(12) United States Patent
Douville et al.

(10) Patent No.: US 12,064,407 B2
(45) Date of Patent: Aug. 20, 2024

(54) ENDOGENOUS RETROVIRUS-K (ERVK) ENCODES AN ALTERNATE ENVELOPE PROTEIN

(71) Applicant: University of Manitoba, Winnipeg (CA)

(72) Inventors: Renée Douville, Winnipeg (CA); Mamneet Gurm, Winnipeg (CA)

(73) Assignee: UNIVERSITY OF WINNIPEG, Winnipeg (CA)

( * ) Notice: Subject to any disclaimer, the term of this patent is extended or adjusted under 35 U.S.C. 154(b) by 567 days.

(21) Appl. No.: 16/756,947

(22) PCT Filed: Oct. 17, 2018

(86) PCT No.: PCT/CA2018/051306
§ 371 (c)(1),
(2) Date: Apr. 17, 2020

(87) PCT Pub. No.: WO2019/075562
PCT Pub. Date: Apr. 25, 2019

(65) Prior Publication Data
US 2023/0064896 A1 Mar. 2, 2023

Related U.S. Application Data

(60) Provisional application No. 62/573,290, filed on Oct. 17, 2017.

(51) Int. Cl.
| *A61K 31/192* | (2006.01) |
| *A61K 31/352* | (2006.01) |
| *A61K 31/40* | (2006.01) |
| *A61K 31/56* | (2006.01) |
| *A61P 31/12* | (2006.01) |
| *A61P 35/00* | (2006.01) |

(52) U.S. Cl.
CPC .......... *A61K 31/192* (2013.01); *A61K 31/352* (2013.01); *A61K 31/40* (2013.01); *A61K 31/56* (2013.01); *A61P 31/12* (2018.01); *A61P 35/00* (2018.01)

(58) Field of Classification Search
CPC ..... A61K 31/352; A61K 31/192; A61P 31/12; A61P 35/00
See application file for complete search history.

(56) References Cited

U.S. PATENT DOCUMENTS

| 7,205,146 B1 | 4/2007 | Keith et al. |
| 7,745,391 B2 | 6/2010 | Mintz et al. |
| 7,776,523 B2 | 8/2010 | Garcia et al. |
| 7,964,341 B2 | 6/2011 | Laderoute et al. |
| 2005/0228172 A9 | 10/2005 | Wang |

OTHER PUBLICATIONS

Adams et al., "Mechanisms of Conotoxin Inhibition of N-Type (Cav2.2) Calcium Channels," Biochim Biophys Acta. 1828(7):1619-1628 (2013).
Alfahad et al., "Retroviruses and Amyotrophic Lateral Sclerosis," Antiviral Res. 99(2):180-187 (2013).
Amy et al., "A Common Functional Allele of the Nogo Receptor Gene, Reticulon 4 Receptor (RTN4R), is Associated With Sporadic Amyotrophic Lateral Sclerosis in a French Population," Amyotroph Lateral Scler Frontotemporal Degener. 16:490-496 (2015).
Anderson., "Bioterrorism Toxins as Weapons," J Pharm Pract. 25(2):121-129

(56) References Cited

OTHER PUBLICATIONS

Buck et al., "The Human Immunodeficiency Virus Type 1 gag Gene Encodes an Internal Ribosome Entry Site," J Virol. 75(1):181-91 (2001).
Buee et al., "Tau Protein Isoforms, Phosphorylation and Role in Neurodegenerative Disorders," Brain Res Rev. 33:95-130 (2000).
Buss et al., "Sequential Loss of Myelin Proteins During Wallerian Degeneration in the Human Spinal Cord," Brain. 128(2):356-364 (2005) (10 pages).
Buzdin et al., "At Least 50% of Human-Specific HERV-K (HML-2) Long Terminal Repeats Serve In Vivo as Active Promoters for Host Nonrepetitive DNA Transcription," J Virol. 80(21):10752-10762 (2006).
Cafferty et al., "The Nogo-Nogo Receptor Pathway Limits a Spectrum of Adult CNS Axonal Growth," J Neurosci. 26(47):12242-12250 (2006).
Caller et al., "Spatial Clustering of Amyotrophic Lateral Sclerosis and the Potential Role of BMAA," Amyotroph Lateral Scler. 13(1):25-32 (2012).
Cappello et al., "Neuromuscular Junction Dismantling in Amyotrophic Lateral Sclerosis," Int J Mol Sci. 18:2092 (2017) (16 pages).
Cascao et al., "Celastrol: A Spectrum of Treatment Opportunities in Chronic Diseases," Front Med. 4:69 (2015) (18 pages).
Chang et al., "Motor Neuron Expression of the Voltage-Gated Calcium Channel Cacophony Restores Locomotion Defects in a Drosophila, TDP-43 Loss of Function Model of ALS," Brain Res. 1584:39-51 (2014).
Chang et al., "Revealing-1 Programmed Ribosomal Frameshifting Mechanisms by Single-molecule Techniques and Computational Methods," Comput Math Methods. 2012:569870 (2012) (9 pages).
Chen et al., "A Mechanistic Overview of Triptolide and Celastrol, Natural Products From Tripterygium Wilfordii Hook F," Front Pharmacol. 9:104 (2018) (13 pages).
Chen et al., "Prognostic Value of Caspase-3 Expression in Cancers of Digestive Tract: A Meta-analysis and Systematic Review," Int J Clin Exp Med. 8(7):10225-10234 (2015).
Chong et al., "Tapping Into the Glial Reservoir: Cells Committed to Remaining Uncommitted," J Cell Biol. 188(3):305-312 (2010).
Christensen., "HERVs in Neuropathogenesis," J Neuroimmune Pharmacol. 5(3):326-335 (2010).
Civetta et al., "Correlated Effects of Sperm Competition and Postmating Female Mortality," Proceedings of the National Academy of Sciences of the United States of America. 97(24):13162-13165 (2000).
Civetta et al., "Quantitative Trait Loci and Interaction Effects Responsible for Variation in Female Postmating Mortality in *Drosophila* Simulans and D. Sechellia Introgression Lines.," Heredity. 94:94-100 (2005).
Contreras-Galindo et al., "Characterization of Human Endogenous Retroviral Elements in the Blood of HIV-1-Infected Individuals," J Virol. 86(1):262-276 (2012).
Daly et al., "Bioactive Cystine Knot Proteins," Curr Opin Chem Biol. 15(3):362-368 (2011).
Daly et al., "NMR and Protein Structure in Drug Design: Application to Cyclotides and Conotoxins," Eur Biophys J. 40(4):359-370 (2011).
Davis et al., "Blood-CNS Barrier Impairment in ALS Patients Versus an Animal Model," Front Cell Neurosci. 8:21 (2014) (9 pages).
De Faria Jr et al., "Activity-dependent central nervous system myelination throughout life," J Neurochem. 148(4):447-461 (2018).
Denne et al., "Physical and Functional Interactions of Human Endogenous Retrovirus Proteins Np9 and Rec With the Promyelocytic Leukemia Zinc Finger Protein," J Virol. 81(11):5607-5616 (2007) (11 pages).
Dewannieux et al., "Identification of a Functional Envelope Protein From the HERV-K Family of Human Endogenous Retroviruses," J Virol. 79(24): 15573-15577 (2005).

Dhamija et al., "Tat Predominantly Associates With Host Promoter Elements in HIV-1-infected T-Cells—Regulatory Basis of Transcriptional Repression of c-Rel," FEBS J. 282(3):595-610 (2015).
Dimos et al., "Induced Pluripotent Stem Cells Generated from Patients with ALS can be Differentiated into Motor Neurons," Science. 321(5893):1218-1221 (2008) (5 pages).
Dinkel et al., "ELM 2016-data Update and New Functionality of the Eukaryotic Linear Motif Resource," Nucleic Acids Res. 44(D1):D294-300 (2016).
Do et al., "Three-Dimensional Imaging of HIV-1 Virological Synapses Reveals Membrane Architectures Involved in Virus Transmission," J Virol. 88(18):10327-10339 (2014).
Douville et al., "Human Endogenous Retrovirus-K and TDP-43 Expression Bridges ALS and HIV Neuropathology," Front Microbiol. 8:1986 (2017) (8 pages).
Douville et al., "Identification of Active Loci of a Human Endogenous Retrovirus in Neurons of Patients With Amyotrophic Lateral Sclerosis," Ann Neurol. 69(1):141-151 (2011).
Dupuis et al., "Nogo Provides a Molecular Marker for Diagnosis of Amyotrophic Lateral Sclerosis," Neurobiol Dis. 10(3):358-365 (2002).
Egawa et al., "Drug Screening for ALS Using Patient-Specific Induced Pluripotent Stem Cells," Sci Transl Med. 4(145):145ra104 (2012) (9 pages).
Eisen et al., "Cortical Influences Drive Amyotrophic Lateral Sclerosis," J Neurol Neurosurg Psychiatry. 88(11):917-924 (2017).
Eldridge et al., "Characterization of a Baculovirus Gene Encoding a Small Conotoxinlike Polypeptide," J Virol. 66(11):6563-6571 (1992).
Estes et al., "Motor Neurons and Glia Exhibit Specific Individualized Responses to TDP-43 Expression in a *Drosophila* Model of Amyotrophic Lateral Sclerosis," Dis Model Mech. 6(3):721-733 (2013).
Fan et al., "Counteraction of Nogo-A and Axonal Growth Inhibitors by Green Tea Polyphenols and Other Natural Products," Neural Regen Res. 11(4):545-546 (2016).
Fancy et al., "Dysregulation of the Wnt Pathway Inhibits Timely Myelination and Remyelination in the Mammalian CNS," Genes Dev. 23(13):1571-1585 (2009) (16 pages).
Fang et al., "High-throughput Study of the Effects of Celastrol on Activated Fibroblast-like Synoviocytes From Patients With Rheumatoid Arthritis," Genes. 8:221 (2017) (12 pages).
Fang et al., "The Nogo/Nogo Receptor (NgR) Signal is Involved in Neuroinflammation through the Regulation of Microglial Inflammatory Activation," J Biol Chem. 290(48):28901-28914 (2015) (15 pages).
Frank et al., "Human Endogenous Retrovirus Expression Profiles in Samples from Brains of Patients with Schizophrenia and Bipolar Disorders," J Virol. 79(17):10890-10901 (2005).
Fu et al., "Gambogic acid inhibits spinal cord injury and inflammation through suppressing the p38 and Akt signaling pathways," Mol Med Rep. 17(1):2026-2032 (2017).
Garcia et al., "Functional domains required for tat-induced transcriptional activation of the HIV-1 long terminal repeat," EMBO J. 7(10):3143-3147 (1988).
Garrison et al., "Transcriptional Errors in Human Immunodeficiency Virus Type 1 Generate Targets for T-cell Responses," Clin Vaccine Immunol. 16(9):1369-1371 (2009).
Ghosh et al., "Study of Pathway Cross-talk Interactions With NF-kappaB Leading to its Activation via Ubiquitination or Phosphorylation: A Brief Review," Gene. 584(1):97-109 (2016).
Ghosh et al., "Targeted Ablation of Oligodendrocytes Triggers Axonal Damage," PLoS One. 6(7):e22735 (2011) (10 pages).
Gifford et al., "The Evolution, Distribution and Diversity of Endogenous Retroviruses," Virus Genes. 26(3):291-316 (2003) (26 pages).
Gomez-Ospina et al., "A Promoter in the Coding Region of the Calcium Channel Gene CACNA1C Generates the Transcription Factor CCAT," PLoS One. 8(4):e60526 (2013) (11 pages).
Gomez-Ospina et al., "The C Terminus of the L-Type Voltage-gated Calcium Channel CAV1.2 Encodes a Transcription Factor," Cell. 127(3):591-606 (2006).
Gonzalez-Hernandez et al., "Regulation of the Human Endogenous Retrovirus K (HML-2) Transcriptome by the HIV-1 Tat Protein," J Virol. 88(16):8924-8935 (2014).

(56) References Cited

OTHER PUBLICATIONS

Gracy et al., "KNOTTIN: The Knottin or Inhibitor Cystine Knot Scaffold in 2007," Nucleic Acids Res. 36:D314-9 (2008).
Griffiths., "Endogenous Retroviruses in the Human Genome Sequence," Genome Biol. 2(6):1017.1-1017.5 (2001) (5 pages).
Hanke et al., "Reconstitution of the Ancestral Glycoprotein of Human Endogenous Retrovirus K and Modulation of its Functional Activity by Truncation of the Cytoplasmic Domain," J Virol. 83(24):12790-12800 (2009).
Hardiman et al., "Amyotrophic Lateral Sclerosis," Nat Rev Dis Primers. 3:17071 (2017) (19 pages).
Ho et al., "Cytolytic CD8+ T Cells Directed Against a Cryptic Epitope Derived From a Retroviral Alternative Reading Frame Confer Disease Protection," J Immunol.176(4):2470-2475 (2006) (7 pages).
Hohn et al., "HERV-K(HML-2), The Best Preserved Family of HERVs: Endogenization, Expression, and Implications in Health and Disease," Front Oncol. 3:246 (2013) (12 pages).
Huang et al., "Comparison of Larval and Adult *Drosophila* Astrocytes Reveals Stage-Specific Gene Expression Profiles," Genes,Genomes,Genetics. 5(4):551-558 (2015).
Hughes et al., "*Drosophila* as a Genetic Model for Studying Pathogenic Human Viruses," Virology. 423(1):1-5 (2012).
Hurtado et al., "Immunohistochemical Overexpression of MAP-2 in the Cerebral Cortex of Rabies-infected Mice," Int J Morphol. 33(2):465-470 (2015).
Ineichen et al., "Nogo-A Antibodies for Progressive Multiple Sclerosis," CNS Drugs. 31(3):187-198 (2017) (12 pages).
International Search Report and Written opinion for International Patent Application No. PCT/CA2018/051306, dated Jan. 22, 2019 (20 pages).
International Preliminary Report on Patentability and Written Opinion for International Patent Application No. PCT/CA2018/051306, dated Apr. 21, 2020 (10 pages).
Iyer et al., "Tying the Knot: The Cystine Signature and Molecular-Recognition Processes of the Vascular Endothelial Growth Factor Family of Angiogenic Cytokines," FEBS J. 278(22):4304-4322 (2011).
Jackson et al., "Structural and Molecular Evolutionary Analysis of Agouti and Agouti-Related Proteins," Chemistry and Biology. 13(12):1297-1305 (2006).
Jang et al., "Gambogic Amide, a Selective Agonist for TrkA Receptor That Possesses Robust Neurotrophic Activity, Prevents Neuronal Cell Death," PNAS. 104(41):16329-16334 (2007).
Jang et al., Transglutaminase 2 Suppresses Apoptosis by Modulating Caspase 3 and NF-kappaB Activity in Hypoxic Tumor Cells, Oncogene. 29(3):356-367 (2010).
Jiang et al., "In-labeled Cystine-knot Peptides Based on the Agouti-related Protein for Targeting Tumor Angiogenesis," J Biomed Biotechnol. 2012:368075 (2012) (8 pages).
Jokic et al., "The Neurite Outgrowth Inhibitor Nogo-A Promotes Denervation in an Amyotrophic Lateral Sclerosis Model," EMBO Rep. 7(11):1162-1167 (2006).
Julien et al., "Crystal Structure of a Soluble Cleaved HIV-1 Envelope Trimer," Science. 342(6165):1477-1483 (2013) (12 pages).
Kalantari et al., "15-deoxy-delta12, 14-prostaglandin J2 Inhibits HIV-1 Transactivating Protein, Tat, Through Covalent Modification," FASEB J. 23(8):2366-2373 (2009).
Kashyap et al., "Molecular Targets of Celastrol in Cancer: Recent Trends and Advancements," Crit Rev Oncol Hematol. 128:70-81 (2018).
Kashyap et al., "Molecular Targets of Gambogic Acid in Cancer: Recent Trends and Advancements," Tumour Biol. 37:12915-12925 (2016).
Kearse et al., "Geneious Basic: An Integrated and Extendable Desktop Software Platform for the Organization and Analysis of Sequence Data," Bioinformatics. 28(12):1647-1649 (2012) (3 pages).
Keller et al., "Functional Independence of the Two Cysteine-Rich Activation Domains in the Yeast Mac1 Transcription Factor," J Biol Chem. 275(38):29193-29199 (2000) (8 pages).

Kesidou et al., Autophagy and Neurodegenerative disorders, Neural Regen Res. 8(24):2275 (2013) (15 pages).
Kim et al., "HIV-1 Tat Interacts with and Regulates the Localization and Processing of Amyloid Precursor Protein," PLoS One. 8(11):e77972 (2013) (12 pages).
Krug et al., "Retrotransposon Activation Contributes to Neurodegeneration in a Drosophila TDP-43 Model of ALS," PLoS genet. 13(3):e1006635 (2017) (34 pages).
Kruman et al., "HIV-1 Protein Tat Induces Apoptosis of Hippocampal Neurons by a Mechanism Involving Caspase Activation, Calcium Overload, and Oxidative Stress," Exp Neurol. 254(2):276-288 (1998).
Kuhlmann et al., "Differentiation Block of Oligodendroglial Progenitor Cells as a Cause for Remyelination Failure in Chronic Multiple Sclerosis," Brain. 131(Pt 7):1749-1758 (2008).
Kwong et al., "TDP-43 Proteinopathy: The Neuropathology Underlying Major Forms of Sporadic and Familial Frontotemporal Lobar Degeneration and Motor Neuron Disease," Acta Neuropathol. 114:63-70 (2007).
Lancaster et al., "Cerebral Organoids Model Human Brain Development and Microcephaly," Nature. 501(7467):373-379 (2003) (18 pages).
Leal et al., "Calcium Dysregulation Links ALS Defective Proteins and Motor Neuron Selective Vulnerability," Frontiers in Cellular Neuroscience. 9:225 (2015) (6 pages).
Lemaitre et al., "The HERV-K Human Endogenous Retrovirus Envelope Protein Antagonizes Tetherin Antiviral Activity," J Virol. 88(23):13626-13637 (2014).
Lesbats et al., "Retroviral DNA Integration," Chem Rev. 116(20):12730-12757 (2016).
Li et al., "Function and Solution Structure of hainantoxin-I, a Novel Insect Sodium Channel Inhibitor From the Chinese Bird Spider Selenocosmia Hainana," FEBS Lett. 55(3):616-622 (2003).
Li et al., "Human Endogenous Retrovirus-κ Contributes to Motor Neuron Disease," Sci Transl Med. 7(307):307ra153 (2015) (27 pages).
Lokossou et al., "Implication of Human Endogenous Retrovirus Envelope Proteins in Placental Functions," Viruses. 6(11):4609-4627 (2014) (20 pages).
Lopez-Lastra et al., "Protein Synthesis in Eukaryotes: The Growing Biological Relevance of Cap-Independent Translation Initiation," Biol Res. 38(2-3):121-146 (2005).
MacFarlane et al., "Allelic Variation of HERV-K(HML-2) Endogenous Retroviral Elements in Human Populations," J Mol Evol. 59:642-656 (2004).
MacGowan et al., "An ALS-like Syndrome With New HIV Infection and Complete Response to Antiretroviral Therapy., " Neurology. 57(6):1094-1097 (2001) (6 pages).
Manghera et al., "Endogenous Retrovirus-K Promoter: A Landing Strip for Inflammatory Transcription Factors," Retrovirology. 10:16 (2013) (11 pages).
Manghera et al., "Endogenous Retrovirus-K and Nervous System Diseases," Curr Neurol Neurosci Rep. 14(10):488 (2014) (10 pages).
Manghera et al., "ERVK Polyprotein Processing and Reverse Transcriptase Expression in Human Cell Line Models of Neurological Disease," Viruses. 7(1):320-332 (2015).
Manghera et al., "NF-kappaB and IRF1 Induce Endogenous Retrovirus K Expression via Interferon-Stimulated Response Elements in its 5 ' Long Terminal Repeat," J Virol. 90(20):9338-9349 (2016).
Manghera et al., "TDP-43 Regulates Endogenous Retrovirus-K Viral Protein Accumulation," Neurobiol Dis. 94:226-236 (2016).
Manghera, Mamneet, Thesis: "Re-Activation of Human Endogenous Retrovirus-K in Neuroinflammatory Disease," Master of Science in Bioscience, Technology, and Public Policy, he University of Winnipeg, 2015 (199 pages).
Marambaud et al., "Calcium Signaling in Neurodegeneration," Mol Neurodegener. 4:20 (2009) (15 pages).
Marchi et al., "Unfixed Endogenous Retroviral Insertions in the Human Population," J Virol. 88(17):9529-9537 (2014).
Marsili et al., "On the Role of Interferon Regulatory Factors in HIV-1 Replication," Ann N Y Acad Sci. 1010:29-42 (2003) (15 pages).

(56) References Cited

OTHER PUBLICATIONS

Matsuzaki et al., "HTLV-I-associated Myelopathy (HAM)/tropical Spastic Paraparesis (TSP) With Amyotrophic Lateral Sclerosis-like Manifestations," J Neuro Virol. 6(6):544-548 (2000).
McCombe et al., "The Role of Immune and Inflammatory Mechanisms in ALS," Curr Mol Med. 11(3):246-254 (2011).
McCormick et al., "Quantification of Reverse Transcriptase in ALS and Elimination of a Novel Retroviral Candidate," Neurology. 70(4):278-283 (2008) (8 pages).
McDonald et al., "Targeting the Nogo Receptor Complex in Diseases of the Central Nervous System," Curr Med Chem. 18(2):234-244 (2011).
McNulty et al., "Structures of the Agouti Signaling Protein," J Mol Biol. 346(4):1059-1070 (2005).
McTigue et al., "The Life, Death, and Replacement of Oligodendrocytes in the Adult CNS," J Neurochem. 107(1):1-19 (2008).
Meininger et al., "Safety and Efficacy of Ozanezumab in Patients With Amyotrophic Lateral Sclerosis: A Randomised, Double-blind, Placebo-Controlled, Phase 2 Trial," Lancet Neurol. 16(3):208-216 (2017).
Meininger et al., "Safety, Pharmacokinetic, and Functional Effects of the Nogo-a Monoclonal Antibody in Amyotrophic Lateral Sclerosis: A Randomized, First-in-human Clinical Trial," PLoS One. 9(5):e97803 (2014) (12 pages).
Miron et al., "Cells of the Oligodendroglial Lineage, Myelination, and Remyelination," Biochim Biophys Acta. 1812(2):184-193 (2011).
Mitchell et al., "Amyotrophic Lateral Sclerosis," Lancet. 369(9578):2031-2041 (2007).
Moisse et al., "Innate Immunity in Amyotrophic Lateral Sclerosis," Biochim Biophys Acta. 1762(11-12):1083-93 (2006).
Monroy-Gomez et al., "Overexpression of MAP2 and NF-H Associated with Dendritic Pathology in the Spinal Cord of Mice Infected with Rabies Virus," Viruses. 10(3):112 (2018) (11 pages).
Mullick et al.,"The Cumate Gene-Switch: A System for Regulated Expression in Mammalian Cells," BMC Biotechnol. 6:43 (2006) (18 pages).
Narayan et al., "Celastrol Inhibits Tat-Mediated Human Immunodeficiency Virus (HIV) Transcription and Replication," J Mol Biol. 410(5):972-983 (2011).
Nielsen et al., "Structure-activity Relationships of Omega-conotoxins at N-type Voltage-sensitive Calcium Channels," J Mol Recognit. 13(2):55-70 (2000) (20 pages).
Norton et al., "Conotoxins Down Under," Toxicon. 48(7):780-98 (2006).
Obafemi et al., "Prolonged Delirium With Psychotic Features From Omega Conotoxin Toxicity," Pain Med. 14(3):447-8 (2013).
Olivera et al., "Diversity of the Neurotoxic Conus Peptides: A Model for Concerted Pharmacological Discovery," Mol Interv. 7(5):251-260 (2007) (11 pages).
Othman et al., "Olig1 is Expressed in Human Oligodendrocytes During Maturation and Regeneration," Glia. 59(6):914-926 (2011).
Paris et al., "Reduction of beta-amyloid Pathology by Celastrol in a Transgenic Mouse Model of Alzheimer's Disease," J Neuroinflammation. 7:17 (2010) (15 pages).
Pernet et al., "Nogo-A and Myelin-Associated Glycoprotein Differently Regulate Oligodendrocyte Maturation and Myelin Formation," Journal of Neuroscience. 28(29):7435-7444 (2008).
Pettersen et al., "UCSF Chimera—A Visualization System for Exploratory Research and Analysis," J Comput Chem. 25(13):1605-1612 (2004) (1 page) (Abstract).
Poniatowski et al., "Analysis of the Role of CX3CL1 (Fractalkine) and its Receptor CX3CR1 in Traumatic Brain and Spinal Cord Injury: Insight into Recent Advances in Actions of Neurochemokine Agents," Mol Neurobiol. 54(3):2167-2188 (2017).
Popper et al., Lower Human Immunodeficiency Virus (HIV) Type 2 Viral Load Reflects the Difference in Pathogenicity of HIV-1 and HIV-2, J Infect Dis. 180(4):1116-1121 (1999).
Pradat et al., "Muscle Nogo-A Expression is a Prognostic Marker in Lower Motor Neuron Syndromes," Ann Neurol. 62(1):15-20 (2007).
Pu et al., "Caspase-3 and Caspase-8 Expression in Breast Cancer: Caspase-3 is Associated With Survival," Apoptosis. 22(3):357-368 (2017).
Reutrakul et al., "Cytotoxic and Anti-HIV-1 Caged Xanthones From the Resin and Fruits of Garcinia Hanburyi," Planta med. 73(1):33-40 (2007).
Rosati et al., "Establishment of Stable Ips-derived Human Neural Stem Cell Lines Suitable for Cell Therapies," Cell Death Dis. 9(1):937 (2018) (16 pages).
Ruggieri et al., "Human Endogenous Retrovirus HERV-K(HML-2) Encodes a Stable Signal Peptide With Biological Properties Distinct From Rec," Retrovirology. 6:17 (2009) (20 pages).
Saini et al., "The Next Generation Non-competitive Active Polyester Nanosystems for Transferrin Receptor-mediated Peroral Transport Utilizing Gambogic Acid as a Ligand," Scientific Reports. 6:29501 (2016) (16 pages).
Salminen et al., "Celastrol: Molecular Targets of Thunder God Vine," Biochem Biophys Res Commun. 394(3):439-42 (2010).
Sato et al., "Binding of Ala-scanning Analogs of Omega-conotoxin MVIIC to N- and P/Q-type Calcium Channels," FEBS Lett. 469(2-3):147-150 (2000).
Schmandke et al., "Nogo-A: Multiple Roles in CNS Development, Maintenance, and Disease," Neuroscientist. 20(4):372-386 (2014) (16 pages).
Schmitt et al., "Transcriptional Profiling of Human Endogenous Retrovirus Group HERV-K(HML-2) Loci in Melanoma," Genome Biol Evol. 5(2):307-328 (2013).
Scotter et al., "TDP-43 Proteinopathy and ALS: Insights into Disease Mechanisms and Therapeutic Targets," Neurotherapeutics. 12(2):352-363 (2015).
Seifarth et al., "Comprehensive Analysis of Human Endogenous Retrovirus Transcriptional Activity in Human Tissues With a Retrovirus-specific Microarray," J Virol. 79(1):341-352 (2005).
Sepe et al., "Proteolytic Control of Neurite Outgrowth Inhibitor NOGO-A by the cAMP/PKA Pathway," Proc Natl Acad Sci USA. 111(44):15729-15734 (2014).
Sheehy et al., "Functional Analysis of Human T Lymphotropic Virus Type 2 Tax Proteins," Retrovirology. 3:20 (2006) (10 pages).
Shin et al., "Human-Specific HERV-K Insertion Causes Genomic Variations in the Human Genome," PLoS One. 8(4):e60605 (2013) (10 pages).
Su et al., "Regulation of N-type Voltage-gated Calcium Channels and Presynaptic Function by Cyclin-Dependent Kinase 5," Neuron. 75(4):675-687 (2012) (28 pages).
Subramanian et al., "Identification, Characterization, and Comparative Genomic Distribution of the HERV-K (HML-2) Group of Human Endogenous Retroviruses," Retrovirology. 8:90 (2011) (22 pages).
Sui et al., "New Insights into the Roles of Nogo-A in CNS Biology and Diseases," Neurochem Res. 40(9):1767-85 (2015).
Szilagyi et al., "Efficient Prediction of Nucleic Acid Binding Function From Low-resolution Protein Structures," J Mol Biol. 358(3):922-933 (2006).
Takata et al., "Clinical Significance of Caspase-3 Expression in Pathologic-stage I, Nonsmall-Cell Lung Cancer," Int J Cancer. 96(Suppl.):54-60 (2001).
Talbott et al., "Endogenous Nkx2.2+/olig2+ Oligodendrocyte Precursor Cells Fail to Remyelinate the Demyelinated Adult Rat Spinal Cord in the Absence of Astrocytes," Exp Neurol. 192(1):11-24 (2005).
Tao et al., "Treatment of Rheumatoid Arthritis With Low Doses of Multi-glycosides of Tripterygium Wilfordii," Chinese Journal of Modern Developments in Traditional Medicine. 10(5):289-91 (1990) (abstract) (1 pages).
Teng et al., "Nogo Signaling and Non-physical Injury-induced Nervous System Pathology," J Neurosci Res. 79(3):273-278 (2005).
Terry et al., "Expression of HERV-K108 Envelope Interferes With HIV-1 Production," Virology. 509:52-59 (2017) (17 pages).
Theotokis et al., "Time Course and Spatial Profile of Nogo-A Expression in Experimental Autoimmune Encephalomyelitis in C57BL/6 Mice," J Neuropathol Exp Neurol. 71(10):907-920 (2012).

(56) References Cited

OTHER PUBLICATIONS

Thompson et al., "Treatment Challenges and Complications With Ziconotide Monotherapy in Established Pump Patients," Pain Physician. 9(2):147-152 (2006).
Timmermann et al., "Distribution of High-Voltage-activated Calcium Channels in Cultured Gamma-aminobutyric Acidergic Neurons From Mouse Cerebral Cortex," J Neurosci Res. 67(1):48-61 (2002).
Tognatta et al., "Contribution of the Oligodendrocyte Lineage to CNS Repair and Neurodegenerative Pathologies," Neuropharmacology. 110(Pt B):539-547 (2016).
Toufaily et al., "Activation of LTRS From Different Human Endogenous Retrovirus (HERV) Families by the HTLV-1 Tax Protein and T-cell Activators," Viruses. 3(11):2146-59 (2011).
Touriol., "Generation of Protein Isoform Diversity by Alternative Initiation of Translation at Non-AUG Codons," Biol Cell. 95(3-4):169-178 (2003).
Ueki et al., "Cryptides: Functional Cryptic Peptides Hidden in Protein Structures," Biopolymers. 88(2):190-8 (2007).
Vagner et al., "Alternative Translation Initiation of the Moloney Murine Leukemia Virus mRNA Controlled by Internal Ribosome Entry Involving the p57/PTB Splicing Factor," J Biol Chem. 270(35):20376-20383 (1995).
Venkatesha et al., "Suppression of Autoimmune Arthritis by Celastrus-derived Celastrol Through Modulation of Pro-Inflammatory Chemokines," Bioorg Med Chem. 20(17):5229-5234 (2012).
Verma et al., "ALS Syndrome in Patients With HIV-1 Infection," J Neurol Sci. 240(1-2):59-64 (2006).
Vincendeau et al., "Modulation of Human Endogenous Retrovirus (Herv) Transcription During Persistent and De Novo HIV-1 Infection," Retrovirology. 12:27 (2015) (17 pages).
Vlahopoulos et al., "Dynamic Aberrant NF-kappaB Spurs Tumorigenesis: A New Model Encompassing the Microenvironment," Cytokine Growth Factor Rev. 26(4):389-403 (2015).
Vocero-Akbani et al., "Transduction of Full-length Tat Fusion Proteins Directly Into Mammalian Cells: Analysis of T Cell Receptor Activation-induced Cell Death," Methods Enzymol. 322:508-521 (2000).
Wang et al., "Gambogic Acid-Induced Degradation of Mutant p53 is Mediated by Proteasome and Related to Chip," J Cell Biochem. 112(2):509-519 (2011).
Wang et al., "Reversal of a Full-length Mutant Huntingtin Neuronal Cell Phenotype by Chemical Inhibitors of Polyglutamine-mediated Aggregation," BMC Neurosci. 6:1 (2005) (12 pages).
Watkins et al., "Distinct Stages of Myelination Regulated by Gamma-secretase and Astrocytes in a Rapidly Myelinating CNS Coculture System," Neuron. 60(4):555-569 (2008).
Weiss, "The Discovery of Endogenous Retroviruses," Retrovirology. 3:67 (2006) (11 pages).
Williams, "Transcriptional Regulation of Interferon-stimulated Genes," Eur J Biochem. 200(1):1-11 (1991).
Wills, "Blockade of the Neurite Outgrowth Inhibitor Nogo-A in Amyotrophic Lateral Sclerosis," Lancet Neurol. 16(3):175-176 (2017).
Wojcik et al., "Increased Expression of Nogo-A in ALS muscle biopsies is not unique for this disease," Acta Myol. 25(3):116-118 (2006).
Wurzer et al., "Caspase 3 Activation is Essential for Efficient Influenza Virus Propagation," EMBO J. 22(11):2717-2728 (2003).
Yan et al., "Sera From Amyotrophic Lateral Sclerosis Patients Reduce High-voltage Activated Ca2+ Currents in Mice Dorsal Root Ganglion Neurons," Neurosci Lett. 235(1-2):69-72 (1997).
Yang et al., "Targeting Signaling Factors for Degradation, an Emerging Mechanism for TRAF Functions," Immunol Rev. 266(1):56-71 (2015).
Yu et al., "Gambogenic Acid Induces Proteasomal Degradation of CIP2A and Sensitizes Hepatocellular Carcinoma to Anticancer Agents," Oncology Reports. 36(6):3611-3618 (2016).
Zhou et al., "Functional Integrity of Nuclear Factor KappaB, Phosphatidylinositol 3'-Kinase, and Mitogen-activated Protein Kinase Signaling Allows Tumor Necrosis Factor Alpha-Evoked Bcl-2 Expression to Provoke Internal Ribosome Entry Site-Dependent Translation of Hypoxia-inducible Factor 1alpha," Cancer Res. 64(24):9041-9048 (2004).
Zhou et al., "Implications of White Matter Damage in Amyotrophic Lateral Sclerosis (Review)," Mol Med Rep. 16(4):4379-4392 (2017).
Zhu et al., "Evolutionary Origin of Inhibitor Cystine Knot Peptides," FASEB J. 17(12):1765-1767 (2003).

Figure 1: Two types of ERVK genomes. The ERVK genome consists of four main Retroviridae genes, which are from 5' to 3': *gag, pro, pol,* and *env*. These viral genes are flanked by long terminal repeats (LTRs) containing U3, R and U5 regions. Two types of ERVK genomes can be distinguished based on a 292 bp deletion in the *env* gene.

FIG 2

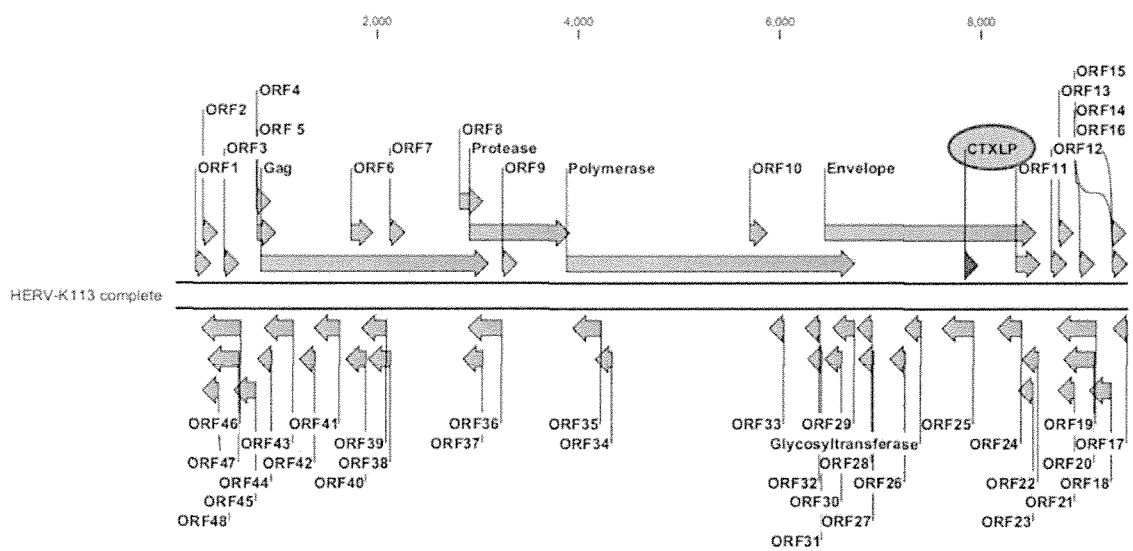

Figure 2: Open reading frames on both strands of the endogenous retrovirus K-113 genome. ORFs bigger than 50 nucleotides (yellow) on both the sense and antisense strands were predicted using CLCbio software. The ERVK conotoxin-like protein (CTXLP) ORF is indicated in red. Any amino acid-encoding codon was accepted as an ORF start, although each ended with a stop codon. Note the overlapping ORFs within known ERVK genes, such as *gag, protease, polymerase* and *envelope*.

FIG 3

| Conotoxin | Sequence | |
|---|---|---|
| *Conus geographus* ⎰ ·GVIA | CKSPGSSCSPTSYNCCRSCNPYTKRC | SEQ ID NO: 4 |
| ·GVIC | CKSPGSSCSPTSYNCCRSCNPYTKRC | SEQ ID NO: 5 |
| ·GVIIA | CKSPGSSCSPTSYNCCRSCNPYTKRC | SEQ ID NO: 6 |
| ·GVIIB | CKSPGTPCSRGMRDCCTSCLLYSNKC | SEQ ID NO: 7 |
| *Conus magus* ⎰ ·MVIIA | CKGKGAKCSRLMYDCCTGSCRSGKC | SEQ ID NO: 8 |
| ·MVIIB | CKGKGASCHRTSYDCCTGSCNRGKC | SEQ ID NO: 9 |
| *Conus textile* ·KK-0 | CKQSGEMCNLLDQNCCDGYCIVLVC | SEQ ID NO: 10 |
| ·NPV CTXLP | CAETGAVCHNDECCSGACSPIFNYC | SEQ ID NO: 11 |
| ·Consensus | C...G..C... .CC...C.....C | |

·ERVK CTXLP   CSDYGINCSHSYGCCSRSCIALFC SEQ ID NO: 12

Figure 3: Alignment of cone snail and viral omega conotoxin domain sequences. Sequences from 3 *Conus* species (black), 1 conotoxin-like protein domain sequence from *Autographa Californica* Nuclear Polyhedrosis Virus (blue), the consensus sequence generated from the aforementioned sequences (red) and the sequence of the putative Endogenous Retrovirus K-113 conotoxin-like protein domain (green). Modified from[1]. Note the characteristic C-C-CC-C-C knottin folding motif[2].

FIG 4

| | | | |
|---|---|---|---|
| | HERV-K113 C... | CSDYGINCSHSYGCCSRSCIALFC | SEQ ID NO: 13 |
| | A8C6C4 | CTEDGRNCQYSYECCSGACSALFC | SEQ ID NO: 14 |
| | A0EYV0 | CTETGRNCKYSYECCSNACSAAFC | SEQ ID NO: 15 |
| NPV CTL Proteins | A9YMX2 | CTETGRNCQYSYECCSGACSAVFC | SEQ ID NO: 16 |
| | CXOL2 | CTETGRNCQYSYECCSGACSAAFC | SEQ ID NO: 17 |
| | D3YGV0 | CTEDGRNCQYNYECCSGACSALFC | SEQ ID NO: 18 |
| | D7FSS1 | CTETGRNCKYSYECCSGACSAAFC | SEQ ID NO: 19 |
| | Q2NP33 | CTETGKNCKYSYECCSGACSAAFC | SEQ ID NO: 20 |
| | Q06KN7 | CTETGRNCKYSYECCSGACSAVFC | SEQ ID NO: 21 |
| | Q8QLC7 | CTDTGRNCKYSYECCSGACSAAFC | SEQ ID NO: 22 |
| | Q9PYR8 | CTETGRNCQYSYECCSGACSAAFC | SEQ ID NO: 23 |

Figure 4: Alignment and sequence logo of the putative endogenous retrovirus K-113 conotoxin-like protein domain and 10 Nuclear Polyhedrosis Virus conotoxin-like protein domain sequences. Sequences were aligned and sequence logo was assessed using Geneious v5 software[3]. Note the conserved C-G-NC-Y-CCS-C-A-FC sequence logo in these viral conotoxin-like proteins.

FIG 5

| | | | | | | | |
|---|---|---|---|---|---|---|---|
| Consensus | CTXYGXNC- | XXSYECCSXXCS- | -XGFC | SEQ ID NO: 115 |
| Sequence Logo | | | | |
| Identity | | | | |
| CTXLP | C YG NC- | SY CCS | C -- | F C SEQ ID NO: 116 |
| NPV\|Similar | CT G NC- | SYECCS | CS | GF C SEQ ID NO: 117 |
| NPV\|Central | CT G NC- | S ECCS | CS | GF C SEQ ID NO: 118 |
| Conus\|Similar | C Y C- | ECCS | C -- | G C SEQ ID NO: 119 |
| Conus\|Central | C G C- | CCS | C -- | C SEQ ID NO: 120 |

Figure 5: **ERVK CTXLP cysteine-rich motif has strong similarity to both nuclear polyhedrosis virus (NPV, 46.2%) and *Conus* (45.8%) conotoxin proteins.** Nuclear Polyhedrosis Virus (NPV) and Cone snail conotoxin sequences which are typical ("Central") or which most closely resemble the ERVK conotoxin-like protein encoded in the human genome ("Similar") were identified in Uniprot and hg38 with reference to the protein database Pfam and the repetitive element database Repbase. These were aligned to the Pfam model of the Conotoxin family and the alignment was trimmed to the knottin domain. For details about which search algorithms and measures of centrality were used, see the methods section below. *Methods:* ERVK sequences were identified with ORFfinder in DNA corresponding to entries in UCSC genome browser track rmskJoinedBaseline, derived from Repbase, whose "name" field matches "%#LTR/ERVK". ORFs matching PF08087 were taken to be CTXLP encoding and these were clustered with cd-hit with default settings, identifying the major variant designated "CTXLP". Cone snail sequences were obtained from Uniprot using the search terms "conus conotoxin". Nuclear Polyhedrosis Virus (NPV) sequences were obtained from Uniprot using the search terms "conotoxin taxonomy:'dsDNA viruses, no RNA stage [35237]'". The results of each search were clustered using cd-hit with default settings. The cluster representative sequences for each group were searched using hmmsearch for hits against the models in Pfam clan CL0083. The sequences corresponding to PF02950 (Conotoxin) and PF08087 (toxin_18) with the highest average pairwise percent identity to all other matches for that HMM were designated "Central". BLAST databases were constructed for sequences matching each HMM, and these were queried with CTXLP using blastp. The result with the lowest e-value from each database was designated "Similar". The two "Central" and two "Similar" sequences, along with CTXLP, were aligned to PF02950 using hmmalign, and this alignment was trimmed to the Knottin domain.

FIG 6

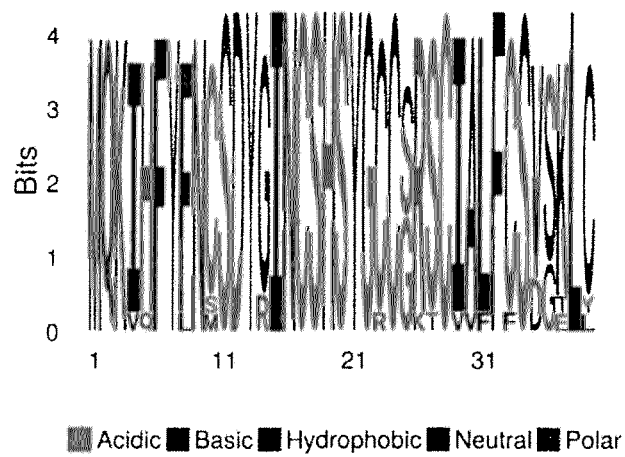

Figure 6: Logo of the knottin domain from cluster representative CTXLP sequences. ERVK CTXLP has 7 cysteines. The amino acid composition includes 1/39 acidic, 5/39 basic, 11/39 hydrophobic, 19/39 polar and 3/39 neutral residues. The bitscores represent the meaningfulness of particular amino-acid residues given their conservation and the composition of the sequences overall. This was produced from a0053/data/ctxlp_variants.cluster.aligned.fasta using the R packages "msa" to load the alignment and "ggseqlogo" to produce the figure.

FIG 7

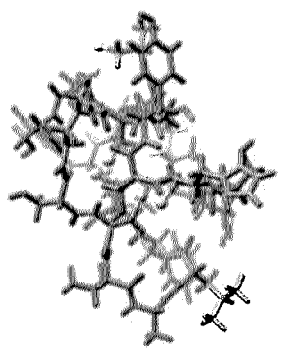

Figure 7: Modeled 3-dimensional structure of the putative Endogenous Retrovirus-K113 conotoxin-like protein domain. Protein tertiary structure was predicted using Knotter1D3D software (gray sticks = carbon, green sticks = hydrogen, red sticks = oxygen, blue sticks = nitrogen and yellow spheres = sulfur). Note the interactions of the yellow cysteine residues, as they form disulfide bonds.

FIG 8

Figure 8: **Aligned overlap of the predicted structures of viral conotoxin-like proteins from ERVK-113 and *Ecotropis obliqua* NPV.** Knotter1D3D was used to predict the structures of putative ERVK-113 CTXLP domain (blue) and *Ecotropis obliqua* NPV CTXLP domain (red). Structure alignment is based on sequence alignment and was prepared using UCSF Chimera software[4].

FIG 9

Figure 9: Aligned overlap of the predicted structures of viral conotoxin-like protein backbones from ERVK-113 and *Ecotropis obliqua* NPV. Knotter1D3D was used to predict the structures of putative ERVK-113 CTXLP domain (blue) and *Ecotropis obliqua* NPV CTXLP domain (red). Structure alignment is based on sequence alignment and was prepared using UCSF Chimera software[4].

FIG 10

CTXLP Cysteine motif sequence logo  CSDYGINCSHSYGCCSRSCIALFCSVSKLC  SEQ ID NO: 24

Figure 10: Predicted inhibitor cysteine knot fold of ERVK CTXLP cysteine-rich peptide. Disulfide bonds connect cysteine 1 to cysteine 4, cysteine 2 to cysteine 5, and cysteine 3 to cysteine 6, resulting in an inhibitor cysteine knot fold.

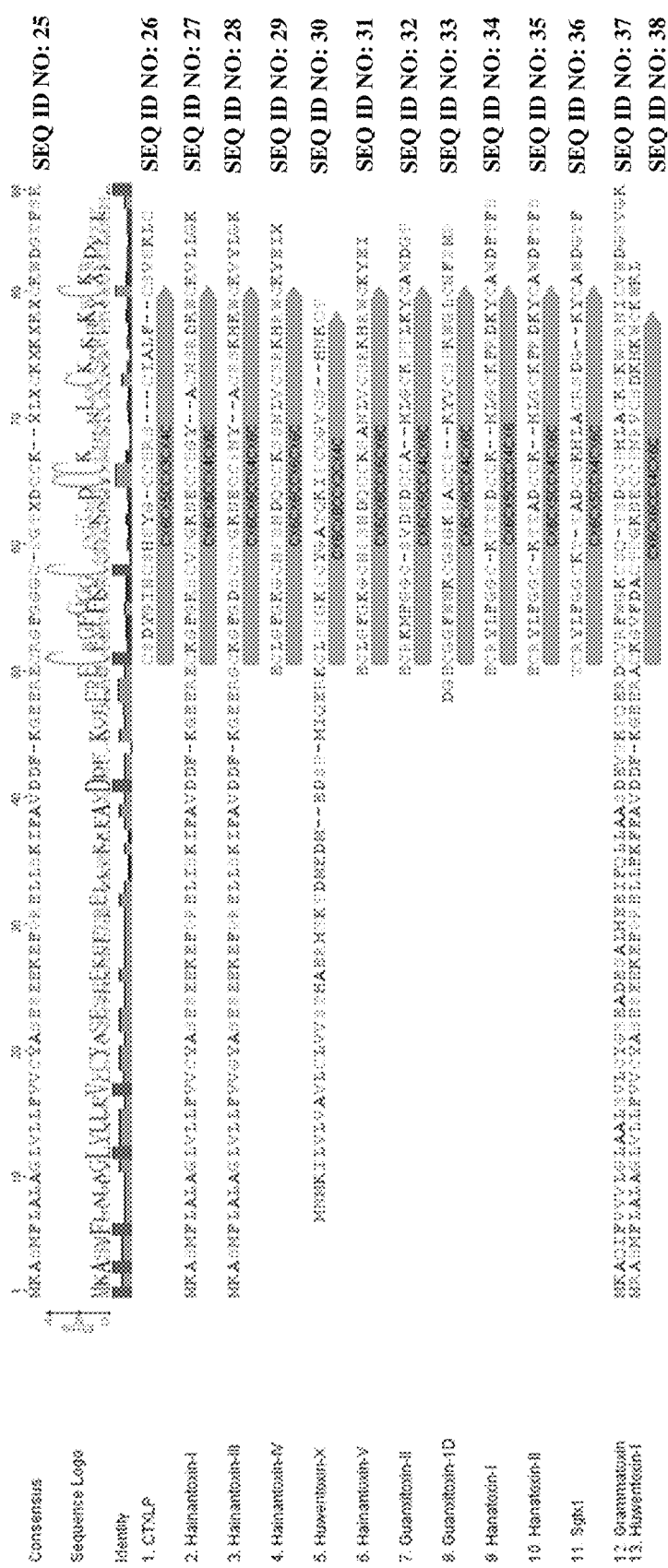

FIG. 11

Figure 11: Alignment and sequence logo of ERVK CTXLP cysteine-rich peptide and 12 spider toxin ICK peptides. Sequences were aligned and sequence logo generated using Geneious Software. A conserved C-C-CC-C-C motif is observed in all sequences. CTXLP, all Hainantoxin and one Guanxitoxin contained a conserved G between the first and second cysteine, as indicated by the star. Grey callouts indicate the cysteine motif spacing of each toxin.

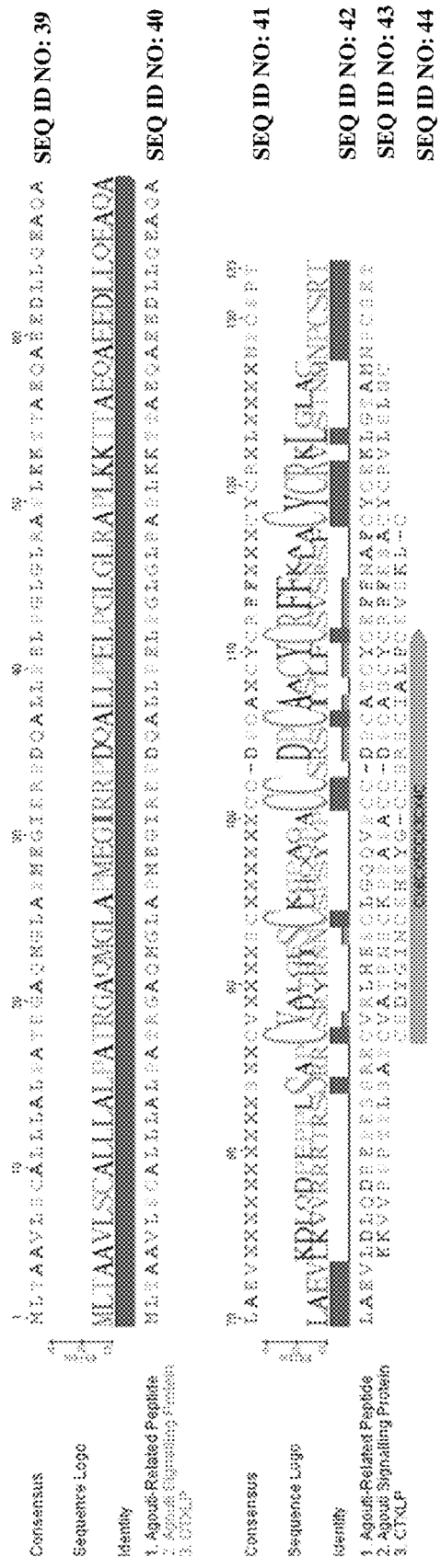
Figure 12: Alignment and sequence logo of ERVK CTXLP cysteine-rich peptide and agouti-related peptide and agouti signalling protein. Sequences were aligned, and sequence logo generated using Geneious Software. A conserved C-C-CC-C-C-C is observed in all sequences.

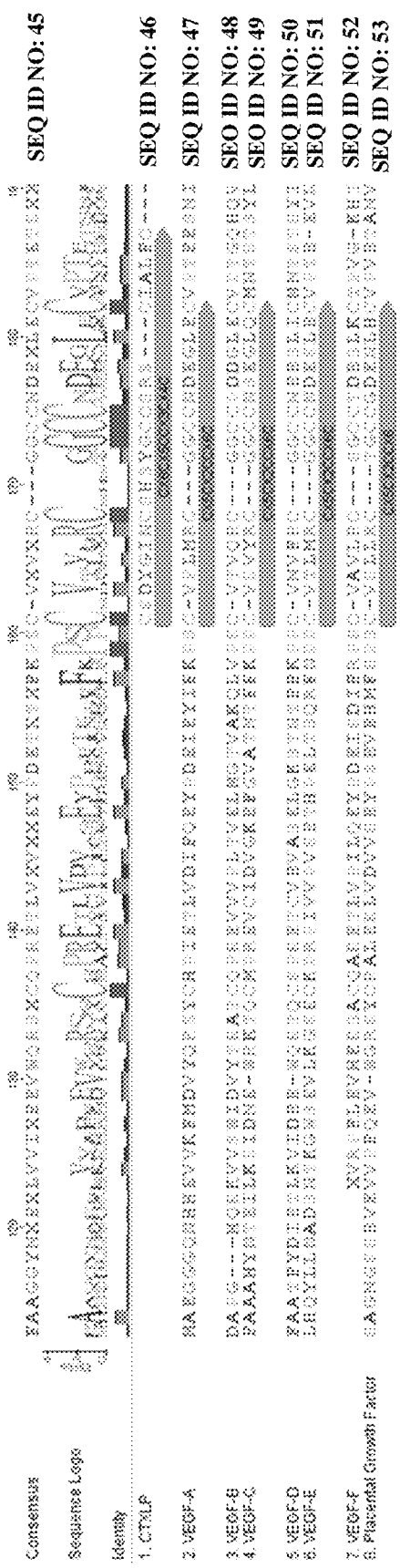

Figure 13: Alignment and sequence logo of ERVK CTXLP cysteine-rich peptide to 7 VEGF Proteins. Sequences were aligned, and sequence logo generated using Geneious Software. No significant conservation was identified between the VEGF proteins and CTXLP, due to the differences in spacing and total number of cysteine residues, as indicated by the grey bar cysteine spacing motif.

Figure 14: Alignment and sequence logo of ERVK CTXLP cysteine-rich peptide and HIV-1 and HIV-2 Tat proteins. Sequences were aligned, and sequence logo generated using Geneious Software. Conservation of 6 of the 7 CTXLP cysteine residues are found in HIV Tat, as well as 1 lysine and 1 leucine residue in the C terminus, between amino acids 75 and 80.

Figure 15: Example Alignment of Chromosome 1 ERVK HML-2 insertions with the DNA sequences for Rec exon 1 and CTXLP. Sequences were aligned, and sequence logo generated using Geneious software. Rec exon 1 aligned with bp 1 to 261 of *env*. CTXLP aligned with bp 1413 to 1505 of *env*.

FIG. 16

Figure 16: Alignment of conotoxin-like peptides of 25 human ERVK HML-2 insertions. Alignment and sequence logo generated using Geneious Software. CTXLP-peptides showed variability in the amino acid sequence. Three distinct alleles were identified, as well as several unique sequences.

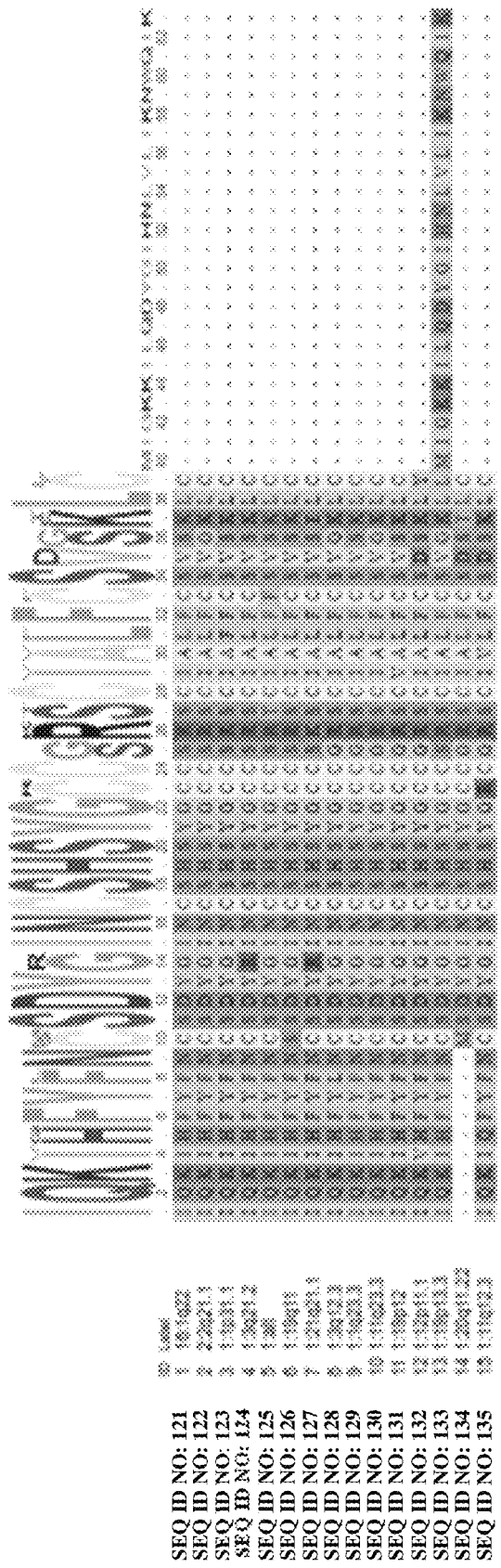

Figure 17: CTXLP variants in the humans, based on genome build GRCh38. Translated open reading frames longer than 59 bp identified in human ERVK loci annotated by RepeatMasker were searched for PF08087 by HMMER. The matching sequences were clustered using cd-hit. In the alignment above we see that the first variant is the most common, with 16 copies, followed by the second with 2. All the following ones are present as unique copies. The last three sequences with a deletion or a mutated cysteine residue are likely to be non-functional.

FIG 18

Figure 18: Schematic representation of CTXLP and amino acid sequence similarities found using NCBI-CDD and Pfam databases. The SU subunit of CTXLP is red and the omega conotoxin domain is in green. The wider portions of the diagram represent the ordered regions of the proteins and the narrow region represent the disordered region as predicted by ELM resource[5].

FIG 19

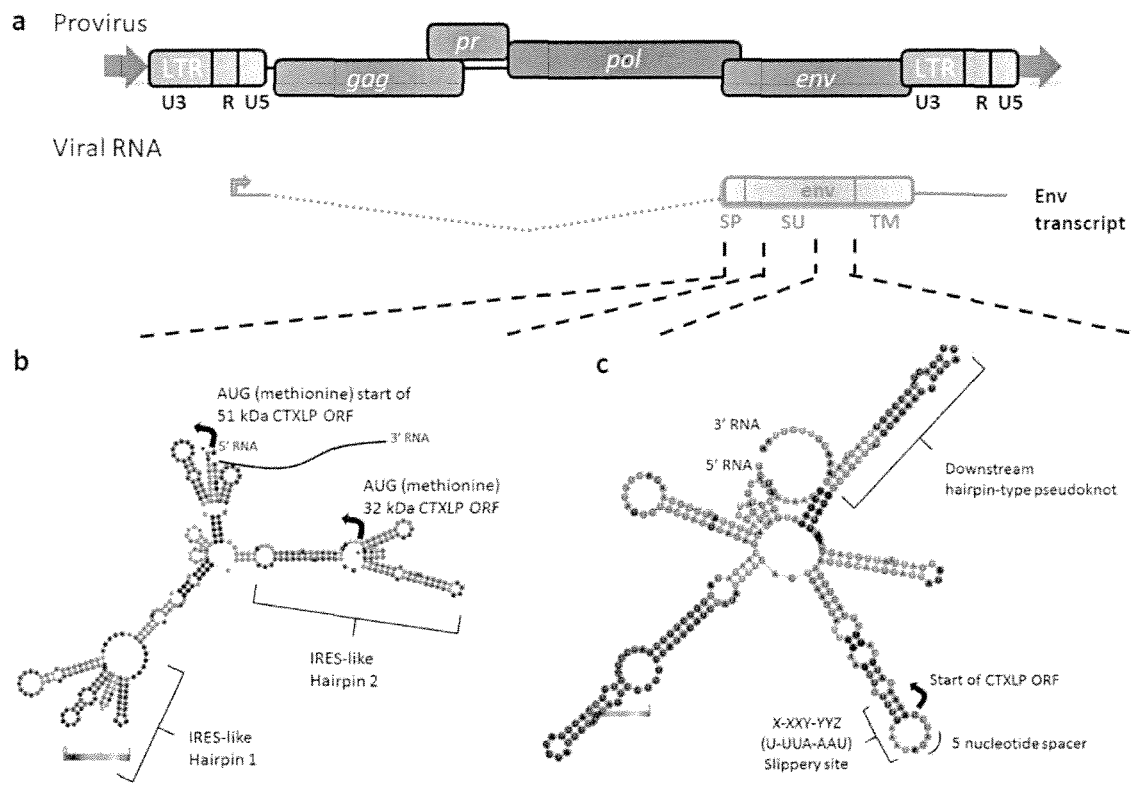

Figure 19: Analysis of the ERVK envelope transcript reveals prototypic RNA secondary structures. A) Formation of the ERVK envelope (Env) transcript from an ERVK provirus. The ERVK Env transcript encodes the viral surface unit (SU) and transmembrane (TM) proteins. **B) Predicted IRES-like RNA hairpin structures in the ERVK *env* transcript. The first 350 bp of ERVK Env-encoding RNA contains numerous AUG (methionine) translational start sites. Two distinct IRES-like hairpins are identified at nucleotides 84-187 and 213-318. tRNA can potentially bind at the AUG start site identified in IRES-like hairpin to produce a smaller isoform of ERVK Env or CTXLP. C) Predicted RNA secondary structure for ERVK-4 *env* transcript upstream and including the CTXLP ORF.** Directly upstream of the CTXLP ORF translational start is a conserved -1 programmed ribosomal frameshifting sequence, which contains three elements i) a slippery site containing an X-XXY-YYZ motif which after frameshifting by -1 results in XXX-YYY reading, ii) a 5 to 10 nucleotide spacer sequence, and iii) a downstream hairpin-type pseudoknot. The ERVK *env* transcript slippery site is encoded by a U-UUA-AAU sequence, followed by a 5 nucleotide spacer. Structure prediction formed with RNAfold Software shows a strong probability of hairpin-loops forming within the CTXLP-coding region, likely providing a downstream hairpin-type pseudoknot.

FIG. 20

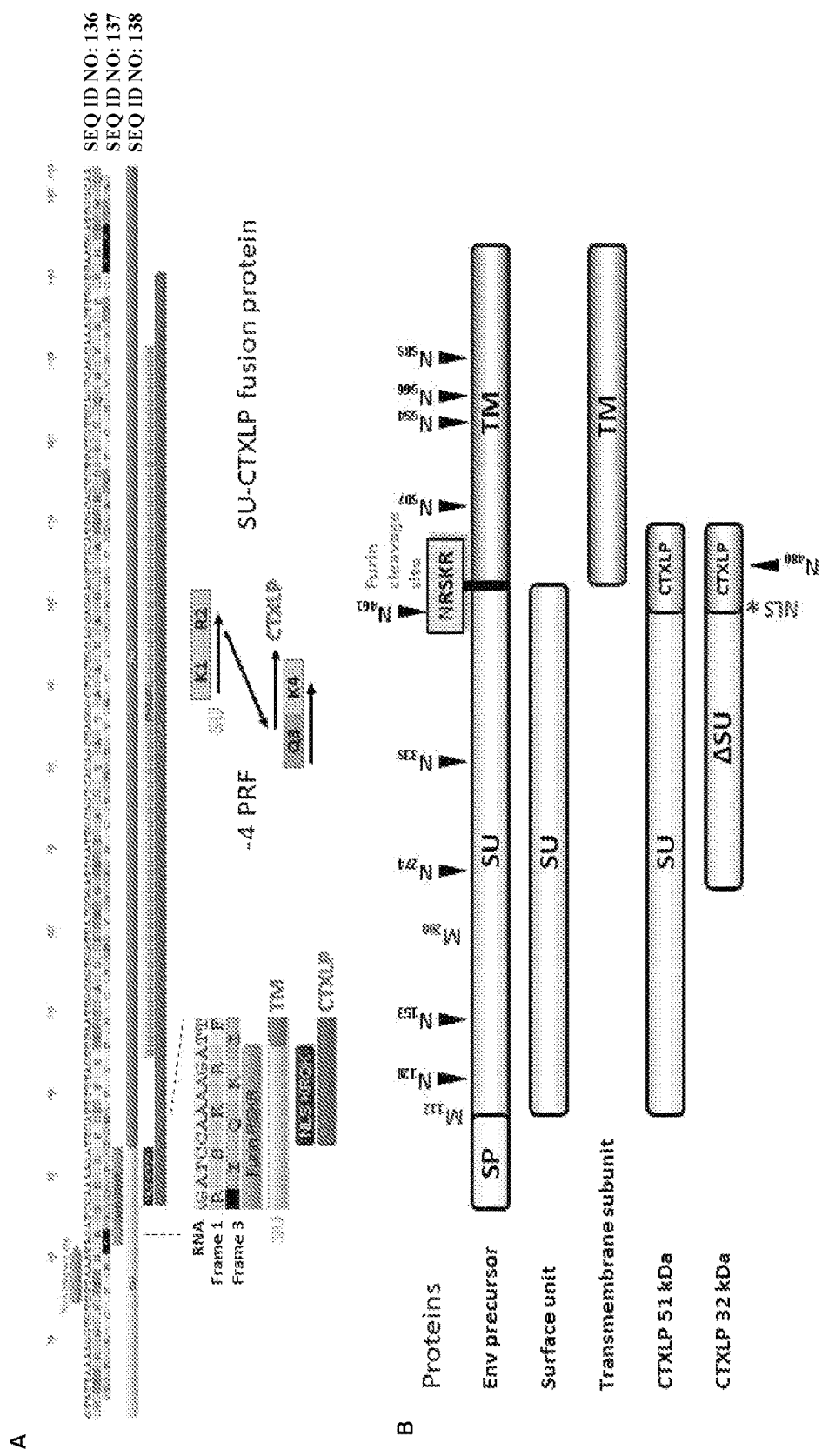

Figure 20: Predicted CTXLP isoforms derived from the ERVK envelope transcript. A) Ribosomal frameshifting event resulting in formation of CTXLP peptide fused to surface unit protein. At the RNA slippery site within the ERVK Env transcript, the ribosome translating the RNA may bounce back by 4 nucleotides and begin reading in an alternate frame. This introduces a canonical KRQK nuclear localization sequence before proceeding into the CTXLP peptide. The resulting protein is a modified SU-CTXLP fusion protein. B) Examination of the known and predicted protein products derived from the ERVK Env transcript. It is well established that ERVK can produce canonical retroviral surface unit (SU) and transmembrane (TM) proteins. We show that ERVK can also produce SU-CTXLP fusion proteins. These CTXLP isoforms contain a nuclear localization sequence (NLS) and an additional N-linked glycosylation site at position 480.

SEQ ID NO:87

SEQ ID NO:88

SEQ ID NO:89

SEQ ID NO:90

SEQ ID NO:91
SEQ ID NO:92

SEQ ID NO:93

SEQ ID NO:94

Figure 21: Bioinformatic identification of CTXLP in the genome of endogenous retrovirus-K. ERVK113 was used as a template for the CTXLP domain in the ERVK envelope gene. The ERVK envelope polyprotein is cleaved by the cellular protease furin downstream of the R-X-R/K-R site. This splits the ERVK Env polyprotein into the surface unit (SU) and transmembrane (TM) proteins which interact to form the viral spike protein on the surface of virions. A -4 programmed ribosomal frameshift (PRF) allows for the translation of the CTXLP cysteine-rich motif (red) at the C-terminal end of the SU protein. Post-translational modification of ERVK SU protein includes glycosylation. N-linked N-X-S/T glycosylation sites are identified in red boxes. Alternative methionine (M) start sites are indicated in green.

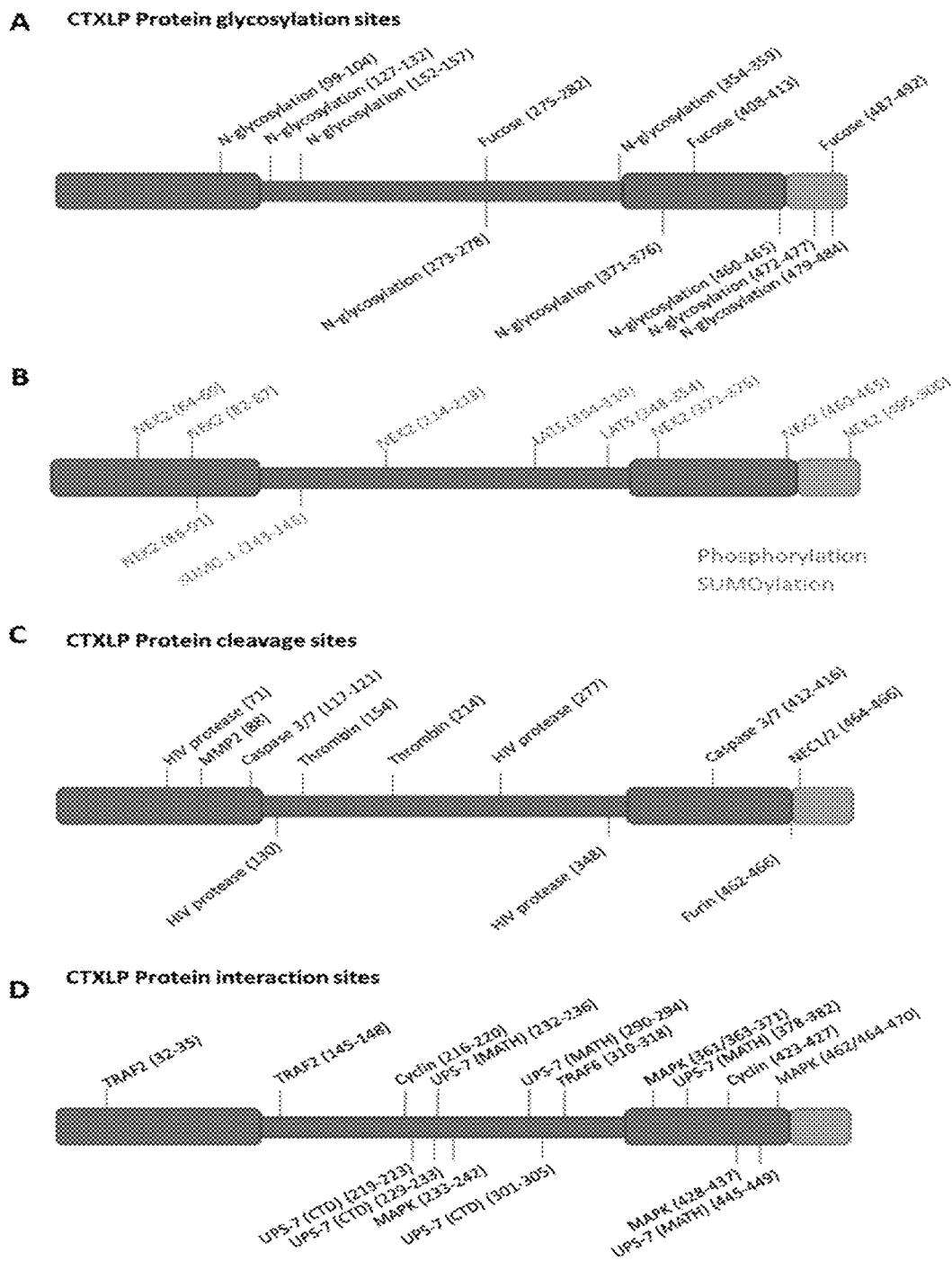
Figure 22: Predicted post-translational modifications and protein interactions of CTXLP. (A) Schematic diagram of predicted glycosylation sites. (B) Schematic diagram of predicted phosphorylation and SUMOylation sites. (C) Schematic diagram of predicted protein cleavage sites. (D) Schematic diagram of predicted protein interaction sites.

FIG 23

Antigen Profiler

Custom Antigen Information
Designed For: Renee Douville_O-conotoxin
Sequence: Length: 39 amino acids.

Protein Sequence and Features

SEQ ID NO: 95
I Q K I H F Y F N C S D Y G I N C S H S Y G C C S R S C I A L F C S V S K L C    39

Antigen Peptide Candidates

| Name | Peptide | Position | Length |
|---|---|---|---|
| OBS-3:8 | KIHFYF SEQ ID NO: 96 | 3 | 6 |
| OBS-5:10 | HFYFNC SEQ ID NO: 97 | 5 | 6 |
| OBS-10:15 | CSDYGI SEQ ID NO: 98 | 10 | 6 |
| OBS-11:16 | SDYGIN SEQ ID NO: 99 | 11 | 6 |
| OBS-11:17 | SDYGINC SEQ ID NO: 100 | 11 | 7 |
| OBS-12:17 | DYGINC SEQ ID NO: 101 | 12 | 6 |
| OBS-18:23 | SHSYGC SEQ ID NO: 102 | 18 | 6 |
| OBS-18:24 | SHSYGCC SEQ ID NO: 103 | 18 | 7 |
| OBS-18:25 | SHSYGCCS SEQ ID NO: 104 | 18 | 8 |
| OBS-19:24 | HSYGCC SEQ ID NO: 105 | 19 | 6 |
| OBS-19:25 | HSYGCCS SEQ ID NO: 106 | 19 | 7 |
| OBS-20:25 | SYGCCS SEQ ID NO: 107 | 20 | 6 |
| OBS-22:27 | GCCSRS SEQ ID NO: 108 | 22 | 6 |
| OBS-25:30 | SRSCIA SEQ ID NO: 109 | 25 | 6 |
| OBS-26:31 | RSCIAL SEQ ID NO: 110 | 26 | 6 |
| OBS-27:32 | SCIALF SEQ ID NO: 111 | 27 | 6 |
| OBS-31:36 | LFCSVS SEQ ID NO: 112 | 31 | 6 |
| OBS-31:39 | LFCSVSKLC SEQ ID NO: 113 | 31 | 9 |
| OBS-34:39 | SVSKLC SEQ ID NO: 114 | 34 | 6 |

Figure 23: Antigenic profile of the ERVK CTXLP domain, and predicted epitopes.

FIG 24

| Fisher Catalog # | Description | Qty | Unit | Unit Price | Lot Price |
|---|---|---|---|---|---|
| SPECIAL #1 | Thermo Scientific Pierce 2 Rabbit 90-Day Protocol, SYN PEP<br>Thermo Scientific Pierce No. HAB2010<br><br>• Project #: FOF1260<br>• Peptide name: O-Conotoxin<br>• Conjugation: 4MG, KLH, EG<br>• Estimated project time: 12 weeks<br>• Elisa titers: bleeds<br>• Hold bulk bleed: yes<br>• Affinity purification: yes<br>• Special instructions: Provided seq. Linear pep, not oxid.<br>• Peptide sequence: IQKIHFYFNCSDYGINCSHSYGCCSRSCIALFCSVSKLC | 1 | EA | $1,912.60 | $1,912.60 |

Figure 24: Rabbit immunization protocol for generation of a polyclonal antibody against the ERVK CTXLP domain.

FIG 25

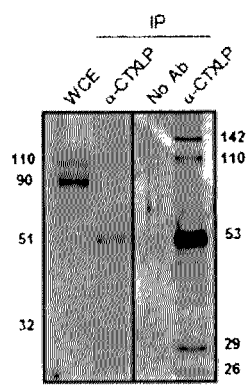

Figure 25: NCCIT spontaneously express ERVK CTXLP protein. NCCIT whole cell extract and immunoprecipitated CTXLP-enriched fractions were run on Western blot CTXLP was detected with custom rabbit anti-CTXLP antibody. The far-right lane in the image, is an image of the left α-CTXLP lane that was over-exposed upon blot development to bring out the details in the bands.

FIG 26

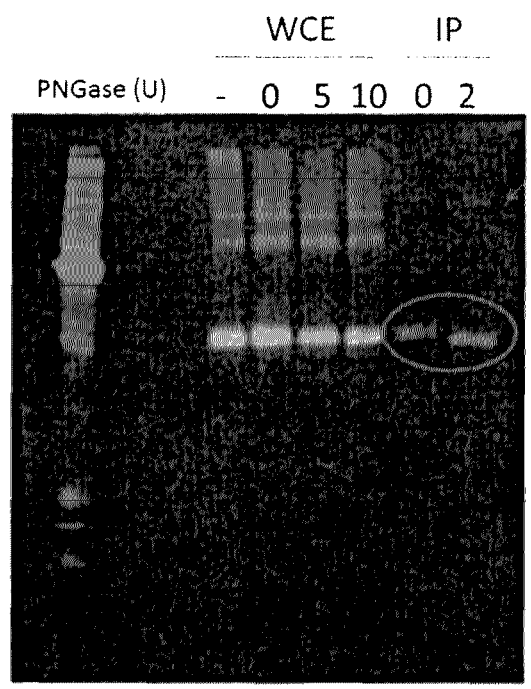

Figure 26: PNGase treatment of IP-purified CTXLP protein results in a decrease in western blot band size associated with removal of N-linked glycosylation moieties. Whole cell extracts and CTXLP enriched by immunoprecipitation were treated with the deglycosylation enzyme PNGase for 1 hour at 37°C. Treated proteins were analysed using western blot. PNGase-treated proteins exhibit a decrease in band size as compared to control indicative of deglycosylation of CTXLP protein isoforms.

FIG 27

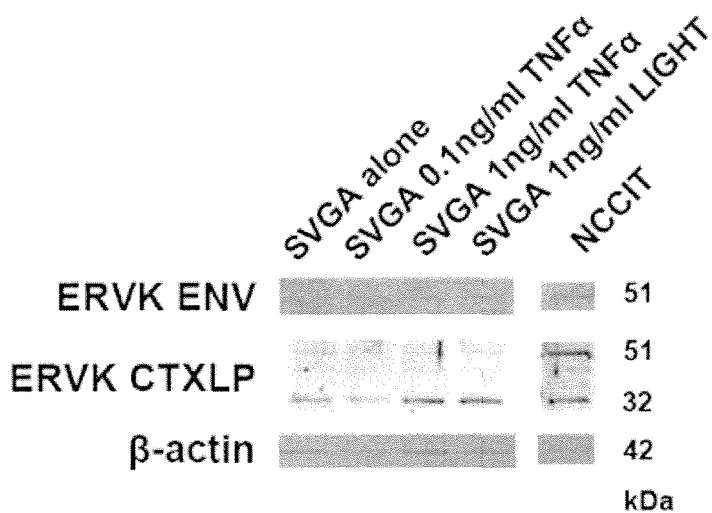

Figure 27: CTXLP expression is inducible in SVGA cells upon exposure to pro-inflammatory stimuli. SVGA cells were cultured in medium alone, TNFα (0.1 ng/ml or 1 ng/ml) or LIGHT (1 ng/ml) for 24 hours. Untreated NCCIT cells were used as a positive culture control. Cell lysates were run on Western blot and incubated with anti-CTXLP antibody. The blot was also incubated anti-β-actin as the loading control (One representative of three independent experiments shown).

Figure 28: ERVK CTXLP is inducible in human neurons. ReNcell-derived neurons were treated with increasing doses of pro-inflammatory cytokines TNFα or LIGHT for 24 hours. CTXLP expression (90kDa form) was enhanced optimally with 1ng/ml TNFα and 10ng/ml LIGHT treatment, n=1.

FIG. 29

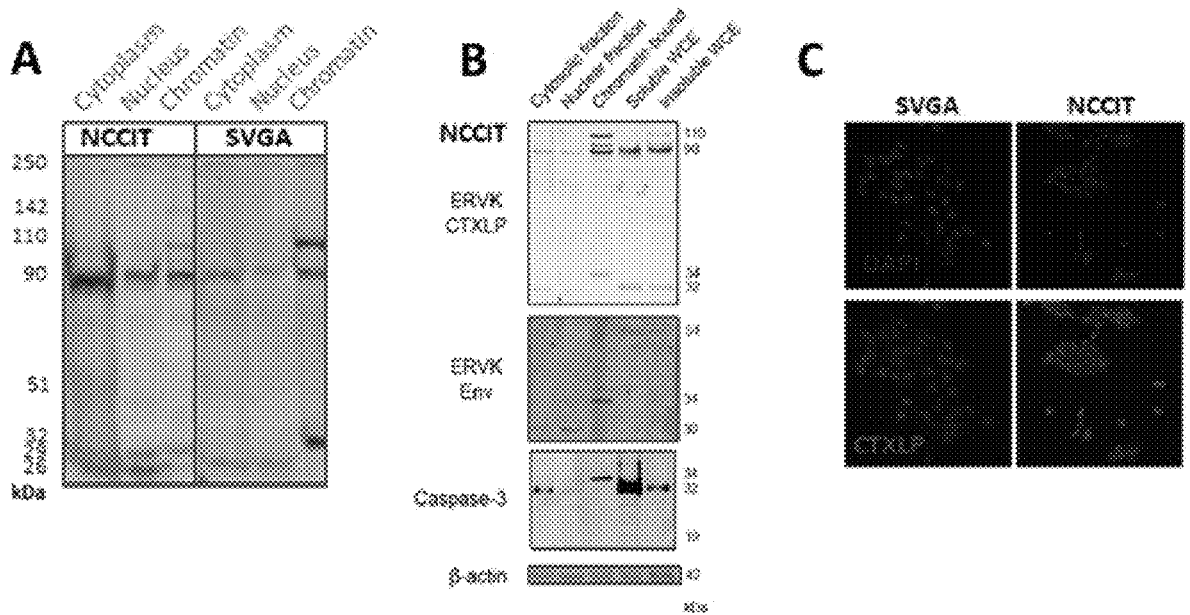

Figure 29: CTXLP protein expression predominantly localizes with chromatin in NCCIT and SVGA cells. NCCIT and SVGA cells in the absence of stimuli, were subject to cytoplasmic, nuclear and chromatin cell fractionation. (A) NCCIT cells exhibited CTXLP expression in all cell lysate fractions (n=4). (B) Additional NCCIT cells cultures were subject to further cell fractionation. CTXLP expression was again identified within all cell fractions, along within soluble and insoluble whole cell lysates. Whereas, ERVK Env 51 kDa isoform was identified in whole cell lysates but not cell fractions, with the exception of a 34kDa band in the chromatin fraction (coinciding with the observed 34 kDa CTXLP band). Caspase-3 expression was predominantly in the cytosolic fraction and the soluble whole cell lysates. β-actin was used as a loading control. (C) Moreover, CTXLP appeared dispersed throughout NCCIT cells in confocal imaging. In contrast, SVGA cells exhibited expression of the small (32kDa) and large (90-110kDa) isoforms of CTXLP in association with the chromatin (A). This was supported by nuclear localization of CTXLP in SVGA cells as shown by confocal microscopy (C).

Figure 30: ERVK CTXLP is inducible in astrocytes with pro-inflammatory cytokines. Confocal analysis of protein expression for ERVK CTXLP (red) and ERVK reverse transcriptase (RT, green) in cells treated with or without TNFα and LIGHT, n=2. Enhanced CTXLP expression precedes increases in RT expression. DAPI stain indicates nuclei (blue).

FIG 31

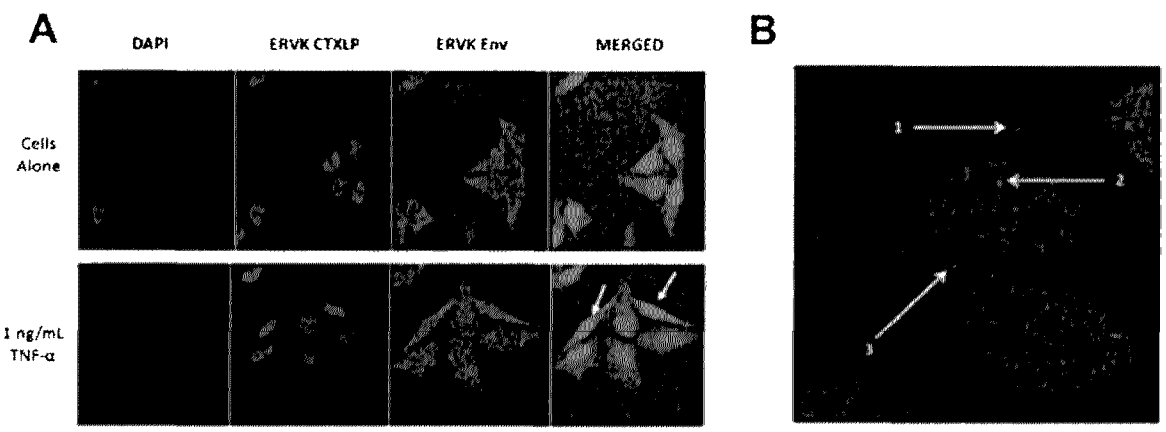

Figure 31: Cellular localization of ERVK CTXLP and SU proteins in human astrocytes. (A) SVGA cells were cultured with medium alone or in the presence of 0.1 ng/mL TNFα for 24 h and analyzed by confocal (400x magnification). Increased CTXLP protein (indicated by arrows) and Env expression were identified (but not co-localized) in TNFα-treated cells compared to controls. (B) SVGA cells were cultured with medium alone (not shown) or in the presence of 10 ng/mL LIGHT for 24 h and analyzed by confocal (600x magnification). Distinct puncta (indicated by arrows) were identified within the 1) cytoplasm, 2) nucleus, and 3) surface membrane of the cell.

Figure 32: **CTXLP overexpression in soluble fractions of SVGA cells enhances the 32 kDa and 90 kDa for

FIG 33

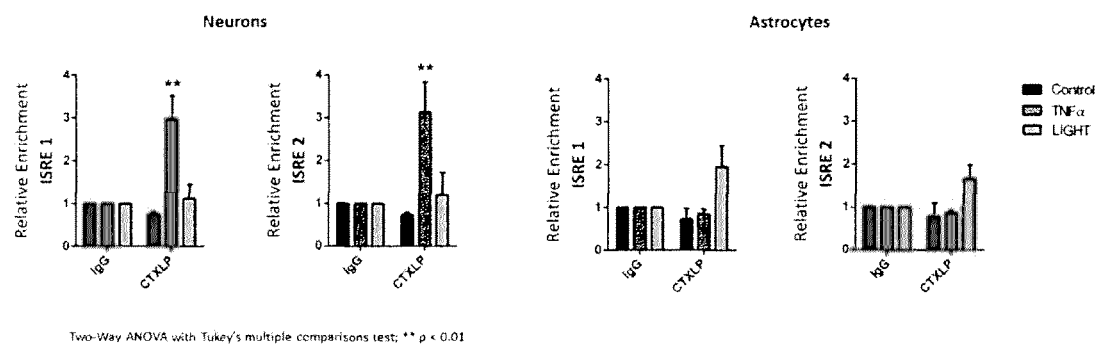

Figure 33: CTXLP binds interferon response elements (ISREs) within the ERVK promoter (5' LTR). CTXLP may regulate ERVK gene expression, as well as other genes containing ISREs. Chromatin immunoprecipitation (ChIP) following 8 hours of 10 ng/ml TNFα or LIGHT treatment in human ReNcell-derived neurons (n=2) and human astrocytic cell line (SVGA) (n=3). Notable increase in CTXLP chromatin binding in neurons upon pro-inflammatory stimulation with the cytokine TNFα.

FIG. 34 CONT'D

Figure 34: ERVK Expression Multidimensional Scaling. Two dimensional plots were produced by reduction of the high dimensional RNA-seq expression data derived from the Sequence Read Archive (SRA) using the R package EdgeR. The plot labels correspond to SRA studies as follows: ALS (SRP064478), Bipolar Disorder (SRP074904), Breast Cancer (SRP058722), HIV/HCV (SRP068424), Multiple Sclerosis (SRP110016), Prostate Cancer (ERP000550), Rheumatoid Arthritis (SRP102685), and Schizophrenia (SRP090259). In these plots each axis represents the leading log-2-scaled fold-change at one particular ERVK locus; the two loci chosen are those with the most extreme values in the majority of the clinical group's samples. Since these represent the biggest difference between samples, if no separation is apparent in these plots, there is no clear difference in transcript profiles. Each sample is represented by its SRA accession number, coloured red for disease-associated samples and black are the control samples. The blue HIV/HCV samples were treated with interferon alpha for 24 hours before sample collection. *Methods:* The expression of each ERVK locus identified in hg38 by RepeatMasker was measured in reads per kilobase per million mapped reads. This measure corresponds to the number of reads aligning to each region normalized by the region length and the number of reads mapped to the genome overall. This number was computed using the R package EdgeR. Read counts were obtained from alignments using samtools. Alignments were produced using bowtie2 to place raw reads onto an unmasked copy of hg38 with appropriate trimming parameters. Raw reads were obtained from the SRA using fastq-dump and trimming parameters were determined using FastQC.

FIG. 35 CONT'D
ERVK by CTXLP Status in Breast Cancer
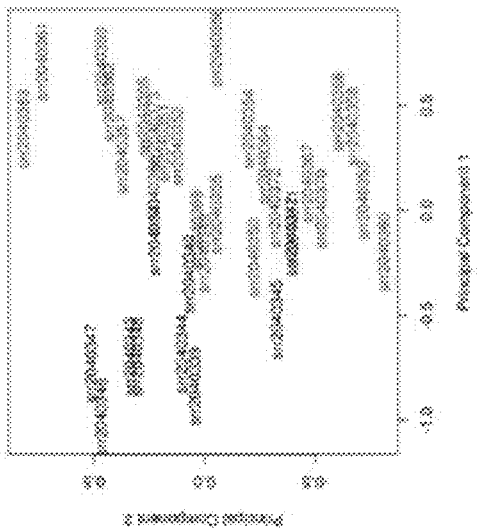
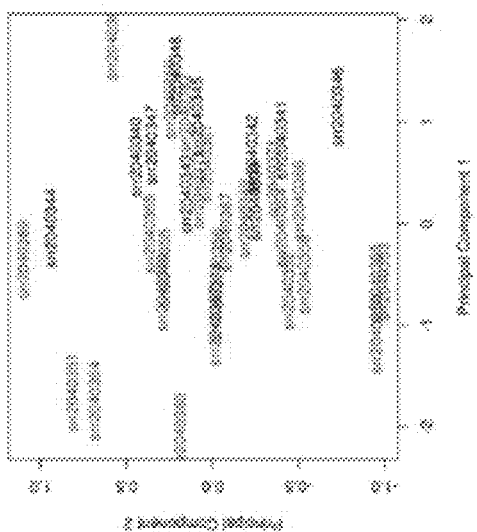
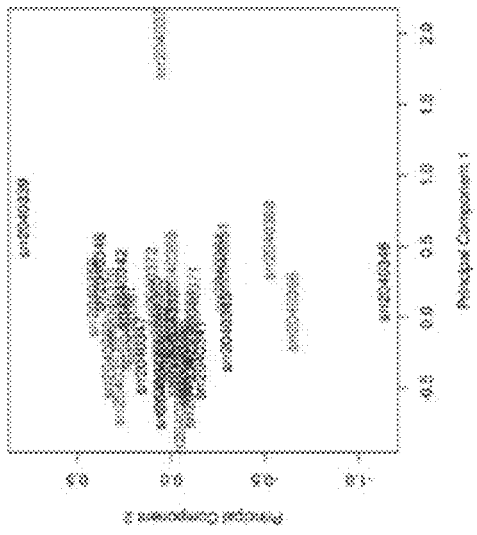

FIG. 35 CONT'D
ERVK by CTXLP Status in Prostate Cancer
CTXLP+
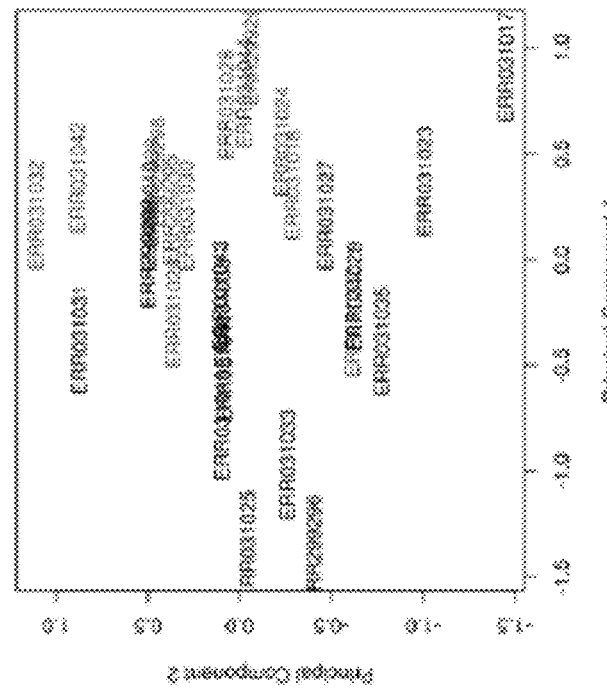
Disrupted
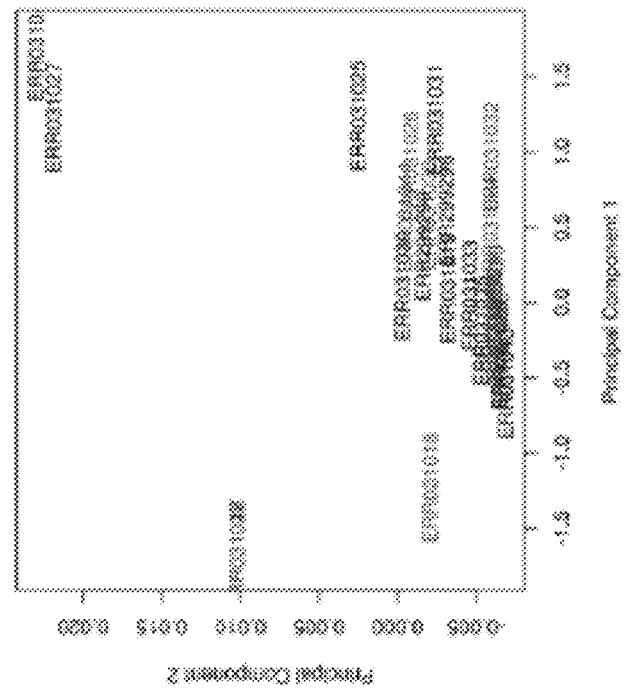
CTXLP−
No Data

FIG. 35 CONT'D

ERVK by CTXLP Status in Schizophrenia

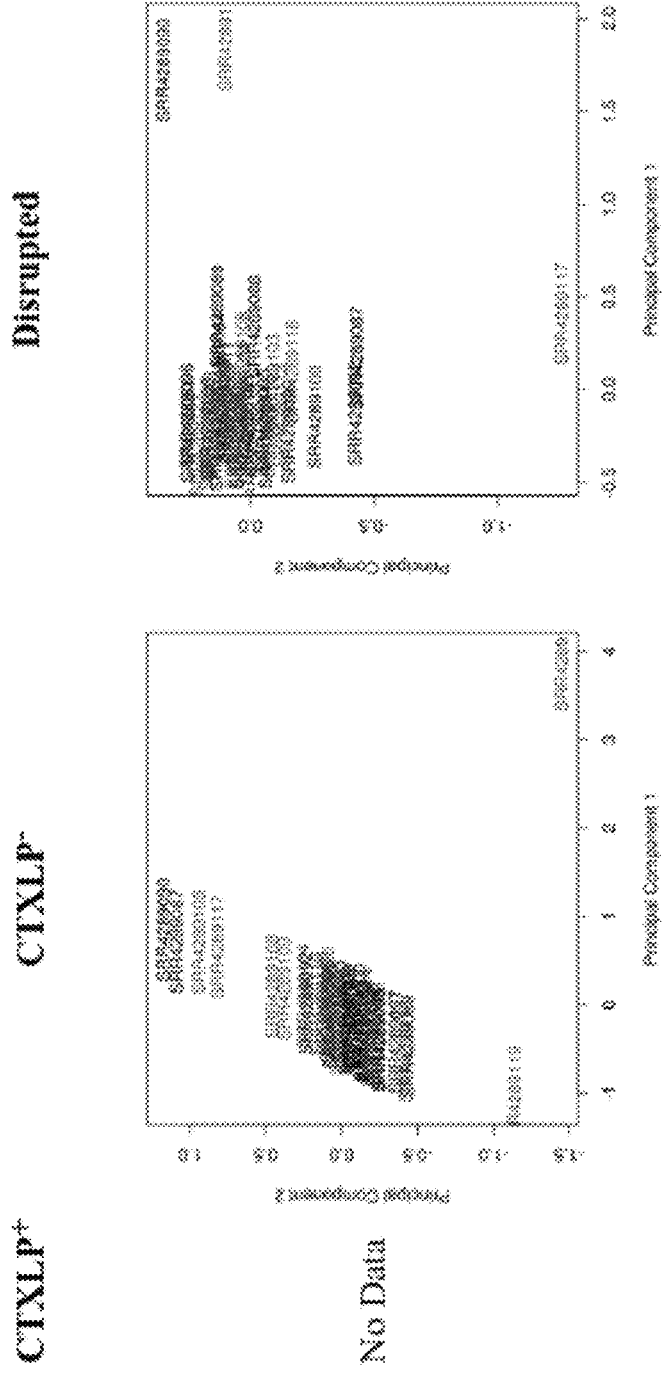

Figure 35: ERVK Multidimensional Scaling by CTXLP status in Human Disease. Each plot was produced as described in Figure 34, except with the modification that ERVK loci were subsetted into three states: "CTXLP+" which could produce CTXLP, "Disrupted" which cannot produce CTXLP but may have had an ancestral loci that produced CTXLP, and finally "CTXLP-" loci which do not and likely never did produce CTXLP from the ERVK env gene. In all cases, samples from the ALS, Bipolar Disorder, Breast Cancer, HIV-1/HCV co-infection, Multiple Sclerosis and Rheumatoid Arthritis cohorts expressed all three types of ERVK env transcripts. In Prostate Cancer and Schizophrenia, there were no loci expressed which were CTXLP+, and so no data is shown for that plot.

FIG. 36 CONT'D

Figure 36: Per-Locus Differential ERVK Expression. Each panel shows in detail the expression of individual ERVK loci encoding envelope in each human disease condition. ERVK loci (black) are plotted against CTXLP+ (red), CTXLP- (blue) and disrupted (grey) loci. The plot labels correspond to SRA studies as follows: ALS (ALS: SRP064478), Bipolar Disorder (BP: SRP074904), Breast Cancer (BC: SRP058722), HIV/HCV (HV; HIV/HCV + interferon (HI): SRP068424), Multiple Sclerosis (MS: SRP110016), Prostate Cancer (PC: ERP000550), Rheumatoid Arthritis (RA: SRP102685), and Schizophrenia (SZ: SRP090259). For each study, controls (C) and indicated to the right of cases. Panel A exclude ERVK loci with very low expression; only loci with a median expression greater than 0 and a mean expression greater than 0.1 are plotted. Panel B shows only loci which were highly expressed; only ERVK loci which had a maximum expression higher than 2 are plotted. *Methods:* FASTQ files for each run from each study were downloaded from the SRA using fastq-dump. Trimming positions for each study were chosen based on examining the output of FastQC. Reads were mapped to an unmasked copy of hg38 obtained from UCSC using bowtie2. All the above were performed on the Compute Canada cluster Orcinus. Mapped reads (SAM files) were downloaded and SAM files were converted to indexed BAM files. Expression of ERVK loci was measured using samtools view to count reads aligning to each locus. Expression data were interpreted using EdgeR.

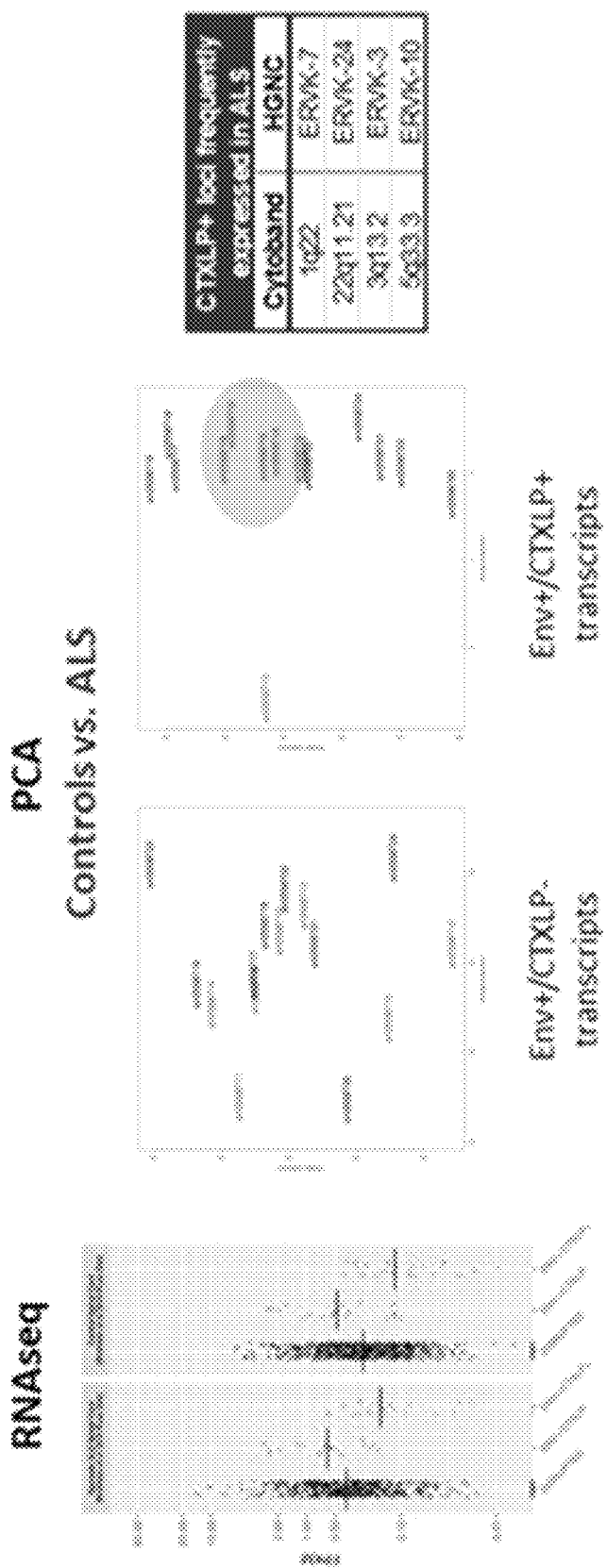

Figure 37: ERVK CTXLP encoding transcripts and CTXLP protein are present in Amyotrophic Lateral Sclerosis (ALS). (A) Re-analysis of RNAseq data² in control (right) and sporadic ALS (left) spinal cords for expression of disrupted non-coding (black), Env+/CTXLP- (blue) and Env+/CTXLP+ (red) env transcripts. Principle component analysis (PCA) reveals ALS patient clustering in terms of CTXLP+ transcript expression, with most frequently expressed CTXLP encoding loci indicated.

FIG 38

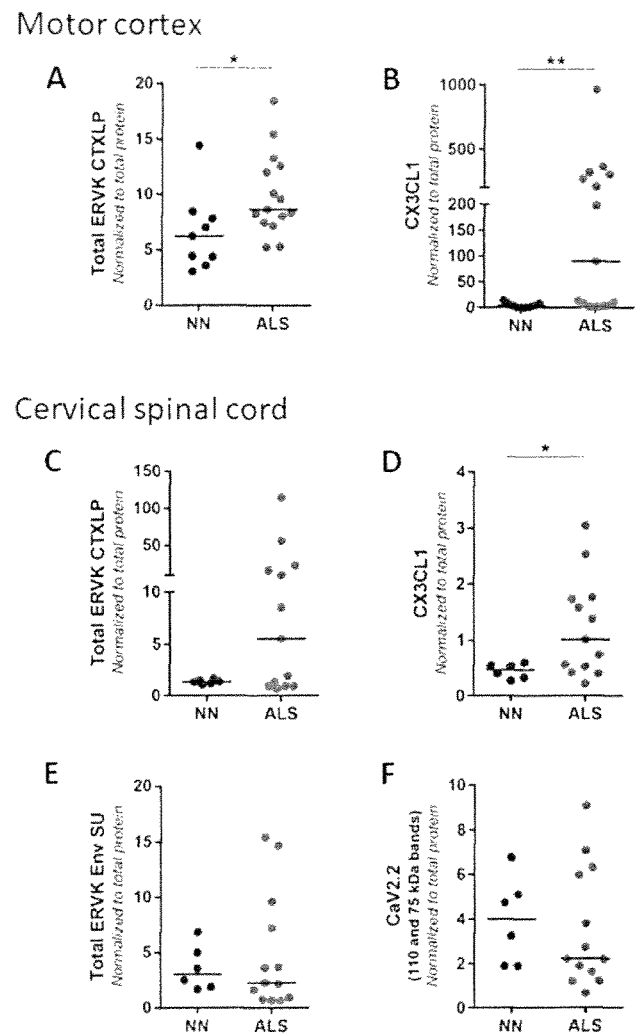

Figure 38: ERVK CTXLP levels are enhanced in autopsy spinal cord and brain tissues of patients with ALS. Graph represents total CTXLP (A) and CX3CL1 (B) quantification in neuronormal (NN) (n=9) and ALS (n=15) motor cortex specimens, as measured by western blot. *Graph represents total CTXLP* (C), CX3CL1 (D), ERVK Env SU (E) and CaV2.2 (F) quantification in NN (n=6) and ALS (n=13) cervical spinal cord specimens, as measured by western blot. Statistical test with unpaired two-tailed t-tests (*p<0.05, **p<0.01, black bars are medians).

FIG 39

A Cervical spinal cord

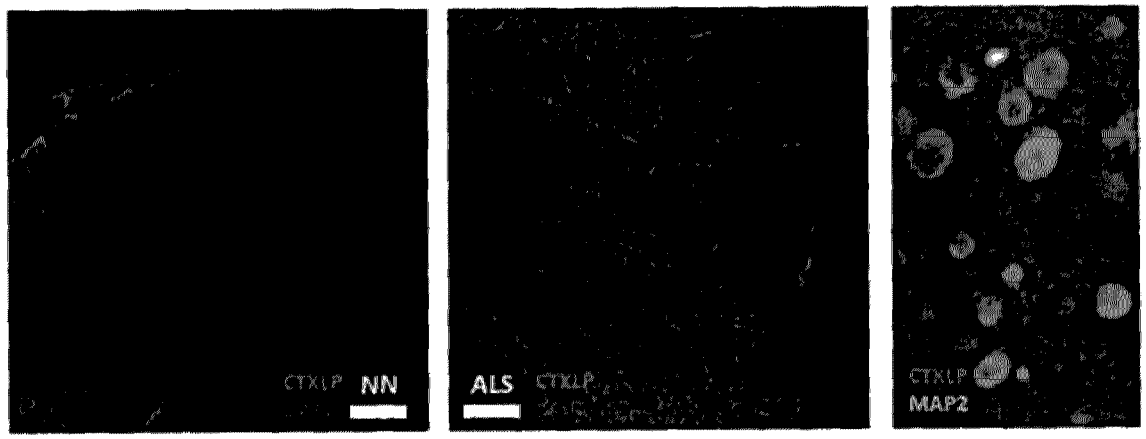

B Motor cortex

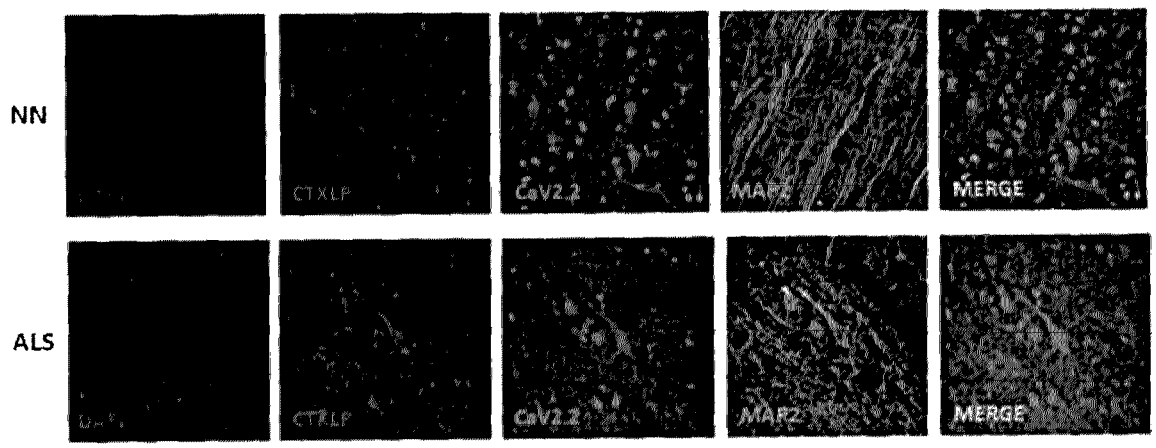

Figure 39: ERVK CTXLP levels are enhanced in autopsy spinal cord and brain tissues of patients with ALS, as measured by confocal microscopy. (A) Representative 10x confocal micrographs of ERVK CTXLP expression in ex vivo cervical spinal cord of a neuronormal control (NN, n=3) and patient with ALS (n=3). DAPI stain depicts nuclei. High magnification reveals staining in cells surrounding MAP2+ axons, suggesting CTXLP+ oligodendrocytes. CTXLP+ rings ranged from 6-16μM in diameter. (B) Representative 40x confocal micrographs of ERVK CTXLP, voltage-gated calcium channel CaV2.2 (C-terminal antibody) and neuronal MAP2 expression in Brodmann area 6 (BA6) motor cortex tissue of a NN control (n=3) and patient with ALS (n=3). Note the translocation of nuclear CTXLP to cytoplasmic aggregates in neurons from an ALS patient, as well as an overall decrease in CaV2.2 expression. DAPI stain depicts nuclei.

FIG 40
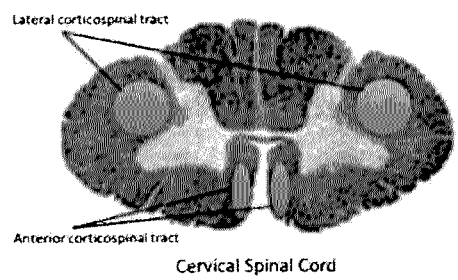
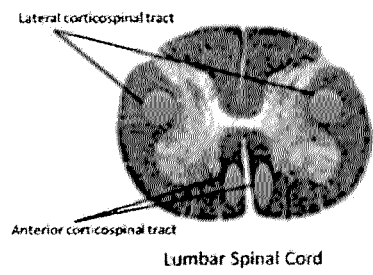
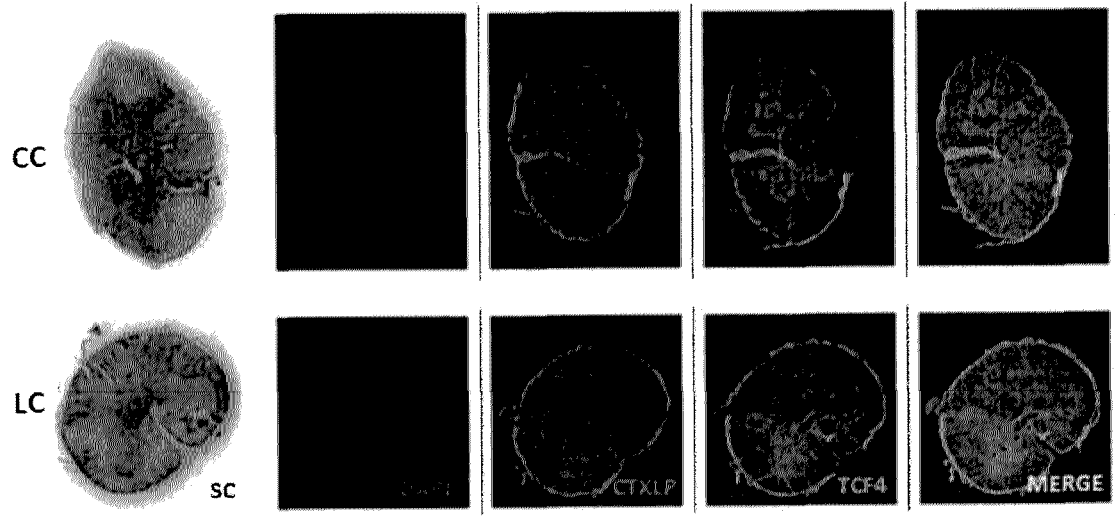
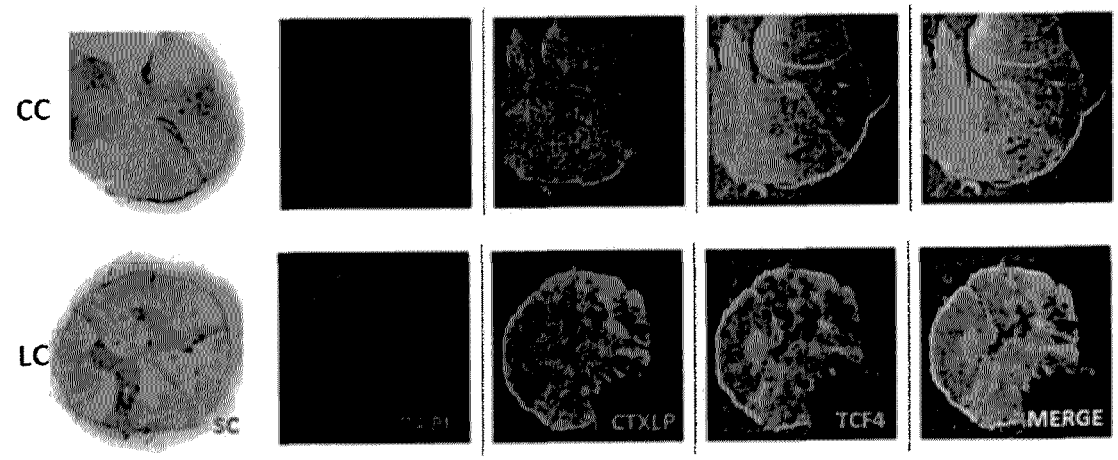

FIG 40 CONT'D

Figure 40: ERVK CTXLP levels are enhanced in autopsy cervical and lumbar spinal cord tissues from patients with ALS, as measured by light and confocal microscopy. Representative 10x confocal micrographs of ERVK CTXLP expression in *ex vivo* cervical (CC) and lumbar (LC) spinal cord of a neuronormal control (NN, n=3) and patients with ALS (n=3). Solochrome cyanine (SC) stain (purple) with eosin counterstain (pink) depicts tissue myelination; pale lesions appear in ALS tissues. These lesioned areas exhibit increased CTXLP expression is in red. Oligodendrocyte precursor marker TCF4 is in green. DAPI stain depicts cellular nuclei. Note that CTXLP expression occurs in either lateral and/or anterior cortical spinal tracts.

FIG 41 CONT'D

Figure 41: ERVK CTXLP levels are associated with demyelination and CTXLP is enhanced in TCF4+Olig1+ oligodendrocyte precursors in cervical spinal cord tissues from patients with ALS. Representative 20x confocal micrographs of ERVK CTXLP expression in *ex vivo* cervical (CC) spinal cord of a neuronormal control (NN, n=3) and a patient with ALS (n=3). Notably decreased myelin stain as measure my MAG protein expression (green) is evident in ALS tissue as compared to control. In ALS tissue, CTXLP expression (red) co-localizes with TCF4 (green) or Olig1 (green) markers indicative of oligodendrocyte precursor cells. DAPI stain depicts cellular nuclei.

FIG 42

ALS VA 110011       ALS NBB 4766

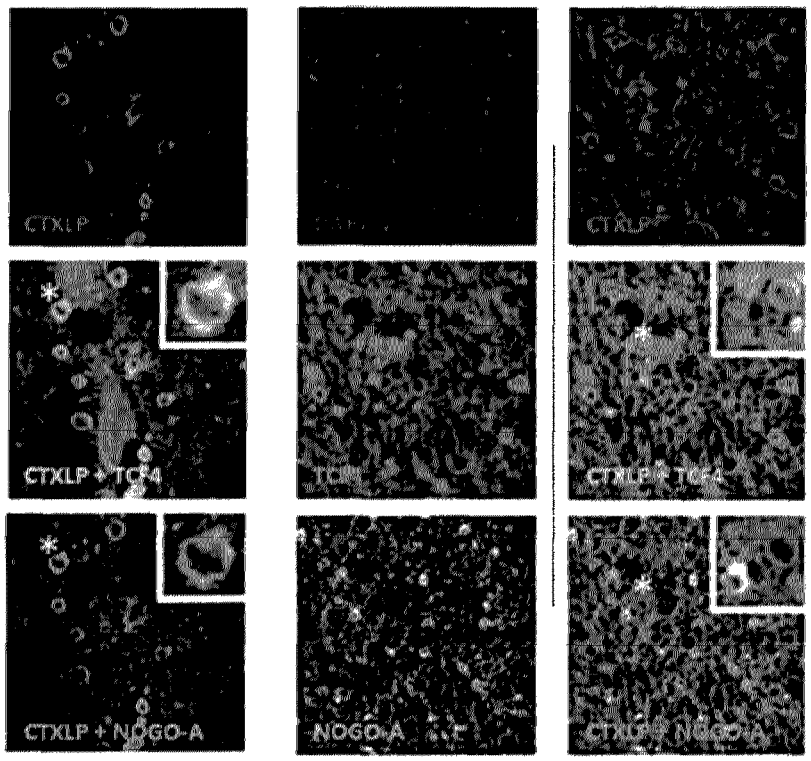

Figure 42: ERVK CTXLP+ oligodendrocyte precursors express myelin inhibitory protein Nogo-A, or are in close proximity to Nogo-A positive cells in spinal cord tissues of patients with ALS. Human *ex vivo* cervical spinal cord tissues were stained for ERVK CTXLP (red), TCF4 (green), Nogo-A (grey) and nuclei (blue) in neuro-normal controls (n=3) and patients with ALS (n=3). Image merging for CTXLP and TCF4 indicate that oligodendrocyte precursors express CTXLP in ALS. Image merging for CTXLP and Nogo-A indicate that oligodendrocyte precursors can express myelin inhibitor protein Nogo-A (left panel) or alternately are in proximity to Nogo-A expressing cells in ALS (right panel). White stars indicate areas that are magnified to depict overlapping protein expression in CTXLP+ rings.

FIG 43

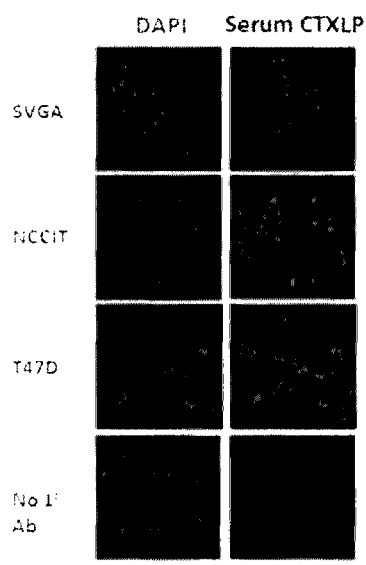

Figure 43: Cancer cells express greater levels of CTXLP as compared to non-cancer cells. Prototypic cell lines for teratocarcinoma (NCCIT) and breast cancer (T47D) were examined for CTXLP expression as compared to astrocytic SVGA cells using confocal microscopy. No antibody negative control is to show that specificity of CTXLP (red) staining requires an antibody targeting ERVK CTXLP. Nuclei are shown in blue using a DAPI stain.

FIG. 44

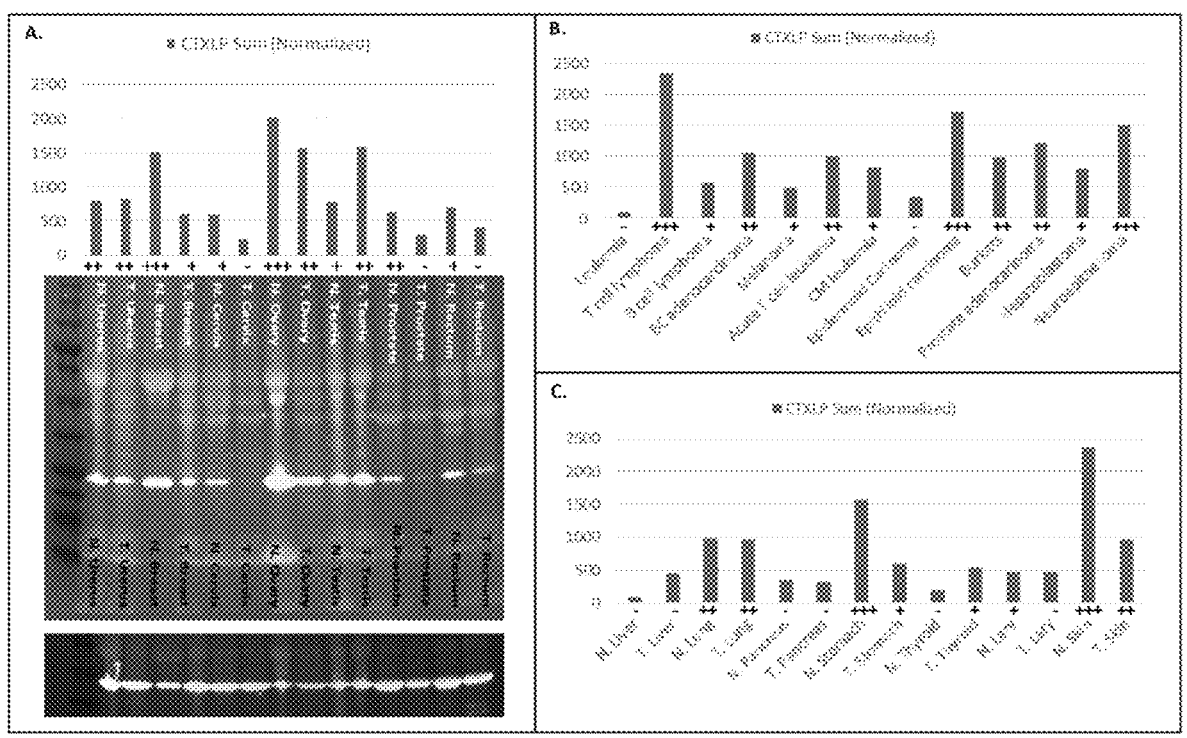

Figure 44: CTXLP expression in G-Bioscience Ready-to-screen cancer tissue and cell line blots. TB56-I (A), TB55 (B) and TB56-II (C) blots were screen for CTXLP expression (blue bars, top blot) normalized to β-actin loading control (lower blot). Enhanced CTXLP expression in noted is several cancer types, including T cell lymphoma, neuroepithelioma, prostate, ovary, testis and skin cancers.

FIG 45

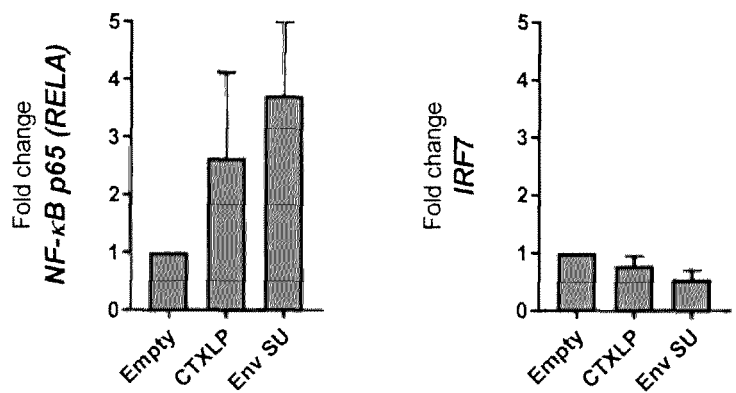

Figure 45: Changes in the gene expression of pro-inflammatory NF-κB p65 and anti-viral IRF7 in response to CTXLP and SU expression. 293T cells were transfected with plasmids encoding empty vector, ERVK CTXLP or ERVK SU for 24 hours. Cell pellets were collected, RNA extracted, and cDNA produced for use in Q-PCR experiments to evaluate relative gene expression of RELA and IRF7. Analysis performed using ΔΔCt method and 18S RNA as a calibrator.

Figure 46: Confocal images of control, CTXLP-expressing and SU-expressing 293T cells. Cells were stained with DAPI nuclear stain, and antibodies against Env SU (green) fluorescent dye, NF-κB p65 (red) fluorescent dye and CTXLP (grey / white) fluorescent dye. Only CTXLP expressing cells exhibit upregulated NF-κB p65 expression. Representative micrographs of n=3 experiments.

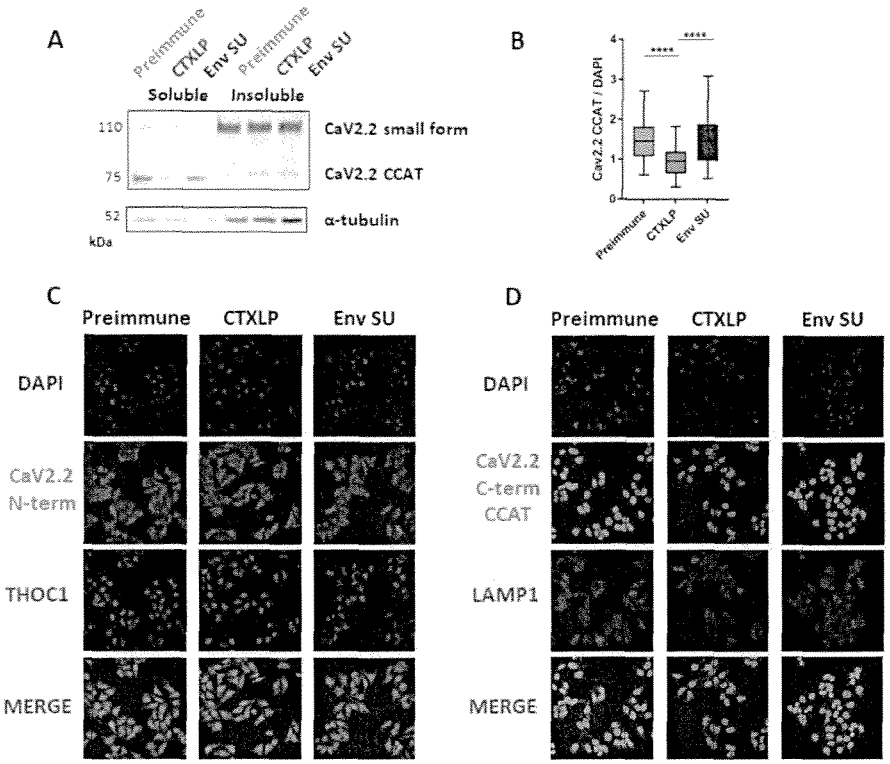

FIG 47

Figure 47: ERVK CTXLP, but not ERVK Env SU, depletes CaV2.2 calcium channel-associated transcription regulator (CCAT). (A) CaV2.2 expression in SVGA cells treated with 5μl of immunoprecipitation (IP) products from NCCIT cell lysates extracted using rabbit pre-immune serum, custom rabbit anti-CTXLP antibody or custom rabbit anti-ERVK Env SU antibody for 24 hours. Membrane-bound forms of CaV2.2 are 240/210 kDa (not shown) and 110 kDa respectively, whereas the CaV2.2 CCAT is 75 kDa. (B) Quantification of CaV2.2 depletion in IP-product treated astrocytes (2hrs), based on confocal quantification (****$p<0.0001$, 80-100 cells per condition quantified). (C & D) Confocal imaging of CaV2.2 (N-terminal antibody) and CaV2.2 CCAT (C-terminal antibody) illustrates that CTXLP depletes nuclear CaV2.2 CCAT within 2 hours, but not the membrane-associated CaV2.2 channel (n=2).

Figure 48: CTXLP administration enhances caspase-3 expression in SVGA cells. (A) Images of live cells after 24 hours taken using EVOS imager, top image depicts untreated control cells and bottom image depicts cells treated with 5μl of CTXLP immunoprecipitated solution. (B) Graphical depiction of caspase-3 expression in control and CTXLP-treated cell after 24 hours.

FIG 49

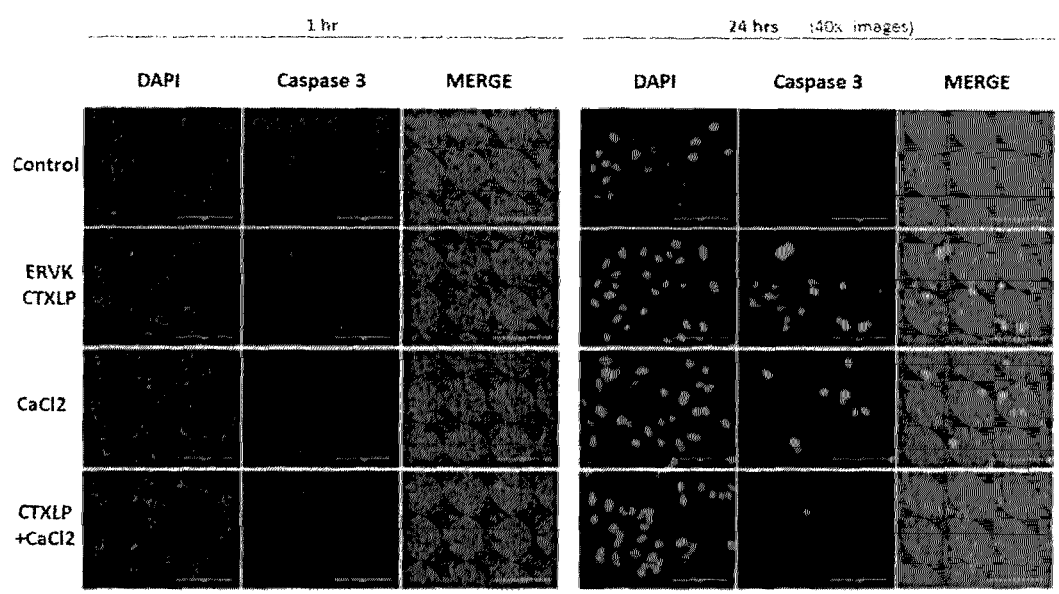

Figure 49: CTXLP induces caspase-3 activation and apoptosis, which can be blocked by excess extracellular calcium. Cell survival 1 hour and 24 hours post treatment with 5μl of buffer, calcium chloride, CTXLP or CTXLP and calcium chloride. Cells were examined using an EVOS microscopy for caspase-3 activation (green) or nuclei (blue), n=2). Excess calcium chloride is known to block the cellular effects of conotoxin proteins[7].

FIG 50

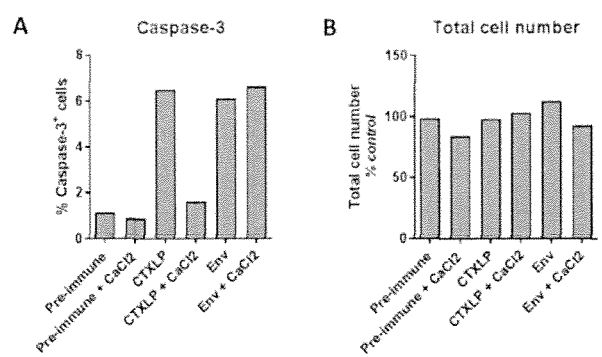

Figure 50: Cell survival and confluency 24 hours post treatment with 5µl of pre-immune serum, pre-immune serum and calcium chloride, CTXLP, CTXLP and calcium chloride, SU, or SU and calcium chloride. (A) Graphical depiction of caspase-3 expression in SVGA cells 24 hours post treatment. (B) Graphical depiction of cell confluency of SVGA cells 24 hours post-treatment. Note that pre-immune serum was used as a negative control as this is the component of immunoprecipitation product.

FIG 51

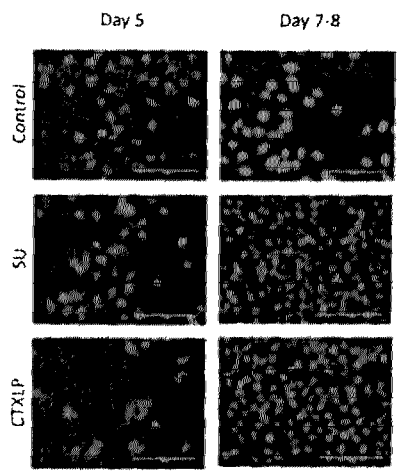

Figure 51: CTXLP induced caspase-3 does not result in cell death. Live cell images of SVGA cells in control, SU-treated and CTXLP-treated conditions stained for caspase-3 using EVOS live cell imaging. Cells in each condition were imaged after 5 days. Control cells were imaged at 7 days and SU and CTXLP-treated cells were imaged after 8 days. Controls cells express greater amounts of the apoptotic marker caspase-3, and have not proliferated to the extent observed in CTXLP and Env treatments.

FIG 52

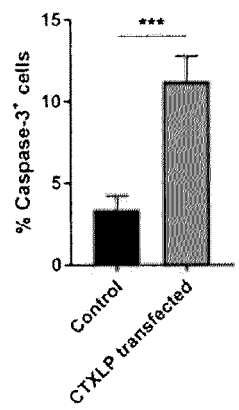

Figure 52: CTXLP-transfection markedly enhances capase-3 expression. Percentage of control and CTXLP-transfected SVGA cells expressing caspase-3 after 24 hours. SVGA cells were transfected with empty vector and lipofectamine LTX (control) or a pcDNA3.1 CTXLP-expressing vector. Graphical depiction of apoptosis marker caspase-3 in control and CTXLP-transfected SVGA cell after 24 hours, as measured by confocal microscopy.

Figure 53: Abnormal cellular morphology in cells exposed to CTXLP. (A) Fluorescent image of CTXLP-treated SVGA cell expressing caspase-3 (green) and stained with DAPI nuclear stain (blue). (B) Confocal image of Env SU expression (green) in a CTXLP-expressing 293T cell.

FIG 54

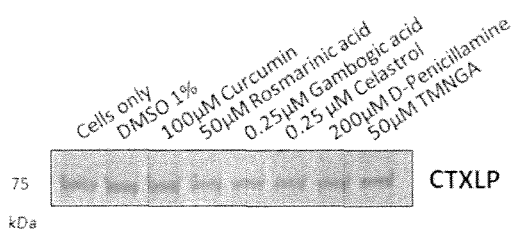

Figure 54: CTXLP-limiting drug screen in human NCCIT teratocarcinoma cells. The ERVK-expressing NCCIT teratocarcinoma cell line was grown in a monolayer in RMPI 1640 media supplemented with FetalGro. Cells were treated for 24 (data not shown) and 48 hours with known $IC_{50}$ concentrations of drugs (NCCIT cells alone, 1% DMSO as drug carrier control, 100μM Curcumin, 50μM Rosmarinic acid, 0.25μM Gambogic acid, 0.25μM Celastrol, 200μM D-Penicillamine and 50μM Tetramethyl Nordihydroguaiaretic acid/TMNGA). Cells were collected, protein extracted, and western blot performed to measure the expression of ERVK CTXLP as compared to β-actin loading control. Results demonstrate that select MAEs can reduce CTXLP expression in NCCIT cells. n = 2.

FIG 55

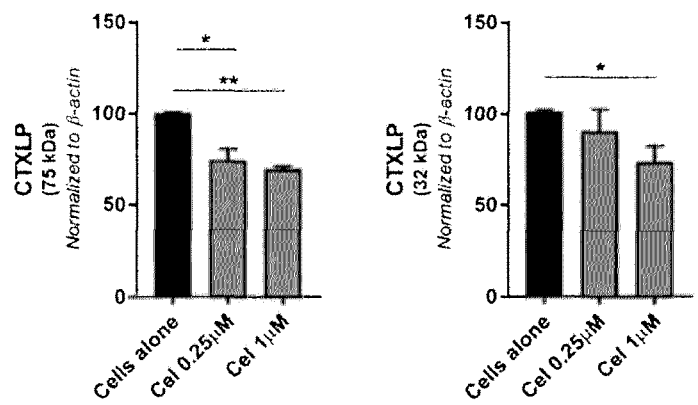

Figure 55: MAE drug Celastrol abrogates CTXLP expression in human NCCIT teratocarcinoma cells. The ERVK-expressing NCCIT teratocarcinoma cell line was grown in a monolayer in RMPI 1640 media supplemented with FetalGro. Cells were treated for 24 hours with increasing doses of celastrol (Cel, 0.1, 0.25, 1 and 2.5μM). Cells were collected, protein extracted, and western blot performed to measure the expression of ERVK CTXLP, as compared to β-actin loading control. Results demonstrate that Cel dose-dependently reduces CTXLP expression in NCCIT cells. n = 4 independent experiments, *p<0.05, **p<0.01, two-tailed paired t-test.

FIG 56

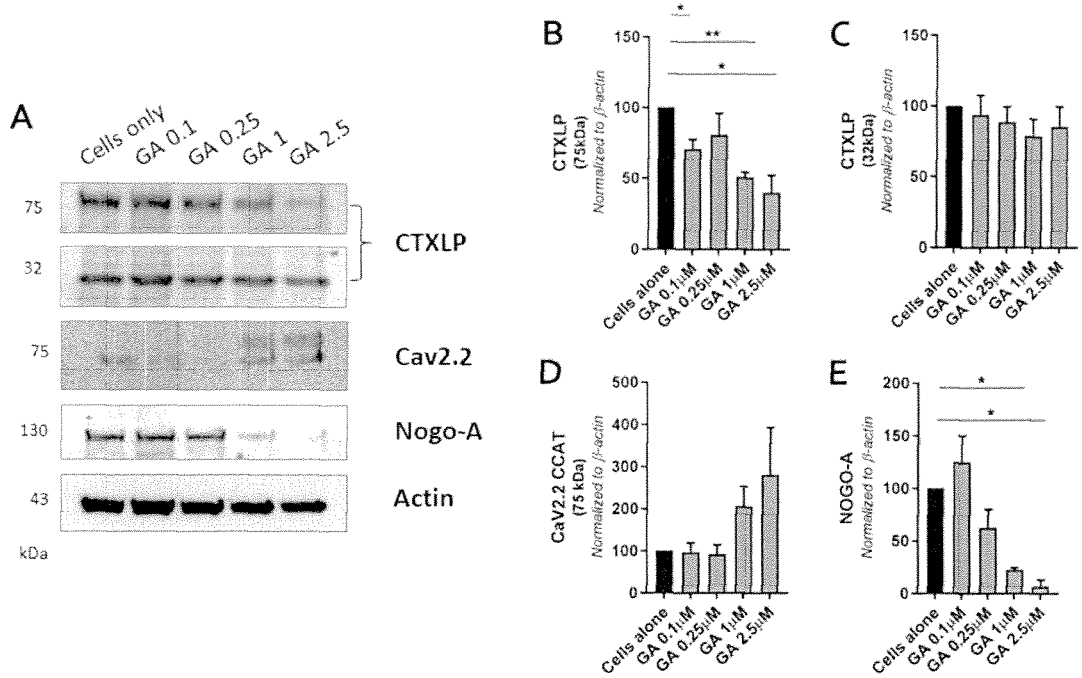

Figure 56: MAE drug Gambogic acid abrogates CTXLP expression in human NCCIT teratocarcinoma cells. The ERVK-expressing NCCIT teratocarcinoma cell line was grown in a monolayer in RMPI 1640 media supplemented with FetalGro. Cells were treated for 24 hours with increasing doses of gambogic acid (GA, 0.1, 0.25, 1 and 2.5μM). Cells were collected, protein extracted, and western blot performed to measure the expression of ERVK CTXLP, CaV2.2 C-terminal calcium channel-associated transcriptional regulator (CaV2.2 CCAT) and NOGO-A, as compared to β-actin loading control. Results demonstrate that GA dose-dependently reduces CTXLP and NOGO-A expression in NCCIT cells. CaV2.2 CCAT is inversely correlated with the expression of ERVK CTXLP in this culture system. n = 3, *$p<0.05$, **$p<0.01$, two-tailed paired t-test.

Figure 57: Endogenous levels of CTXLP in human astrocytes can be depleted in the presence of gambogic acid. Human astrocytic cell line SVGA were treated with increasing doses of gambogic acid in the low micromolar range (0.25 and 0.5µM). CTXLP expression was measured by western blot. n = 4, *p<0.05, one-tailed paired t-test.

FIG 58

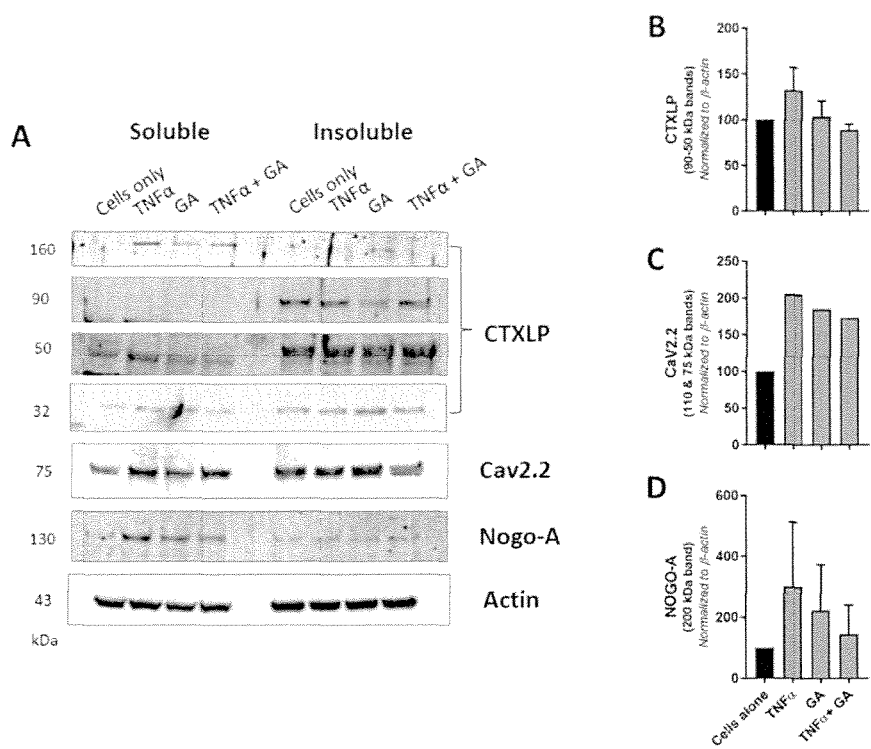

Figure 58: Gambogic acid blocks TNFα-induced CTXLP expression in human neurospheres. The ReNcell CX neuroprogenitor cell line was grown in suspension to produce human neurospheres (approximately 0.5mm diameter). Neurospheres were treated for 24 hours in neurobasal media alone, or with or without 1ng/ml TNFα and/or 0.5μM gambogic acid (GA). Cells were collected, protein extracted, and western blot performed to measure the expression of soluble (standard lysis) and insoluble (RIPA lysis) proteins for ERVK CTXLP CaV2.2 C-terminal calcium channel-associated transcriptional regulator (CaV2.2 CCAT) and NOGO-A, as compared to β-actin loading control. Results demonstrate that TNFα enhances CTXLP and NOGO-A expression in neurons, whereas in the presence of GA this effect is blocked. CaV2.2 CCAT is inversely correlated with the expression of ERVK CTXLP in this neuronal culture system. n = 2.

```
                                                                          SEQ ID NOs:
Representative Sequences from Each Species
gorilla     526948   IQKIHFYFNCSDYGINCSHSYGCCGRSCIALFCSVGKLC 315
mangabey   1353842   IQKIHFYFNCSDYGINCSHSYSLCGRSCIALFCSDSKLC 316
chimpanzee   13529   IQKIHFYFNCSDYGINCSHSYGCCGRSCIALFCSVSKLC 317
human         1227   IQKIHFYFNCSDYGINCSHSYGCCSRSCIALFCSVGKLC 318
```

Figure 59: tBLASTx results from orthologous and non-orthologous sets with at least one Toxin_18+ ORF. Examination of CTXLP encoding loci in three non-human primate genomes, *Pan troglodytes* (Common chimpanzee), *Gorilla gorilla gorilla* (Western lowland gorilla), and *Cercocebus atys* (Sooty Mangabey), as well as humans reveals orthologous loci and conservation of the Toxin_18 cysteine motif (yellow). The name of each sequence is the Douville lab Retroexplorer database retroelement identification number of the locus encoding it. Entries with overlapping genomic regions were treated as one single entry during the tBLASTx search and merged accordingly. Orthology was determined by pairwise best BLAST matches of whole Retroexplorer retroelement entries and their flanking 1000bp, which mostly correspond to entire ERVs, but which sometimes were fragments. Three and four-way orthology was determined from pairwise orthology. Some loci do not have any species-specific sequence in the alignment, as the orthologous region in that species did not return a tBLASTx result. Non-orthologous sequences represent entries for which no orthologue was identified (possible paralogues or unique insertions). Representative sequences from each from each primate species highlights the degree of conservation in the Toxin_18 cysteine motif (yellow).

FIG 60

Figure 60: Different mutational patterns between orthologues and paralogues of ERVK env genes. Represented is a combined set of heatmaps generated by superheat from frames 0 (CTXLP) and 1 (Envelope) of the human and gorilla orthologues ORFs, which where both are positive for Toxin_18 positive (CTXLP). The sequences which are orthologues are indicated by black squares in the center of each space (paralogues do not have black squares). Blue is an ω (dN/dS ratio) less than 1, indicating purifying selection and similarity between the sequences. Yellow is an ω more than 1, indicating diversifying selection and dissimilarity between the sequences. Grey indicates that ω could not be computed (in all cases dS = 0, indicating no synonymous differences between the two sequences). Sequences which are identical along the diagonal are blacked out. The cytological bands are based on the human genome, with Gorilla designations indicating their respective human orthologue/paralogue coordinate. It is notable that orthologous sequences have a low ω when it is defined (when undefined it still has a low dN value). This suggests that there is more conservation between orthologues in different species than between paralogues from the same species. This pattern is much more apparent for CTXLP than for Env reading frame, where differences are smaller if present at all.

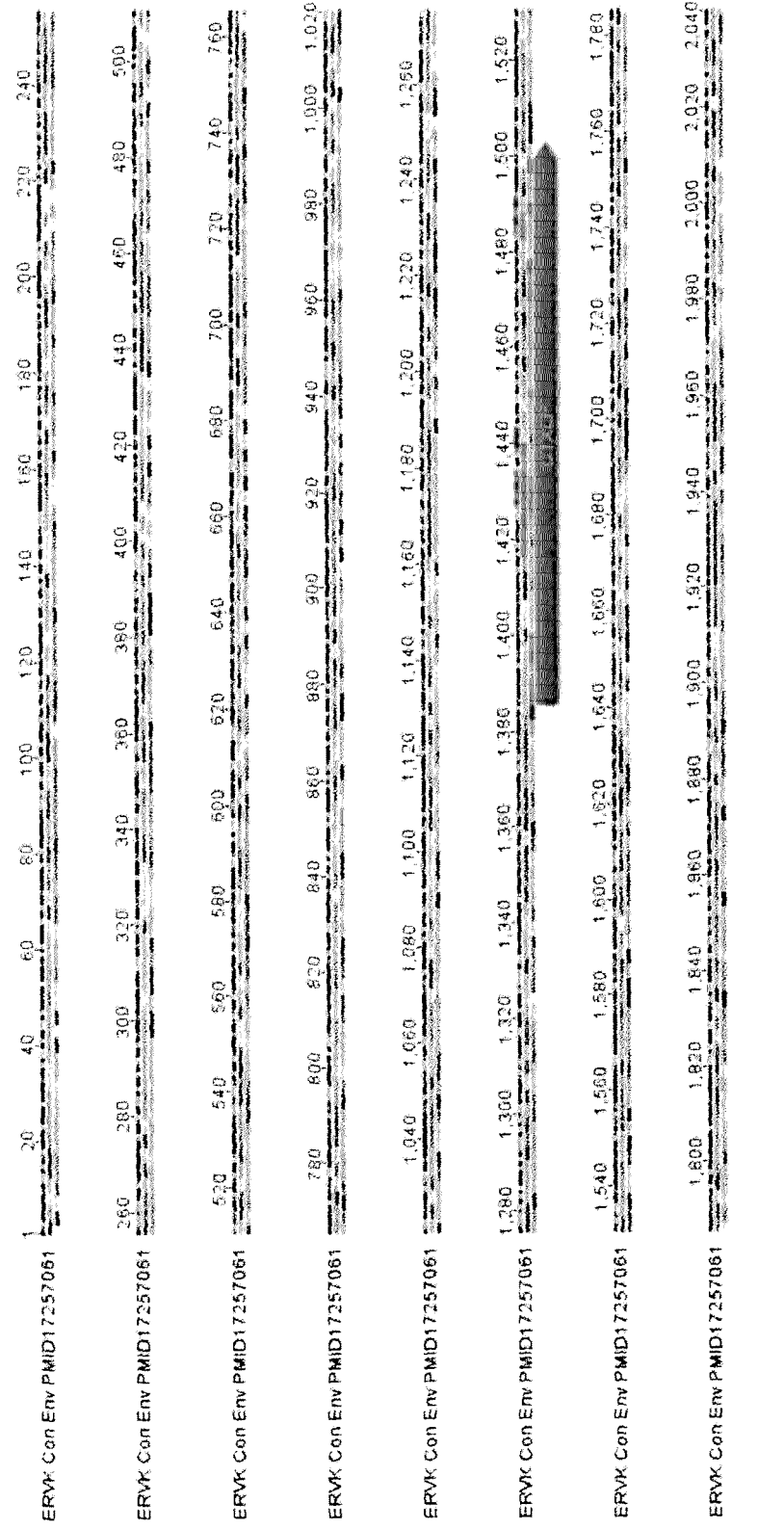
Figure 61: The transgene employed in the generation of ERVK envelope transgenic mice encodes CTXLP. The viral gene insert for Figure 62: Alignment of ERVK113 CTXLP sequence and the ERVK Consensus sequence found in the ERVK envelope transgenic mice[8]. Note the similarity and retention of key cysteine motif.

FIG 63

Figure 63: The ERVK Env and CTXLP proteins. Env is composed of the SU and TM subunits and is the prototypical gene product of the *env* gene. CTXLP is composed of the SU subunit and a C-terminal omega conotoxin domain and is encoded in an alternate open reading frame and may be produced due to ribosomal frameshifting.

FIG 64

Figure 64: Illustration of the disruption of voltage-gated calcium channel CaV2.2 by ERVK CTXLP. Both canonical endogenous retrovirus-K (ERVK) envelope protein and conotoxin-like protein (CTXLP) can be produced from the ERVK *env* gene. ERVK CTXLP disrupts CaV2.2 on multiple levels, by decreasing CaV2.2 channel expression, as well as depleting the CaV2.2 calcium channel-associated transcription regulator (CCAT) in the nucleus. CTXLP inhibition of voltage gated calcium ion channel CaV2.2 may preventing neurotransmitter release and the continuation of signal transduction in the postsynaptic neurons.

FIG 65

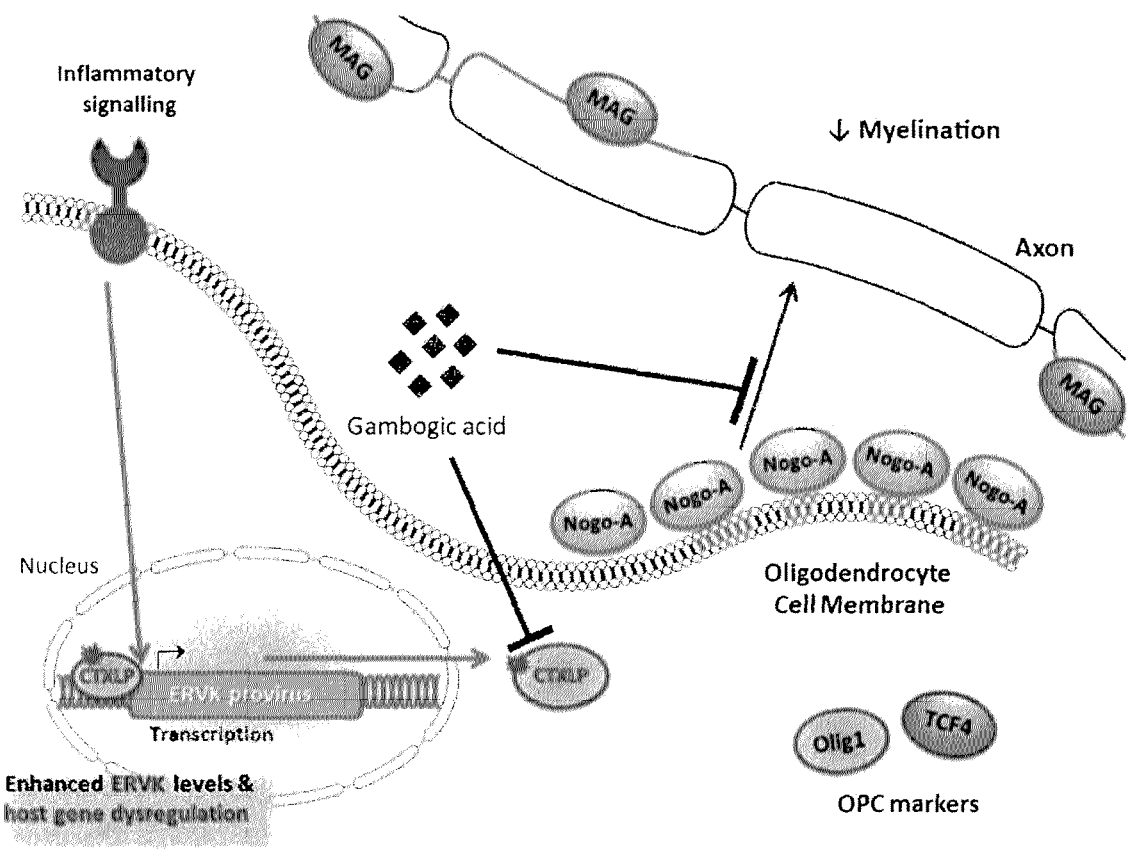

Figure 65: Pathological implications of CTXLP expression in oligodendrocyte precursor cells. CTXLP expression is enhanced in the presence of pro-inflammatory cytokines, including TNFα. Increased CTXLP protein levels in *ex vivo* human spinal cord tissue coincides with an increase in oligodendrocyte precursor cell (OPC) markers, transcription factor 4 (TCF4) and Olig1, along with elevated neurite outgrowth inhibitor A (Nogo-A) levels in adjacent cells and decreased myelin associated glycoprotein (MAG) axonal/myelin expression, which all suggest oligodendrocyte (OL) pathology. Nogo-A is a regulator of OPC differentiation, inhibitor of OL myelination, and axonal growth cone collapse during axon regeneration in the CNS. MAG is a marker for differentiated OLs and highly expressed in myelinating OLs. Based on expression patterns of OPC and OL markers, this suggests that heightened CTXLP expression in ALS is associated with OPCs being arrested in an immature state and inhibition of OL myelination. Treatment with CTXLP inhibitors, including gambogic acid, may reduce inflammatory signalling and decrease OPC and OL pathology by inhibiting increased Nogo-A expression.

ENDOGENOUS RETROVIRUS-K (ERVK) ENCODES AN ALTERNATE ENVELOPE PROTEIN

SEQUENCE LISTING

The instant application contains a Sequence Listing which has been submitted electronically in ASCII format and is hereby incorporated by reference in its entirety. Said ASCII copy, created May 21, 2021, is named 51012-032001_Sequence_Listing_5_21_21_ST25 and is 130,650 bytes in size.

FIELD

The present disclosure relates generally an endogenous Retrovirus-K (ERVK) alternate envelope protein.

BACKGROUND

Conotoxins are neurotoxic peptides found in the *Conus* genus of marine snails used to immobilize prey[22]. *Conus* species are distinct in their ability to produce hundreds of different toxic peptides[23]. Conotoxins are disulfide-rich and are usually 10-30 amino acids in length[22]. Conotoxins act as antagonists to specific voltage and ligand-gated ion channels[22]. In humans, symptoms of conotoxin exposure include poor coordination, blurred vision, speech difficulties, and nausea[23]. Conotoxins have also been associated with episodes of delirium and psychosis[24].

The O-superfamily of conotoxins exhibits an ICK fold. Members of the O-superfamily include μ-conotoxins, which inhibit voltage-gated sodium channels, and d-conotoxins, which delay sodium channel inactivation[25]. K-Conotoxins are inhibitors of voltage-gated potassium channels; ω-conotoxins inhibit N-type voltage-gated calcium channels (VGCCs)[25]. N-type VGCCs are located in presynaptic nerve terminals and are involved in neurotransmitter release[26]. ω-Conotoxin's selectivity for N-type VGCCs has allowed for their development as therapeutic agents. The ω-conotoxin MVIIA has been developed into a drug for relief of chronic and inflammatory pain[27].

Genes encoding an ω-conotoxin-like protein (CTXLP) have also been identified in certain viruses. Nuclear polyhedrosis viruses (NPV) have been shown to secrete a small conotoxin-like peptide[28]. NPVs are insect pathogens belonging to the family baculoviridae[28]. Although NPV-CTXLP's function has not been elucidated, its structure was found to have a nearly identical structure to the conserved ω-conotoxin's cysteine motif[28].

SUMMARY

In one aspect there is described an isolated polypeptide that comprises or consists of: an amino acid sequence having at least about 90% identity with the amino acid sequence set forth in SEQ ID NO:1 (CSDYGINCSHSYGCCSRS-CIALFC).

In one example the isolated polypeptide comprises or consists of an amino acid sequence having at least about 95% identity with the amino acid sequence set forth in SEQ ID NO:1.

In one example the isolated polypeptide comprises or consists of the amino acid sequence set forth in SEQ ID NO:1.

In one aspect there is described an isolated nucleic acid molecule comprising a nucleotide sequence encoding a peptide comprising or consisting of an amino acid sequence having at least about 90% identity with the amino acid sequence set forth in SEQ ID NO:1.

In one example the isolated nucleic acid molecule comprises or consists of a nucleotide sequence having at least about 90% identity with the nucleotide acid sequence encoding the polypeptide of SEQ ID NO: 1.

In one example the isolated nucleic acid molecule comprises a nucleotide sequence having at least about 95% identity with the nucleotide acid sequence encoding the polypeptide of SEQ ID NO: 1.

In one aspect there is described a vector comprising the nucleic acid molecule according to any one of claims 4 to 6.

In one aspect there is described a mammalian cell comprising the nucleic acid molecule of any one of claims 4 to 6.

In one example said mammalian cell is a human cell or non-human primate cell.

In one aspect there is described a host cell comprising the nucleic acid molecule of any one of claims 4 to 6.

In one example said host cell is a mammalian cell, an insect cell (such as *Drosophila melanogaster*), a bacteria cell, or a fungal cell.

In one aspect there is described a method for producing the peptide comprising: culturing a mammalian cell, or a host cell in a culture medium; and isolating the peptide from the mammalian cell, or host cell, or culture medium thereof.

In one aspect there is described an antibody that specifically recognizes the peptide of any one claims 1 to 3.

In one example said antibody is a monoclonal antibody or a polyclonal antibody.

In one aspect there is described a method for treating or preventing conditions or disorders associated with CTXLP in a subject, comprising: administering to a subject in need thereof a therapeutically effective amount of active agent optionally in a physiological carrier, or a pharmaceutically acceptable salt thereof, wherein the active agent blocks or inhibits the CTXLP activity and/or CTXLP associated pathology.

In one aspect there is described a method for treating or preventing conditions or disorders associated with ERVK in a subject, comprising: administering to a subject in need thereof a therapeutically effective amount of an active agent optionally in a physiological carrier, or a pharmaceutically acceptable salt thereof, wherein the active agent blocks or inhibits CTXLP activity and/or CTXLP associated pathology.

In one example said condition or disorder is an infectious disease.

In one example said infection disease is HSV infection, HIV infection, EBV infection, HTLV infection, *Toxoplasma Gondii* infection, HSV infection, or prion disease.

In one example said condition or disorder is a neurological disease.

In one example said neurological disease is amyotrophic lateral sclerosis (ALS), bipolar disorder, Kennedy's disease, multiple sclerosis, or schizophrenia.

In one example said condition or disorder is a cancer.

In one example said cancer is breast cancer, chronic myelogenous leukemia, colon cancer, gastric cancer, germ cell tumours, germinogenic tongue tumours, gonadoblastomas, hepatocellular carcinoma, adenocarcinoma, epithloid carcinoma, Acute T-cell leukemia, leukemia, lymphoma, T-cell lymphoma, Burkitt's lymphoma, neuroepithelioma, melanoma, myelodysplastic syndrome, nasopharyngeal carcinoma, ovarian cancer, pancreatic cancer, prostate cancer, testicular cancer, lung cancer, stomach cancer, skin cancer, trophoblastic tumours, tumorigenesis (e.g., via AR interaction), thyroid adenoma, or ERVK in cancerous tissues.

In one example said associated pathology is a change in CNS function of said subject, a developmental disorder, a stroke, Alzheimer's disease, spinal cord injury, cerebral ischemia, Huntington's disease, Parkinson's disease, a peripheral neuropathy, or epilepsy ocular disease.

In one example said active agent a small molecule, an antibody, a nucleic acid, an aptamer, or a peptide.

In one example said active agent comprises a Michael acceptor electrophile (MAE).

In one example said active agent comprises gambogic acid.

In one example said active agent comprises celastrol.

In one example said active agent is a small molecule inhibitor of HIV Tat, for example a Michael acceptor electrophile (MAE) such as curcumin, rosmarinic acid, gambogic acid, celastrol (15-deoxy-Δ(12,14)-prostaglandin J(2) (15d-PGJ(2)), cyclopentenone prostaglandins (CyPG), such as 15-deoxy-Delta(12,14)-PGJ(2) (15d-PGJ(2)), N-acetyl-cysteine amide (NACA), or D-penicillamine (also called Cuprimine); a sulfhydryl compound with chelating properties such as N-(2-Mercapto-propionyl)-glycin (MPG), 2,3-Dimercapto-propanol (DMP), 2,3-Dimercapto-propane-sulfonic acid (DMPS), Nitric oxide (NO), or sulphated polysaccharides; or a Thioredoxin reductase 1 (TRR1) inhibitor, such as B5 (curcumin analog).

In one example said active agent is a small molecule or antibody reversing CTXLP blockade on oligodendrocyte precursor cell maturation and oligodendrocyte myelination, such as clemastine fumarate.

In one example further comprising administering a human anti-Nogo-A antibody.

In one example said active agent is a small molecule enhancer of CaV2.2 and its calcium channel associated transcription regulator (CaV2.2 CCAT) expression or activity, such as EGTA, or glutamate.

In one aspect there is described a use of a therapeutically effective amount of active agent optionally in a physiological carrier, or a pharmaceutically acceptable salt thereof, wherein the active agent blocks or inhibits the CTXLP activity and/or CTXLP associated pathology for treating or preventing conditions or disorders associated with CTXLP in a subject.

In one aspect there is described a use of a therapeutically effective amount of active agent optionally in a physiological carrier, or a pharmaceutically acceptable salt thereof, wherein the active agent blocks or inhibits the CTXLP activity and/or CTXLP associated pathology in the manufacture of a medicament for treating or preventing conditions or disorders associated with CTXLP in a subject.

In one aspect there is described a use of a therapeutically effective amount of an active agent optionally in a physiological carrier, or a pharmaceutically acceptable salt thereof, wherein the active agent blocks or inhibits CTXLP activity and/or CTXLP associated pathology for treating or preventing conditions or disorders associated with ERVK in a subject.

In one aspect there is described a use of a therapeutically effective amount of an active agent optionally in a physiological carrier, or a pharmaceutically acceptable salt thereof, wherein the active agent blocks or inhibits CTXLP activity and/or CTXLP associated pathology in the manufacture of a medicament for treating or preventing conditions or disorders associated with ERVK in a subject.

In one example said condition or disorder is an infectious disease.

In one example said infection disease is HSV infection, HIV infection, EBV infection, HTLV infection, *Toxoplasma Gondii* infection, HSV infection, or prion disease.

In one example said condition or disorder is a neurological disease.

In one example said neurological disease is amyotrophic lateral sclerosis (ALS), bipolar disorder, Kennedy's disease, multiple sclerosis, or schizophrenia.

In one example said condition or disorder is a cancer.

In one example said cancer is breast cancer, chronic myelogenous leukemia, colon cancer, gastric cancer, germ cell tumours, germinogenic tongue tumours, gonadoblastomas, hepatocellular carcinoma, adenocarcinoma, epithloid carcinoma, Acute T-cell leukemia, leukemia, lymphoma, T-cell lymphoma, Burkitt's lymphoma, neuroepithelioma, melanoma, myelodysplastic syndrome, nasopharyngeal carcinoma, ovarian cancer, pancreatic cancer, prostate cancer, testicular cancer, lung cancer, stomach cancer, skin cancer, trophoblastic tumours, tumorigenesis (e.g., via AR interaction), thyroid adenoma, or ERVK in cancerous tissues.

In one example said associated pathology is a change in CNS function of said subject, a developmental disorder, a stroke, Alzheimer's disease, spinal cord injury, cerebral ischemia, Huntington's disease, Parkinson's disease, a peripheral neuropathy, or epilepsy ocular disease In one example said active agent a small molecule, an antibody, a nucleic acid, an aptamer, or a peptide.

In one example said active agent comprises a Michael acceptor electrophile (MAE).

In one example said active agent comprises gambogic acid.

In one example said active agent comprises celastrol.

In one example said active agent is a small molecule inhibitor of HIV Tat, for example a Michael acceptor electrophile (MAE) such as curcumin, rosmarinic acid, gambogic acid, celastrol (15-deoxy-Δ(12,14)-prostaglandin J(2) (15d-PGJ(2)), cyclopentenone prostaglandins (CyPG), such as 15-deoxy-Delta(12,14)-PGJ(2) (15d-PGJ(2)), N-acetyl-cysteine amide (NACA), or D-penicillamine (also called Cuprimine); a sulfhydryl compound with chelating properties such as N-(2-Mercapto-propionyl)-glycin (MPG), 2,3-Dimercapto-propanol (DMP), 2,3-Dimercapto-propane-sulfonic acid (DMPS), Nitric oxide (NO), or sulphated polysaccharides; or a Thioredoxin reductase 1 (TRR1) inhibitor, such as B5 (curcumin analog).

In one example said active agent is a small molecule or antibody reversing CTXLP blockade on oligodendrocyte precursor cell maturation and oligodendrocyte myelination, such as clemastine fumarate.

In one example further comprising the use of a human anti-Nogo-A antibody.

In one example said active agent is a small molecule enhancer of CaV2.2 and its calcium channel associated transcription regulator (CaV2.2 CCAT) expression or activity, such as EGTA, or glutamate.

In one aspect there is described a method for transcriptional activation, comprising contacting a DNA molecule comprising a gene with a peptide of any one of claims 1 to 3.

In one aspect there is described a diagnostic reagent for use in the detection of CTXLP protein in a subject, comprising an antibody.

In one aspect there is described a diagnostic reagent for use in the detection of CTXLP mRNA in a subject, comprising an isolated nucleic acid according to any one of claims 4 to 6.

In one aspect there is described a diagnostic reagent for use in the detection CTXLP activity in a subject, comprising a peptide of any one of claims 1 to 3.

In one aspect there is described a method for treating or preventing conditions or disorders associated with CTXLP in a subject, comprising: measuring an amount of CTXLP polypeptide, or CTXLP activity, or CTXLP mRNA; and administering to a subject in need thereof a therapeutically effective amount of an active agent optionally in a physiological carrier or a pharmaceutically acceptable salt thereof when the amount of CTXLP polypeptide, or CTXLP activity, or CTXLP mRNA, is high, optionally compared to a control, wherein the active agent blocks or inhibits the CTXLP activity and/or CTXLP associated pathology.

In one aspect there is described a method for treating or preventing conditions or disorders associated with ERVK in a subject, comprising: measuring an amount of CTXLP polypeptide, or CTXLP activity, or CTXLP mRNA; and administering to a subject in need thereof a therapeutically effective amount of an active agent optionally in a physiological carrier or a pharmaceutically acceptable salt thereof when the amount of CTXLP polypeptide, or CTXLP activity, or CTXLP mRNA, is high, optionally compared to a control, wherein the active agent blocks or inhibits the CTXLP activity and/or CTXLP associated pathology.

In one example said condition or disorder is an infectious disease.

In one example said infection disease is HSV infection, HIV infection, EBV infection, HTLV infection, *Toxoplasma Gondii* infection, HSV infection, or prion disease.

In one example said condition or disorder is a neurological disease.

In one example said neurological disease is amyotrophic lateral sclerosis, bipolar disorder, Kennedy's disease, multiple sclerosis, or schizophrenia.

In one example said condition or disorder is a cancer.

In one example said cancer is breast cancer, chronic myelogenous leukemia, colon cancer, gastric cancer, germ cell tumours, germinogenic tongue tumours, gonadoblastomas, hepatocellular carcinoma, adenocarcinoma, epithloid carcinoma, Acute T-cell leukemia, leukemia, lymphoma, T-cell lymphoma, Burkitt's lymphoma, neuroepithelioma, melanoma, myelodysplastic syndrome, nasopharyngeal carcinoma, ovarian cancer, pancreatic cancer, prostate cancer, testicular cancer, lung cancer, stomach cancer, skin cancer, trophoblastic tumours, tumorigenesis (e.g., via AR interaction), thyroid adenoma, or ERVK in cancerous tissues.

In one example said associated pathology is a change in CNS function of said subject, a developmental disorder, a stroke, Alzheimer's disease, spinal cord injury, cerebral ischemia, Huntington's disease, Parkinson's disease, a peripheral neuropathy, or epilepsy ocular disease In one example said active agent a small molecule, an antibody, a nucleic acid, an aptamer, or a peptide.

In one example said active agent comprises a Michael acceptor electrophile (MAE).

In one example said active agent comprises gambogic acid.

In one example said active agent comprises celastrol.

In one example said active agent is a small molecule inhibitor of HIV Tat, for example a Michael acceptor electrophile (MAE) such as curcumin, rosmarinic acid, gambogic acid, celastrol (15-deoxy-Δ(12,14)-prostaglandin J(2) (15d-PGJ(2)), cyclopentenone prostaglandins (CyPG), such as 15-deoxy-Delta(12,14)-PGJ(2) (15d-PGJ(2)), N-acetyl-cysteine amide (NACA), or D-penicillamine (also called Cuprimine); a sulfhydryl compound with chelating properties such as N-(2-Mercapto-propionyl)-glycin (MPG), 2,3-Dimercapto-propanol (DMP), 2,3-Dimercapto-propane-sulfonic acid (DMPS), Nitric oxide (NO), or sulphated polysaccharides; or a Thioredoxin reductase 1 (TRR1) inhibitor, such as B5 (curcumin analog).

In one example said active agent is a small molecule or antibody reversing CTXLP blockade on oligodendrocyte precursor cell maturation and oligodendrocyte myelination, such as clemastine fumarate.

In one example, further comprising administering a human anti-Nogo-A antibody.

In one example said active agent is a small molecule enhancer of CaV2.2 and its calcium channel associated transcription regulator (CaV2.2 CCAT) expression or activity, such as EGTA, or glutamate.

In one example the amount of CTXLP polypeptide is determined using an antibody.

In one aspect there is described a kit comprising: (a) a container comprising a pharmaceutical composition containing the peptide, and/or a nucleic acid, and/or a vector, a mammalian cell, a host cell, and/or an antibody, in solution or in lyophilized form; (b) optionally, a second container containing a diluent or reconstituting solution for the lyophilized formulation; and (c) optionally, instructions for use.

In one example further comprising one or more of (iii) a buffer, (iv) a diluent, (v) a filter, (vi) a needle, or (v) a syringe.

In one aspect there is described a method identifying CTXLP inhibitors, comprising: contacting a mammalian cell or a host cell, such as an insect cell (such as *Drosophila melanogaster*), a bacteria cell, or a fungal cell, with a test compound or test composition, and measuring an amount of CTXLP protein, CTXLP-mRNA, CTXLP-regulated gene, or CTXLP-associate biomarker.

In one aspect there is described a method identifying CTXLP inhibitors, comprising: contacting a organoid, with a test compound or test composition, and measuring an amount of CTXLP protein, CTXLP-mRNA, CTXLP-regulated gene, or CTXLP-associate biomarker

BRIEF DESCRIPTION OF THE DRAWINGS

Embodiments of the present disclosure will now be described, by way of example only, with reference to the attached Figures.

FIG. 2 depicts open reading frames on both strands of the endogenous retrovirus K-113 genome. ORFs (yellow) on both the sense and antisense strands were predicted using CLCbio software. Any amino acid-encoding codon was accepted as an ORF start, although each ended with a stop codon. Note the overlapping ORFs within known ERVK genes, such as gag, protease, polymerase and envelope.

FIG. 3 depicts alignment of cone snail and viral omega conotoxin domain sequences. Sequences from 3 *Conus* species (black), 1 conotoxin-like protein domain sequence from Autographa Californica Nuclear Polyhedrosis Virus (blue), the consensus sequence generated from the aforementioned sequences (red) and the sequence of the putative Endogenous Retrovirus K-113 conotoxin-like protein domain. Modified from[28]. Note the characteristic C-C-CC-C-C knottin folding motif[29]

FIG. 4 depicts an alignment and sequence logo of the putative endogenous retrovirus K-113 conotoxin-like protein domain and 10 Nuclear Polyhedrosis Virus conotoxin-like protein domain sequences. Sequences were aligned and sequence logo was assessed using Geneious v5 software[30]. Note the conserved C-G-NC-Y-CCS-C-A-FC sequence logo in these viral conotoxin-like proteins.

FIG. 5 depicts an alignment of the ERVK CTXLP cysteine-rich motif which has strong similarity to both nuclear polyhedrosis virus (NPV, 46.2%) and *Conus* (45.8%) conotoxin proteins.

FIG. 6 depicts the amino acid logo of the knottin domain from cluster representative CTXLP sequences.

FIG. 7 depicts modeled 3-dimensional structure of the putative Endogenous Retrovirus-K113 conotoxin-like protein domain. Protein tertiary structure was predicted using Knotter1D3D software (gray sticks=carbon, green sticks=hydrogen, red sticks=oxygen, blue sticks=nitrogen and yellow spheres=sulfur). Note the interactions of the yellow cysteine residues, as they form disulfide bonds.

FIG. 8 depicts aligned overlap of the predicted structures of viral conotoxin-like proteins from ERVK-113 and Ecotropis obliqua NPV. Knotter1D3D was used to predict the structures of putative ERVK-113 CTXLP domain (blue) and Ecotropis obliqua NPV CTXLP domain (red). Structure alignment is based on sequence alignment and was prepared using UCSF Chimera software[31].

FIG. 9 depicts an aligned overlap of the predicted structures of viral conotoxin-like protein backbones from ERVK-113 and Ecotropis obliqua NPV. Knotter1D3D was used to predict the structures of putative ERVK-113 CTXLP domain (blue) and Ecotropis obliqua NPV CTXLP domain (red). Structure alignment is based on sequence alignment and was prepared using UCSF Chimera software[31].

FIG. 10 depicts a predicted inhibitor cysteine knot fold of ERVK CTXLP cysteine-rich peptide. Disulfide bonds connect cysteine 1 to cysteine 4, cysteine 2 to cysteine 5, and cysteine 3 to cysteine 6, resulting in an inhibitor cysteine knot fold.

FIG. 11 depicts an alignment and sequence logo of ERVK CTXLP cysteine-rich peptide and 12 spider toxin ICK peptides. Sequences were aligned and sequence logo generated using Geneious Software. A conserved C-C-CC-C-C motif is observed in all sequences. CTXLP, all Hainantoxin and one Guanxitoxin contained a conserved G between the first and second cysteine, as indicated by the star. Grey callouts indicate the cysteine motif spacing of each toxin.

FIG. 12 depicts alignment and sequence logo of ERVK CTXLP cysteine-rich peptide and agouti-related peptide and agouti signalling protein. Sequences were aligned and sequence logo generated using Geneious Software. A conserved C-C¬CC-C-C-C is observed in all sequences.

FIG. 13 depicts alignment and sequence logo of ERVK CTXLP cysteine-rich peptide to 7 VEGF Proteins. Sequences were aligned and sequence logo generated using Geneious Software. No significant conservation was identified between the VEGF proteins and CTXLP, due to the differences in spacing and total number of cysteine residues, as indicated by the grey bar cysteine spacing motif.

FIG. 16 depicts alignment of conotoxin-like peptides of 25 human ERVK HML-2 insertions. Alignment and sequence logo generated using Geneious Software. CTXLP-peptides showed variability in the amino acid sequence. Three distinct alleles were identified, as well as several unique sequences.

FIG. 17 depicts CTXLP variants in the humans, based on genome build GRCh38.

FIG. 18 depicts schematic representation of CTXLP and amino acid sequence similarities found using NCBI-CDD and Pfam databases. The SU subunit of CTXLP is red and the omega conotoxin domain is in green. The wider portions of the diagram represent the ordered regions of the proteins and the narrow region represent the disordered region as predicted by ELM resource56.

FIG. 19 depicts analysis of the ERVK envelope transcript reveals prototypic RNA secondary structures. Shown is the predicted IRES-like RNA hairpin structures in the ERVK env transcript. The first 350 bp of ERVK Env-encoding RNA contains numerous AUG (methionine) translational start sites. Two distinct IRES-like hairpins are identified at nucleotides 84-187 and 213-318. tRNA can potentially bind at the AUG start site identified in IRES-like hairpin to produce a smaller isoform of ERVK Env or CTXLP. Alos shown is the predicted RNA secondary structure for ERVK-4 env transcript upstream and including the CTXLP ORF. Directly upstream of the CTXLP ORF translational start is a conserved −1 programmed ribosomal frameshifting sequence, which contains three elements i) a slippery site containing an X-XXY-YYZ motif which after frameshifting by −1 results in XXX-YYY reading, ii) a 5 to 10 nucleotide spacer sequence, and iii) a downstream hairpin-type pseudoknot. The ERVK env transcript slippery site is encoded by a U-UUA-AAU sequence, followed by a 5 nucleotide spacer. Structure prediction formed with RNAfold Software shows a strong probability of hairpin-loops forming within the CTXLP-coding region, likely providing a downstream hairpin-type pseudoknot.

FIGS. 20A and 20B depict the predicted CTXLP isoforms derived from the ERVK envelope transcript. Ribosomal frameshifting event resulting in formation of CTXLP peptide fused to surface unit protein. At the RNA slippery site within the ERVK Env transcript, the ribosome translating the RNA may bounce back by 4 nucleotides and begin reading in an alternate frame. This introduces a canonical KRQK nuclear localization sequence before proceeding into the CTXLP peptide. The resulting protein is a modified SU-CTXLP fusion protein. We show that ERVK can also produce SU-CTXLP fusion proteins. These CTXLP isoforms contain a nuclear localization sequence (NLS) and an additional N-linked glycosylation site at position 480.

FIG. 21 depicts bioinformatic identification of CTXLP in the genome of endogenous retrovirus-K. ERVK113 was used as a template for the CTXLP domain in the ERVK envelope gene. The ERVK envelope polyprotein is cleaved by the cellular protease furin downstream of the R-X-R/K-R site. This splits the ERVK Env polyprotein into the surface unit (SU) and transmembrane (TM) proteins which interact to form the viral spike protein on the surface of virions. A −1 programmed ribosomal frameshift (−1 PRF) allows for the translation of the CTXLP cysteine-rich motif at the C-terminal end of the SU protein. Post-translational modification of ERVK SU protein includes glycosylation. N-linked N-X-S/T glycosylation sites are identified in red boxes.

FIG. 22 depicts predicted post-translational modifications and protein interactions of CTXLP. (A) Schematic diagram of predicted glycosylation sites. (B)Schematic diagram of predicted phosphorylation and SUMOylation sites. (C) Schematic diagram of predicted protein cleavage sites. (D) Schematic diagram of predicted protein interaction sites.

FIG. 23 depicts antigenic profile of the ERVK CTXLP domain, and predicted epitopes.

FIG. 24 depicts rabbit immunization protocol for generation of a polyclonal antibody against the ERVK CTXLP domain.

FIG. 25 depicts Western blot of ERVK-expressing NCCIT whole cell extract and immunoprecipitated CTXLP-enriched fraction. The far-right lane in the image is an image of the left α-CTXLP lane that was over-exposed to bring out the details in the bands.

FIG. 26 depicts PNGase treatment of IP-purified CTXLP protein results in a decrease in western blot band size associated with removal of N-linked glycosylation moieties.

FIG. 27 depicts ERVK Env, and CTXLP expression in SVGA cells treated with 0.1 ng/mL TNFα, 1 ng/mL TNFα, and 1 ng/mL LIGHT. NCCIT cells were used as a positive control and β-actin as a loading control. n=3.

FIG. 29 depicts CTXLP protein expression predominantly localizes with chromatin in NCCIT and SVGA cells. CTXLP expression was also identified in the cytosolic and nuclear fraction and soluble and insoluble whole cell lysates of NCCIT cells. Moreover, CTXLP appeared dispersed throughout NCCIT cells in confocal imaging. In contrast, SVGA cells exhibited expression of the small (32 kDa) and large (90-110 kDa) isoforms of CTXLP in association with the chromatin (A). This was supported by nuclear localization of CTXLP in SVGA cells as shown by confocal.

FIG. 31 depicts the cellular localization of ERVK CTXLP and SU proteins in human astrocytes. Increased CTXLP protein and Env expression were identified (but not co-localized) in TNFα-treated cells compared to controls. Increased CTXLP expression indicated by arrows. Distinct puncta were identified within the 1) cytoplasm, 2) nucleus, and 3) surface membrane of the cell.

FIG. 33 depicts that CTXLP binds interferon response elements (ISREs) within the ERVK promoter (5' LTR). CTXLP may regulate ERVK gene expression, as well as other genes containing ISREs. Chromatin immunoprecipitation (ChIP) following 8 hours of 10 ng/ml TNFα or LIGHT treatment in human ReNcell-derived neurons (n=2) and human astrocytic cell line (SVGA) (n=3). Notable increase in CTXLP chromatin binding in neurons upon pro-inflammatory stimulation with the cytokine TNFα.

FIG. 37 depicts ERVK CTXLP encoding transcripts and CTXLP protein are present in Amyotrophic Lateral Sclerosis (ALS). Re-analysis of RNAseq data6 in sporadic ALS and control spinal cords for expression of disrupted non-coding (black), Env+/CTXLP− (blue) and Env+/CTXLP+ (red) env transcripts. Principle component analysis (PCA) reveals ALS patient clustering in terms of CTXLP+ transcript expression, with most frequently expressed CTXLP encoding loci indicated.

FIG. 38 depicts ERVK CTXLP levels are enhanced in autopsy spinal cord and brain tissues of patients with ALS, as measured by western blot analysis. Bar graph represents total CTXLP (A) and CX3CL1 (B) quantification in NN (n=9) and ALS (n=15) motor cortex specimens, as measured by western blot. Bar graph represents total CTXLP (C), CX3CL1 (D), ERVK Env SU (E) and CaV2.2 (F) quantification in NN (n=6) and ALS (n=13) cervical spinal cord specimens, as measured by western blot.

FIG. 39 depicts confocal micrographs of ERVK CTXLP levels being enhanced in autopsy spinal cord and brain tissues of patients with ALS. (A) Representative 10× confocal micrographs of ERVK CTXLP expression in ex vivo cervical spinal cord of a neuronormal control (NN, n=3) and patient with ALS (n=3). DAPI stain depicts nuclei. High magnification reveals staining in cells surrounding MAP2+ axons, suggesting CTXLP+ oligodendrocytes. CTXLP+ rings ranged from 6-16 μM in diameter. (B) Representative 40× confocal micrographs of ERVK CTXLP, voltage-gated calcium channel CaV2.2 (C-terminal antibody) and neuronal MAP2 expression in Brodmann area 6 (BA6) motor cortex tissue of a NN control (n=3) and patient with ALS (n=3). Note the translocation of nuclear CTXLP to cytoplasmic aggregates in neurons from an ALS patient, as well as an overall decrease in CaV2.2 expression. DAPI stain depicts nuclei.

FIG. 40 depicts micrographs showing that ERVK CTXLP levels are enhanced in autopsy cervical and lumbar spinal cord tissues from patients with ALS, as measured by light and confocal microscopy. Representative 10× confocal micrographs of ERVK CTXLP expression in ex vivo cervical (CC) and lumbar (LC) spinal cord of a neuronormal control (NN, n=3) and patients with ALS (n=3). Solochrome cyanine (SC) stain (purple) with eosin counterstain (pink) depicts tissue myelination; pale lesions appear in ALS tissues. These lesioned areas exhibit increased CTXLP expression is in red. Oligodendrocyte precursor marker TCF4 is in green. DAPI stain depicts cellular nuclei. Note that CTXLP expression occurs in either lateral and/or anterior cortical spinal tracts.

FIG. 42 depicts confocal micrographs showing ERVK CTXLP+ oligodendrocyte precursors express myelin inhibitory protein Nogo-A, or are in close proximity to Nogo-A positive cells in spinal cord tissues of patients with ALS. Human ex vivo cervical spinal cord tissues were stained for ERVK CTXLP (red), TCF4 (green), Nogo-A (grey) and nuclei (blue) in neuro-normal controls (n=3) and patients with ALS (n=3). Image merging for CTXLP and TCF4 indicate that oligodendrocyte precursors express CTXLP in ALS. Image merging for CTXLP and Nogo-A indicate that oligodendrocyte precursors can express myelin inhibitor protein Nogo-A (left panel) or alternately are in proximity to Nogo-A expressing cells in ALS (right panel). White stars indicate areas that are magnified to depict overlapping protein expression in CTXLP+ rings.

FIG. 43 depicts cancer cells express greater levels of CTXLP as compared to non-cancer cells. Prototypic cell lines for teratocarcinoma (NCCIT) and breast cancer (T47D) were examined for CTXLP expression as compared to astrocytic SVGA cells using confocal microscopy. No antibody negative control is to show that specificity of CTXLP (red) staining requires an antibody targeting ERVK CTXLP. Nuclei are shown in blue using a DAPI stain.

FIG. 44 depicts CTXLP expression in G-Bioscience Ready-to-screen cancer tissue and cell line blots. TB56-I (A), TB55 (B) and TB56-II (C) blots were screen for CTXLP expression (blue bars, top blot) normalized to β-actin loading control (lower blot). Enhanced CTXLP expression in noted is several cancer types, including T cell lymphoma, neuroepithelioma, prostate, ovary, testis and skin cancers.

FIG. 45 depicts changes in the gene expression of pro-inflammatory NF-κB p65 and anti-viral IRF7 in response to CTXLP and SU expression. 293T cells were transfected with plasmids encoding empty vector, ERVK CTXLP or ERVK SU for 24 hours. Cell pellets were collected, RNA extracted and cDNA produced for use in Q-PCR experiments to evaluate relative gene expression of RELA and IRF7. Analysis performed using ΔΔCt method and 18S RNA as a calibrator.

FIG. 47 depict western blot and confocal micrographs of ERVK CTXLP, but not ERVK Env SU, depleting CaV2.2 calcium channel-associated transcription regulator (CCAT). CaV2.2 expression in SVGA cells treated with 5 μl of immunoprecipitation (IP) products from NCCIT cell lysates extracted using rabbit pre-immune serum, custom rabbit anti-CTXLP antibody or custom rabbit anti-ERVK Env SU antibody for 24 hours. Quantification of CaV2.2 depletion in IP-product treated astrocytes (2 hrs), based on confocal quantification (****$p<0.0001$, 80-100 cells per condition quantified). Confocal imaging of CaV2.2 (N-terminal antibody) and CaV2.2 CCAT (C-terminal antibody) illustrates that CTXLP depletes nuclear CaV2.2 CCAT within 2 hours, but not the membrane-associated CaV2.2 channel (n=2).

FIG. 49 depicts CTXLP induces caspase-3 activation and apoptosis, which can be blocked by excess extracellular calcium. Cell survival 1 hour and 24 hours post treatment with 5 μl of buffer, calcium chloride, CTXLP or CTXLP and calcium chloride. Cells were examined using an EVOS microscopy for caspase-3 activation (green) or nuclei (blue), n=2). Excess calcium chloride is known to block the cellular effects of conotoxin proteins[81].

FIG. 50 depicts cell survival and confluency 24 hours post treatment with 5 μl of pre-immune serum, pre-immune serum and calcium chloride, CTXLP, CTXLP and calcium chloride, SU, or SU and calcium chloride. (A) Graphical depiction of caspase-3 expression in SVGA cells 24 hours post treatment. (B) Graphical depiction of cell confluency of SVGA cells 24 hours post-treatment. Note that pre-immune serum was used as a negative control as this is the component of immunoprecipitation product.

FIG. 51 depicts Live cell images of SVGA cells in control, SU-treated and CTXLP-treated conditions stained for caspase-3 using EVOS live cell imaging. Cells in each condition were imaged after 5 days. Control cells were imaged at 7 days and SU and CTXLP-treated cells were imaged after 8 days. Controls cells express greater amounts of the apoptotic marker caspase-3, and have not proliferated to the extent observed in CTXLP and Env treatments.

FIG. 52 depicts percentage of control and CTXLP-transfected SVGA cells expressing caspase-3 after 24 hours. Graphical depiction of apoptosis marker caspase-3 in control and CTXLP-transfected SVGA cell after 24 hours.

FIG. 54 depicts CTXLP-limiting drug screen in human NCCIT teratocarcinoma cells. The ERVK-expressing NCCIT teratocarcinoma cell line was grown in a monolayer in RMPI 1640 media supplemented with FetalGro. Cells were treated for 24 (data not shown) and 48 hours with known IC50 concentrations of drugs (NCCIT cells alone, 1% DMSO as drug carrier control, 100 μM Curcumin, 50 μM Rosmarinic acid, 0.25 μM Gambogic acid, 0.25 μM Celastrol, 200 μM D-Penicillamine and 50 μM Tetramethyl Nordihydroguaiaretic acid/TMNGA). Cells were collected, protein extracted, and western blot performed to measure the expression of ERVK CTXLP, as compared to β-actin loading control. Results demonstrate that select MAEs can reduce CTXLP expression in NCCIT cells.

FIG. 55 depicts that MAE drug Celastrol abrogates CTXLP expression in human NCCIT teratocarcinoma cells. The ERVK-expressing NCCIT teratocarcinoma cell line was grown in a monolayer in RMPI 1640 media supplemented with FetalGro. Cells were treated for 24 hours with increasing doses of celastrol (Cel, 0.1, 0.25, 1 and 2.5 μM). Cells were collected, protein extracted, and western blot performed to measure the expression of ERVK CTXLP, as compared to β-actin loading control. Results demonstrate that Cel dose-dependently reduces CTXLP expression in NCCIT cells.

FIG. 56 depicts that MAE drug Gambogic acid abrogates CTXLP expression in human NCCIT teratocarcinoma cells. The ERVK-expressing NCCIT teratocarcinoma cell line was grown in a monolayer in RMPI 1640 media supplemented with FetalGro. Cells were treated for 24 hours with increasing doses of gambogic acid (GA, 0.1, 0.25, 1 and 2.5 μM). Cells were collected, protein extracted, and western blot performed to measure the expression of ERVK CTXLP, CaV2.2 C-terminal calcium channel-associated transcriptional regulator (CaV2.2 CCAT) and NOGO-A, as compared to β-actin loading control. Results demonstrate that GA dose-dependently reduces CTXLP and NOGO-A expression in NCCIT cells. CaV2.2 CCAT is inversely correlated with the expression of ERVK CTXLP in this culture system.

FIG. 58 depicts that Gambogic acid blocks TNFα-induced CTXLP expression in human neurospheres. The ReNcell CX neuroprogenitor cell line was grown in suspension to produce human neurospheres (approximately 0.5 mm diameter). Neurospheres were treated for 24 hours in neurobasal media alone, or with or without 1 ng/ml TNFα and/or 0.5 μM gambogic acid (GA). Cells were collected, protein extracted, and western blot performed to measure the expression of soluble (standard lysis) and insoluble (RIPA lysis) proteins for ERVK CTXLP, CaV2.2 C-terminal calcium channel-associated transcriptional regulator (CaV2.2 CCAT) and NOGO-A, as compared to β-actin loading control. Results demonstrate that TNFα enhances CTXLP and NOGO-A expression in neurons, whereas in the presence of GA this effect is blocked. CaV2.2 CCAT is inversely correlated with the expression of ERVK CTXLP in this neuronal culture system.

FIG. 59 depicts alignments of orthologous and non-orthologous ERVK loci with at least one Toxin_18+ ORF. Examination of CTXLP encoding loci in three non-human primate genomes, *Pan troglodytes* (Common chimpanzee), *Gorilla gorilla gorilla* (Western lowland gorilla), and *Cercocebus atys* (Sooty Mangabey), as well as humans reveals orthologous loci and conservation of the Toxin_18 cysteine motif (yellow). Orthology was determined by pairwise best BLAST matches of whole Retroexplorer retroelement entries and their flanking 1000 bp, which mostly correspond to entire ERVs, but which sometimes were fragments. Three and four-way orthology was determined from pairwise orthology. Some loci do not have any species-specific sequence in the alignment, as the orthologous region in that species did not return a tBLASTx result. Non-orthologous sequences represent entries for which no orthologue was identified (possible paralogues or unique insertions). Representative sequences from each from each primate species highlights the degree of conservation in the Toxin_18 cysteine motif (yellow).

FIG. 60 depicts different mutational patterns between orthologues and paralogues of ERVK env genes. Represented is a combined set of heatmaps generated by superheat from frames 0 (CTXLP) and 1 (Envelope) of the human and gorilla orthologues ORFs, which where both are positive for Toxin_18 positive (CTXLP). The sequences which are orthologues are indicated by black squares in the center of each space (paralogues do not have black squares). Blue is an ω (dN/dS ratio) less than 1, indicating purifying selection and similarity between the sequences. Yellow is an ω more than 1, indicating diversifying selection and dissimilarity between the sequences. Grey indicates that ω could not be computed (in all cases dS=0, indicating no synonymous differences between the two sequences). Sequences which are identical along the diagonal are blacked out. The cytological bands are based on the human genome, with Gorilla designations indicating their respective human orthologue/paralogue coordinate. It is notable that orthologous sequences have a low ω when it is defined (when undefined it still has a low dN value). This suggests that there is more conservation between orthologues in different species than between paralogues from the same species. This pattern is much more apparent for CTXLP than for Env reading frame, where differences are smaller if present at all.

FIG. 61 depicts that the transgene employed in the generation of ERVK envelope transgenic mice encodes CTXLP. The viral gene insert for the vector used in the generation of ERVK envelope transgenic mice8, was analysed for the potential to encode and produce ERVK CTXLP. The red annotation indicates the location of CTXLP in the transgene insert.

FIG. 63 depicts the ERVK Env and CTXLP proteins. Env is composed of the SU and TM subunits and is the prototypical gene product of the env gene. CTXLP is composed of the SU subunit and a C-terminal omega conotoxin domain and is encoded in an alternate open reading frame and may be produced due to ribosomal frameshifting.

FIG. 64 depicts illustration of the disruption of voltage-gated calcium channel CaV2.2 by ERVK CTXLP. Both canonical endogenous retrovirus-K (ERVK) envelope protein and conotoxin-like protein (CTXLP) can be produced from the ERVK env gene. ERVK CTXLP disrupts CaV2.2 on multiple levels, by decreasing CaV2.2 channel expression, as well as depleting the CaV2.2 calcium channel-associated transcription regulator (CCAT) in the nucleus. CTXLP inhibition of voltage gated calcium ion channel CaV2.2 may preventing neurotransmitter release and the continuation of signal transduction in the postsynaptic neurons.

FIG. 65 depicts the putative pathological implications of CTXLP expression in oligodendrocyte precursor cells. CTXLP expression is enhanced in the presence of pro-inflammatory cytokines, including TNFα. Increased CTXLP protein levels in ex vivo human spinal cord tissue coincides with an increase in oligodendrocyte precursor cell (OPC) markers, transcription factor 4 (TCF4) and Olig1, along with elevated neurite outgrowth inhibitor A (Nogo-A) levels in adjacent cells and decreased myelin associated glycoprotein (MAG) axonal/myelin expression, which all suggest oligodendrocyte (OL) pathology. Nogo-A is a regulator of OPC differentiation, inhibitor of OL myelination, and axonal growth cone collapse during axon regeneration in the CNS. MAG is a marker for differentiated OLs and highly expressed in myelinating OLs. Based on expression patterns of OPC and OL markers, this suggests that heightened CTXLP expression in ALS is associated with OPCs being arrested in an immature state and inhibition of OL myelination. Treatment with CTXLP inhibitors, including gambogic acid, may reduce inflammatory signalling and decrease OPC and OL pathology by inhibiting increased Nogo-A expression.

DETAILED DESCRIPTION

Figure 1:
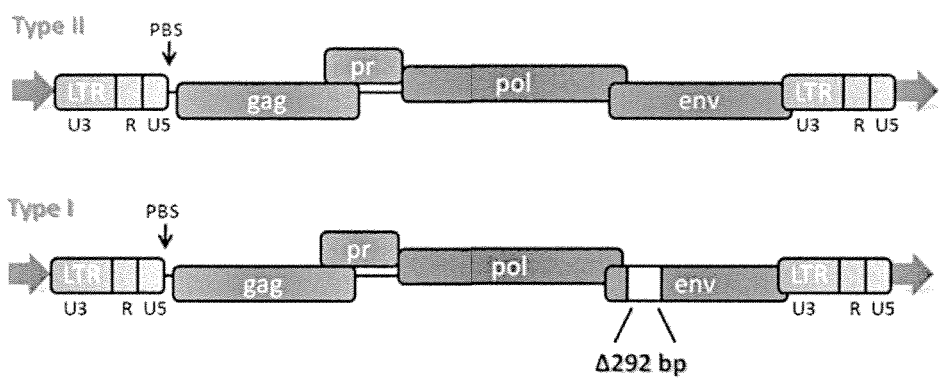
FIG. 1 depicts two types of ERVK genomes. The ERVK genome consists of four main Retroviridae genes, which are from 5' to 3': gag, pro, pol, and env. These viral genes are flanked by long terminal repeats (LTRs) containing U3, R and U5 regions. Two types of ERVK genomes can be distinguished based on a 292 bp deletion in the env gene.

In one aspect, there is described herein the identification of a region in the ERVK provirus DNA which encodes a conotoxin-like polypeptide, and which may have significance in ERVK pathogenesis. In a specific example, the polypeptide is CTXLP (CSDYGINCSHSYGCCSRS-CIALFC) (SEQ ID NO: 1).

In one example, there is described an isolated polypeptide that comprises or consists of: an amino acid sequence having at least about 70% identity with the amino acid sequence set forth in SEQ ID NO:1. In another example, the isolated polypeptide comprises or consists of an amino acid sequence having at least about 75% identity with the amino acid sequence set forth in SEQ ID NO:1. In another example, the isolated polypeptide comprises or consists of an amino acid sequence having at least about 80% identity with the amino acid sequence set forth in SEQ ID NO:1. In another example, the isolated polypeptide comprises or consists of an amino acid sequence having at least about 85% identity with the amino acid sequence set forth in SEQ ID NO:1. In another example, the isolated polypeptide comprises or consists of an amino acid sequence having at least about 90% identity with the amino acid sequence set forth in SEQ ID NO:1. In another example, the isolated polypeptide comprises or consists of an amino acid sequence having at least about 95% identity with the amino acid sequence set forth in SEQ ID NO:1. In another example, the isolated polypeptide comprises or consists of an amino acid sequence having at least about 99% identity with the amino acid sequence set forth in SEQ ID NO:1. In another example, the isolated polypeptide comprises or consists of an amino acid sequence having at least about 100% identity with the amino acid sequence set forth in SEQ ID NO:1. In another example, the isolated polypeptide comprises or consists of an amino acid sequence having at least about 70% identity to about 100% identify with the amino acid sequence set forth in SEQ ID NO:1.

In one example, there is described an isolated nucleic acid molecule comprising a nucleotide sequence encoding a peptide comprising or consisting of an amino acid sequence having at least about 70% identity with the amino acid sequence set forth in SEQ ID NO:1. In another example the isolated nucleic acid encoding a peptide comprising or consisting of an amino acid sequence having at least about 75% identity with the amino acid sequence set forth in SEQ ID NO:1. In another example the isolated nucleic acid encoding a peptide comprising or consisting of an amino acid sequence having at least about 80% identity with the amino acid sequence set forth in SEQ ID NO:1. In another example the isolated nucleic acid encoding a peptide comprising or consisting of an amino acid sequence having at least about 85% identity with the amino acid sequence set forth in SEQ ID NO:1. In another example the isolated nucleic acid encoding a peptide comprising or consisting of an amino acid sequence having at least about 90% identity with the amino acid sequence set forth in SEQ ID NO:1. In another example the isolated nucleic acid encoding a peptide comprising or consisting of an amino acid sequence having at least about 95% identity with the amino acid sequence set forth in SEQ ID NO:1. In another example the isolated nucleic acid encoding a peptide comprising or consisting of an amino acid sequence having at least about 99% identity with the amino acid sequence set forth in SEQ ID NO:1. In another example the isolated nucleic acid encoding a peptide comprising or consisting of an amino acid sequence having at least about 100% identity with the amino acid sequence set forth in SEQ ID NO:1. In another example the isolated nucleic acid encoding a peptide comprising or consisting of an amino acid sequence having at least about 70% to about 100% identity with the amino acid sequence set forth in SEQ ID NO:1.

The term "isolated", as used herein, refers to altered or removed from the natural state. For example, a polypeptide or nucleic acid naturally present in a living animal is not "isolated," but the same nucleic acid or peptide partially or completely separated from the coexisting materials of its natural state is "isolated." An isolated nucleic acid or polypeptide can exist in substantially purified form, or can exist in a non-native environment such as, for example, a host cell.

Unless otherwise specified, a "nucleotide sequence encoding a polypeptide" (and the like) includes all nucleotide sequences that are degenerate versions of each other and that encode the same amino acid sequence. The phrase nucleotide sequence that encodes a polypeptide protein or an RNA may also include introns to the extent that the nucleotide sequence encoding the protein may in some version contain an intron(s).

The terms "peptide," "polypeptide," and "protein", as used herein are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

In some examples, there is described a vector comprising the nucleic acid molecule described above and herein.

The term "vector" or "expression vector" as used herein refers to a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide. In on example, the vector is a pcDNA3.1 vector.

The term "homologous" as used herein refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Similarity", for example between two peptides, may be determined by comparing the amino acid sequence and its conserved amino acid substitutes of one polypeptide to a sequence of a second polypeptide. Variants are defined to include peptide sequences different from the original sequence, for example, different from the original sequence in less than 40% of residues per segment of interest, different from the original sequence in less than 25% of residues per segment of interest, different by less than 10% of residues per segment of interest, or different from the original protein sequence in just a few residues per segment of interest and at the same time sufficiently homologous to the original sequence to preserve the functionality of the original sequence.

The term "sequence identity" of a polypeptide or polynucleotide as used herein refers to a degree of sameness in an amino acid residue or a base in a specific region of two sequences that are aligned to best match each other for comparison. The sequence identity is a value obtained via alignment and comparison of the two sequences in the specific region for comparison, in which a partial sequence in the specific region for comparison may be added or deleted with respect to a reference sequence. The sequence identity represented in a percentage may be calculated by, for example, comparing two sequences that are aligned to best match each other in the specific region for comparison, determining matched sites with the same amino acid or base in the two sequences to obtain the number of the matched sites, dividing the number of the matched sites in the two sequences by a total number of sites in the compared specific regions (i.e., a size of the compared region), and multiplying a result of the division by 100 to obtain a sequence identity as a percentage. The sequence identity as a percentage may be determined using a known sequence comparison program, for example, BLASTP or BLASTN (NCBI), CLC Main Workbench (CLC bio), or MegAlign™ (DNASTAR Inc).

A polypeptide of may be synthesized by conventional techniques. For example, the peptides may be synthesized by chemical synthesis using solid phase peptide synthesis. These methods employ either solid or solution phase synthesis methods. Automated synthesis may be used.

In some example, a polypeptide may be produced by culturing a cell comprising a nucleic acid which encoded the polypeptide, and isolating the polypeptide from the host cell or culture medium thereof.

The peptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts to a standard translation reaction.

In some examples, the polypeptides described herein may include unnatural amino acids formed by post-translational modification or by introducing unnatural amino acids during translation. A variety of approaches are available for introducing unnatural amino acids during protein translation.

A "cell" or "host cell" refers to an individual cell or cell culture that can be or has been a recipient of any recombinant vector(s), isolated polynucleotide, or polypeptide. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a recombinant host cell.

In one example, the host cell is a cell obtained or derived from a subject.

The term "subject" or "patient" as used herein, refers to an animal, and can include, for example, domesticated animals, such as cats, dogs, etc., livestock (e.g., cattle, horses, pigs, sheep, goats, etc.), laboratory animals (e.g., mouse, rabbit, rat, guinea pig, etc.), mammals, non-human mammals, primates, non-human primates, rodents, birds, reptiles, amphibians, fish, and any other animal. The subject may be an infant, a child, an adult, or elderly. In a specific example, the subject is a human.

In one example the cell host is a human cell.

In one example, the cell is SVGA (astrocytes), RenCell CX (neuroprogenitor cells), or NCCIT (teratocarcinoma).

In some examples, there is described an antibody that specifically binds to a polypeptide as described herein. In one example, the polypeptide comprises or consists of the sequence of SEQ ID NO: 1.

The term "antibody" or "antibodies" is used herein refers to both polyclonal and monoclonal antibodies. In addition to intact or "full" immunoglobulin molecules, also included in the term "antibodies" are fragments (e.g., CDRs, Fv, Fab and Fc fragments) or polymers of those immunoglobulin molecules and humanized versions of immunoglobulin molecules, as long as they exhibit any of the desired properties according to the description.

Antibodies of the description may also be generated using well-known methods.

In some examples, a polypeptide may be used for generating an antibody of the description may be partially or fully purified from a natural source, or may be produced using recombinant DNA techniques.

In some examples, the antibodies may be purchased commercially.

In some examples, the generation of two or more different sets of monoclonal or polyclonal antibodies may maximize or increase the likelihood of obtaining an antibody with the specificity and affinity required for its intended use.

The antibodies produced may tested for their desired activity by known methods, in accordance with the purpose for which the antibodies are to be used (e.g., Immunoblooting, ELISA, immunohistochemistry, immunotherapy, etc).

For example, antibodies may be tested in ELISA assays or, Western blots, immunohistochemical staining of formalin-fixed or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity.

Monoclonal antibodies may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods.

In some example, the antibodies are humanized antibodies. Methods for humanizing non-human antibodies are well known in the art.

In some examples, antibodies may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography.

Examples of probes may include, but are not limited to, fluorescein, rhodamine, eosin and other fluorophores, radioisotopes, gold, gadolinium and other lanthanides, paramagnetic iron, fluorine-18 and other positron-emitting radionuclides. Antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art.

In one example, there is described a method for treating or preventing conditions or disorders associated with CTXLP in a subject, comprising: administering to a subject in need thereof a therapeutically effective amount of an active agent or a pharmaceutically acceptable salt thereof, wherein the active agent blocks or inhibits the CTXLP activity.

In one example, there is described a method for treating or preventing conditions or disorders associated with ERVK in a subject, comprising: administering to a subject in need thereof a therapeutically effective amount of an active agent or a pharmaceutically acceptable salt thereof, wherein the active agent blocks or inhibits the CTXLP activity.

In one example, the active agent is a CTXLP inhibitors.

In one example, a CTXLP inhibitors inhibits or reduces the activity of CTXLP polypeptide.

In one example, a CTXLP inhibitors inhibits or reduces the level or amount of CTXLP polypeptide.

In one example, a CTXLP inhibitors inhibits or reduces the level or amount of of CTXLP mRNA.

In some example, a CTXLP inhibitor may be, without being limiting thereto, a small molecule, an antibody, a nucleic acid, an aptamer, a peptide.

The term "small molecule" as used herein refers to a molecule of less than about 1,000 daltons, in particular organic or inorganic compounds.

In one example, the small molecule may be a small molecule inhibitor of HIV Tat. In one example, the small molecule inhibitor of HIV Tat is a Michael acceptor electrophile (MAE). In one example, the MAE is curcumin, rosmarinic acid, gambogic acid, celastrol (15-deoxy-Δ(12, 14)-prostaglandin J(2) (15d-PGJ(2)), cyclopentenone prostaglandins (CyPG), such as 15-deoxy-Delta(12,14)-PGJ(2) (15d-PGJ(2)), N-acetylcysteine amide (NACA), or D-penicillamine (also called Cuprimine). In one example, the small molecule inhibitor of HIV Tat is a sulfhydryl compound with chelating properties. In one example, the sulfhydryl compound with chelating properties is N-(2-Mercapto-propionyl)-glycin (MPG), 2,3-Dimercapto-propanol (DMP), 2,3-Dimercapto-propane-sulfonic acid (DMPS), Nitric oxide (NO), or sulphated polysaccharides. In one example the small molecule inhibitor of HIV Tat is a Thioredoxin reductase 1 (TRR1) inhibitor. In one example, the Thioredoxin reductase 1 (TRR1) inhibitor is B5 (curcumin analog).

In one example, the CTXLP inhibitor is a nucleic acid molecule interfering specifically with CTXLP expression. In some example, the nucleic acid CTXLP inhibitor may be an antisense against CTXLP, a siRNA against CTXLP, a shRNA against CTXLP, or a ribozyme.

The term "RNAi" or "interfering RNA" refers an RNA, which is capable of down-regulating the expression of the targeted polypeptide, such as CTXLP. It encompasses small interfering RNA (siRNA), double-stranded RNA (dsRNA), single-stranded RNA (ssRNA), micro-RNA (miRNA), and short hairpin RNA (shRNA) molecules. RNA interference, designates a phenomenon by which dsRNA specifically suppresses expression of a target gene at post-translational level. In normal conditions, RNA interference is initiated by double-stranded RNA molecules (dsRNA) of several thousand base pairs in length. In vivo, dsRNA introduced into a cell is cleaved into a mixture of short dsRNA molecules called siRNA. The enzyme that catalyzes the cleavage, Dicer, is an endo-RNase that contains RNase III domains siRNA are usually designed against a region 50-100 nucleotides downstream the translation initiator codon, whereas 5'UTR (untranslated region) and 3'UTR are usually avoided. The chosen siRNA target sequence should be subjected to a BLAST search against EST database to ensure that the only desired gene is targeted. Various products are commercially available to aid in the preparation and use of siRNA. In a preferred embodiment, the RNAi molecule is a siRNA of at least about 15-50 nucleotides in length, preferably about 20-30 base nucleotides.

RNAi can comprise naturally occurring RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end of the molecule or to one or more internal nucleotides of the RNAi, including modifications that make the RNAi resistant to nuclease digestion.

RNAi may be administered in free (naked) form or by the use of delivery systems that enhance stability and/or targeting, e.g., liposomes, or incorporated into other vehicles, such as hydrogels, cyclodextrins, biodegradable nanocapsules, bioadhesive microspheres, or proteinaceous vectors. They may also be administered in the form of their precursors or encoding DNAs.

Antisense nucleic acid can also be used to down-regulate the expression of CTXLP. The antisense nucleic acid can be complementary to all or part of a sense nucleic acid encoding CTXLP e.g., complementary to the coding strand of a double-stranded cDNA molecule or complementary to an mRNA sequence, and is thought to interfere with the translation of the target mRNA.

An antisense nucleic acid can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. Particularly, antisense RNA can be chemically synthesized, produced by in vitro transcription from linear (e.g. PCR products) or circular templates (e.g., viral or non-viral vectors), or produced by in vivo transcription from viral or non-viral vectors.

Antisense nucleic acid may be modified to have enhanced stability, nuclease resistance, target specificity and improved pharmacological properties. For example, antisense nucleic acid may include modified nucleotides designed to increase the physical stability of the duplex formed between the antisense and sense nucleic acids, e.g., phosphorothioate derivatives and acridine substituted nucleotides.

Ribozyme molecules can also be used to block the expression of CTXLP. Ribozymes are catalytic RNA molecules with ribonuclease activity which are capable of cleaving a single-stranded nucleic acid, such as an mRNA, to which they have a complementary region. Thus, ribozymes can be used to catalytically cleave mRNA transcripts to thereby inhibit translation of the protein encoded by the mRNA. Ribozyme molecules specific for CTXLP can be designed, produced, and administered by methods commonly known to the art.

The term "aptamer" refers to a molecule of nucleic acid or a peptide able to bind specifically to CTXLP polypeptide.

The term "administering" as used herein includes all means of introducing the compounds and compositions described herein to the subject, including, but are not limited to, oral (po), intravenous (iv), intramuscular (im), subcutaneous (sc), transdermal, inhalation, and the like. The compounds and compositions described herein may be administered in unit dosage forms and/or formulations containing conventional nontoxic pharmaceutically-acceptable carriers, adjuvants, and vehicles.

Non limiting examples of oral administration include tablets, capsules, elixirs, syrups, and the like.

Non limiting examples of parenteral administration include intravenous, intraarterial, intraperitoneal, epidurial, intraurethral, intrasternal, intramuscular and subcutaneous, as well as any other art recognized route of parenteral administration.

Non limiting examples of means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound(s) depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

In one example, examples of ERVK associated diseases may include but are not limited to infectious diseases, autoimmune diseases, neurological diseases, cancer, and other conditions such as idiopathic nephrotic syndrome.

In one example, examples of CTXLP associated diseases may include but are not limited to infectious diseases, autoimmune diseases, neurological diseases, cancer, and other conditions such as idiopathic nephrotic syndrome.

Infectious disease, including but not limited to HSV infection, HIV infection, EBV infection, HTLV infection, *Toxoplasma Gondii* infection, HSV infection, or prion disease.

Autoimmune disease, including but not limited to, Insulin dependent diabetes mellitus, morphea, Psoriasis, rheumathoid arthritis, systemic lupus erythematosus, Type 2 diabetes mellitus (in people with SCZ).

Neurological disease, including but not limited to, amyotrophic lateral sclerosis, bipolar disorder, Kennedy's disease, multiple sclerosis, Schizophrenia Cancer, including but not limited to, Breast cancer, Chronic myelogenous leukemia, Colon cancer, Gastric cancer, Germ cell tumours, Germinogenic tongue tumours, Gonadoblastomas, Hepatocellular carcinoma, Leukemia, Lymphoma, Melanoma, Myelodysplastic syndrome, Nasopharyngeal carcinoma, Ovarian cancer, Pancreatic cancer, Prostate cancer, Trophoblastic tumours, Tumorigenesis (via AR interaction), Thyroid adenoma, ERVK in cancerous tissues.

Other, including but not limited to, Idiopathic nephrotic syndrome.

In one example, there is described a method for transcriptional activation, comprising contacting a DNA molecule comprising a gene with a polypeptide as described herein.

In one example, there is described a diagnostic reagent for use in the detection of CTXLP polypeptide in a subject, comprising an antibody specific for CTXLP polypeptide.

In one example, there is described a diagnostic reagent for use in the detection of CTXLP mRNA in a subject, comprising an isolated nucleic acid specific for CTXLP.

In one example, there is described a diagnostic reagent for use in the detection CTXLP activity in a subject, comprising a polypeptide as described herein.

In one example, there is described a method for treating or preventing conditions or disorders associated with CTXLP in a subject, comprising: measuring an amount of CTXLP polypeptide, or CTXLP activity, or CTXLP mRNA; and administering to a subject in need thereof a therapeutically effective amount of an active agent or a pharmaceutically acceptable salt thereof when the amount of CTXLP polypeptide, or CTXLP activity, or CTXLP mRNA, is high, optionally compared to a control, wherein the active agent blocks or inhibits the CTXLP activity.

In one example, there is described a method for treating or preventing conditions or disorders associated with ERVK in a subject, comprising: measuring an amount of CTXLP polypeptide, or CTXLP activity, or CTXLP mRNA; and administering to a subject in need thereof a therapeutically effective amount of an active agent or a pharmaceutically acceptable salt thereof when the amount of CTXLP polypeptide, or CTXLP activity, or CTXLP mRNA, is high, optionally compared to a control, wherein the active agent blocks or inhibits the CTXLP activity.

Method are conveniently practiced by providing the compounds and/or compositions used in such method in the form of a kit. Such kit preferably contains the composition. Such a kit preferably contains instructions for the use thereof.

In one example, there is described a kit comprising: (a) a container comprising a pharmaceutical composition containing a polypeptide as described herein, and/or a nucleic acid as described herein, and/or an expression vector, and/or a host cell, and/or an antibody as described herein, in solution or in lyophilized form; (b) optionally, a second container containing a diluent or reconstituting solution for the lyophilized formulation; and (c) optionally, instructions for use.

In one example, the kit further comprising one or more of (iii) a buffer, (iv) a diluent, (v) a filter, (vi) a needle, or (v) a syringe.

To gain a better understanding of the invention described herein, the following examples are set forth. It should be understood that these examples are for illustrative purposes only. Therefore, they should not limit the scope of this invention in anyway.

EXAMPLES

Endogenous retroviruses (ERVs) are host genetic elements originating from prior infection of host germ-line cells that are subsequently inherited through the germline. ERVs represent approximately 8% of human genomic DNA. ERVs can benefit their host, or in other contexts are proposed to be involved in pathogenesis and disease. Notably, our interest in ERVK CTXLP lies in its association to motor neuron conditions such as Amyotrophic Lateral Sclerosis (ALS), as well in cancers.

ERVK CTXLP Bioinformatics: Endogenous retrovirus-K (ERVK) conotoxin-like protein (CTXLP) is produced following a ribosomal frameshifting event and is subject to post-translational modifications (PTMs). PTMs and alternative start sites allow for a variety of CTXLP isoforms which may drive distinct pathogenic mechanisms. The prevalence and polymorphic variability of ERVK CTXLP-encoding insertions suggests that CTXLP is a pervasive and conserved ERVK protein. The molecular characterization of CTXLP revealed a conotoxin domain which predicts that it acts as antagonist to specific voltage-gated calcium channels. CTXLP also contains a cysteine motif that aligned to multiple cone snail, spider and viral toxins, which are known to function as antagonists to voltage-gated ion channels. This intrinsic capacity to interfere with calcium channels through these motifs suggests a putative mechanism by which ERVK can act in the pathogenesis of motor neuron diseases such as ALS.

CTXLP biological characterization: CTXLP protein isoform expression in NCCIT and SVGA cells was elucidated by Western blots which indicated presumed isoform sizes of 32 kDa, 51 kDa, and 90/110 kDa. In NCCIT cells, endogenous CTXLP is ubiquitously expressed in the nucleus, and also identified in the cytoplasm and cell membrane, based on cell fractionation and confocal experiments. In contrast, in SVGA cells basal CTXLP levels are limited, but highly inducible by pro-inflammatory stimuli. In addition, CTXP expression is almost exclusively in the chromatin fraction and demonstrates a prominence in the nucleus upon confocal imaging. The notable exception is that after pro-inflammatory activation for 24 hours CTXLP puncta appear in the cytoplasm and on cellular membranes reminiscent of pathogenic protein aggregates. Moreover, the localization pattern in response to pro-inflammatory activators resulting in a prominence in the nucleus ability to bind chromatin suggests that CTXLP may be involved in viral transcription. A primary candidate as a viral transcription factor is the 32 kDa CTXLP isoform, as small cysteine-rich proteins have previously been identified as transcriptional activators, as per HIV-1 Tat (15 kDa) and HTLV Tax (40 kDa) role as viral transcription co-activators.

CTXLP Expression in disease states: ERVK CTXLP localized to the motor cortex in spinal cord sections from autopsy samples of patients with ALS, but not neuro-normal controls. Concomitantly, CTXLP expression was substantially enhanced in diseased ALS tissues, aligning with oligodendrocytes, Nogo-A expression and demyelinated lesions. In addition, cancer cell lines and tissue expressed greater levels of CTXLP relative to normal controls. Together, these findings provide significant evidence for the activity of CTXLP in ALS and certain cancers.

Pathological consequences of CTXLP expression: ERVK CTXLP has the capacity to enhance NF-κB p65 and p50 proteins that play a critical role in ALS pathogenesis. In addition, CTXLP administration or transfection induced significant levels of capase-3. The induction of caspase-3 activation and apoptosis by CTXLP was inhibited by excess extracellular calcium pointing to a calcium channel mediated activation of toxicity. Remarkably, despite the initial die off of cells, cells remaining in the cultures appeared to demonstrate appreciable cellular proliferation relative to control suggesting the induction of a carcinogenic process. CTXLP also had a notable effect on the depletion of CaV2.2 voltage-gated calcium channel-associated transcriptional regulator (CaV2.2 CCAT) from the nucleus.

ERVK CTXLP can be targeted by small molecule therapeutics: A drug screen revealed that celastrol and gambogic acid have the capacity to inhibit endogenous CTXLP expression in NCCIT cancer cell line. Moreover, gambogic acid was able to reduce inducible CTXLP expression the presence of TNFα and ameliorate the concomitant expression of pathogenic marker Nogo-A. This strongly suggests that therapeutic targeting of CTXLP in human disease could be an agent in the efforts to ameliorate the devastation of ALS.

Development of cell and animal models to investigate CTXLP pathogenesis: Human tissue and animal models for the study of CTXLP in ALS and cancer are needed. We are actively working to further develop our human tissue culture models. In addition, together with Dr. Alberto Civetta, we are in the process of developing a model in *Drosophilia* at the University of Winnipeg. Importantly, we will continue to pursue mammalian models with our collaborators which offer an opportunity to explore multiple features of pathogenesis as we continue to elucidate the processes involved in CTXLP pathogenesis.

ERVK CTXLP is a novel pathological target for the development of therapeutics for inflammatory, neurological and oncogenic diseases.

ABBREVIATIONS

Abbreviations used in text.
AGRP Agouti-related peptide
ALS Amyotrophic lateral sclerosis
ASIP Agouti-signalling protein
BA6 Brodmann area 6
BLAST Basic local alignment search tool
BMAA Beta-N-methylamino-L-alanine
CC Cervical spinal cord
CCAT Calcium channel-associated transcription regulator
cDNA Complimentary deoxyribonucleic acid
CEL Celastrol
ChIP Chromatin immunoprecipitation
CNS Central nervous system
CTXLP Conotoxin-like protein
CX3CL1 Chemokine (C-X3-C motif) ligand 1
DAPI 4',6-diamidino-2-phenylindole
DNA Deoxyribonucleic acid
Env Envelope
ERV Endogenous retrovirus
ERVH Endogenous retrovirus-H
ERVK Endogenous retrovirus-K
ERVW Endogenous retrovirus-W
GA Gambogic acid
HAART Highly active antiretroviral therapy
HAUSP/USP7 Herpesvirus-associated ubiquitin-specific protease/Ubiquitin-specific-processing protease 7
HCV Hepatitis C virus
HIV Human Immunodeficiency virus
HTLV Human T-lymphotrophic virus
HML Human Mouse mammary tumour virus-like
ICK Inhibitor cysteine knot
IP Immunoprecipitation
IRES Internal ribosomal entry site
IRF7 Interferon regulatory factor 7
ISRE Interferon response element
LATS Large tumor suppressor kinase
LC Lumbar spinal cord
LIGHT Homologous to lymphotoxin, exhibits inducible expression and competes with HSV glycoprotein D for binding to herpesvirus entry mediator, a receptor expressed on T lymphocytes
LTR Long terminal repeat
MAE Michael acceptor electrophile
MAG Myelin-associated glycoprotein
MAP2 Microtubule-associated protein 2
MAPK Mitogen-activated protein kinases
MC1 R Melanocortin receptor 1
MMTV Mouse mammary tumour virus
MOG Myelin oligodendrocyte glycoprotein
mRNA Messenger ribonucleic acid
MS Multiple sclerosis
MUSCLE MUltiple Sequence Comparison by Log-Expectation
NCCIT National Cancer Center Institute Tokyo, teratocarcinoma cell line
NF-κB Nuclear factor κB
NCBI National Centre for Biotechnology Information
NEC-1/2 Necrostatin-1/2
NgR1 Nogo-A receptor
NN Neuronormal
NLS Nuclear localization signal
NPV Nuclear polyhedrosis virus
Olig1/2 Oligodendrocyte transcription factor 1/2
OPC Oligodendrocyte precursor cell
ORF Open reading frame
PCA Principle component analysis
PLP Proteolipid protein
PRF Programmed ribosomal frameshift
PTM Post-translational modification
Q-PCR Quantitative polymerase chain reaction
RA Rheumatoid arthritis
RelA REL-associated protein
RNA Ribonucleic acid
RT Reverse transcriptase
RTN4R Reticulon 4 receptor
SC Solochrome cyanine
SRA Sequence Read Archive
SU Surface unit
SVGA SV40 T antigen glial astrocytes
Tat Trans-activator of transcription
Tax Transactivator from the X-gene region
TCF4 Transcription factor 4
TDP-43 TAR DNA-binding protein 43
TM Transmembrane
TM EV Theiler's Murine Encephalomyelitis Virus
TNFα Tumour necrosis factor α
TRAF-2/6 TNF receptor associated factor
VEGF Vascular endothelial growth factors
VGCC Voltage gated calcium channel
WCE Whole cell extract

Endogenous Retroviruses

Retroviruses are single-stranded RNA viruses that replicate through reverse transcription[1]. Retroviruses use the enzyme reverse transcriptase to convert their genomic RNA to DNA, and then use a viral integrase to insert itself into a host genome[2]. Retroviruses are categorized as being either exogenous or endogenous[3]. Examples of exogenous retroviruses include Human-Immunodeficiency virus (HIV) and Human T-lymphotropic virus (HTLV). Alternatively, endogenous retroviruses (ERVs) are genetic elements originating from prior infection of host germ-line cells, allowing them to be inherited through Mendelian genetics[3]. ERVs represent approximately 8% of human genomic DNA[4]. ERVs can benefit their hosts, or in other contexts are proposed to be involved in pathogenesis and disease[6].

Endogenous Retrovirus-K (ERVK) is the most recently endogenated retrovirus in the human genome[1]. ERVK is a group of similar viruses that are categorized into 10 clades (sub-groups). ERVK (HML-2 clade) first entered the human genome approximately 28 million years ago, occurring before the divergence of hominids and old-world monkeys[7]. More recent insertions of ERVK occurred up to 200,000 years ago, and are specific to the human lineage. This has resulted in several human-specific ERVK insertions[8]. Approximately 1000 ERVK loci have been identified in the human genome[9]. Although the majority of ERVK insertions have been silenced through mutations and negative selection, there are an estimated 24 fixed loci capable of producing viral proteins[3,6]. ERVs are also found to be highly polymorphic between individuals and different ethnic groups[7]. ERVK expression has been detected in several tissues throughout the body at varying levels between individuals[3,10].

ERVK Genome

The ERVK genome consists of the essential retroviral genes gag-pro-pol-env, along with its own accessory genes[1] (FIG. 1). The group specific antigen (gag) gene encodes structural proteins including the viral capsid[8,11]. The protease (pro) gene encodes a protease which cleaves newly synthesized viral proteins[1]. The polymerase (pol) gene encodes for proteins including reverse transcriptase and integrase[2,11]. The envelope (env) gene encodes the glycoproteins of the viral envelope[11]. The ERVK genome is flanked by long terminal repeats (LTRs), which were assistive in retroviral DNA insertion into the host[12]. Once inserted into the host genome, the virus is considered a provirus. LTRs contain elements of enhancers and promoters, including transcription factor binding-sites and interferon-stimulated response elements that regulate both retroviral and host gene expression[6,11].

ERVK can be organized into two types based on their genome. Type 1 proviruses contain a 292 base-pair deletion near the 5' end of env not found in type 2 proviruses[13]. The presence or absence of this deletion affects the accessory proteins the provirus produces[13,14].

ERVK Envelope Protein

The ERVK envelope (Env) protein is initially translated as a large, inactive polyprotein[15,16]. The polyproteins dimerizes or trimerizes and are then cleaved by the cellular protease furin, forming a surface unit (SU) and transmembrane (TM) subunit[15]. Like other retroviral envelope proteins, the assembled Env trimer is heavily glycosylated and is expressed on the viral capsid membrane, as well as infected host cell membranes, allowing for incorporation of the virus into host cells[15,17].

Cysteine Knot Proteins

Cysteine knots are protein structural motifs found throughout animals, fungi and plants[18]. Cysteine knot proteins are known for their stability, attributed to their 3 disulfide bonds; two of the disulfide bonds and their peptide backbone form a ring that the third bond goes through, thus forming a "knot" structure[18]. Cysteine knot proteins are categorized as cyclic cysteine knots, growth factor cysteine knots, or inhibitor cysteine knots (ICK). Cyclic cysteine knots are found in plants and often have defense functions as bactericides and insecticides[18]. Growth factor cysteine knots are found in extracellular signaling molecules and are involved in various functions including cell-cell communication and embryonic development[19]. Examples include the vascular endothelial growth factors (VEGFs), and nerve growth factor[19]. ICK proteins are found in fungi, plants and animals and act as antagonists to a variety of receptors and ion channels[18].

ICK proteins include a vast array of peptides found in various living organisms. The ICK structure consists of six conserved (connected as Cys1-CysIV, CysII-CysV, and CysIII-CysVI) cysteine residues and an otherwise variable peptide backbone[18] (FIG. 3). Within the animal kingdom, ICK peptides are found in the venoms of spiders, scorpions, and marine snails, and function either as pore-blockers or gate-modifiers of ion channels[18]. Mammalian ICK peptides have also been identified, including agouti-signalling protein (ASIP) and agouti-related peptide (AGRP)[20].

Animal ICKs are proposed to be a result of divergent evolution[21]. Functional constraints during evolution have resulted in spider, snail, and scorpion ICKs maintaining a similar gene structure, protein fold, and target receptor, which are all evidence for a common ancestor[21]. Alternatively, plant and fungi ICK do not have these similarities to animal ICKs, suggesting they are a product of convergent evolution[21]. In certain baculoviruses, a cysteine-rich ORF has been detected, that potentially translates into an ICK fold[21]. The putative ICK motif resembles the animal ICKs, suggesting that viruses may have obtained this genetic sequence by a gene transfer event after infecting an ICK-carrying host[21].

Conotoxins

Conotoxins are neurotoxic peptides found in the *Conus* genus of marine snails used to immobilize prey[22]. *Conus* species are distinct in their ability to produce hundreds of different toxic peptides[23]. Conotoxins are disulfide-rich and are usually 10-30 amino acids in length[22]. Conotoxins act as antagonists to specific voltage and ligand-gated ion channels[22]. In humans, symptoms of conotoxin exposure include poor coordination, blurred vision, speech difficulties, and nausea[23]. Conotoxins have also been associated with episodes of delirium and psychosis[24].

The O-superfamily of conotoxins exhibits an ICK fold. Members of the O-superfamily include μ-conotoxins, which inhibit voltage-gated sodium channels, and δ-conotoxins, which delay sodium channel inactivation[25]. К-Conotoxins are inhibitors of voltage-gated potassium channels; ω-conotoxins inhibit N-type voltage-gated calcium channels (VGCCs)[25]. N-type VGCCs are located in presynaptic nerve terminals and are involved in neurotransmitter release[26]. ω-Conotoxin's selectivity for N-type VGCCs has allowed for their development as therapeutic agents. The ω-conotoxin MVIIA has been developed into a drug for relief of chronic and inflammatory pain[27].

Genes encoding an ω-conotoxin-like protein (CTXLP) have also been identified in certain viruses. Nuclear polyhedrosis viruses (NPV) have been shown to secrete a small conotoxin-like peptide[28]. NPVs are insect pathogens belonging to the family baculoviridae[28]. Although NPV-CTXLP's function has not been elucidated, its cysteine bridges were found to have a nearly identical structure to the conserved ω-conotoxin's cysteine motif[28]. We have discovered a novel CTXLP ORF in the envelope gene of ERVK. The full pathogenic potential of ERVK CTXLP domain remains unknown.

ERVK CTXLP Bioinformatics

Identification of a Conotoxin-Like Domain in the ERVK Genome

Splicing and Conserved Domains in the ERVK Genome (Start Codon-Biased Analysis)

NetGene2 splice site prediction yielded a large number of predicted splice junctions (105-119 per ERVK sequence). However, after exhaustive analysis, none of these splice junctions resulted in the creation of domains that could be identified using the Conserved Domains Database. However, the predicted splicing patterns resulted in the identification of between 27 and 46 newly created ORFs per ERVK sequence.

Conserved Domains (Start Codon-Unbiased Analysis)

After finding no conserved domains in the initial analysis, the requirement for a start codon (ATG, CTG, TTG, GTG or ATT) at the beginning of each ORF was removed, because a start codon could be introduced through splicing and thus was not strictly necessary. The removal of this requirement resulted in slightly different ORFs, which can be seen in FIG. 2. Analysis of these ORFs identified a previously undescribed region that would generate a peptide with significant homology to known proteins. This ORF occurred in both type 1 and type 2 genomes (that is, it was not affected by the 292-base pair deletion). DNA with the potential to encode a peptide containing a domain with homology to the O-conotoxin superfamily was identified in a region of env, but in a different reading frame, from nucleotide 7863 to nucleotide 7934 in the 5'-3' direction. This ORF did not contain the typical methionine codon that is often used as a start codon for translation.

Conotoxin-Like Domain

The putative conotoxin-like domain contained six characteristic cysteine residues and one characteristic glycine residue, indicating that it is most similar to the ω-conotoxin family. Another group of viruses, Nuclear Polyhedrosis Viruses, which are insect-infecting Baculoviruses, produce a similar conotoxin-like protein (NPV CTXLP). The putative ERVK CTXLP showed the greatest similarity to these viral proteins. FIG. 3 shows the sequences of several ω-conotoxins produced by 3 cone snail species, as well as the sequence of a Nuclear Polyhedrosis Virus conotoxin-like domain. Although these sequences differ from each other in notable ways, 7 conserved residues (6 cysteines and 1 glycine) are found in all of them. These residues are also observed in the ERVK CTXLP domain.

The ERVK CTXLP sequence showed the greatest homology to NPV CTXLP sequences (E-value=$1.09 \times 10^{-5}$). FIG. 4 shows the sequence logo for ERVK CTXLP and 10 NPV sequences, in which several more amino-acid residues (in addition to the 7 described above) are conserved.

FIG. 5 summarizes the *Conus* and NPV sequences with greatest similarity and centrality to ERVK CTXLP. FIG. 6 shows the logo of the knotin domain of CTXLP and its amino acid composition.

Three-Dimensional Modeling of the ERVK Conotoxin-Like Protein

Conotoxins adopt a knot-like conformation, called a knottin domain, which is important for their action. Omega-conotoxin and NPV CTXLP knottins include 3 disulfide bonds. Tertiary structure prediction of the ERVK-113 CTXLP protein using Knotter 1D3D software resulted in the conclusion that it too could form these characteristic features. The predicted 3-dimensional structure of the ERVK-113 CTXLP domain is shown in FIG. 7.

This predicted structure was then superimposed on the predicted structure of an NPV CTXLP domain to examine the similarity between the two. This structure alignment (FIG. 8) is based on sequence alignment and was prepared using UCSF Chimera software[31].

The root mean square deviation between 24 atom pairs in this alignment is 0.426 angstroms. However, it can be difficult to see how similar the predicted structure of these two protein domains are from this image (FIG. 8). As such, the structures were reduced to their respective peptide backbones. The resultant image can be seen in FIG. 9.

Conotoxin-Like Proteins are Not Encoded by Other Retroviruses

After identifying that these two distantly related groups of viruses (ERVK and NPVs) both contain conotoxin-like protein coding capacity, we also searched for conotoxin-like domains within translations of all three reading frames of the env region of several other retroviral genomes (HIV-1, HTLV-1, MMTV, ERVW, ERVH). No conotoxin-like domains were identified in any of these retroviruses from our analysis.

Alignments of ERVK CTXLP and Other Cysteine-Rich Proteins

The ERVK CTXLP ORF is 39 amino acids long, with the cysteine-rich motif accounting for 30/39 amino acids (CSDYGINCSHSYGCCSRSCIALFCSVSKLC). The CTXLP cysteine-rich sequence was aligned to inhibitor cysteine knot (ICK) proteins and other cysteine-rich proteins using Geneious software (Version R8)[30]. A sequence logo was generated from the alignment to assess amino acid conservation between CTXLP and known cysteine-rich proteins (FIG. 10). Geneious alignment software was used to compare ERVK CTXLP's cysteine-rich amino acid sequence to other cysteine-rich proteins (Table 1) to further understand CTXLP's structure and potential function.

TABLE 1

Proteins and peptides from various organisms and their respective accession numbers compared to CTXLP cysteine-rich motif found using Geneious software.

| Protein/Peptide | Organism | Accession # |
|---|---|---|
| Guanxitoxin-2 | Spider | P84837.1 |
| Guanxitoxin-1D | Spider | P84836.1 |
| Hainantoxin-I | Spider | D2Y1X6.1 |
| Hainantoxin-III | Spider | D2Y1X9.1 |
| Hainantoxin-IV | Spider | 1NIY_A |
| Hainantoxin-V | Spider | P60975.1 |
| Hanatoxin-1 | Spider | P56852.1 |
| Hanatoxin-2 | Spider | P56853.1 |
| Sgtx | Spider | 1LA4_A |
| Grammotoxin | Spider | P60590.2 |
| Huwentoxin-I | Spider | P56676.2 |
| Huwentoxin-X | Spider | P68424.2 |
| agouti-related peptide | Human | O00253.1 |
| agouti-signalling protein | Human | 1Y7K_A |
| VEGF-A | Human | P15692.2 |
| VEGF-B | Human | P49765.2 |
| VEGF-C | Human | CAA63907.1 |
| VEGF-D | Human | BAA24264.1 |
| VEGF-E | Human | ABA00650.1 |
| VEGF-F | Snake | 1WQ8_A |
| Placental Growth Factor | Human | AAH07789.1 |
| Tat | HIV-1 | CCD30501.1 |
| Tat | HIV-2 | AAA76845.1 |
| Tax | HTLV-1 | BAD95659.1 |

TABLE 1-continued

Proteins and peptides from various organisms and their respective accession numbers compared to CTXLP cysteine-rich motif found using Geneious software.

| Protein/Peptide | Organism | Accession # |
|---|---|---|
| Tax | HTLV-2 | AFC76143.1 |
| Tax | HTLV-3 | Q0R5R1.1 |
| Envelope | HTLV-4 | CAA29690.1 |
| Envelope | Jaagsiekte Sheep Retrovirus | AAK38688.1 |

Several spiders are known to utilize ICK peptides in their toxins[32]. The putative ERVK CTXLP cysteine motif was aligned to 12 spider toxins from various species of spiders. FIG. 11 shows ERVK CTXLP peptide had significant similarity to the Hainantoxin-I and Hainantoxin-IV ICK motifs, with a pairwise identity above 25% suggesting conserved protein function (NCBI).

The sequence logo generated showed that the cysteine knot (C-C-CC-C-C) motif is conserved in ERVK CTXLP and the spider toxins examined. Although there was significant sequence diversity in other amino acids, each sequence contained the essential 6 cysteine residues for an ICK. Five of the 12 spider toxins also contained a glycine residue in an identical position to ERVK CTXLP's characteristic glycine. The overall cysteine spacing of the CTXLP motif was unique when compared with spider toxins, suggesting that despite forming an ICK fold, the overall protein conformations are likely divergent. This could explain receptor binding specificity of each toxin species. Spider toxins and CTXLP were then examined for conserved motifs (Table 2). Overall, there was little conservation outside of the ICK motif, with the most significant conservation found in Hainantoxin-I, a voltage gated sodium channel inhibitor.

of 21.9% with CTXLP), suggesting structural similarity and possible functional overlap (FIG. 12).

Seven of ten cysteine residues found in the agouti family peptides aligned with ERVK CTXLP. Agouti proteins use 8 cysteines to form an ICK structure[33], whereas CTXLP only has 7 cysteines and is likely to take on a simpler ICK fold. Agouti-like proteins are the only known ICK domain containing protein in humans; however, these findings suggest that CTXLP may also be a human-derived ICK protein.

ERVK CTXLP was also aligned to 7 VEGF proteins, which utilize a growth factor cysteine knot. Although there was some alignment between the cysteine residues and some similar motifs (ex. GCC) identified, the large gaps in spacing and the different spacing of cysteine residues in the VEGF proteins suggests that there is no significant similarity to ERVK CTXLP (all with identity≤7.7%) (FIG. 13). The dissimilarity suggests that CTXLP does not take on a growth factor cysteine knot structure.

Figure 14:
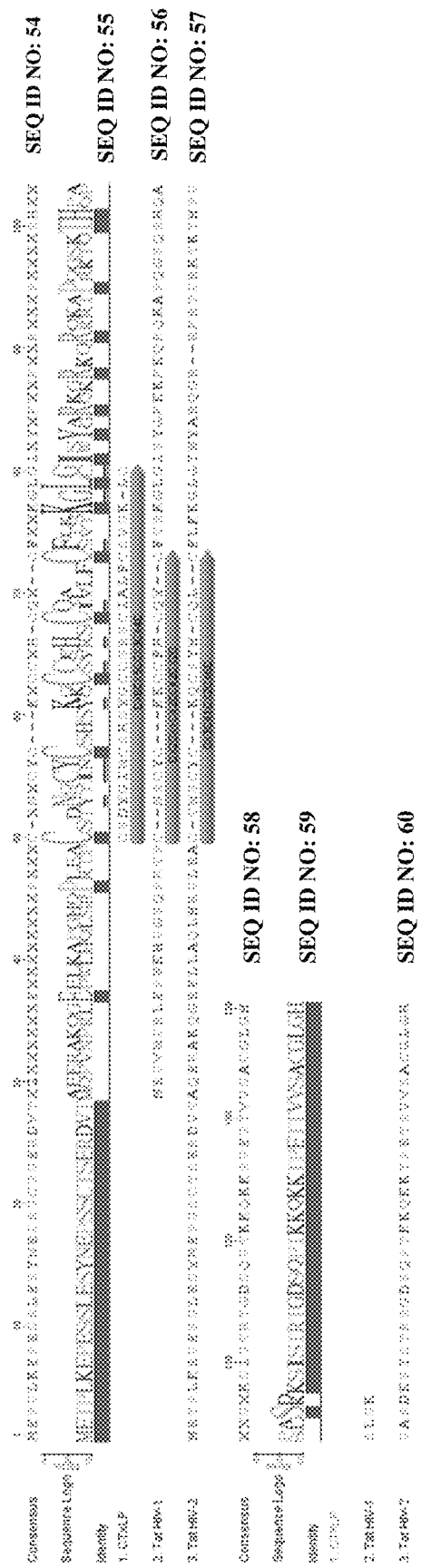
FIG. 14 depicts alignment and sequence logo of ERVK CTXLP cysteine-rich peptide and HIV-1 and HIV-2 Tat proteins. Sequences were aligned and sequence logo generated using Geneious Software. Conservation of 6 of the 7 CTXLP cysteine residues are found in HIV Tat, as well as 1 lysine and 1 leucine residue in the C terminus, between amino acids 75 and 80.

When ERVK CTXLP was aligned to the retroviral accessory protein Tat from HIV-1 and HIV-2, some degree of similarity was detected (identity 19.4% and 16.1%, respectively) (FIG. 14). Tat (HIV-1 and HIV-2) contains a conserved C-C-CC-C-C motif that has a much tighter spacing than ERVK CTXLP. In contrast to HIV-1 Tat and CTXLP, HIV-2 Tat did not contain a central "CC" pair of cysteine residues. ERVK CTXLP was also aligned with Tax proteins from HTLV-1, HTLV-2, and HTLV-3 along with envelope from HTLV-4 and envelope from Jaagsiekte retrovirus, and no homology was detected (data not shown). The conservation of a cysteine motif and central "CC" cysteine pair in HIV-1 Tat and CTXLP is a potential basis for conserved structure and function of these viral proteins.

Aligning ERVK CTXLP to several cysteine-rich peptides provided insight into the potential function of the CTXLP protein domain. ERVK CTXLP showed the greatest simi-

TABLE 2

Spider toxins, host species and target receptors show similarity and conserved motifs with ERVK CTXLP.

| Toxin | Species | Target Receptors | Identity with CTXLP (%) | Conserved Amino Acid Motifs |
|---|---|---|---|---|
| Grammotoxin | Grammostola spatulata | P/Q, N-type VGCC | 16.7 | G (56), S (59), SK(73) |
| Huwentoxin-I | Selenocosmia huwena | Presynaptic N-type VGCC | 12.5 | D (56), K (76) |
| Huwentoxin-X | Selenocosmia huwena | N-type VGCC (Dorsal Root Ganglion) | 10.3 | G (55), K (77) |
| Hainantoxin-I | Selenocosmia hainana | Voltage Gated Sodium Channel | 26.5 | G (55), K (78) |
| Hainantoxin-III | Selenocosmia hainana | Neuronal tetrodotoxin-sensitive Voltage Gated Sodium Channel | 23.5 | G (55), K (78), SK (75) |
| Hainantoxin-IV | Selenocosmia hainana | Voltage Gated Sodium Channel | 25.8 | G (55), S (61), S (68) |
| Hainantoxin-V | Selenocosmia hainana | Voltage Gated Sodium Channel | 23.5 | G(55), S (61) |
| Guanxitoxin-I | Plesiophrictus guangxiensis | Voltage Gated Potassium Channel (Kv2.1 subtype) | 17.1 | None |
| Guanxitoxin-II | Plesiophrictus guangxiensis | Voltage Gated Potassium Channels | 17.1 | None |
| Hanatoxin-I | Grammostola rosea | Voltage Gated Potassium Channel (Kv2.1 subtype) | 16.7 | K (78) |
| Hanatoxin-II | Grammostola rosea | Voltage Gated Potassium Channels | 16.7 | K (78) |
| Sgtx-I | Scodra griseipes | Voltage Gated Potassium Channel (Kv2.1 subtype) | 13.9 | K (78) |

When ERVK CTXLP peptide was aligned to the human ICK proteins agouti-signalling protein (ASIP) and agouti-related peptide (AGRP), significant similarity was found in the conserved cysteine domain (both with a pairwise identity larity to ICK peptides. The cysteine knot motif was conserved in all of the spider toxins examined, and Hainantoxin-I showed the greatest similarity to CTXLP with an identity of 26.5%, suggesting similarity in function (NCBI).

All other amino acid residues were highly variable, suggesting that the conservation of the cysteine residues and the tertiary structure are more important for peptide function rather than the primary amino acid sequence. The spider toxins function as antagonists to voltage gated ion channels, suggesting CTXLP may have a similar function[18]. Hainantoxin-I is a voltage-gated sodium channel inhibitor[34]; thus, CTXLP may function as a voltage-gated sodium channel inhibitor. Although the ERVK CTXLP had significant similarity to Hainantoxin-I, ERVK CTXLP still had the greatest similarity (25.9-33.3%) to the cone snail ω-conotoxins, suggesting CTXLP functions as a VGCC inhibitor. Previous studies have also shown that ω-conotoxin's amino acid residues threonine 11, tyrosine 13, lysine 2, lysine 4, and arginine 22 are important for calcium channel receptor binding[35]. CTXLP has some similar conserved residues including a tyrosine in position 12 and an arginine in position 17. CTXLP may alternatively utilize different amino acid residues to bind to cognate VGCC targets.

ERVK CTXLP also showed significant identity to the human agouti-family proteins, specifically ASIP and AGRP peptides. ASIP and AGRP are mammalian ICK peptides that both function as antagonists to melanocortin receptors 1, 3 and 4 (MC1R, MC3R, and MC4R)[36]. ASIP is produced in the skin to promote pigment production, while AGRP is involved in metabolism[36]. The agouti-family of peptides contains a unique ICK pattern[33]. CTXLP is only capable of forming 3 of the 4 cysteine bridges identified in agouti, suggesting that CTXLP takes on the basic ICK fold. The similarity between ERVK CTXLP to the agouti family of peptides provides further support for CTXLP's structure as an ICK peptide, along with first evidence for the presence of viral ICK peptides in humans.

Vascular endothelial growth factors (VEGFs) contain a growth factor cysteine knot motif, and are signalling molecules involved in angiogenesis[19]. ERVK CTXLP did not show significant similarity (≤7.7%) to the VEGF proteins. A dissimilar cysteine motif with a different spacing of cysteine residues and a significant difference in overall protein size (12-47 kDa for VEGF versus 32 and 51 kDa for CTXLP), suggests that ERVK CTXLP does not function in a growth factor or cytokine manner[19]. CTXLP's similarity to the ICK peptides and dissimilarity to VEGF suggests that ERVK CTXLP likely functions as a receptor antagonist via an ICK motif.

Cysteine-rich peptides have also been identified in exogenous retroviruses. ERVK CTXLP has some sequence similarity with the Tat accessory protein of HIV-1 and HIV-2. Although Tat is not an ICK peptide and has a slightly different cysteine spacing pattern to ERVK CTXLP, a similar cysteine rich motif was identified in both proteins (19.6%). The cysteine-rich motif of Tat endows this protein with neurotoxic properties[37]. Tat expression in the brains of HIV-1 infected patients has been associated with neuronal apoptosis via caspase activation and calcium accumulation[38]. The structural similarities between Tat and ERVK CTXLP may suggest that they both use similar mechanisms for pathogenicity. HIV-2 is known to be a less pathogenic than HIV-1[39]. A partial explanation to this decreased pathogenicity may lie in the structural differences between their respective Tat proteins. HIV-2 Tat has a deletion of one cysteine, losing the "CC" motif. Interestingly, all ERVK CTXLP domains examined contained a "CC" motif. The mechanisms surrounding HIV Tat neurotoxicity are diverse and manifold[38,40,41], suggesting that substantial research may be required to address potential ERVK CTXLP cellular toxicity in the CNS. The cysteine motif in HIV Tat has also been associated with increased HIV transactivation, by translocating to the nucleus and interacting with transcriptional machinery[38]. HIV Tat can also transactivate ERVK[42]. Thus, the multiple functions of HIV-1 and HIV-2 Tat suggest that CTXLP's conserved cysteine motif may also contribute to neurotoxicity and retroviral transcription. Other retroviral proteins examined (HTLV Tax) did not show any homology to ERVK CTXLP, suggesting that this pathogenic mechanism is not conserved among all retroviruses.

Identification of CTXLP-Encoding ERVK Loci in the Human Genome

Figure 15:
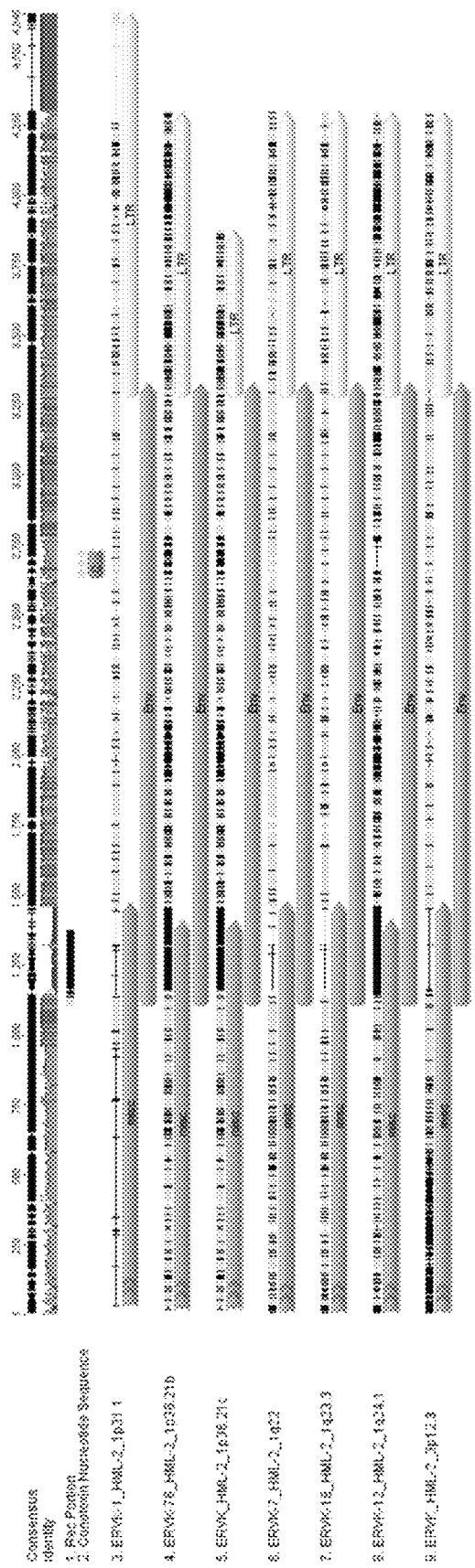
FIG. 15 depicts example Alignment of Chromosome 1 ERVK HML-2 insertions with the DNA sequences for Rec exon 1 and CTXLP. Sequences were aligned and sequence logo generated using Geneious software. Rec exon 1 aligned with bp 1 to 261 of env. CTXLP aligned with bp 1413 to 1505 of env.

Nomenclature for each ERVK loci is based on their common names, as well as their chromosome location. Geneious was used to align both ERVK rec exon 1 and the predicted CTXLP DNA sequence with 95 ERVK HML-2 insertions identified in the human genome. After the ERVK insertions were aligned, many insertions (33) were excluded from further analysis due to the absence of an intact env. The ERVK insertions with an intact env were then aligned to both the rec gene and CTXLP cysteine motif nucleotide sequences. FIG. 15 shows an example of the rec exon 1 and CTXLP nucleotide alignments against intact ERVK envelope genes. The CTXLP sequence was found at bp 1413 of env, just at the 3' end of the coding region for the envelope SU protein. This location is the cleavage site of the envelope polyprotein, where there is a junction between the SU and TM proteins. The aligned nucleotide sequences were then translated into an amino acid sequence and examined for intact Rec and CTXLP coding sequences. Table 3 shows that there are 25 ERVK insertions (out of the 62 examined) capable of producing a CTXLP protein, with 5 proviruses also capable of producing Rec.

TABLE 3

Sixty-two ERVK HML-2 human insertions and their chromosomal location examined for an intact Rec and Intact CTXLP ORF along with any known disease associations with Multiple Sclerosis, Cancer or Schizophrenia.

| Accession number | Genomic location | ERVK insertion | Intact Rec? | Intact Conotoxin? |
|---|---|---|---|---|
| JN675007 | 1p31.1 | ERVK-1$^a$__HML-2__1p31.1__75842771 | No | Yes |
| JN675010 | 1p36.21b | ERVK-76$^b$__HML-2__1p36.21b__13458305 | No | No |
| JN675011 | 1p36.21c | ERVK-76$^b$__HML-2__1p36.21c__13678850 | No | No |
| JN675013 | 1q23.3 | ERVK-18$^a$__HML-2__1q23.3__160660575 | No | Yes |
| JN675014 | 1q22 | ERVK-7$^a$__HML-2__1q22__155596457 | No | Yes |
| JN675015 | 1q24.1 | ERVK-12$^b$__HML-2__1q24.1__166574603 | No | No |
| JN675016 | 1q32.2 | ERVK__HML-2__1q32.2__207808457 | No | No |
| JN675018 | 2q21.1 | ERVK__HML-2__2q21.1__130719538 | No | Yes |
| JN675019 | 3p12.3 | ERVK__HML-2__3p12.3__75600465 | No | No |
| JN675020 | 3p25.3 | ERVK-2$^{a,b}$__HML-2__3p25.3__9889346 | No | No |

TABLE 3-continued

Sixty-two ERVK HML-2 human insertions and their chromosomal location examined for an intact Rec and Intact CTXLP ORF along with any known disease associations with Multiple Sclerosis, Cancer or Schizophrenia.

| Accession number | Genomic location | ERVK insertion | Intact Rec? | Intact Conotoxin? |
|---|---|---|---|---|
| JN675021 | 3q12.3 | ERVK-5[a]_HML-2_3q12.3_ 101410737 | No | Yes |
| JN675022 | 3q13.2 | ERVK-3[a]_HML-2_3q13.2_112743479 | No | Yes |
| JN675023 | 3q21.2 | ERVK-4[a]_HML-2_3q21.2_ 125609302 | No | Yes |
| JN675025 | 3q27.2 | ERVK-11[a]_HML-2_3q27.2_185280336 | No | Yes |
| JN675026 | 4p16.1a | ERVK-17[b]_HML-2_4p16.1a_9123515 | No | No |
| JN675027 | 4p16.1b | ERVK-50c[b]_HML-2_4p16.1b_9659588 | No | No |
| JN675029 | 4p16.3b | ERVK-7[b]_HML-2_4p16.3b_3980069 | No | No |
| JN675030 | 4q13.2 | ERVK_HML-2_4q13.2_463709 | No | No |
| JN675032 | 4q32.3 | ERVK-13[a]_HML-2_4q32.3_5916840 | No | No |
| JN675034 | 5p12 | ERVK_HML-2_5p12_46000159 | No | No |
| JN675035 | 5p13.3 | ERVK-104[b]_HML-2_5p13.3_30487114 | No | Yes |
| JN675036 | 5q33.2 | ERVK-18b[b]_HML-2_5q33.2_154016502 | No | No |
| JN675037 | 5q33.3 | ERVK-10[a]_HML-2_5q33.3_156084717 | No | Yes |
| JN675039 | 6p21.1 | ERVK-OLD35587[b].HML-2_6p22.1_42861409 | No | No |
| JN675040 | 6p22.1 | ERVK-69.HML-2.6p22.128650367 | No | No |
| JN675041 | 6q14.1 | ERVK-9[a]_HML-2_6q14.1_78427019 | Yes | Yes |
| JN675043 | 7p22.1a | ERVK-14[a]_HML-2_4622057 | Yes | Yes |
| JN675044 | 7p22.1b | ERVK-14[a]_HML-2_4630561 | Yes | Yes |
| JN675049 | 8p23.1a | ERVK-8[a]_HML-2_8p23.1a_7355397 | No | Yes |
| JN675050 | 8p23.1b | ERVK-27[b]_HML-2_8p23.1b_8054700 | No | No |
| JN675051 | 8p23.1c | ERVK_HML-2_8p23.1_12073970 | No | No |
| JN675052 | 8p23.1d | ERVKOLD130352[b]_HML-2.8p23.1d_12316492 1 | No | No |
| JN675053 | 8q11.1 | ERVK-70[b]_HML-2_8q11.1_47175650 | No | No |
| JN675057 | 9q34.11 | ERVK-31[b]_HML-2_9q34.11_131612515 | No | No |
| JN675058 | 10p12.1 | ERVK-103[b]_HML-2_10p12.1_27182399 | No | Yes |
| JN675059 | 10p14 | ERVK-16[a]_HML-2_10p14_6867109 | No | No |
| JN675060 | 10q24.2 | ERVK-17[a]_HML-2_10q24.2_101580569 | No | No |
| JN675061 | 11p15.4 | ERVK3-4[a]_HML-2_11p15.4_ 3468656 | No | No |
| JN675062 | 11q12.1 | ERVK_HML-2_11q12.1.58767448 | No | No |
| JN675063 | 11q12.3 | ERVK-OLDAC004127[b]_HML-2_11q12.3_ 62135963 | No | No |
| JN675064 | 11q22.1 | ERVK-25[a]_HML-2_11q22.1_ 101565794 | Yes | Yes |
| JN675065 | 11q23.3 | ERVK-20[a]_HML-2_ 11q23.3_118591724 | No | Yes |
| JN675066 | 12p11.1 | ERVK-50E[b]_HML-2_12p11.1.34772555 | No | No |
| JN675067 | 12q13.2 | ERVK_HML-2_12q13.2_ 55727215 | No | Yes |
| JN675068 | 12q14.1 | ERVK-21[b]_HML-2_12q14.1_ 58721242 | No | Yes |
| JN675073 | 15q25.2 | ERVK_HML-2_15q25.2_84829020 | No | No |
| JN675074 | 16p11.2 | ERVK_HML-2_16p11.2_ 34231474 | No | Yes |
| JN675075 | 17p13.1 | ERVK_HML-2_17p13.1_7960357 | No | No |
| JN675076 | 19p12a | ERVK52[b]_HML-2_ 19p12a 20387400 | No | No |
| JN675077 | 19p12b | ERVK113[b]_HML-2_19p12b_21841536 | Yes | Yes |
| JN675078 | 19p12c | ERVK51[b]_HML-2_19p12c_22757824 | No | Yes |
| JN675080 | 19q11 | ERVK-19[b]_HML-2_19q11_228128498 | Yes | No |
| JN675081 | 19q13.12a | ERVK_HML-2_19q13.12a_36063207 | No | No |
| JN675082 | 19q13.12b | ERVKOLD12309_HML-2_19q13.12b_37597549 | No | No |
| JN675083 | 19q13.41 | ERVK3-6[a]_HML-2_19q13.41_53248274 | No | No |
| JN675084 | 19q13.42 | LTR13[b]_HML-2_19q13.42_53862348 | No | No |
| JN675085 | 20q11.22 | ERVK59[b]_HML-2_20q11.22_32714750 | No | Yes |
| JN675086 | 21q21.1 | ERVK-23[a]_HML-2_21q21.1_19933916 | No | Yes |
| JN675087 | 22q11.21 | ERVK-24[a]_HML-2_22q11.21_18926187 | No | Yes |
| JN675088 | 22q11.23 | ERVK-KOLD345b_HML-2_22q11.23_23879930 | No | No |
| JN675090 | Xq11.1 | ERVK_HML-2_Xq11.1_61959549 | No | No |
| JN675094 | Yp11.2 | ERVK_HML-2_ Yp11.2_6 826441 | No | No |

Disease associations: MS (yellow,) MS (No CTXLP; pale yellow). Cancer (Green), Cancer (No CTXLP; dark green), Schizophrenia (blue).
[a]Mayer, J., Blomberg, J., & Seal, R. L. (2011). A revised nomenclature for transcribed human endogenous retroviral loci. Mobile DNA, 2(1), 7.
[b]Subramanian, R. P., Wildschutte, J. H., Russo, C., & Coffin, J. M. (2011). Identification, characterization, and comparative genomic distribution of the HERV-K (HML-2) group of human endogenous retroviruses. Retrovirology, 8(1), 90.

Of the 95 ERVK DNA sequences, 33 were excluded due to an incomplete env sequence. The remaining 62 sequences were then translated and examined for an intact CTXLP in the appropriate reading frame. The resulting CTXLP peptide sequences were aligned and a sequence logo and consensus sequence were generated to assess amino acid conservation and detect polymorphisms (FIG. 16).

In total, 25 ERVK insertions containing the CTXLP cysteine motif were analysed for overall conservation of the peptide sequence and to identify specific variants. FIG. 16 shows that although each CTXLP peptide has a nearly identical amino acid sequence (identity 95.6%), there are distinct CTXLP polymorphisms identified.

Ten distinct CTXLP polymorphisms were detected. The most prevalent polymorphism is found in ERVK-3, ERVK-104, ERVK-10, ERVK-9, ERVK-14, ERVK-14(b), ERVK-8, ERVK-103, ERVK-25, ERVK-7, ERVK-21, ERVK-16p11.2, and ERVK-113 (Allele 1). The second most prevalent substitutes glycine for serine, relative to the consensus, at two alignment positions (Ser16Gly, Ser27Gly) and is found in ERVK-5 and ERVK-20 (Allele 2). ERVK-HML-2_2q21.2 differs only at the latter Serine (Ser27Gly).

ERVK-18 differs only at the former Serine (Ser16Gly). ERVK-51 has the former variation as well as a valine in position 20 (Ser16Gly, Ile20Val). ERVK-1 has phenylalanine at position 22 (Leu22Phe). ERVK-4 contains arginine at position 5 (Gly5Arg). ERVK-HML-2_12q13.2 contained an asparagine at position 16 (Ser16Asn). ERVK-23 shows three polymorphisms at positions 5, 17, and 27 (Gly5Arg, Arg17Lys, Val26Glu). The prevalence and polymorphic variability of ERVK CTXLP-encoding insertions suggests that CTXLP is a pervasive and conserved ERVK protein.

Out of the identified CTXLP encoding proviruses, 20 of 25 ERVK insertions were human-specific[43]. ERVK-18, ERVK-5, ERVK-69, ERVK-20, ERVK-HML-2_16p21, and ERVK-51 are found in other primates including orangutan, chimpanzee, and rhesus monkey, demonstrating that ERVK CTXLP is an evolutionarily conserved protein, which either entered the genome of a common primate ancestor or through cross-species infection with a specific CTXLP-encoding ERVK virus[16] (See FIG. 59 below in "primate models" section). The evolutionary age and clade of ERVK retroviruses that encode CTXLP suggests that CTXLP is unique to primates[43,44], and that the human genome has an enrichment of this type of ERVK proviruses.

A re-analysis of CTXLP variants in the human genome using a different methodology resulted in similar conclusion regarding the polymorphic nature of CTXLP+ ERVK genomes (FIG. 17).

ERVK CTXLP Domain and Disease Associations

CTXLP was identified in both type 1 and type 2 ERVK (FIG. 1). The prevalence of CTXLP in both types of ERVK suggests that CTXLP originated early on in ERVK evolution, being present before the divergence of ERVK A env genomes[45]. Select CTXLP+ loci had known disease associations (Table 3). Out of the 25 CTXLP-encoding ERVK insertions examined, no insertions were associated with ALS—most likely due to a lack of research on this topic. Two of the 25 insertions (ERVK-18 and ERVK-10) were associated with the psychiatric condition schizophrenia. Two out of 3 insertions associated with MS contained CTXLP-encoding insertions. ERVK expression has previously been associated with neurological disease[6], suggesting that CTXLP may be one mechanism for neurotoxicity. Surprisingly, 9 CTXLP-encoding insertions were associated with cancer. ERVK env expression has previously been identified in several cancers[46]. As we demonstrate below (see "CTXLP and disease" section, FIGS. 25, 36, 43 and 44), there is a notable association between CTXLP and cancer, suggesting that currently identified (Table 3) and other CTXLP-encoding loci with no known disease association may serve as future biomarkers for cancer. The different polymorphisms of CTXLP identified did not associate with any specific disease conditions. Any effects these polymorphisms have on CTXLP function remains unknown.

Identification of ERVK CTXLP—An Alternate Form of the ERVK Envelope Protein

Predicted Full ERVK CTXLP Protein Sequence

The results of both the Pfam and NCBI-CDD databases indicated that the predicted CTXLP amino acid sequence (used to produce the CTXLP plasmids described below) shares similarities with both ERVK Rec, an oncogenic alternate splice product of the env gene, and ERVK Env. These results support the prediction that CTXLP is partially composed of the SU unit of the Env glycoprotein. The NCBI-CDD database also indicated the presence of a surface glycoprotein signal peptide domain. Lastly, the C-terminal portion of the CTXLP sequence was found to share similarities with the O-conotoxin superfamily, which ω-conotoxins are a part of. Lastly, the DUF4408 domain corresponds to a domain of unknown function which is primarily found in plants. Together, these results suggest that CTXLP is composed of the ERVK Env SU unit with a C-terminal ω-conotoxin domain (FIG. 18).

Programmed Frameshifting and Internal Ribosomal Entry Site

Since the reading frames of ERVK env (frame +1) and CTXLP (frame +3) differed by −1, the ERVK env transcript (FIG. 19) was examined for evidence of −1 programmed ribosomal frameshifting (-1 PRF), using ERVK-1, ERVK-18, ERVK-7, ERVK_HML-2_2q21.1, ERVK-5, ERVK-3, ERVK-4, ERKV-104, and ERVK-10 insertions.

RNAfold Analysis of RNA Structures in the ERVK Env Transcript

Our biomedical experiments suggested that there were CTXLP isoforms of different sizes, therefore we examined whether the conventional and alternative methionine start sites could be used to make both long and short CTXLP proteins. The first 350 bp of the ERVK Env-encoding RNA was inserted into RNAfold software to predict RNA secondary structure (iltrna.tbi.univie.ac.at/cgi-bin/RNAfold.cgi). FIG. 19B suggests that the CTLXP proteins can originate from the conventional Env methionine start or potentially use IRES-like RNA hairpins to initiate translation at a downstream methionine.

This alternative mechanism for CTXLP expression is the use of internal ribosomal entry site (IRES), using an alternative translational start site (FIG. 19B). The 51 and 32 kDa isoforms of CTXLP likely form using the start of the env ORF (nucleotide position 1) or an IRES in the env reading frame, starting from one of its many methionine start codons (specifically amino acid position 200). Translating env from alternative start codons would result in different sized isoforms of CTXLP. Certain viruses, including HIV, use IRES to allow for mRNA translation to begin in the middle of the transcript[48,49]. The mRNA forms a hairpin structure that allows the binding of the 40S RNA subunit followed by protein translation[50]. Using RNAfold software to predict mRNA secondary structure upstream of CTXLP, an RNA fold structure similar to HIV IRES was predicted (nucleotide 84 to 187, and 213 to 318 in env transcript), that could take advantage of alternate methionine start codon.

ERVK env nucleotide sequences were also inserted into RNAfold starting from 150 base pairs upstream of the CTXLP ORF to predict RNA secondary structure. RNA secondary structure was examined for evidence of -1 programmed ribosomal frameshifting motifs, including a slippery site with the X-XXY-YYZ form, a 5-10 nucleotide spacer and a downstream pseudoknot or hairpin structure (FIG. 19C). The 1-350 bp region of the ERVK env gene was also examined for RNA secondary structure motifs, as it contains numerous alternative methionine start sites. RNA secondary structure was then examined for potential internal ribosomal entry site (IRES) binding sites, which take the form of complex RNA hairpins4[8.] The likelihood that these ERVK RNA secondary structures represent an IRES was determined using IRES prediction software called IRESite {http://iresite.org/IRESite_web.php), and reported as a similarity with known cellular and viral IRES 2D structures.

PRF can occur when three elements are combined: i) a slippery site containing an X-XXY-YYZ motif which after frameshifting by -1 results in XXX-YYY reading, ii) a 5 to 10 nucleotide spacer sequence, and iii) a downstream hairpin-type pseudoknot. ERVK CTXLP-encoding insertions contained an appropriate U-UUA-AAU slippery site to allow for −1 frameshifting to UUU-AAA. After the slippery site there was a 5 nucleotide spacer sequence before the CTXLP ORF. All sequences examined showed a strong probability of forming a hairpin-type pseudoknot within the RNA sequence encoding the CTXLP cysteine-rich motif (FIG. 19C). Paradoxically, if the envelope protein translates past the CTXLP ORF start and frameshifts by −4, this introduces a conserved KRQK nuclear localization sequence (NLS) into the hypothetical protein (FIG. 20). Another transcription factor that contains a KRQK NLS is NE-κB p50[51]. There are no other known NLS in either the ERVK envelope protein or the predicted ERVK CTXLP proteins.

If CTXLP encoding originates from the conventional start site in the env transcript, followed by a −1 PRF then it may produce a 51 kDa CTXLP protein. Alternatively, if CTXLP encoding originates from an IRES site using an alternate methionine in the env transcript (FIG. 20), followed by a −1 PRF then it may produce a 32 kDa CTXLP protein. The insertions that showed the highest probability of forming a potential IRES binding site upstream of the CTXLP ORF were ERVK-113 and ERVK-4. These sequences analysed by IRESite software predict that the IRES-like RNA hairpins most resemble those found in HIV, Theiler's Murine Encephalomyelitis Virus (TMEV), and Hepatitis C virus (HCV).

Figure 28:
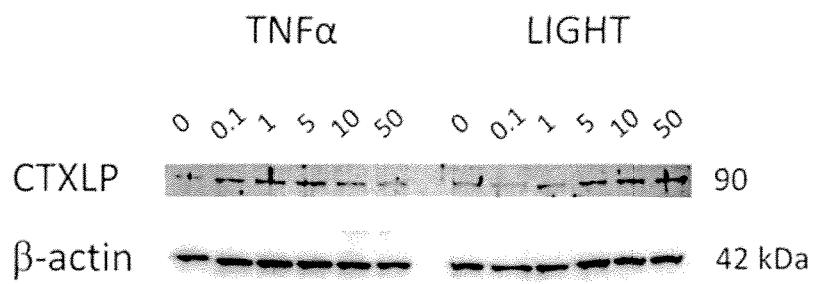
FIG. 28 depicts ERVK CTXLP is inducible in human neurons. ReNcell-derived neurons were treated with increasing doses of pro-inflammatory cytokines TNFα or LIGHT for 24 hours. CTXLP expression (90 kDa form) was enhanced optimally with 1 ng/ml TNFα and 10 ng/ml LIGHT treatment, n=1.

We had previously hypothesized that ERVK CTXLP be produced via alternative splicing of the Rec transcript. Although alternative splicing is a common mechanism in retroviruses, only 4 of 25 CTXLP-encoding insertions also had intact Rec protein. The prevalence of CTXLP-encoding insertions in the absence of Rec suggests that alternative splicing is not the mechanism of CTXLP formation. Upstream and downstream of the CTXLP ORF are several stop codons. One mechanism that retroviruses use to compensate for stop codons or a lack of methionine starts is called programmed minus-one ribosomal frameshifting[52]. This involves the formation of an H-type pseudoknot in the RNA transcript at the site of frameshifting. The H-type pseudoknot would likely halt the ribosome from continuing translation, leading to the −1 PRF[52]. The slippery site UUU-AAA-U would re-establish ribosomal tRNA and mRNA base pairing and allow for the continuation of translation after frameshifting[52]. We predict that this mechanism could be used to extend the ORF of the ERVK SU protein by adding on a C-terminal CTXLP domain (FIGS. 19 & 20). Although the predicted structural stability of the ERVK env RNA H-type pseudoknot (FIG. 18) was stronger in some ERVK insertions than others, the presence of this RNA secondary structure was conserved in all sequences examined using RNAfold. To our knowledge, frameshifting under conditions of inflammation has not been previously described. Enhanced frameshifting due to inflammation may be a unique mechanism in retroviruses, particularly upon exposure to TNFα (FIGS. 27 and 28).

Together, this data suggests that ERVK CTXLP is likely expressed as a cryptic peptide through frameshifted translation of the env transcript (FIGS. 19 & 20). Alternative forms of viral env proteins (CTXLP proteins may be considered isoforms of env) may be translated under specific physiological conditions[53,54]. When ERVK env is translated in this proposed alternative ORF, the CTXLP peptide would be expressed within the translated env as a cryptic peptide. Cryptic peptides are proposed to have significantly different functions than their precursor protein[55]. Cryptic epitopes within modified HIV proteins have been shown to be immunogenic[56,57].

Therefore, ERVK CTXLP is likely formed from a −4 PRF occurring slightly upstream of the furin cleavage site in env. An IRES sequence likely allows for a shorter ERVK CTXLP protein isoform to be produced, explaining the distinct isoforms of CTXLP identified.

Prediction of Post-Translational Modifications for CTXLP

ERVK CTXLP is predicted to have the following post-translational modifications, including, but not limited to phosphorylation, SUMOylation, glycosylation and lipid addition (FIGS. 20 & 21, Tables 4-8) using ELM software[47] and other resources.

TABLE 4

Predicted phosphorylation sites within ERVK CTXLP protein

| Kinase | Predicted phosphorylation sites | ELM | NetPhos3.1 | Motif Scan |
|---|---|---|---|---|
| CDC2 | 41 | | ● | |
| | 213 | | ● | |
| | 279 | | ● | |
| | 281 | | ● | |
| | 321 | | ● | |
| | 374 | | ● | |
| | 376 | | ● | |
| | 417 | | ● | |
| | 438 | | ● | |
| | 475 | | ● | |
| | 482 | | ● | |
| CDK | 184-191 | ● | | |
| CDK5 | 72 | | ● | |
| | 187 | | ● | |
| | 288 | | ● | |
| | 329 | | ● | |
| CK1 | 187-193 | ● | | |
| | 190-196 | ● | ● | |
| | 198-204 | ● | | |
| | 235-241 | ● | | |
| | 276-282 | ● | | |
| | 281-287 | ● | | |
| | 293-299 | ● | | |
| | 329-335 | ● | | |
| | 373-379 | ● | | |
| CK2 | 32-35 | ● | ● | ● |
| | 116-119 | | | ● |
| | 260-263 | | | ● |
| | 293 | | ● | ● |
| | 331-334 | ● | ● | ● |
| | 411-414 | | | ● |
| DNAPK | 298 | | ● | |
| | 374 | | ● | |
| | 400 | | ● | |
| EGFR | 272 | | ● | |
| GSK3 | 54-61 | ● | | |
| | 82-89 | ● | | |
| | 210-217 | ● | | |
| | 281-288 | ● | | |
| | 350-357 | ● | | |
| | 397-404 | ● | | |
| | 409-416 | ● | | |
| INSR | 160 | | ● | |
| LATS | 304-310 | ● | | |
| MAPK/PDK | 69-75 | ● | | |
| | 184-190 | ● | | |
| | 285-291 | ● | | |
| | 326-332 | ● | | |
| | 443-349 | ● | | |
| NEK2 | 64-69 | ● | | |
| | 82-87 | ● | | |
| | 86-91 | ● | | |
| | 371-376 | ● | | |
| | 460-465 | ● | | |
| | 495-500 | ● | | |

TABLE 4-continued

Predicted phosphorylation sites within ERVK CTXLP protein

| Kinase | Predicted phosphorylation sites | ELM | NetPhos3.1 | Motif Scan |
|---|---|---|---|---|
| PIKK | 54-60 | ● | | |
| | 67-79 | ● | | |
| | 276-282 | ● | | |
| | 397-403 | ● | | |
| PKA | 54-60 | ● | | |
| | 155 | | ● | |
| | 190-196 | ● | | |
| | 250 | | ● | |
| | 340-346 | ● | | |
| | 353 | | ● | |
| | 491 | | ● | |
| PKC | 24-26 | | ● | ● |
| | 41-43 | | ● | ● |
| | 57 | | ● | |
| | 117 | | ● | |
| | 193 | | ● | |
| | 200-203 | | ● | ● |
| | 216-218 | | ● | ● |
| | 279 | | ● | |
| | 281 | | ● | |
| | 298 | | ● | |
| | 309 | | ● | |
| | 321-324 | | ● | ● |
| | 343 | | ● | |
| | 360 | | ● | |
| | 376 | | ● | |
| | 381 | | ● | |
| | 412 | | ● | |
| | 417 | | ● | |
| | 462-464 | | ● | ● |
| PLK | 414-420 | ● | | |
| p38 MAPK | 72 | | ● | |
| | 187 | | ● | |
| | 329 | | ● | |

TABLE 5

Predicted SUMOylation and SUMO interaction sites within ERVK CTXLP protein

| | ELM | GPS-SUMO |
|---|---|---|
| Predicted SUMOylation sites | | |
| 143-146 | ● | ● |
| 397 | | ● |
| Predicted SUMO interaction sites | | |
| 123-127 | | ● |
| 180-184 | ● | ● |
| 367-374 | ● | |
| 424-428 | | ● |

TABLE 6

Predicted glycosylation sites within ERVK CTXLP protein

| Sugar attachment | Predicted glycosylation sites | ELM | Netglyc4.0 | Motif Scan |
|---|---|---|---|---|
| Fucose | 275-282 | ● | | |
| | 408-413 | ● | | |
| | 487-492 | ● | | |
| Glycosaminoglycan | 197-200 | ● | | |
| | 249-252 | ● | | |
| | 275-278 | ● | | |
| | 283-286 | ● | | |

TABLE 6-continued

Predicted glycosylation sites within ERVK CTXLP protein

| Sugar attachment | Predicted glycosylation sites | ELM | Netglyc4.0 | Motif Scan |
|---|---|---|---|---|
| | 331-334 | ● | | |
| | 352-355 | ● | | |
| N-glycosylation | 99-102 | ● | ● | |
| | 127-130 | ● | ● | |
| | 152-155 | ● | ● | |
| | 273-276 | ● | ● | |
| | 354-357 | ● | ● | |
| | 371-374 | ● | ● | |
| | 460-463 | ● | ● | |
| | 472-475 | ● | ● | |
| | 479-482 | ● | ● | |
| O-glycosylation | 213 | | | ● |
| | 217 | | | ● |
| | 235 | | | ● |
| | 284 | | | ● |
| | 288 | | | ● |
| | 321 | | | ● |

TABLE 7

Predicted lipid attachment sites within ERVK CTXLP protein

| Lipid attachment | Predicted lipid addition sites | CSS-Palm | GPS-Lipid |
|---|---|---|---|
| S-Farnesylation | 497 | | ● |
| | 503 | | ● |
| S-Geranylgeranylation | 503 | | ● |
| S-palmitoylation | 140 | ● | |
| | 141 | ● | |
| | 227 | | ● |
| | 275 | | ● |
| | 382 | ● | |
| | 408 | | ● |
| | 487 | ● | ● |
| | 488 | | ● |

The N-linked glycosylation of ERVK CTXLP has been verified experimentally using PNGase treatment of CTXLP protein fractions, followed by western blot analysis for shifts in high molecular weight protein banding patterns (FIG. 26, n=3). Phosphorylation is postulated to occur to ERVK CTXLP when bound to chromatin, as seen in the 32 kDa band shift in FIG. 30.

Moreover, bioinformatic predictions also predicted protein cleavage and interaction sites within CTXLP (Table 8) using the PROSPER website (https://prosper.erc.monash.edu.au/home.html). Among the proteins predicted to cleave CTXLP were HIV protease, furin, NEC1, and NEC2. The predicted furin cleavage site is consistent with the location of the known furin cleavage site that typically cleaves the Env polyprotein into discrete SU and TM peptide chains that are then assembled into multimer proteins. However, it is unclear how an overlapping NRS N-linked glycosylation site would impact the ability of furin the cleave the site. As well, the predicted cleavage by HIV protease is interesting as ERVK interactions with HIV proteins have been previously reported[42,58,59]. Of note, cleavage predictions only take into account primary amino acid sequence only, and do not account for how viral protein tertiary structure and cellular factors come into play.

TABLE 8

Predicted protease cleavage sites within CTXLP, as predicted by PROSPER.

| Merops ID | Protease Name | Position | P4-P4' site | N-fragment (kDa) | C-fragment (kDa) | Cleavage score |
|---|---|---|---|---|---|---|
| A02.001 | HIV-1 retropepsin | SEQ ID NO: 139 | 130 TEVL\|WEEC | 15.57 | 30.67 | 1.24 |
| A02.001 | HIV-1 retropepsin | SEQ ID NO: 140 | 348 KGVL\|IQKI | 41.54 | 4.69 | 1.05

TABLE 8-continued

Predicted protease cleavage sites within CTXLP, as predicted by PROSPER.

| Merops ID | Protease Name | | Position | P4-P4' site | N-fragment (kDa) | C-fragment (kDa) | Cleavage score |
|---|---|---|---|---|---|---|---|
| M10.004 | matrix metallopeptidase-9 | SEQ ID NO: 169 | 138 | VANS\|VVIL | 16.48 | 29.75 | 1.08 |
| M10.004 | matrix metallopeptidase-9 | SEQ ID NO: 170 | 275 | KPPY\|MLW | 32.89 | 13.34 | 1.08 |
| M10.004 | matrix metallopeptidase-9 | SEQ ID NO: 171 | 182 | VDSD\|LTES | 21.59 | 24.64 | 1.07 |
| M10.004 | matrix metallopeptidase-9 | SEQ ID NO: 172 | 38 | EEEG\|MMIN | 4.48 | 41.75 | 1.06 |
| M10.004 | matrix metallopeptidase-9 | SEQ ID NO: 173 | 339 | SIHI\|LTEI | 40.46 | 5.78 | 1.05 |
| M10.004 | matrix metallopeptidase-9 | SEQ ID NO: 174 | 4 | MVTP\|VTWM | 0.42 | 45.81 | 1.05 |
| M10.004 | matrix metallopeptidase-9 | SEQ ID NO: 175 | 274 | VKPP\|YMLV | 32.73 | 13.5 | 1.05 |
| M10.004 | matrix metallopeptidase-9 | SEQ ID NO: 176 | 362 | SDYG\|INCS | 43.37 | 2.86 | 1.04 |
| M10.004 | matrix metallopeptidase-9 | SEQ ID NO: 177 | 281 | VVGN11VIK | 33.62 | 12.61 | 1.04 |
| M10.004 | matrix metallopeptidase-9 | SEQ ID NO: 178 | 351 | LIQK\|IHFY | 41.91 | 4.32 | 1.03 |
| M10.004 | matrix metallopeptidase-9 | SEQ ID NO: 179 | 266 | LTVP\|LQSC | 31.88 | 14.35 | 1.03 |
| M10.004 | matrix metallopeptidase-9 | SEQ ID NO: 180 | 313 | HRIL\|LVRA | 37.36 | 8.88 | 1.02 |
| M10.004 | matrix metallopeptidase-9 | SEQ ID NO: 181 | 347 | LKGV\|LIQK | 41.43 | 4.81 | 1.02 |
| M10.004 | matrix metallopeptidase-9 | SEQ ID NO: 182 | 39 | EEGM\|MINI | 4.61 | 41.62 | 1.01 |
| M10.004 | matrix metallopeptidase-9 | SEQ ID NO: 183 | 385 | SVSK\|LC | 46.02 | 0.21 | 0.99 |
| M10.005 | matrix metallopeptidase-9 | SEQ ID NO: 184 | 173 | CPSA\|QVSP | 20.69 | 25.54 | 1.16 |
| M10.005 | matrix metallopeptidase-9 | SEQ ID NO: 185 | 137 | CVAN\|SWI | 16.4 | 29.84 | 1.02 |
| M10.005 | matrix metallopeptidase-9 | SEQ ID NO: 186 | 288 | KPASIQTIT | 34.33 | 11.9 | 0.99 |
| M10.005 | matrix metallopeptidase-9 | SEQ ID NO: 187 | 276 | PPYM\|LWG | 33.03 | 13.21 | 0.96 |
| S01.001 | chymotrypsin A (cattle-type) | SEQ ID NO: 188 | 142 | WILI\|QNNE | 16.91 | 29.33 | 1.02 |
| S01.001 | chymotrypsin A (cattle-type) | SEQ ID NO: 189 | 83 | RFTY\|HMVS | 9.85 | 36.39 | 1.01 |
| S01.001 | chymotrypsin A (cattle-type) | SEQ ID NO: 190 | 228 | PELW\|RLTV | 27.29 | 18.95 | 0.97 |
| S01.131 | elastase-2 | SEQ ID NO: 191 | 219 | ISPV\|SGPE | 26.14 | 20.1 | 1.41 |
| S01.131 | elastase-2 | SEQ ID NO: 192 | 352 | IQKI\|HFYF | 42.02 | 4.21 | 1.37 |
| S01.131 | elastase-2 | SEQ ID NO: 193 | 140 | NSW \|ILQN | 16.68 | 29.55 | 1.21 |
| S01.131 | elastasc-2 | SEQ ID NO: 194 | 377 | RSCI\|ALFC | 45.19 | 1.05 | 1.18 |

TABLE 8-continued

| Predicted protease cleavage sites within CTXLP, as predicted by PROSPER. | | | | | | | |
|---|---|---|---|---|---|---|---|
| Merops ID | Protease Name | | Position | P4-P4' site | N-fragment (kDa) | C-fragment (kDa) | Cleavage score |
| S01.131 | elastase-2 | SEQ ID NO: 195 | 52 | YPPI\|CLGR | 6.23 | 40.01 | 1.18 |
| S01.131 | elastase-2 | SEQ ID NO: 196 | 20 | NDSV\|WVPG | 2.29 | 43.95 | 1.17 |
| S01.131 | elastase-2 | SEQ ID NO: 197 | 315 | ILLV\|RARE | 37.57 | 8.66 | 1.16 |
| S01.131 | elastase-2 | SEQ ID NO: 198 | 43 | MINI\|SIGY | 5.08 | 41.15 | 1.12 |
| S01.131 | elastase-2 | SEQ ID NO: 199 | 278 | YMLV\|VGNI | 33.24 | 13 | 1.11 |
| S01.131 | elastase-2 | SEQ ID NO: 200 | 86 | YHMV\|SGMS | 10.21 | 36.02 | 1.09 |
| S01.131 | elastase-2 | SEQ ID NO: 201 | 237 | SHHI\|RIWS | 28.3 | 17.93 | 1.09 |
| S01.131 | elastase-2 | SEQ ID NO: 202 | 349 | GVLIIQKIH | 41.65 | 4.58 | 1.09 |
| S01.131 | elastase-2 | SEQ ID NO: 203 | 65 | MPAV\|QNWL | 7.73 | 38.51 | 1.09 |
| S01.131 | elastase-2 | SEQ ID NO: 204 | 41 | GMMI\|NISI | 4.86 | 41.38 | 1.08 |
| S01.131 | elastase-2 | SEQ ID NO: 205 | 5 | VTPV\|TWMD | 0.52 | 45.71 | 1.07 |
| S01.131 | elastase-2 | SEQ ID NO: 206 | 233 | LTVA\|SHHI | 27.83 | 18.41 | 1.07 |
| S01.131 | elastase-2 | SEQ ID NO: 207 | 151 | GTII\|DWAP | 18.04 | 28.19 | 1.07 |
| S01.131 | elastase-2 | SEQ ID NO: 208 | 45 | NISI\|GYHY | 5.28 | 40.95 | 1.04 |
| S01.131 | elastase-2 | SEQ ID NO: 209 | 129 | NTEV\|LWEE | 15.45 | 30.78 | 1.02 |
| S01.131 | elastase-2 | SEQ ID NO: 210 | 325 | WIPV\|STDR | 38.88 | 7.35 | 1 |
| S01.133 | Cathepsin G | SEQ ID NO: 211 | 214 | PRPK\|IISP | 25.63 | 20.61 | 1.33 |
| S01.133 | cathepsin G | SEQ ID NO: 212 | 160 | GQFY\|HNCS | 19.28 | 26.96 | 1.24 |
| S01.133 | cathepsin G | SEQ ID NO: 213 | 40 | EGMM\|INIS | 4.74 | 41.49 | 1.18 |
| S01.133 | cathepsin G | SEQ ID NO: 214 | 277 | PYML\|VVGN | 33.14 | 13.09 | 1.17 |
| S01.133 | cathepsin G | SEQ ID NO: 215 | 260 | IDLN\|SILT | 31.27 | 14.96 | 1.11 |
| S01.133 | cathepsin G | SEQ ID NO: 216 | 15 | IEVY\|VNDS | 1.77 | 44.46 | 1.1 |
| S01.133 | cathepsin G | SEQ ID NO: 217 | 240 | IRIW\|SGNQ | 28.76 | 17.48 | 1.09 |
| S01.133 | cathepsin G | SEQ ID NO: 218 | 8 | VTWM\|DNPI | 0.94 | 45.29 | 1.06 |
| S01.133 | cathepsin G | SEQ ID NO: 219 | 83 | RFTY\|HMVS | 9.85 | 36.39 | 1.05 |
| S01.133 | cathepsin G | SEQ ID NO: 220 | 47 | SIGY\|HYPP | 5.62 | 40.61 | 1.04 |
| S01.133 | cathepsin G | SEQ ID NO: 221 | 313 | HRIL\|LVRA | 37.36 | 8.88 | 1.03 |
| S01.133 | cathepsin G | SEQ ID NO: 222 | 276 | PPYM\|LVVG | 33.03 | 13.21 | 1.01 |
| S01.133 | cathepsin G | SEQ ID NO: 223 | 199 | QSFY\|LWEW | 23.68 | 22.56 | 0.99 |
| S01.133 | cathepsin G | SEQ ID NO: 224 | 321 | REGM\|WIPV | 38.38 | 7.85 | 0.99 |
| S01.133 | cathepsin G | SEQ ID NO: 225 | 39 | EEGM\|MINI | 4.61 | 41.62 | 0.96 |
| S01.133 | cathepsin G | SEQ ID NO: 226 | 361 | CSDY\|GINC | 43.2 | 3.04 | 0.94 |
| S01.133 | cathepsin G | SEQ ID NO: 227 | 7 | PVTW\|MDNP | 0.81 | 45.42 | 0.93 |
| S01.133 | cathepsin G | SEQ ID NO: 228 | 89 | VSGM\|SLRP | 10.6 | 35.63 | 0.92 |
| S01.217 | thrombin | SEQ ID NO: 229 | 214 | PRPK\|IISP | 25.63 | 20.61 | 1.03 |
| S01.269 | glutamyl peptidase I | SEQ ID NO: 230 | 319 | RARE\|GMWI | 38.08 | 8.15 | 1.04 |

TABLE 8-continued

Predicted protease cleavage sites within CTXLP, as predicted by PROSPER.

| Merops ID | Protease Name | Position | P4-P4' site | N-fragment (kDa) | C-fragment (kDa) | Cleavage score |
|---|---|---|---|---|---|---|
| S01.269 | glutamyl peptidase I | SEQ ID NO: 231 | 185 DLTE\|SLDK | 21.94 | 24.3 | 1 |
| S26.008 | thylakoidal processing peptidase | SEQ ID NO: 232 | 102 QDFS\|YQRS | 12.12 | 34.11 | 0.94 |
| S26.010 | signalase (animal) 21 kDa component | SEQ ID NO: 233 | 107 LVRA\|REGM | 37.8 | 8.44 | 0.95 |

Lastly, the predicted protein interactions of cellular proteins and CTXLP were equally intriguing (Table 9). Among the predicted interactions were proteins involved in cell cycle regulation such as MAPK and LATS. As well, interactions were also predicted with proteins involved in innate immunity such as UPS-7/HAUSP, TRAF-2 and TRAF-6, which are upstream of NF-κB in inflammatory signalling.

TABLE 9

Predicted protein interaction partners of CTXLP using ELM software.

| Predicted protein interaction partner | Predicted CTXLP interaction sites |
|---|---|
| BRCA1 | 216-220 |
| Calcineurin | 90-93 |
|  | 375-378 |
| Cyclin | 216-220 |
|  | 423-427 |
| Dyenein | 66-72 |
| MAPKs | 233-242 |
|  | 361-371 |
|  | 363-371 |
|  | 428-437 |
|  | 462-470 |
|  | 464-470 |
| MAPKs (ERK1/2 and p38 subfamilies) | 425-437 |
|  | 427-439 |
| Pin1 | 69-74 |
|  | 184-189 |
|  | 285-290 |
|  | 326-331 |
|  | 443-448 |
| Protein phosphatase 1 (catalytic subunit) | 112-119 |
|  | 214-221 |
|  | 465-471 |
| STAT5 | 63-66 |
|  | 101-104 |
|  | 106-109 |
|  | 126-129 |
|  | 208-211 |
|  | 367-370 |
|  | 471-474 |
| SUMO | 179-185 |
|  | 367-374 |
| TRAF2 | 32-35 |
|  | 145-148 |
| TRAF6 | 310-318 |
| USP7/HAUSP | 219-223 |
|  | 225-229 |
|  | 229-233 |
|  | 232-236 |
|  | 290-294 |
|  | 301-305 |
|  | 378-382 |
|  | 445-449 |

Design of a Custom ERVK CTXLP Antibody

Pierce Custom antibody services has produced a CTXLP-specific polyclonal rabbit antibody, used in all the experiments described below. The predicted epitopes are listed in FIG. 22. The rabbit protocol and immunization plan is stated in FIG. 23.

Design of a Custom ERVK CTXLP Vector, and Complementary ERVK Env and ERVK SU Vector GenScript custom plasmid services has produced an ERVK CTXLP-expressing vector within a pcDNA3.1 backbone, used in all the experiments described below. We also synthesized a matching ERVK SU vector as a complementary plasmid devoid of the CTXLP domain. The sequences used to produce the vectors are listed below:

```
ERVK SU + ERVK CTXLP
(Based on ERVK113): 57.14 kDa
                                    [SEQ ID NO: 2]
MNPSEMQRKAPPRRRRHRNRAPLTHKMNKMVTSEEQM

KLPSTKKAEPPTWAQLKKLTQLATKYLENTKVTQTP

ESMLLAALMIVSMVVSLPMPAGAAAANYTYWAYVPF

PPLIRAVTWMDNPIEIYVNDSVWVPGPTDDCCPAKP

EEEGMMINISIGYRYPPICLGRAPGCLMPAVQNWLV

EVPTVSPISRFTYHMVSGMSLRPRVNYLQDFSYQRS

LKFRPKGKPCPKEIPKESKNTEVLVWEECVANSAVI

LQNNEFGTLIDWAPRGQFYHNCSGQTQSCPSAQVSP

AVDSDLTESLDKHKHKKLQSFYPWEWGEKGISTARP

KIISPVSGPEHPELWRLTVASHHIRIWSGNQTLETR

DRKPFYTIDLNSSLTVPLQSCVKPPYMLVVGNIVIK

PDSQTITCENCRLLTCIDSTFNWQHRILLVRAREGV

WIPVSMDRPWEASPSVHILTEVLKGVLNRSKRQKIH

FYFNCSDYGINCSHSYGCCSRSCIALFCSVSKLC
```

First portion is ERVK Env SU, aa residues 1-465 (furin cleavage site) of ERVK 113 (19p12b) with normal frame. Second portion is ERVK CTXLP, aa residues 463-500 of ERVK 113 (19p12b) with +3 reading frame and no start codon bias. Env SU ends at KR before bolded font indicating where Env CTXLP starts (QK). Bolded portion of sequence represents the allele 1 portion of Env CTXLP.

NRS is an N-linked glycosylation site, RSKR is the furin cleavage site, KRQK is the nuclear localization sequence (NLS). NRS may mask furin site allowing for NLS function.

```
ERVK Env (Based on ERVK113): 79.2 kDa
                              [SEQ ID NO. 234]
MNPSEMQRKAPPRRRRHRNRAPLTHKMNKMVTSEEQ

MKLPSTKKAEPPTWAQLKKLTQLATKYLENTKVTQT

PESMLLAALMIVSMVVSLPMPAGAAAANYTYWAYVP

FPPLIRAVTWMDNPIEIYVNDSVWVPGPTDDCCPAK

PEEEGMMINISIGYRYPPICLGRAPGCLMPAVQNWL

VEVPTVSPISRFTYHMVSGMSLRPRVNYLQDFSYQR

SLKFRPKGKPCPKEIPKESKNTEVLVWEECVANSAV

ILQNNEFGTLIDWAPRGQFYHNCSGQTQSCPSAQVS

PAVDSDLTESLDKHKHKKLQSFYPWEWGEKGISTAR

PKIISPVSGPEHPELWRLTVASHHIRIWSGNQTLET

RDRKPFYTIDLNSSLTVPLQSCVKPPYMLVVGNIVI

KPDSQTITCENCRLLTCIDSTFNWQHRILLVRAREG

VWIPVSMDRPWEASPSVHILTEVLKGVLNRSKRFIF

TLIAVIMGLIAVTATAAVAGVALHSSVQSVNFVNDW

QNNSTRLWNSQSSIDQKLANQINDLRQTVIWMGDRL

MSLEHRFQLQCDWNTSDFCITPQIYNESEHHWDMVR

CHLQGREDNLTLDISKLKEQIFEASKAHLNLVPGTE

AIAGVADGLANLNTVTWVKTIGSTTIINLILILVCL

FCLLLVYRCTQQLRRDSDHRERAMMTMVVLSKRKGG

NVGKSKRDQIVTVSV*
```

→aa residues 1-465 (furin cleavage site—R-X-K/R-R↓) of ERVK 113 (19p12b).
→aa residues 466-699 (furin cleavage site to end of aa sequence) of ERVK 113 (19p12b). Bolded portion of sequence represent the ISU domain of ERVK TM.

```
ERVK SU (Based on ERVK113): 52.86 kDa
                              [SEQ ID NO: 3]
MNPSEMQRKAPPRRRRHRNRAPLTHKMNKMVTSEEQ

MKLPSTKKAEPPTWAQLKKLTQLATKYLENTKVTQT

PESMLLAALMIVSMVVSLPMPAGAAAANYTYWAYVP

FPPLIRAVTWMDNPIEIYVNDSVWVPGPTDDCCPAK

PEEEGMMINISIGYRYPPICLGRAPGCLMPAVQNWL

VEVPTVSPISRFTYHMVSGMSLRPRVNYLQDFSYQR

SLKFRPKGKPCPKEIPKESKNTEVLVWEECVANSAV

ILQNNEFGTLIDWAPRGQFYHNCSGQTQSCPSAQVS

PAVDSDLTESLDKHKHKKLQSFYPWEWGEKGISTAR

PKIISPVSGPEHPELWRLTVASHHIRIWSGNQTLET

RDRKPFYTIDLNSSLTVPLQSCVKPPYMLVVGNIVI

KPDSQTITCENCRLLTCIDSTFNWQHRILLVRAREG

VWIPVSMDRPWEASPSVHILTEVLKGVLNRSKR*
```

→aa residues 1-465 (furin cleavage site—R-X-K/R-R↓) of ERVK 113 (19p12b).

CTXLP Biological Characterization

The ERVK CTXLP Domain is Found in Several Distinct Proteinaceous Forms

Western Blot Analysis of ERVK-Expressing NCCIT Cells

Whole cell extract of ERVK-expressing NCCIT cells and an immunoprecipitated (IP) fraction enriched for CTXLP were analyzed by Western blot (FIG. 25). In the whole cell extract, major bands were identified at 90 and 110 kDa, suggesting this may be the predominant form of CTXLP found in the cell. Unmodified CTXLP would be expected to correspond to a 51 kDa band; thus, is it possible that heavier bands are due to PTM such as glycosylation, phosphorylation or sumoylation. It should be noted that higher molecular weight bands are also observed in other cell types (see below). It is likely that these heavier bands reflect PTM including phosphorylation (≈2 kDa) and glycosylation (≥2 kDa) (FIGS. 21 and 26) or sumoylation. The possibility that the higher molecular weights reflect post-translational modification of the 32 and 51 kDa CTXLP isoforms through glycosylation, would be in accordance with the results of the bioinformatic analysis which indicate that ERVK Env and CTXLP proteins are heavily glycosylated (FIG. 21, Table 6, FIG. 26)[15,60,61]. Another possibility for observing larger than expected protein bands is detergent-resistant multimerization, as retroviral envelope proteins form trimers[15]. Light bands were also observed at 51 kDa and 32 kDa, the latter form possibly due to an alternative start site within or cleavage of CTXLP protein.

In the CTXLP-enriched fraction, the most heavily enriched band was detected at 51 kDa. In this fraction, CTXLP-reactive bands were also found at 110 and 142 kDa, which are also possible results of protein PTM or multimerization. Lighter bands were found at 26 and 29 kDa, again these bands suggest CTXLP cleavage or alternative methionine start site products.

ERVK CTXLP is Inducible Through the Action of Pro-Inflammatory Signalling

Astroctye Expression of ERVK CTXLP in the Presence of Pro-Inflammatory Agents

NCCIT, used as control cells, were cultured along side-SVGA cells. In addition to higher molecular weight bands (not shown) NCCIT cells demonstrated a 51 kDa band and 32 kDa band. Unlike NCCIT cells, in the astrocytic cell line SVGA ERVK CTXLP protein is spontaneously expressed at low levels, with a minor 32 kDa protein being apparent (FIG. 25). However, CTXLP expression in SVGA cells was upregulated upon treatment with pro-inflammatory cytokines tumor neurosis factor (TNFα) and LIGHT (lymphotoxin-like inducible member of the TNF superfamily protein) (FIG. 27). In contrast to CTXLP expression, Env protein expression was not induced by pro-inflammatory stimulus.

As with NCCIT cells, larger 90/110 kDa CTXLP reactive bands were also observed upon TNFα or LIGHT treated SVGA andReNcell neurons (FIGS. 28, 30, 56 and 58). As detailed above, these larger bands may represent post-translational modification (PTM) of CTXLP isoforms.

The Localization of ERVK CTXLP Expression is Cell Type and Inflammation Dependent Ubiquitous Expression of ERVK CTXLP Expression in NCCIT Cells The localization of CTXLP protein expression was examined through Western blot analysis of cellular fractions and confocal imaging. In NCCIT cells, endogenous CTXLP protein appeared ubiquitously expressed and localizes to the cytoplasm, nucleus and chromatin enriched fractions. CTXLP protein was also found in both the soluble and insoluble NCCIT whole cell lysates (FIGS. 29A and B). The latter further suggests that there is interaction of CTXLP with cell membranes. The ubiquitous nature of CTXLP was supported by confocal imaging (FIG. 27 C).

CTLXP expression was also associated with indicators of autophagy in NCCIT cells (FIG. 29B). Autophagy occurs when dysfunctional proteins and damaged organelles accumulate within a cell, and has been associated with cell dysfunction in neurodegenerative disease[62]. NCCIT cells exhibited insoluble caspase-3, which is an indicator for autophagy[63]. There was also evidence of LC3B cleavage (data not shown) which occurs during autophagy.

Nuclear Localization of ERVK CTXLP Expression in SVGA Cells

Figure 30:
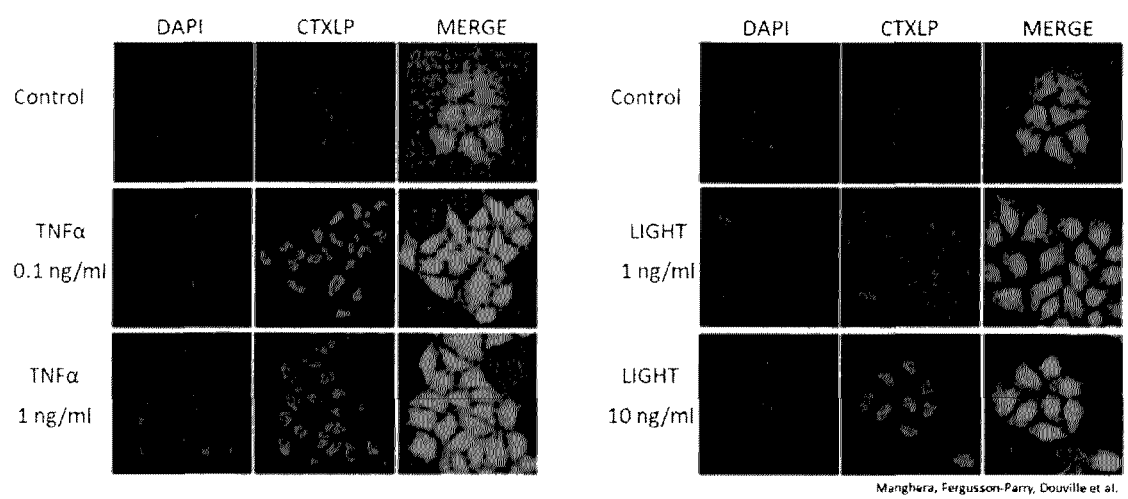
FIG. 30 depicts ERVK CTXLP is inducible in astrocytes with pro-inflammatory cytokines. Confocal analysis of protein expression for ERVK CTXLP (red) and ERVK reverse transcriptase (RT, green) in cells treated with or without TNFα and LIGHT, n=2. Enhanced CTXLP expression precedes increases in RT expression. DAPI stain indicates nuclei (blue).

In contrast to NCCIT cells, in SVGA cells endogenous CTXLP protein localization occurred predominantly in the chromatin cellular fraction (FIG. 29A) and was poorly detected by confocal imaging (FIG. 29C). However, CTXLP protein levels were strongly elevated in the nucleus upon treatment of 0.1 and 1 ng/mL TNFα when compared to cells alone (FIG. 30). This increase in CTXLP expression upon treatment of astroctyes with low levels of TNFα or LIGHT, suggests that chronic, low level inflammation may augment CTXLP levels physiologically. Moreover, with pro-inflammatory cytokine exposure, CTXLP puncta formed within the nucleus, but staining was excluded from the nucleoli (FIG. 31). Higher resolution images of CTXLP expressing astrocytes showed that CTXLP puncta also formed in the cytoplasm and on the cell surface, suggesting that potential isoforms of CTXLP may have location-specific functions (FIG. 31 B).

Enhanced CTXLP expression was also associated with enhanced cytoplasmic RT expression (FIG. 30), suggesting regulation of global ERVK gene expression may be linked. Pro-inflammatory cytokines have been shown to induce ERVK expression[64-67]. During inflammatory events, ERVK Env has been shown to be either neuroprotective[68] and neuropathological[69]. Indeed, chronic exposure to TNFα may facilitate frameshifting in ERVK env translation leading to CTXLP being produced as a cryptic protein. TNFα expression and its subsequent downstream signalling cascade products may result in enhanced IRES-dependant translation[70], promoting the formation of the smaller CTXLP isoform. Nonetheless, the observation that ERVK CTXLP did not co-localize with ERVK Env protein which localized (FIG. 31), suggesting that these proteins may have different localization sequences and/or patterns. Thus, the relationship between CTXLP and Env in ERVK gene regulation remain unclear.

Figure 32:
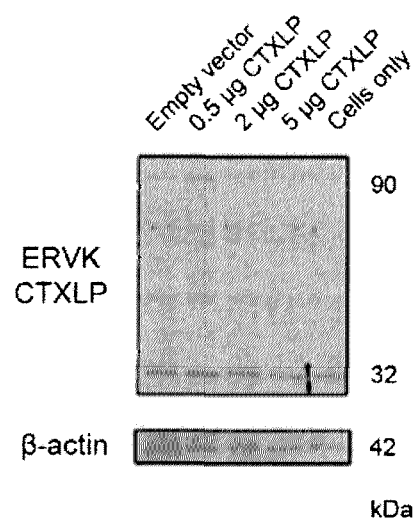
FIG. 32 depicts CTXLP overexpression in soluble fractions of SVGA cells enhances the 32 kDa and 90 kDa forms of endogenous CTXLP. SVGA cells were transfected using Lipofectamine LTX with 5 μg Empty Vector, or 0.5, 2 and 5 μg CTXLP cysteine-rich construct for 48 hr.
Figure 34:
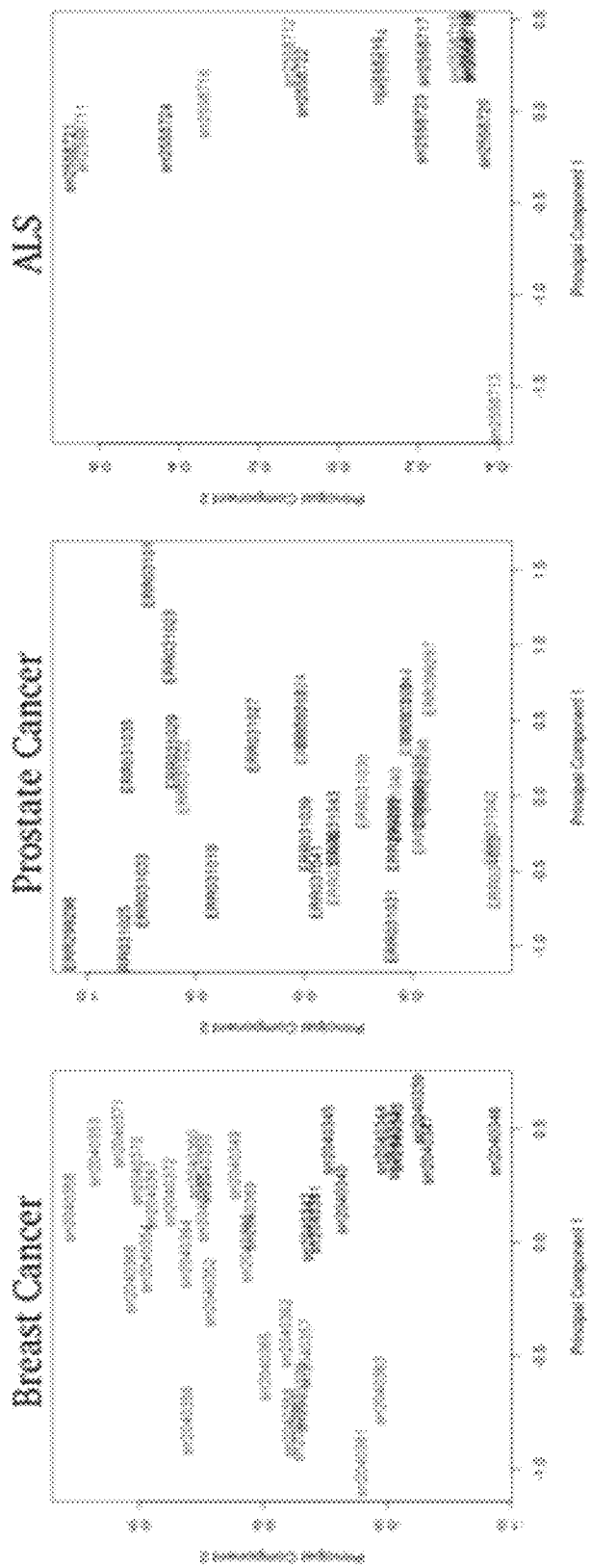
FIG. 34 depicts ERVK Expression Multidimensional Scaling. Two dimensional plots were produced by reduction of the high dimensional RNA-seq expression data derived from the Sequence Read Archive (SRA) using the R package EdgeR. The plot labels correspond to SRA studies as follows: ALS (SRP064478), Bipolar Disorder (SRP074904), Breast Cancer (SRP058722), HIV/HCV (SRP068424), Multiple Sclerosis (SRP110016), Prostate Cancer (ERP000550), Rheumatoid Arthritis (SRP102685), and Schizophrenia (SRP090259). In these plots each axis represents the leading log-2-scaled fold-change at one particular ERVK locus; the two loci chosen are those with the most extreme values in the majority of the clinical group's samples. Since these represent the biggest difference between samples, if no separation is apparent in these plots, there is no clear difference in transcript profiles. Each sample is represented by its SRA accession number, coloured red for disease-associated samples and black are the control samples.
Figure 34:
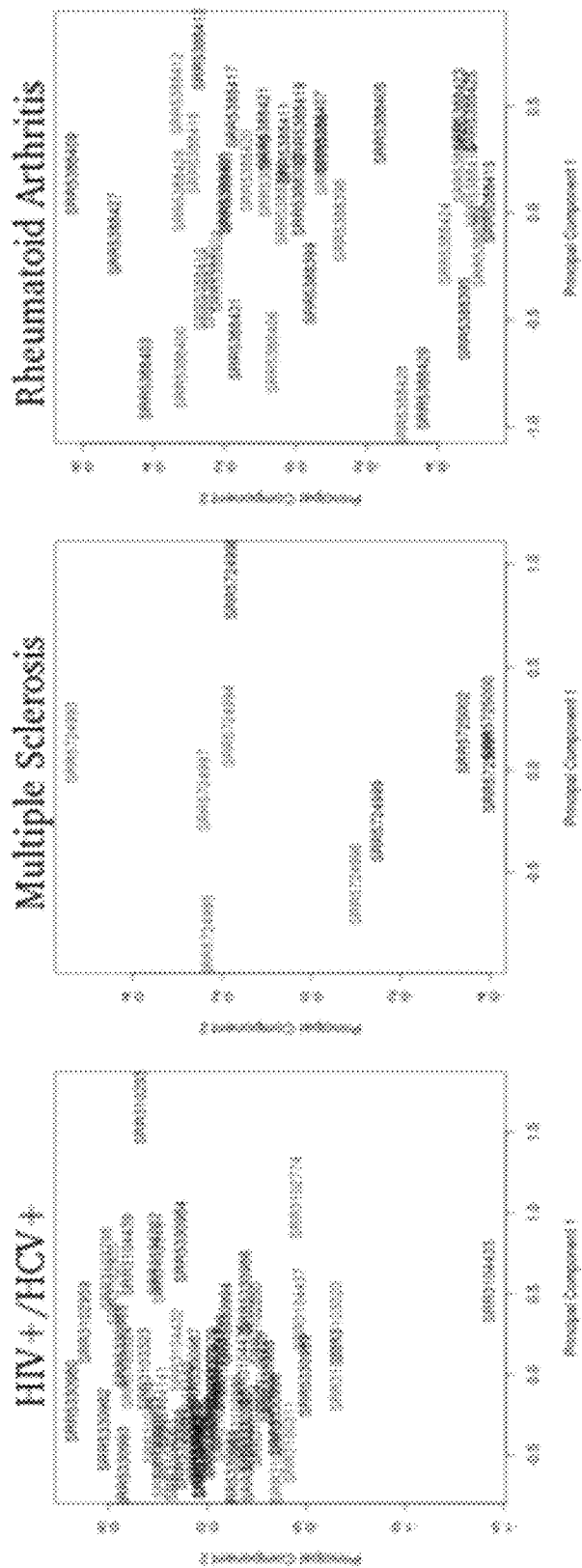
Figure 34:
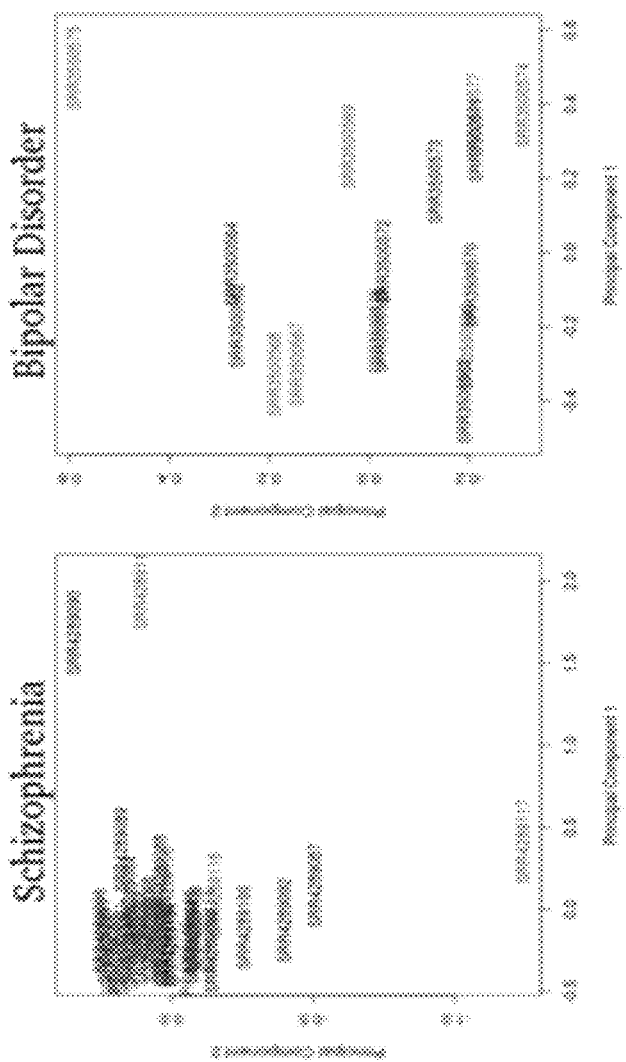
Figure 35:
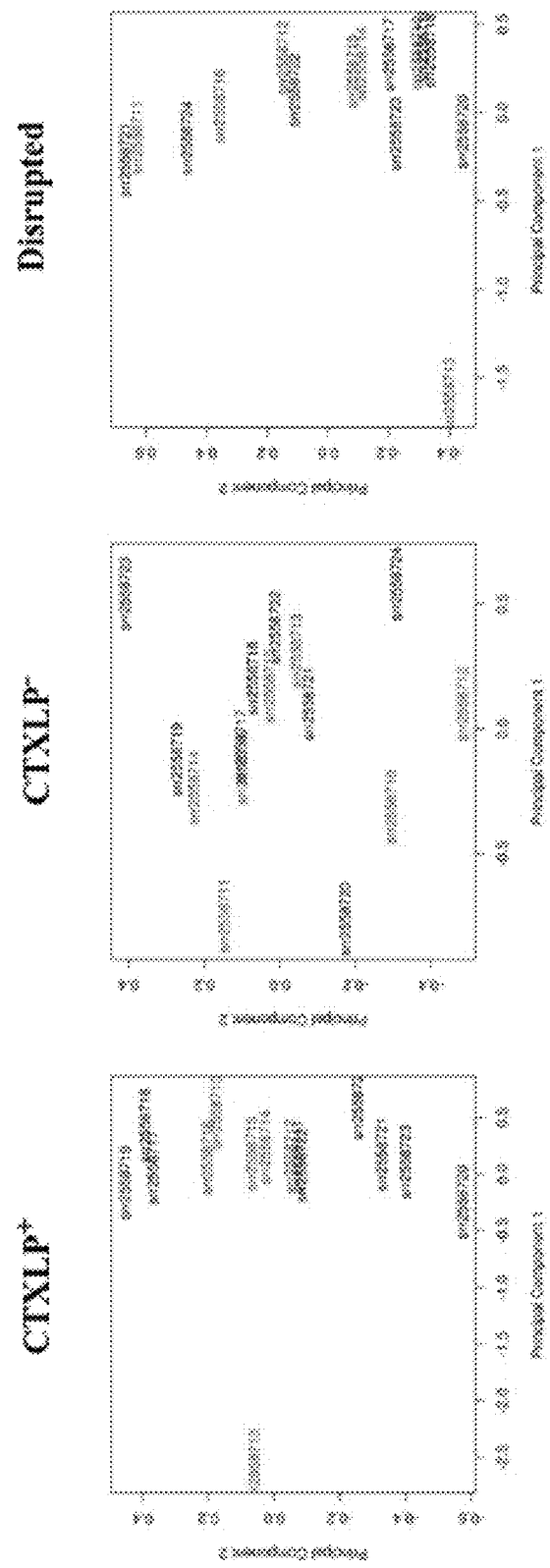
FIG. 35 depicts ERVK Multidimensional Scaling by CTXLP status in Human Disease. Each plot was produced as described in FIG. 34, except with the modification that ERVK loci were subsetted into three states: "CTXLP+" which could produce CTXLP, "Disrupted" which cannot produce CTXLP but may have had an ancestral loci that produced CTXLP, and finally "CTXLP−" loci which do not and likely never did produce CTXLP from the ERVK env gene. In all cases, samples from the ALS, Bipolar Disorder, Breast Cancer, HIV-1/HCV co-infection, Multiple Sclerosis and Rheumatoid Arthritis cohorts expressed all three types of ERVK env transcripts.
Figure 35:
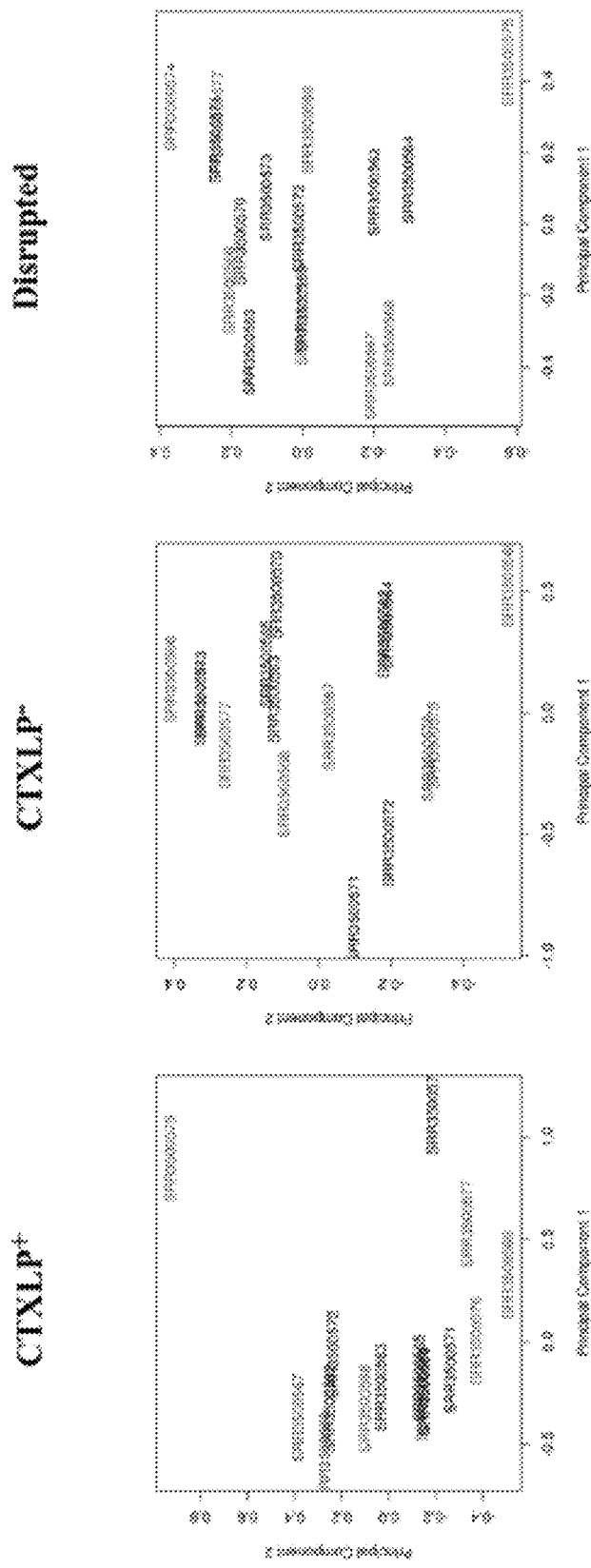
Figure 35:
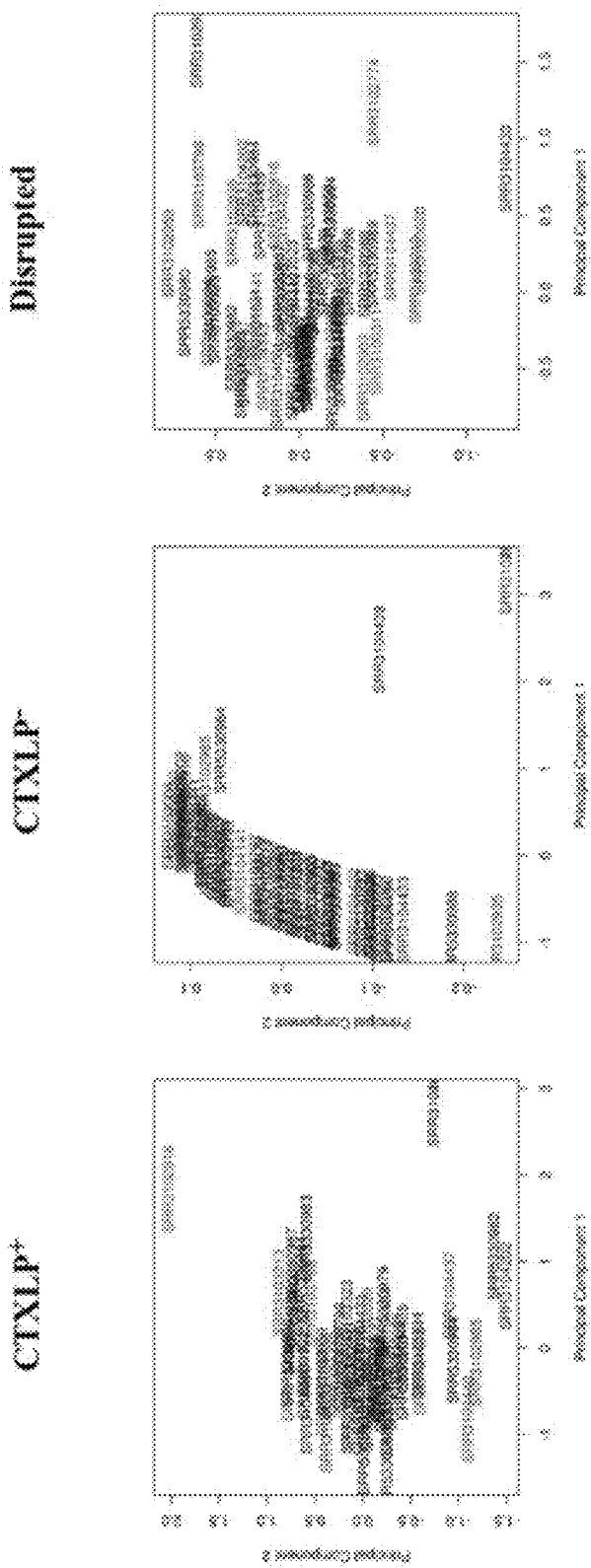
Figure 35:
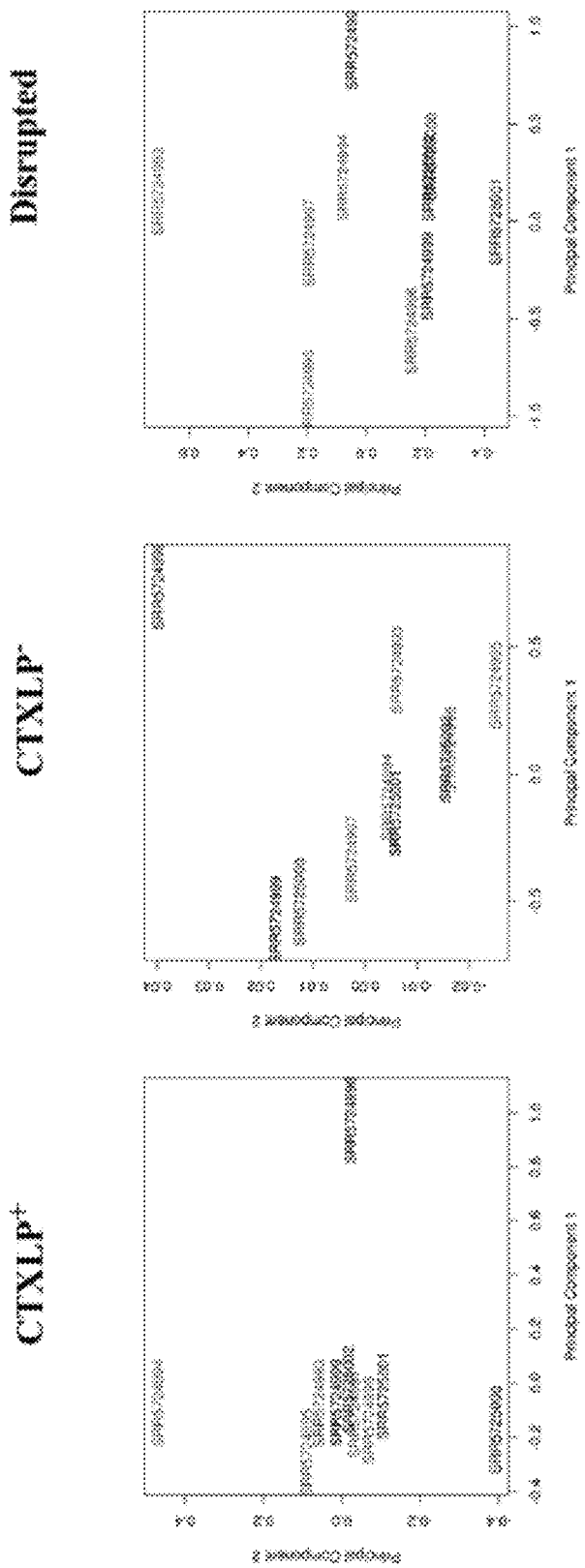
Figure 35:
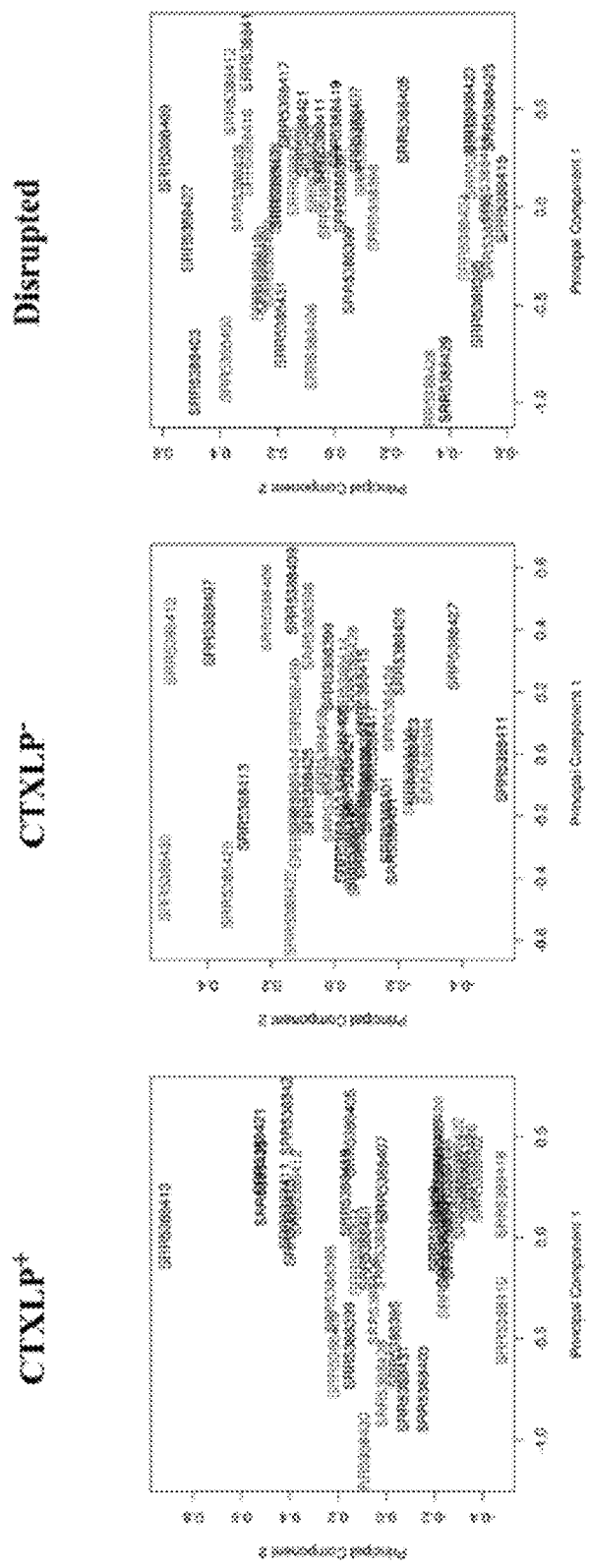
Figure 36:
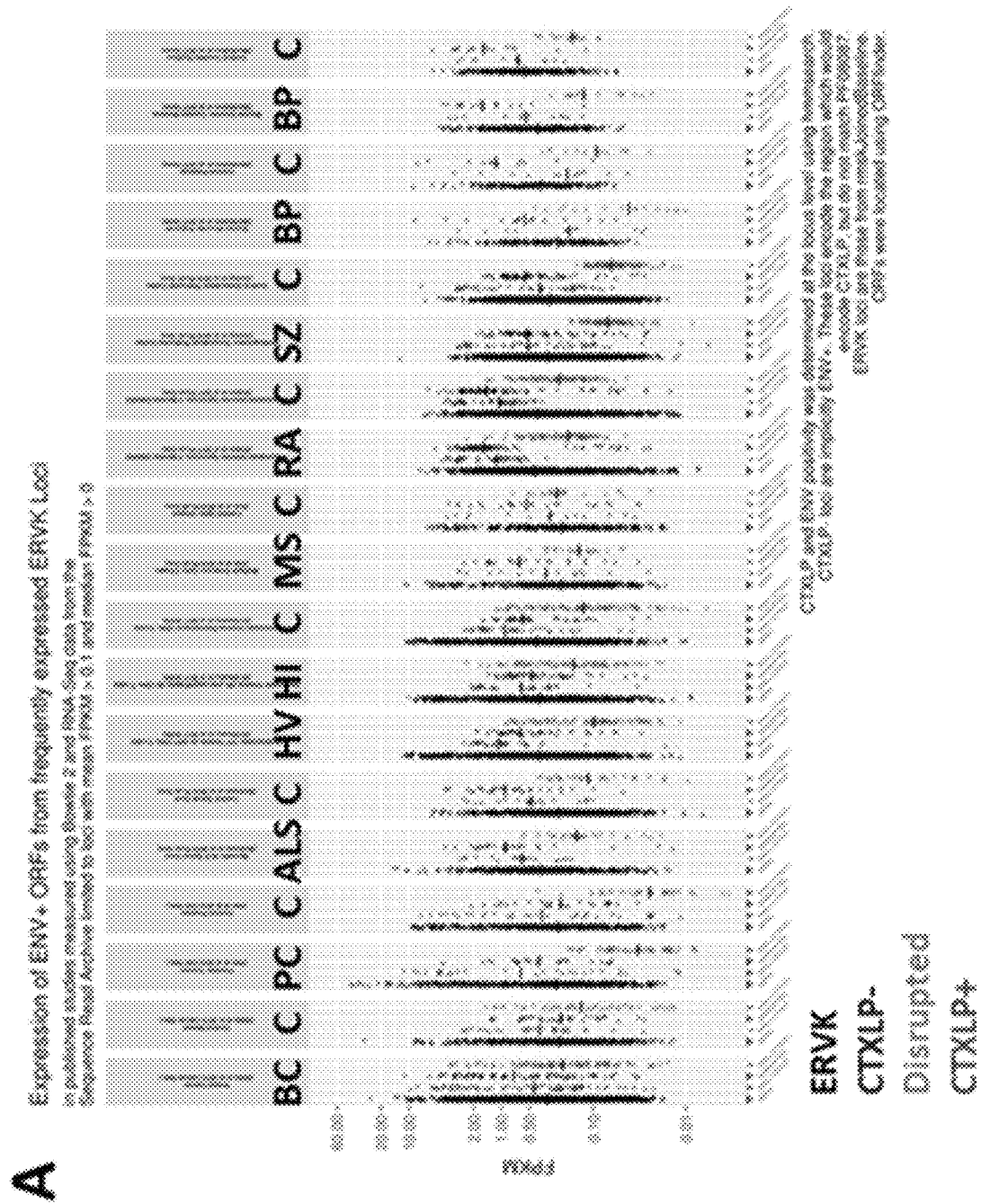
FIG. 36 depicts Per-Locus Differential ERVK Expression. Each panel shows in detail the expression of individual ERVK loci encoding envelope in each human disease condition. ERVK loci (black) are plotted against CTXLP+ (red), CTXLP− (blue) and disrupted (grey) loci. The plot labels correspond to SRA studies as follows: ALS (ALS: SRP064478), Bipolar Disorder (BP: SRP074904), Breast Cancer (BC: SRP058722), HIV/HCV (HV; HIV/HCV+interferon (HI): SRP068424), Multiple Sclerosis (MS: SRP110016), Prostate Cancer (PC: ERP000550), Rheumatoid Arthritis (RA: SRP102685), and Schizophrenia (SZ: SRP090259). For each study, controls (C) and indicated to the right of cases. Panel A exclude ERVK loci with very low expression; only loci with a median expression greater than 0 and a mean expression greater than 0.1 are plotted. Panel B shows only loci which were highly expressed; only ERVK loci which had a maximum expression higher than 2 are plotted.
Figure 36:
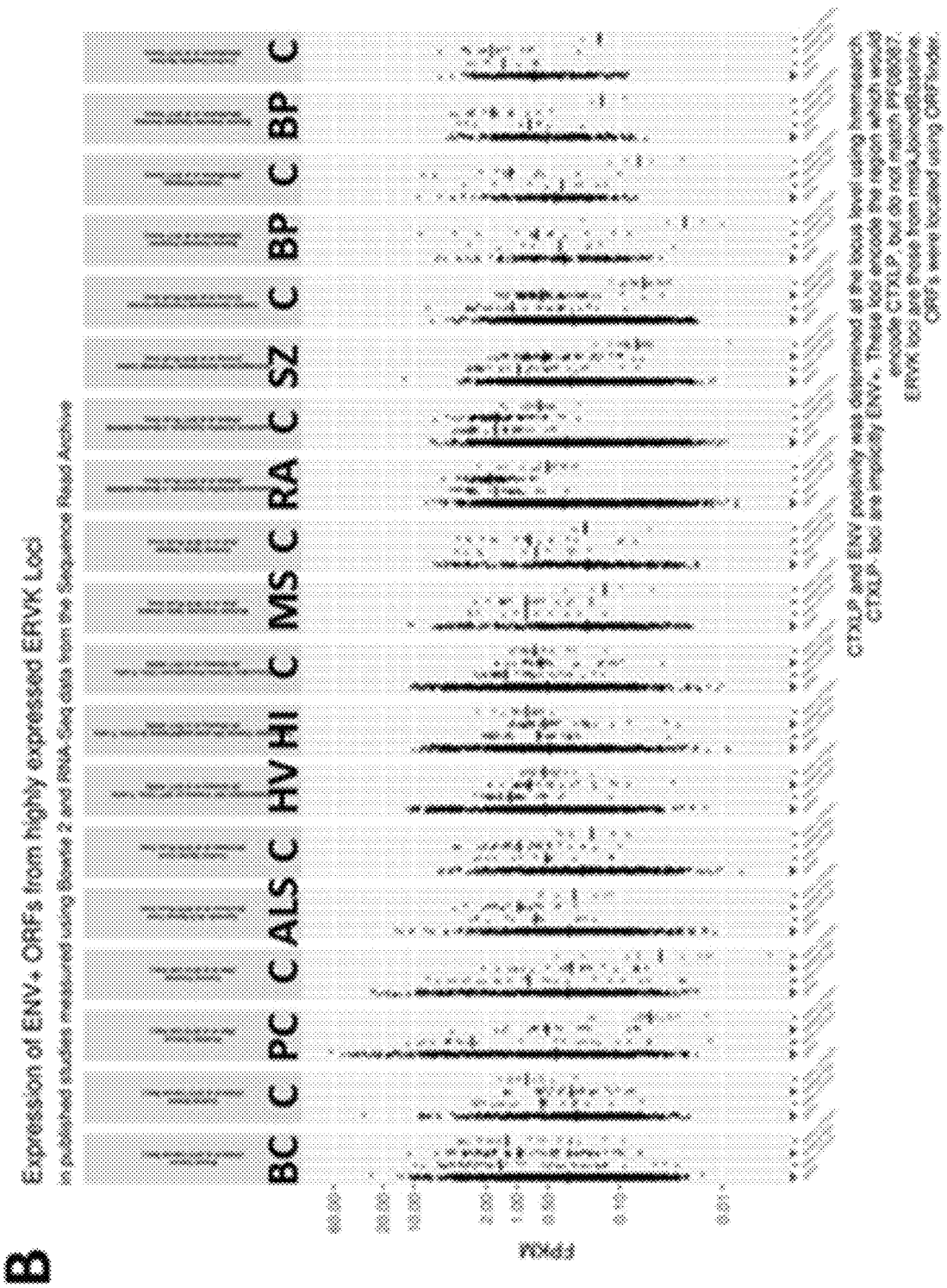

Overexpression of the CTXLP cysteine-rich domain in SVGA cells also resulted in increased CTXLP 32 kDa and 90/110 kDa protein bands (FIG. 32), suggesting that this protein domain is sufficient to enhance its own expression.

ERVK CTXLP Binds Chromatin

Consistent with our observation that CTXLP is enriched in the chromatin fraction (FIG. 29), DNABIND prediction (dnabind.szialab.org/)71 predicts that CTXLP binds DNA. Prediction parameters were as follows: false positive rate of 6%, expected sensitivity of 58.7%, expected Matthews correlation coefficient of 0.55, score threshold is set to 1.577 (threshold probability of 0.8288). Prediction results of the CTXLP sequence were a score of 1.771 and a probability of DNA binding of 0.8546.

An analysis is DNA interactions revealed that CTXLP bound the interferon response elements (ISREs) within the ERVK viral promoter (5' LTR) (FIG. 33). This binding is enhanced in the presence of inflammatory cytokine stimuli, and is distinct in select cell types (FIG. 33). This suggests that CTXLP, and specifically the 32 kDa form of CTXLP (FIG. 24), may bind DNA and regulate gene expression. Indeed, preliminary data suggest that CTXLP can alter both ERVK expression (FIG. 32) and the transcription of NF-κB transcripts (see below). Further, CTXLP may alter the gene expression patterns of numerous viral and cellular genes containing an ISRE elements in their promoters[72,73]. Thus, CTXLP may regulate ERVK gene expression, as well as other genes containing ISREs.

In summary, CTXLP protein isoform expression in NCCIT and SVGA cells was elucidated by Western blots which indicated presumed isoform sizes of 32 kDa, 51 kDa, and 90/110 kDa. In NCCIT cells, endogenous CTXLP is ubiquitously expressed being present in the nucleus and also identified in the cytoplasm and cell membrane, based on cell fractionation and confocal experiments. In contrast, in SVGA cells basal CTXLP levels are limited, but highly inducible by pro-inflammatory stimuli. In addition, CTXP expression in almost exclusively in the chromatin fraction and demonstrates a prominence in the nucleus upon confocal imaging. The notable exception is that after pro-inflammatory activation for 24 hours CTXLP puncta appear in the cytoplasm and on cellular membranes reminiscent of pathogenic protein aggregates. Moreover, the localization pattern in response to pro-inflammatory activators resulting in a prominence in the nucleus (FIGS. 29-31), ability to bind chromatin (FIGS. 29 and 33) and absence from the nucleoli (FIG. 31) suggests that CTXLP may be involved in viral transcription. A primary candidate as a viral transcription factor is the 32 kDa CTXLP isoform, as small cysteine-rich proteins have previously been identified as transcriptional activators[74,75], as per HIV-1 Tat (15 kDa) and HTLV Tax (40 kDa) role as viral transcription co-activators[76,77]. Additionally, low basal CTXLP staining in non-diseased cells suggests that it might have a role in normal physiology and gene regulation processes.

CTXLP Expression in Disease States

CTXLP is Expressed In Vivo in Humans

RNAseq Analysis of CTXLP+ Transcripts in Disease States

To evaluate the significance of CTXLP in disease, we evaluated the expression of CTXLP encoding ERVK loci in publicly available RNA-Seq datasets in the Sequence Read

TABLE 10

RNA-Seq datasets in the Sequence Read Archive (SRA) used for the analysis of ERVK expression.
Characteristics of RNA-Seq Studies

| Study | Condition | Tissue | Instrument | Strategy | Source | Selection | Layout | Read Length |
|---|---|---|---|---|---|---|---|---|
| SRP090259 | schizophronia | dorsolateral prefrontal cortex | AB SOLiD 4 System | RNA-Seq | transcriptomic | cDNA | single | 50 bp |
| SRP074904 | bipolar disorder | putamen or candidate nucleus | Illumina HiSeq 2000 | RNA-Seq | transcriptomic | cDNA | single | 99 bp |
| SRP110016 | multiple sclerosis | optic chiasm | Illumina HiSeq 3000 | RNA-Seq | transcriptomic | cDNA | single | 50 bp |
| SRP102685 | rheumatoid arthritis | synovium | Illumina HiSeq 2000 | RNA-Seq | transcriptomic | cDNA | paired | 101/99 bp |
| SRP068424 | HIV+/HCV+ | CD4+ T-cells | Illumina HiSeq 2500 | RNA-Seq | transcriptomic | random PCR | paired | 100/100 bp |

Archive (SRA) (Table 10). This analysis is summarized in Table 11 and FIGS. 34-37. These loci were identified by searching the SRA by disease affiliation and then evaluating each potential study based on samples size, tissue and sequencing quality. Preference was given to studies with large sample sizes, autologous controls, ex vivo disease-relevant tissue, and high sequencing quality. Paired-end reads were preferred to single-end. We focused on studies with fewer measures selecting for particular RNA sub-populations, which could have depleted ERVK RNA from the input.

The studies examine included breast cancer, prostate cancer, Amyotrophic Lateral Sclerosis (ALS), Multiple Sclerosis (MS), Rheumatoid Arthritis (RA), schizophrenia, bipolar disorder and HIV+/HCV+ infection. ERVK expression by HML group is summarized in Table 11. We found that the overall expression of ERVK in these disease states was low, and all HML groups were expressed. ERVK expression was highest in blood and cancerous tissue. In addition, we found loci with significantly different expression between patients and controls, but these were different for each study. Breast cancer, prostate cancer, and Multiple Sclerosis datasets contained expression patterns which could potentially distinguish patients from controls. These patterns were driven by differences in expression of CTXLP– loci and loci with inactivating Env mutations.

TABLE 11

ERVK expression by HML group in RNAseq datasets

| study | hml | Minimum | Median | Mean | SD | Maximum |
|---|---|---|---|---|---|---|
| SRP090259 | HML1 | 0 | 0.0125001 | 0.1179662 | 0.3213379 | 11.465101 |
|  | HML10 | 0 | 0.0389112 | 0.1801432 | 0.3599358 | 5.855237 |
|  | HML2 | 0 | 0.0214437 | 1.0386104 | 28.9656795 | 2800.179981 |
|  | HML3 | 0 | 0.0085536 | 0.0772390 | 0.1934535 | 5.249185 |
|  | HML4 | 0 | 0.0274862 | 0.0863698 | 0.1811918 | 3.655131 |
|  | HML5 | 0 | 0.0000000 | 0.0859580 | 0.2350117 | 4.212269 |
|  | HML6 | 0 | 0.0000000 | 0.1133778 | 0.3016479 | 4.628222 |
|  | HML7 | 0 | 0.0128447 | 0.0602345 | 0.1412095 | 3.037872 |
|  | HML8 | 0 | 0.0193117 | 0.2915583 | 11.7006947 | 1289.465670 |
|  | K14C | 0 | 0.0000000 | 0.0542510 | 0.1667601 | 3.168318 |
|  | LTR22B1#LTR/ERVK | 0 | 0.0000000 | 0.1161527 | 0.3674700 | 8.431398 |
|  | LTR22B2#LTR/ERVK | 0 | 0.0000000 | 0.1241151 | 0.3284346 | 2.537287 |
|  | LTR22C2#LTR/ERVK | 0 | 0.0000000 | 0.0826217 | 0.2326312 | 2.358517 |
|  | LTR22E#LTR/ERVK | 0 | 0.0000000 | 0.1423927 | 0.3607523 | 3.823776 |
|  | LTR3B_#LTR/ERVK | 0 | 0.0000000 | 0.0855171 | 0.2227743 | 3.975364 |
| SRP074904 | HML1 | 0 | 0.0000000 | 0.1061961 | 0.3018500 | 3.824492 |
|  | HML10 | 0 | 0.0000000 | 0.1789209 | 0.4687300 | 7.527670 |
|  | HML2 | 0 | 0.0072385 | 0.1691623 | 1.8123759 | 197.784008 |
|  | HML3 | 0 | 0.0000000 | 0.0917908 | 0.3355194 | 12.499732 |
|  | HML4 | 0 | 0.0000000 | 0.1252037 | 0.2851307 | 5.880441 |
|  | HML5 | 0 | 0.0000000 | 0.0909087 | 0.3553731 | 9.824726 |
|  | HML6 | 0 | 0.0000000 | 0.1070234 | 0.2950223 | 3.474829 |
|  | HML7 | 0 | 0.0000000 | 0.0786869 | 0.2005897 | 2.337186 |
|  | HML8 | 0 | 0.0000000 | 1.0845542 | 56.4008441 | 5752.139071 |
|  | K14C | 0 | 0.0000000 | 0.0566177 | 0.1889185 | 2.725355 |
|  | LTR22B1#LTR/ERVK | 0 | 0.0000000 | 0.0929150 | 0.2638750 | 4.531172 |
|  | LTR22B2#LTR/ERVK | 0 | 0.0000000 | 0.1643443 | 0.5538800 | 6.122761 |
|  | LTR22C2#LTR/ERVK | 0 | 0.0000000 | 0.0697017 | 0.2267312 | 3.086240 |
|  | LTR22E#LTR/ERVK | 0 | 0.0000000 | 0.1307125 | 0.3980359 | 4.137923 |
|  | LTR3B_#LTR/ERVK | 0 | 0.0000000 | 0.1079325 | 0.4247868 | 11.348338 |
| SRP110016 | HML1 | 0 | 0.0000000 | 0.0939917 | 0.4084061 | 6.709148 |
|  | HML10 | 0 | 0.0246443 | 0.1977949 | 0.6106722 | 8.991545 |
|  | HML2 | 0 | 0.0748145 | 0.1923879 | 0.7013925 | 25.584209 |
|  | HML3 | 0 | 0.0207453 | 0.0850121 | 0.4052984 | 14.993567 |
|  | HML4 | 0 | 0.0676325 | 0.2055983 | 0.5833871 | 17.361348 |
|  | HML5 | 0 | 0.0000000 | 0.0627547 | 0.2304348 | 4.292697 |
|  | HML6 | 0 | 0.0000000 | 0.1176631 | 0.3652445 | 4.943406 |
|  | HML7 | 0 | 0.0165461 | 0.0571758 | 0.1534795 | 2.665017 |
|  | HML8 | 0 | 0.0237677 | 0.0779974 | 0.5586158 | 31.923344 |
|  | K14C | 0 | 0.0000000 | 0.0319094 | 0.1170643 | 1.377055 |

TABLE 11-continued

ERVK expression by HML group in RNAseq datasets

| study | hml | Minimum | Median | Mean | SD | Maximum |
|---|---|---|---|---|---|---|
| | LTR22B1#LTR/ERVK | 0 | 0.0000000 | 0.0744216 | 0.2581293 | 2.729679 |
| | LTR22B2#LTR/ERVK | 0 | 0.0000000 | 0.1462319 | 0.6989967 | 4.712645 |
| | LTR22C2#LTR/ERVK | 0 | 0.0000000 | 0.0341152 | 0.1244866 | 1.373369 |
| | LTR22E#LTR/ERVK | 0 | 0.0000000 | 0.0483235 | 0.1773740 | 1.849842 |
| | LTR3B_#LTR/ERVK | 0 | 0.0000000 | 0.0478708 | 0.1685803 | 2.643292 |
| SRP102685 | HML1 | 0 | 0.0000000 | 0.1268767 | 0.3353742 | 4.052137 |
| | HML10 | 0 | 0.0304281 | 0.1950971 | 0.3455298 | 2.487003 |
| | HML2 | 0 | 0.0229832 | 0.1938948 | 1.8896213 | 219.947046 |
| | HML3 | 0 | 0.0000000 | 0.1223329 | 0.3815171 | 10.135953 |
| | HML4 | 0 | 0.0237879 | 0.1731327 | 0.3562414 | 5.434816 |
| | HML5 | 0 | 0.0000000 | 0.1089093 | 0.3043274 | 7.381214 |
| | HML6 | 0 | 0.0000000 | 0.1585309 | 0.3921706 | 4.257929 |
| | HML7 | 0 | 0.0000000 | 0.0912298 | 0.2878545 | 7.654548 |
| | HML8 | 0 | 0.0081154 | 2.0901303 | 98.5146905 | 8515.001781 |
| | K14C | 0 | 0.0000000 | 0.0706536 | 0.2391837 | 3.356916 |
| | LTR22B1#LTR/ERVK | 0 | 0.0000000 | 0.1234718 | 0.3168124 | 5.835195 |
| | LTR22B2#LTR/ERVK | 0 | 0.0000000 | 0.1937394 | 0.7134805 | 5.204694 |
| | LTR22C2#LTR/ERVK | 0 | 0.0000000 | 0.0902775 | 0.2336134 | 2.321173 |
| | LTR22E#LTR/ERVK | 0 | 0.0000000 | 0.1764475 | 0.4852693 | 4.627528 |
| | LTR3B_#LTR/ERVK | 0 | 0.0000000 | 0.1258778 | 0.3518004 | 4.700366 |
| SRP068424 | HML1 | 0 | 0.0000000 | 0.1546103 | 0.9128325 | 32.738476 |
| | HML10 | 0 | 0.0000000 | 0.1910084 | 0.5156409 | 8.690614 |
| | HML2 | 0 | 0.0000000 | 0.2408015 | 2.7415319 | 195.191293 |
| | HML3 | 0 | 0.0000000 | 0.1016756 | 0.7212861 | 32.342361 |
| | HML4 | 0 | 0.0000000 | 0.3064975 | 1.5651906 | 56.983694 |
| | HML5 | 0 | 0.0000000 | 0.1737037 | 0.9668251 | 22.605106 |
| | HML6 | 0 | 0.0000000 | 0.1513285 | 0.7387770 | 15.850478 |
| | HML7 | 0 | 0.0000000 | 0.0647419 | 0.2488850 | 5.277685 |
| | HML8 | 0 | 0.0000000 | 0.2023157 | 6.0970185 | 705.290157 |
| | K14C | 0 | 0.0000000 | 0.0794524 | 0.4541036 | 8.772424 |
| | LTR22B1#LTR/ERVK | 0 | 0.0000000 | 0.1325097 | 0.6447649 | 13.163549 |
| | LTR22B2#LTR/ERVK | 0 | 0.0000000 | 0.0693838 | 0.2707259 | 2.985159 |
| | LTR22C2#LTR/ERVK | 0 | 0.0000000 | 0.0440100 | 0.1820465 | 2.502976 |
| | LTR22E#LTR/ERVK | 0 | 0.0000000 | 0.0989893 | 0.3236325 | 4.761848 |
| | LTR3B_#LTR/ERVK | 0 | 0.0000000 | 0.1085489 | 0.5031198 | 8.617390 |
| SRP064478 | HML1 | 0 | 0.0000000 | 0.0601878 | 0.1912765 | 3.648491 |
| | HML10 | 0 | 0.0046214 | 0.1085939 | 0.2846323 | 3.347339 |
| | HML2 | 0 | 0.0114172 | 0.1068918 | 1.0920575 | 60.595378 |
| | HML3 | 0 | 0.0000000 | 0.0663053 | 0.2855648 | 11.555712 |
| | HML4 | 0 | 0.0122422 | 0.0818699 | 0.2004683 | 2.824911 |
| | HML5 | 0 | 0.0000000 | 0.0544799 | 0.1695744 | 3.303590 |
| | HML6 | 0 | 0.0000000 | 0.0687535 | 0.1899200 | 1.844958 |
| | HML7 | 0 | 0.0000000 | 0.0453627 | 0.1214706 | 1.274142 |
| | HML8 | 0 | 0.0000000 | 1.6252062 | 86.0880409 | 9238.633200 |
| | K14C | 0 | 0.0000000 | 0.0356487 | 0.1248000 | 2.091446 |
| | LTR22B1#LTR/ERVK | 0 | 0.0000000 | 0.0603075 | 0.1706618 | 3.324758 |
| | LTR22B2#LTR/ERVK | 0 | 0.0000000 | 0.0890397 | 0.3238018 | 2.795000 |
| | LTR22C2#LTR/ERVK | 0 | 0.0000000 | 0.0532044 | 0.1480141 | 1.725137 |
| | LTR22E#LTR/ERVK | 0 | 0.0000000 | 0.0890193 | 0.2572100 | 2.633204 |
| | LTR3B_#LTR/ERVK | 0 | 0.0000000 | 0.0548118 | 0.1628587 | 2.074693 |
| SRP058722 | HML1 | 0 | 0.0000000 | 0.1099929 | 0.5374086 | 19.771974 |
| | HML10 | 0 | 0.0000000 | 0.3120755 | 4.0788949 | 209.074420 |
| | HML2 | 0 | 0.0000000 | 0.3083341 | 7.0141530 | 716.132793 |
| | HML3 | 0 | 0.0000000 | 0.0819258 | 0.5721171 | 44.512233 |
| | HML4 | 0 | 0.00556(2 | 0.1631802 | 0.5669411 | 15.160832 |
| | HML5 | 0 | 0.0000000 | 0.0740519 | 0.2991551 | 8.570903 |
| | HML6 | 0 | 0.0000000 | 0.1508548 | 0.7572169 | 35.954051 |
| | HML7 | 0 | 0.0000000 | 0.0721502 | 0.2653196 | 7.406958 |
| | HML8 | 0 | 0.0000000 | 0.1347603 | 5.6620404 | 1058.007060 |
| | K14C | 0 | 0.0000000 | 0.0942404 | 1.3013323 | 77.419996 |
| | LTR22B1#LTR/ERVK | 0 | 0.0000000 | 0.1381469 | 1.3368361 | 54.714245 |
| | LTR22B2#LTR/ERVK | 0 | 0.0000000 | 0.1202672 | 0.6000457 | 6.857656 |
| | LTR22C2#LTR/ERVK | 0 | 0.0000000 | 0.0524224 | 0.3472964 | 9.886468 |
| | LTR22E#LTR/ERVK | 0 | 0.0000000 | 0.1179183 | 0.5986011 | 19.318676 |
| | LTR3B_#LTR/ERVK | 0 | 0.0000000 | 0.0871452 | 0.4722096 | 17.621088 |
| ERP000550 | HML1 | 0 | 0.0000000 | 0.0913613 | 0.6721108 | 25.754908 |
| | HML10 | 0 | 0.0000000 | 0.5265347 | 3.7211529 | 104.449407 |
| | HML2 | 0 | 0.0000000 | 0.3829747 | 9.4737435 | 494.573463 |
| | HML3 | 0 | 0.0000000 | 0.0758083 | 0.6113529 | 24.861316 |
| | HML4 | 0 | 0.0000000 | 0.1226314 | 0.5223547 | 39.400311 |
| | HML5 | 0 | 0.0000000 | 0.0545070 | 0.3573734 | 15.142432 |
| | HML6 | 0 | 0.0000000 | 0.1665188 | 1.1979633 | 46.109402 |
| | HML7 | 0 | 0.0000000 | 0.0653212 | 0.5217105 | 11.243053 |
| | HML8 | 0 | 0.0000000 | 0.0792274 | 2.3560620 | 344.064632 |
| | K14C | 0 | 0.0000000 | 0.0208334 | 0.0993372 | 1.730934 |
| | LTR22B1#LTR/ERVK | 0 | 0.0000000 | 0.0496653 | 0.2114473 | 3.282185 |

TABLE 11-continued

ERVK expression by HML group in RNAseq datasets

| study | hml | Minimum | Median | Mean | SD | Maximum |
|---|---|---|---|---|---|---|
| | LTR22B2#LTR/ERVK | 0 | 0.0000000 | 0.1243072 | 0.6755299 | 6.645951 |
| | LTR22C2#LTR/ERVK | 0 | 0.0000000 | 0.0542908 | 0.3050922 | 6.011783 |
| | LTR22E#LTR/ERVK | 0 | 0.0000000 | 0.0386306 | 0.1391434 | 2.082330 |
| | LTR3B_#LTR/ERVK | 0 | 0.0000000 | 0.0649027 | 0.4006698 | 8.956652 |

The lack of differential total RNA expression in controls versus the ALS cohort (FIG. 37), which is intriguing given data from protein immunostaining showing obvious differences between clinical groups (see below, FIGS. 38-42). PCA analysis reveals that expression of select ERVK CTXLP+ loci cluster in controls versus the ALS cohort (FIG. 37), suggesting that specific CTXLP loci may drive the expression of CTXLP protein in ALS.

ERVK CTXLP Expression is Enhanced in CNS Tissues from Patients with Amyotrophic Lateral Sclerosis (ALS)

ALS pathology involves degeneration of upper (brain) and lower (spinal cord) motor neurons, leading to muscle weakness and paralysis (reviewed in [78-80]). Brain and spinal cord inflammation is a hallmark of ALS (reviewed in [81,82]). The majority of ALS cases are sporadic, and the cause of this disease remains unknown. Here, we focus on the connection between neuropathology associated with ALS and ERVK CTXLP, such as proteinopathy[83,84], aberrant calcium signalling[85], demyelination[86], and oligodendrocyte dysfunction[87].

To show that CTXLP protein is not only expressed in in vitro cell cultures, but also in ex vivo (autopsy) human tissues, spinal cord and brain tissues from neuro-normal controls and patients with ALS were assayed for CTXLP by western blot (FIG. 38) and confocal microscopy (FIGS. 39-42). Western blot analysis of motor cortex specimens from neuronormal controls and patients with ALS reveals significantly enhanced CTXLP expression in ALS (FIG. 38A, p<0.05). CTXLP was concomitantly expressed with inflammation and tissue injury marker CX3CL1 (FIG. 38B)[88]. Analysis of cervical spinal cord tissues also demonstrates elevated CTXLP and CX3CL1 expression in ALS as compared to controls, alongside a modest decrease in levels of voltage-gated calcium channel CaV2.2 in ALS (FIG. 38, C-F). Together, these results point to tissue injury and inflammation in CTXLP+ tissues from patients with ALS.

In addition, confocal microscopy of cervical spinal cord (FIG. 39A) and motor cortex specimens (FIG. 39B) from neuro-normal controls and patients with ALS reveals substantially enhanced CTXLP expression in ALS. In the motor cortex, CTXLP+ cells were neurons (based on MAP2 neuronal marker). This is consistent with previous observations of ERVK proteins present in the motor cortex of patients with ALS[67,89,90]. Notably, basal CTXLP expression was mostly nuclear in neuronormal tissues, whereas CTXLP exhibited a pattern of cytoplasmic aggregation in motor cortex tissues from patients with ALS (FIG. 39B). Enhanced MAP2 staining in the axon hillock of CTXLP+ pyramidal neurons may be an indicator of virus activity, as seen during rabies infection[91,92]. This pattern of CTXLP expression coincided with a notable decrease in CaV2.2 expression in ALS as compared to controls. Based on staining pattern, this decrease may represent a loss of CaV2.2 expressing pyramidal neurons, as well as smaller CaV2.2+ cells[93]. Remarkably, CTXLP patterning in the cervical spinal cord exhibited a ring pattern surrounding MAP2+ neurons (MAP2 marks neuronal axons in grey, FIG. 39A, far right panel).

Our evidence further indicates that CTXLP can alter oligodendrocyte behavior. In the CNS, highly specialized cells called oligodendrocytes protect neuronal axons by wrapping them in an extensive plasma membrane compacted to produce the myelin sheath[94]. Oligodendrocyte precursor cells (OPCs) are a pool of immature oligodendrocytes, which express characteristic markers such TCF4, Olig1 and Olig2 [95,96]. Upon differentiation into mature oligodendrocytes, they begin to express myelin proteins such as PLP, MOG and MAG[95]. Oligodendrocytes must myelinate early post-differentiation and myelination occurs within a short timeframe (12-18 hours), where their extended processes ensheath 50-60 axonal segments simultaneously[97]. Some CNS regions (spinal cord, brainstem and visual cortex) exhibit early myelination during human development, whereas other regions undergo myelination into adulthood (prefrontal cortex and association fibers). Pools of OPCs can remain in tissues and are capable of migration and later differentiation into mature oligodendrocytes, often in response to brain injury[98]. However, in many disease states, an attempt at remyelination is most often unsuccessful[98]. A prevailing theory surrounding defects in remyelination is that despite increased numbers of OPCs in injured tissue, these precursor cells become stalled in an immature state and fail to properly differentiate into mature oligodendrocytes[96,98]. Alterations in OPC markers, such as enhanced TCF4 and Olig1 occurs in tissue lesions from patients with MS[99,100].

Our observations show that CTXLP expression occurs in either lateral and/or anterior cortical spinal tracts in ALS (FIG. 40). Strong CTXLP+ staining coincides with demyelinating lesions, as shown by solochrome cyanine staining of adjacent tissues (FIG. 40). Increased TCF4 (oligodendrocyte precursor marker) is also evident in association with CTXLP expression in tissue from patients with ALS (FIG. 40).

Figure 41:
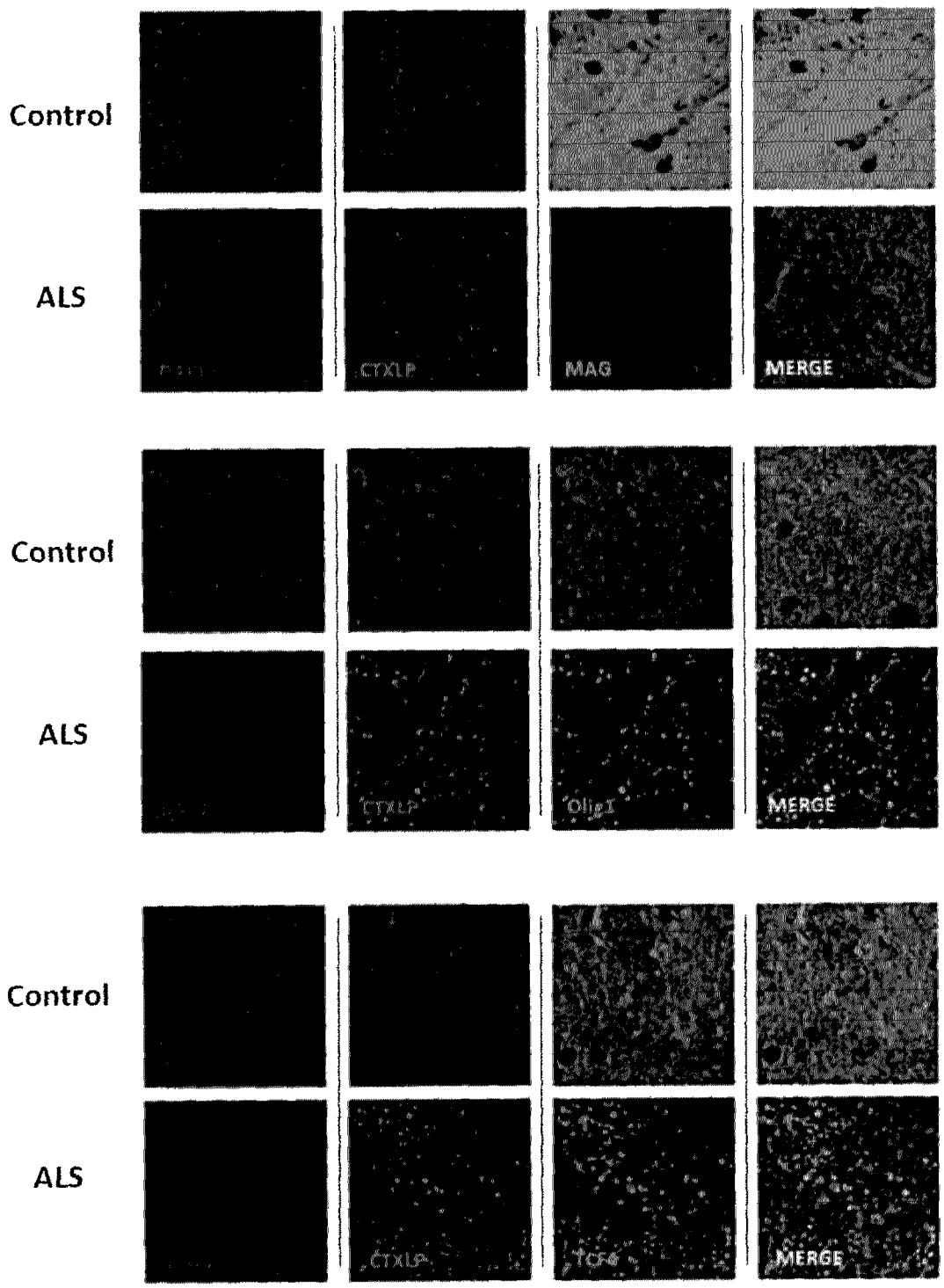
FIG. 41 depicts confocal micrographs of ERVK CTXLP levels are associated with demyelination and CTXLP is enhanced in TCF4+Olig1+ oligodendrocyte precursors in cervical spinal cord tissues from patients with ALS. Representative 20× confocal micrographs of ERVK CTXLP expression in ex vivo cervical (CC) spinal cord of a neuronormal control (NN, n=3) and a patient with ALS (n=3). Notably decreased myelin stain as measure my MAG protein expression (green) is evident in ALS tissue as compared to control. In ALS tissue, CTXLP expression (red) co-localizes with TCF4 (green) or Olig1 (green) markers indicative of oligodendrocyte precursor cells. DAPI stain depicts cellular nuclei.

FIG. 41 depicts increased numbers of TCF4+ and Olig1+ cells expressing CTXLP in cervical spinal cord tissue from patients with ALS, as compared to controls. This indicates that CTXLP expression in the spinal cord of patients with ALS does indeed occur in oligodendrocytes (FIGS. 39-41), specifically in cells expressing OPC markers.

Neurite outgrowth inhibitor (Nogo-A) is a key regulator of oligodendrocyte precursor cell (OPC) differentiation; when OPCs express Nogo-A they are unable to progress towards a mature oligodendrocyte phenotype, which is capable of myelination[101,102]. Thus, enhanced expression of Nogo-A in OPCs in the context of inflammation and disease states prevents axonal regeneration by restricting OPC maturation[103-105]. As an example, demyelinated MS lesions show an increased abundance of Nogo-A+ OPCs, yet the inability of OPCs to mature is proposed as the mechanism driving a non-permissive environment leading to remyelination failure[103,106,107]. In mature oligodendrocytes, Nogo-A expression prevents axonal sprouting and is expressed in these cells until the initiation of active myelination.

Nogo-A is implicated in a variety of neurological conditions, such as spinal cord injury, peripheral neuropathies, stroke, temporal lobe epilepsy, Alzheimer's disease, ALS, MS and schizophrenia[101,108-110]. Nogo-A has been identified as a prognostic marker and therapeutic target in ALS due to its substantial expression in muscle tissue from patients with motor neuron disease[111,112]. Mechanistically, Nogo-A expression destabilizes neuromuscular junctions[113-116]. Indeed, clinical trials using human anti-Nogo-A antibodies have been performed (ATI 355 from Novartis Pharma and Ozanezumab and GSK1223249 from GlaxoSmithKline)[101,117,118]. These therapies were designed to target Nogo-A expression in the periphery (intravenous infusions), but may fail to block Nogo-A expression in the CNS (FIG. 42), thus explaining the negative results in Phase II clinical ALS trials with Ozanezumab[119,120]. Of note, genetic polymorphism reticulon 4 receptor (RTN4R) gene encoding the Nogo-A receptor (NgR1), is associated with sporadic ALS[121].

FIG. 42 demonstrates that CTXLP expression in the spinal cord of patients with ALS is associated with elevated Nogo-A expression, specifically in OPCs and other cell types. This specifically occurs in areas of myelin depletion (see FIG. 41). It has been demonstrated in human spinal cord, that select myelin protein rings (PLP, MOG, but not MAG) are detectable by immunohistochemistry even 3 years after injury in degenerating fibre tracts exhibiting the absence of intact axons[122]. Nogo-A expression also persists in degenerating spinal tissue and may create a non-permissive environment for axon regeneration[122]. Furthermore, it has been shown that Nogo-A favours a pro-inflammatory context[123], one that would promote ERVK expression via modulation of NF-κB and pro-inflammatory cytokine secretion[67].

ERVK CTXLP Expression is Enhanced in Cancer Cells

To further evaluate the potential pathogenic activity of CTXLP, we examined CTXLP levels in cancer to follow-up on our observation that NCCIT human embryonic carcinoma line spontaneously expressed CTXLP. The localization pattern that included the cytoplasm also suggested that this represented a stage in course of aberrant CTXLP expression. Thus, we assayed prototypic teratocarcinoma (NCCIT) and breast cancer cells (T47D) for CTXLP expression as compared to the karyotypically normal, non-cancerous, cell lines astrocytic SVGA cells (FIG. 43). Cancer cells clearly show higher levels of ERVK CTXLP as compared to non-cancerous cells. A cancer screen also reveals several cancers exhibiting enhanced CTXLP levels, including T cell lymphoma, Acute T-cell leukemia, epithelioid carcinoma, Burkitt's lymphoma, neuroepithelioma, prostate, breast, ovary, testis and skin cancers (FIG. 44).

In summary, ERVK CTXLP localized to the motor cortex and spinal cord sections from autopsy samples of patients with ALS, but not neuronormal controls. Concomitantly, CTXLP expression was substantially enhanced in diseased ALS tissues aligning with oligodendrocytes, Nogo-A expression and demyelinated lesions. In addition, cancer cell lines and tissue expressed greater levels of CTXLP relative to normal controls. Together, these findings provide significant evidence for the activity of CTXLP in ALS and certain cancers.

Pathological Consequences of CTXLP Expression

ERVK CTXLP Enhances NF-κB Protein Expression, Whereas ERVK Env Does Not

Real Time PCR analysis of Transfected 293T Cells

To investigate how cells may react to the expression of CTXLP and SU, RT-PCR analysis was used to measure the expression of the pro-inflammatory NF-κB p65 subunit and the anti-viral response protein IRF7. This analysis showed that both CTXLP and SU triggered a marked increase in the mRNA expression of NF-κB p65. Conversely, neither protein was able to trigger an upregulation of IRF7 (FIG. 45). The upregulation of NF-κB p65 may be beneficial to the ERVK provirus as it is able to 1) act as a direct transcriptional activator of the ERVK LTR, and 2) trigger inflammatory conditions that are conducive to ERVK activation[64,67].

Confocal Microscopy Analysis of Transfected 293T Cells

Figure 46:
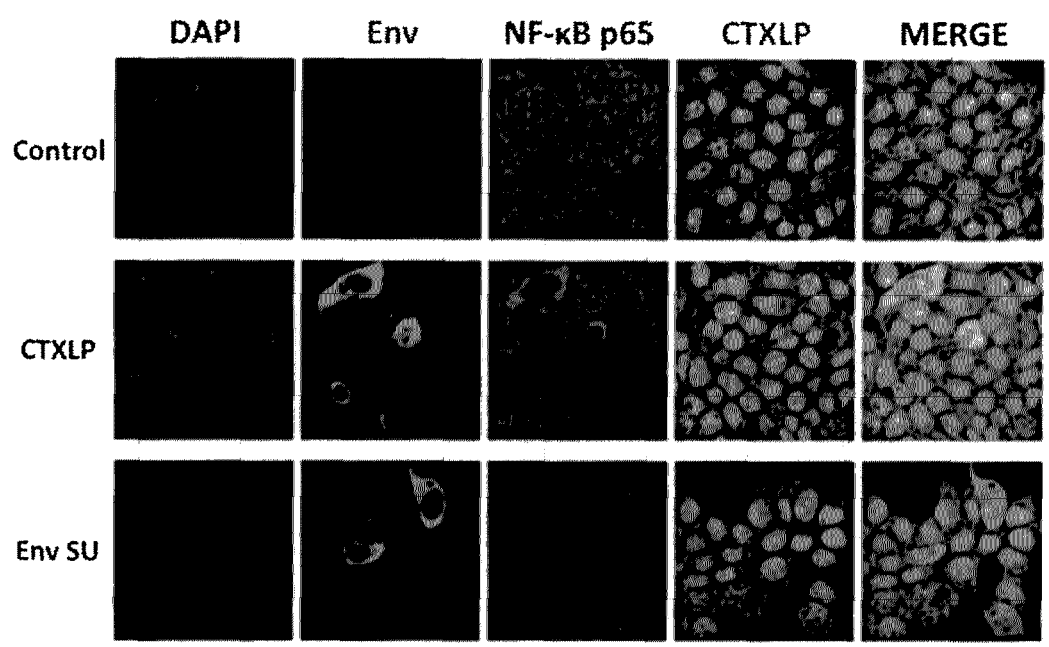
FIG. 46 depicts confocal images of control, CTXLP-expressing and SU-expressing 293T cells. Cells were stained with DAPI nuclear stain, and antibodies against Env SU (green) fluorescent dye, NF-KB p65 (red) fluorescent dye and CTXLP (grey/white) fluorescent dye. Only CTXLP expressing cells exhibit upregulated NF-KB p65 expression. Representative micrographs of n=3 experiments.

SU and CTXLP transfected 293T cells were also stained to determine whether the presence of either of these proteins was sufficient to trigger the expression of NF-κB p65. It was observed that CTXLP was able to trigger NF-κB p65 protein expression, whereas SU was unable (FIG. 46). This was in stark contrast to the RT-PCR results in FIG. 45, where both ERVK SU and CTXLP induced NF-κB p65 transcription. As expected, there was a marked increase in SU expression in CTXLP-expressing cells, as the epitope for the SU antibody binds to either SU or CTXLP as both proteins contain the SU amino acid sequence.

To further confirm whether the effect of NF-κB induction by CTXLP is a general phenomenon occurring the multiple cell types, astrocytic SVGA cells were also transfected as described above and evaluated for NF-κB protein expression. Interestingly, both NF-κB p65 and p50 proteins were induced by CTXLP, but not ERVK SU overexpression (n=4). This finding is notable, considering we have shown that ERVK transcription is mediated by IRF1, p50 and p65 transcription factors, and impacts ERVK expression in ALS[67]. It is also intriguing considering TRAF proteins were predicted to be interacting partners of CTXLP, and may alter NF-κB signalling[124,125].

ERVK CTXLP Depletes CaV2.2 CCAT Protein Expression

A surprising feature of several voltage-gated calcium channels (VGCCs) is the ability of their C-terminal fragments to translocate to the nucleus and impact gene expression. Termed calcium channel-associated transcription regulator (CCAT) by Gomez-Ospina et al. in 2006[126], these novel gene products encoded within the VGCC sequences. In most cases, an antibody targeting a C-terminal CACNA1 epitope will identify an approximately 75 kDa CCAT fragment with a cellular distribution within the nucleus (or nuclear fractions), unlike the intact channel protein localized to the cytoplasm and membrane[126,127]. VGCC CCAT proteins can be regulated by cell signalling events. For example, cellular signals that promote CaV1.2 CCAT nuclear localization include treatment of neurons with 2.5 mM EGTA (a chelator which reduces free extracellular calcium), whereas 65 mM KCl treatment (mimicking tonic activity of VGCC) decreased nuclear CCAT levels[126]. Several signals which drive high intracellular calcium levels in neurons, including 100 µM glutamate, depolarization and NMDA signalling, lead to decreased nuclear CCAT levels[126].

We have previously demonstrated an inverse correlation between CTXLP and voltage-gated calcium channel CaV2.2 expression in ALS brain and spinal cord tissues (FIGS. 38 and 39). To further extend this observation, we performed in vitro experiments of CTXLP and ERVK SU exposure by overlaying immunoprecipitation products on human astrocytes (FIG. 47). Treatment of SVGA cells with CTXLP, but not ERVK SU, resulted in the depletion of Cav2.2 CCAT (75 kDa), as measured by western blot analysis and confocal microscopy. A decreased in the full size CaV2.2 channel (220 kDa) was also observed (n=2, data not shown). Thus, CTXLP in the CNS may lead to an overall decrease in CaV2.2 channel and CaV2.2 CCAT expression, thus explaining the observed decreased expression of CaV2.2 in ALS (FIGS. 38 and 39). The regulatory role of CaV2.2 on cellular transcription is currently unknown.

Figure 48:
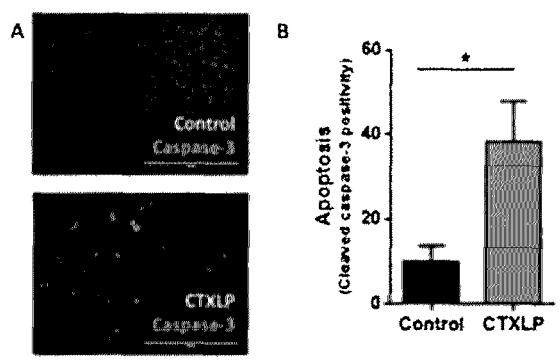
FIG. 48 depicts Caspase-3 expression in SVGA cells in control and CTXLP-treated conditions after 24 hours. (A) Images of live cells after 24 hours taken using EVOS imager, top image depicts untreated control cells and bottom image depicts cells treated with 5 μl of CTXLP immuno-precipitated solution. (B) Graphical depiction of caspase-3 expression in control and CTXLP-treated cell after 24 hours.

ERVK CTXLP is Toxic Via Mechanisms that Differ from ERVK Env-Mediated Toxicity Treatment of SVGA Astrocyte Cells with ERVK Env Proteins Isolated Via Immunoprecipitation To determine the neurotoxicity of CTXLP, SVGA astrocyte cells were treated with CTXLP proteins isolated from NCCIT cells via immunoprecipitation (IP). This simulates conditions wherein CTXLP would enter the cell from the outside and possibly exert its effects by binding to cell surface receptors (such as calcium channels). There was considerable variation in the neurotoxicity assays, which may be due in part to the fact that cells were dosed by volume of CTXLP. There was no reliable way to measure the concentration of the protein in the IP product, as protein concentration was well below sensitivity of our in-house BCA assay (20 μg/ml). However, a much higher number of cells treated with CTXLP expressed caspase-3 (apoptosis marker used in the toxicity assays) than control cells demonstrating that CTXLP was toxic to astrocytes, even at unmeasurably low concentrations (FIG. 48).

A separate toxicity assay was performed by treating astrocytes with SU and CTXLP (respectively) in the presence and absence of calcium. Theoretically, if CTXLP does in fact contain an ω-conotoxin domain, by flooding cells with calcium and thus saturating calcium channels, it's ability to exert toxic effects on cells via calcium channel binding should be blocked. This is what was seen in CTXLP, but not SU, toxicity assays. In the presence of calcium, the levels of caspase expression in CTXLP-treated cells were similar to controls conditions. They were also less than those of cells treated with CTXLP in the absence of calcium. Further, cells treated with SU in the presence and absence of calcium expressed similar levels of caspase-3 in comparison to CTXLP alone (FIGS. 49 and 50).

Cells in this same toxicity assay were also analyzed at later time points. It was observed that CTXLP and SU-treated cells appeared to be able to continue to replicate despite high levels of caspase expression. After 8 days, cells in both conditions increased in cell density despite high levels of caspase-3 expression and without the addition of media. These observations suggest that these cells may have been transformed oncogenically[129-131]. Conversely, control cells were not viable after 8 days in culture (FIG. 51). It is interesting to note that some viruses, such as the influenza virus, require caspase expression to replicate efficiently[132]. Moreover, HIV Tat, the viral transactivator, induces caspase activation as part of its neurotoxic mechanism[38].

It is notable that the trend of enhanced caspase-3 positivity is seen in both treated (FIGS. 48-51) and transfected cells (FIG. 52), suggesting that exposure to CTXLP and/or cellular production of CTXLP in vivo may be toxic to cells.

ERVK CTXLP Expression Drives Morphological Changes in Cells

Figure 53:
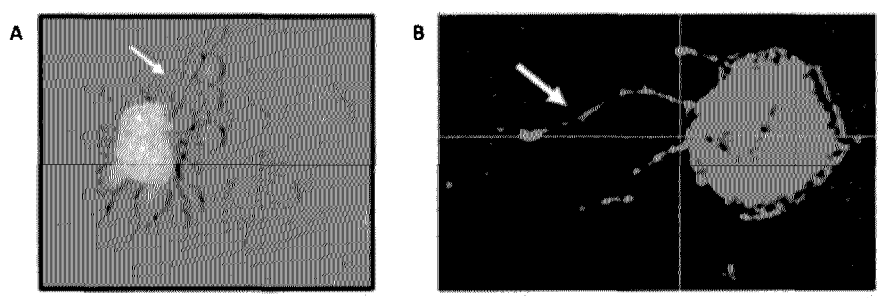
FIG. 53 depicts abnormal cellular morphology in cells exposed to CTXLP. (A) Fluorescent image of CTXLP-treated SVGA cell expressing caspase-3 (green) and stained with DAPI nuclear stain (blue). (B) Confocal image of Env SU expression (green) in a CTXLP-expressing 293T cell.

ERVK CTXLP-treated SVGAs and 293T cells transfected with ERVK CTXLP-encoding plasmids were imaged to observe the cellular morphology. Though many of the cells looked normal in appearance, it was observed that an increased number of the cells produced long filipodia (FIG. 53). As well, the formation of syncytia (multinucleated cells) was also observed amongst cells exposed to CTXLP. These features are characteristic of retrovirus-infected cells and are known to promote virus transfer between cells[133].

This data indicates that ERVK CTXLP expression has the capacity to enhance NF-κB p65/p50 and CaV2.2 proteins that play a critical role in ALS pathogenesis. In addition, CTXLP administration or transfection induced significant levels of capase-3. The induction of caspase-3 activation and apoptosis by CTXLP was inhibited by excess extracellular calcium pointing to a calcium channel mediated activation of toxicity. Remarkably, despite the initial die off of cells, cells remaining in the cultures appeared to demonstrate appreciable cellular proliferation relative to control suggesting the induction of a carcinogenic process.

ERVK CTXLP can be Targeted by Small Molecule Therapeutics

Taken together this data strongly indicates that targeting CTXLP would have significant therapeutic value in ALS. To this end, we have began investigating A small molecule inhibitors to capable of counteracting the pathological effects associated with CTXLP expression is of therapeutic value. A drugs screen in ERVK CTXLP-expressing NCCIT cells was performed to evaluate potential efficacity against CTXLP (FIG. 54). Michael acceptor electrophile (MAE) compounds are known to inhibit HIV Tat-dependent transcription by interfering with thiols in its cysteine-rich domain[134,135]. As CTXLP and HIV Tat share commonality in their cysteine-rich domains (FIG. 14), we evaluated a series of MAE compounds including curcumin, rosmarinic acid, gambogic acid and celastrol. Two MAE drugs, celastrol (Cel) and gambogic acid (GA), were identified as suppressing CTXLP expression in NCCIT cells in the low micromolar range (FIG. 54).

Derived as an active compound from the Thunder God vine (Tripterygium wilfordii Hook F), celastrol (pubchem.ncbi.nlm.nih.ciov/compound/celastrol) is a plant-derived triterpene with antioxidant, anti-viral and anti-inflammatory activity[134,136,137]. Celastrol is currently used as a therapeutic agent for rheumatoid arthritis (RA) and lupus in China[136,138]. Celastrol has also been shown to impact pathological outcomes and symptoms in animal models of RA[139], as well as inflammatory markers in activated fibroblast-like synoviocytes from patients with rheumatoid arthritis[140]. Celastrol has been shown to limit beta-amyloid pathology and neuronal degeneration in Alzheimer's disease models[141]. Its anti-cancer properties are also under investigation[142].

Gambogic acid (pubchem.ncbi.nlm.nih.ciov/compound/16072310) is an active compound from the Gamboge tree (Garcinia hanburyi), with antioxidant, anti-viral and anti-inflammatory properties)[134,143-145]. It has been shown to be neuroprotective[146], and inhibit spinal cord injury and inflammation in a rat model[147]. Both celastrol and gambogic acid can prevent mutant huntingtin protein aggregation and its neuronal toxicity[148]. The anti-cancer properties of gambogic acid are also under investigation[144,145].

Improvements on drug efficacy, toxicity and tissue-targeting are possible by using MAE-derivatives, related compounds (Table 12), soluble analogues and nanosystem delivery to the brain[149,150]. Here we provide proof-of-concept that CTXLP is druggable using small molecules (FIGS. 54-58); further drug development may improve upon the anti-CTXLP effects of celastrol and gambogic acid.

TABLE 12

Compounds with similar structures and/or bioactivities with celastrol and gambogic acid found using PubChem open chemistry database.

| Celastrol (CID 122724) | PubChem CID | Gambogic Acid (CID 16072310) | PubChem CID |
| --- | --- | --- | --- |
| Celestrol methyl ester | 10004662 | Gambogic acid | 86767267 |
| Salaspermic acid | 44593364 | Gambogic amide | 6710783 |
| Demethylzeylasteral | 10322911 | Gambogellic Acid | 10651612 |
| Wilforol A | 10096097 | Isomorellin | 12313004 |
| Isoiguesterin | 11373102 | Gambogin | 15298998 |
| Tingenone | 441687 | Isogambogenic acid | 15299002 |
| ZXENWDWQTWYUGY-DIS-OOBLMSA-N | 122852 | Gambogic acid | 15559465 |
| JFACETXYABVHFD-YDUKQFKJSA-N | 90488873 | Desoxymorellin | 16078248 |
| JFACETXYABVHFD-ZAZHEN-ERSA-N | 86280086 | Isomorellin | 16078249 |
| Tripterygone | 197388 | Morellic acid | 16078251 |
| JFACETXYABVHFD-NLFRDL-PRSA-N | 51455907 | Forbesione | 16078254 |
| Maitenin | 101520 | Cochinchinone C | 70697833 |
| Sandorinic acid C | 11048975 | Cochinchinone C | 73019072 |
| Bryonolic acid | 472768 | Neogambogic acid | 6438568 |
| Bryonolic acid | 6712218 | Neogambogic acid | 92132426 |
| Tingenone | 355376 | Gambogic acid | 99639195 |
| Isoiguesterin | 328559 | Isogambogenic acid | 101389903 |
| Pristimerine | 264268 | Gambogin | 101690778 |
| Polpunonic acid | 169521 | Gaudichaudione A | 101949804 |
| 22-Hydroxytingenone | 73147 | Gambogenic Acid | 102004807 |
| Iguesterin | 46881919 | Gambogin | 102004809 |
| Celastrol methyl ester | 159516 | Neogambogic acid | 102004925 |
| 3-Oxoglycyrrhetinic acid | 111253 | Forbesione | 102303099 |
| Tri pterin | 4274774 | Morellic acid | 102533562 |
| QVCXDBCRBHXXAD-WFVGHVPHSA-N | 24861322 | Gambogic acid | 126963722 |
| KQJSQWZMSAGSHN-PA-COHSDFSA-N | 16757868 | Gambogic acid | 134129562 |
| 20alpha-Hydroxytingenone | 10717799 | Gambogenic Acid | 9895478 |
| JFACETXYABVHFD-LQSRW-FAZSA-N | 16757909 | Gambogic acid | 9852185 |
| 20beta-Hydroxytingenone | 44559597 | Gambogic acid | 11599836 |
| ZTCAJLZRROIDHU-WAFCJU-BUSA-N | 44572792 | Gambogic amide | 25252739 |
| FXLVCCDIUNLGKU-BRUCSKOJSA-N | 5701992 | Gambogellic Acid | 52945437 |
| RemangiloneD | 44558996 | Morellic acid | 54580250 |
| ZKJXUKUIPQCUMI-QSZQY-ENJSA-N | 10624078 | Gambogic acid | 3451 |

TABLE 12-continued

Compounds with similar structures and/or bioactivities with celastrol and gambogic acid found using PubChem open chemistry database.

| Celastrol (CID 122724) | PubChem CID | Gambogic Acid (CID 16072310) | PubChem CID |
|---|---|---|---|
| AIXBDINLSQYZGS-JWNVRJNBSA-N | 45482038 | Acetyl isogambogic acid | 6857789 |
| GSIDIGLXCWJQPN-YMEQZMBDSA-N | 25424418 | Gambogin | 11753679 |
| DMHJWMODPYSFCD-DUSJHGMNSA-N | 71498413 | Gambogic amide | 56951189 |
| PDMJIWXURDBAOZ-CIFOREJBSA-N | 45482047 | Gambogic acid | 91668478 |
| 21-Oxopristimerine | 50907761 | Gambogic acid | 5281632 |
| Dispermoquinone | 53320376 | Gambogic acid | 5380091 |
| QHYPSOWPDMYTTQ-UNNRZNSMSA-N | 71498452 | Gambogic acid | 5353639 |
| QIRUFAFQGKOTKA-YKUCPAPWSA-N | 389017 | Isomorellic acid | 9915833 |
| OQLDDXDMTOPTDO-QRARIYCASA-N | 10695614 | Gambogenic Acid | 10794070 |
| QGWDYPREORDRIT-DGRUGRQQSA-N | 16745529 | Gambogic acid | 20054919 |
| QGWDYPREORDRIT-DSIOGZMYSA-N | 229868 | Isogambogenic acid | 70639870 |
| ZNFSSQAJGMMWBY-WXPPGMDDSA-N | 25197280 | Gambogic acid | 70639872 |
| WHDKOWNIOGJXHK-PTRAYGLTSA-N | 45482045 | 10-Hydroxygambogic Acid | 71450485 |
| OQLDDXDMTOPTDO-PEKWGEHZSA-N | 44289021 | BLDWFKHVHHINGR-UHFFFAOYSA-N | 125071 |
| GAPWCQHXCIXKLV-RKHSXEAASA-N | 6708798 | Deoxymorellin | 635828 |
| QGWDYPREORDRIT-UHFFFAOYSA-N | 3129312 | Morellic acid | 5319893 |
| RRRZQVJZDVPAJN-ZRCCSVPJSA-N | 25197172 | Isomorellin | 5364585 |
| Polpunonic acid | 169521 | Isomorellic acid | 5366120 |
| KZCZQJNPWZPAEJ-ZRCCSVPJSA-N | 25195610 | DRRWWKSGTSQOON-DXMWQDMHSA-N | 52947871 |
| Dihydrocelastrol | 10411574 | 7-Methoxyepigambogic acid | 45270567 |
| FATJTRUVRFSESL-HZYNXAPGSA-N | 44566365 | UONSIJYWYKPEDK-NXWWLHKBSA-N | 45272194 |
| Isoiguesterinol | 10477355 | BIGAHFWHALQTRA-TYAVBBKTSA-N | 45272195 |
| Wilfolic acid C | 44559659 | GJFGYTWPUIBTJN-UOCUBHIGSA-N | 45272197 |
| HVRSOVWJUJGHSI-JHGSJXKWSA-N | 44558965 | UJUARHDVFLLQMF-KELXBUOKSA-N | 45272281 |
| 11-Oxoursonic acid | 22210052 | BMPKGNCYXQRUMA-BLACGAOQSA-N | 52941797 |
| 6-Oxopristimerol | 11754914 | JEWKRGWMKMUBBF-JFDIIJRYSA-N | 52943022 |
| MAAVNXPPBHQXNL-INMPMWFSSA-N | 6710688 | ORRQVYBMKAECLD-KMIBLQPDSA-N | 52946647 |
| GZKMFYLBPHPWEI-DGRUQNLJSA-N | 363631 | QQQNFIABWPXSFD-PUYFONRISA-N | 52946668 |

TABLE 12-continued

Compounds with similar structures and/or bioactivities with celastrol and gambogic acid found using PubChem open chemistry database.

| Celastrol (CID 122724) | PubChem CID | Gambogic Acid (CID 16072310) | PubChem CID |
|---|---|---|---|
| LUSKWXDBHNQVEL-JXZIT-WAVSA-N | 53323497 | JTTOKKDLXZMVBA-IHECDDROSA-N | 52947870 |
| QGWDYPREORDRIT-NFGWGJPRSA-N | 73758286 | XSDFUWMDPUDYHN-CLKBEGISSA-N | 52948934 |
| CDOKUYLTAYCBST-GKMFGOQDSA-N | 9869964 | Gaudichaudione H | 57345562 |
| CPFUJAKVJBYWJA-BTRWLOMLSA-N | 10411393 | 6-Hydroxycluvenone | 57390441 |
| YXEPIOPYEDGEEP-IITIDZKMSA-N | 71498373 | KCALBYYRHOKKBO-BCFMDSCZSA-N | 57395879 |
| KGQOHECLTONQOT-HKFGFSCZSA-N | 10645721 | CSIZKMXLDPOBKM-PQIHDOCZSA-N | 57395880 |
| QEACUYQTRMGOSD-MZRSIZMESA-N | 14465806 | XZPYBDPGHSLINX-OHTINKFRSA-N | 71720741 |
| CVAILKMOFONEDU-KRJMWWHISA-N | 15765122 | KCYKVBCVFBSOKZ-RWPPGCTJSA-N | 118737824 |
| 2-Picenecarboxylic acid | 23757062 | PVRDWAUIIJESEC-WFSGSTODSA-N | 118737833 |
| QLTFHGMEDZMMTF-VUQPYPCZSA-N | 44298352 | OIZCJCKDTJMDFV-CVTCUNNCSA-N | 118737835 |
| OKOGABAEYJRJOB-JSJVQHDDSA-N | 46184390 | KSEYPOHNDKJEPF-ILHGWRPKSA-N | 45267055 |
| UZEJIMRGSSLBIV-SAQIBKBSSA-N | 25197281 | Dimethyl gambogate | 6857785 |
| Fupenzic acid | 12045007 | Garcinolic acid | 6857794 |
| WZAUFGYINZYCKH-AQCDROMSSA-N | 6708673 | Methyl gambogate | 12113746 |
| Amazoquinone | 44559090 | Decahydrogambogic acid | 5149276 |
| Dihydrocelastryl diacetate | 9828620 | REDMIYQFNIRTDF-WIKVJIRTSA-N | 16758035 |
| 20-Epi-isoiguesterinol | 21575471 | VZXLWEWYBUGLJA-SAABBMRESA-N | 44449775 |
| TTWPKNPRMGVGJO-QZLVDJLTSA-N | 49797930 | FJRORJDZZLUAPP-BUJCIKCXSA-N | 25208438 |
| 23-Nor-Blepharodol | 53320826 | Dimethyl-Ga | 44449753 |
| GSIDIGLXCWJQPN-BRLXHVQISA-N | 5336986 | 7-Methoxygambogic acid | 45268014 |
| SAOOBRUHTPONGX-UANCAJPASA-N | 6708713 | 7-Methoxygambogellic acid | 25208761 |
| PLXMKOYILCBYGS-UXDHXBHYSA-N | 6710689 | VZIUOBFNNRUPAK-QBEIJZEMSA-N | 71717656 |
| QGWDYPREORDRIT-VLYMFKARSA-N | 44435792 | JDGCURVTMMXMDY-TYTBCFIUSA-N | 71718886 |
| DQHHRVQZUPBARM-LRRZNWEGSA-N | 90233240 | FTTRVECHPLAERQ-UZTNAXEXSA-N | 71717668 |
| YQUGEUGWFBESNQ-WXPPGMDDSA-N | 118408942 | UCIJDAOAFDHFEA-XYBONBLRSA-N | 71717669 |
| QOGSXJHNNDQXSS-YN-JIRTJXSA-N | 88303297 | PUDIAMZKKXFSOI-UZTNAXEXSA-N | 71717674 |
| SKMCTUIWOMRTKB-RLLZTQLFSA-N | 68198583 | CDIIOQLRYIQLOZ-JSJFTWSHSA-N | 71717675 |
| GAVQRDLYJPTRLX-NGXGXHCGSA-N | 68028960 | KKPBMYHMXYLZMU-KDBWZQHXSA-N | 71718259 |

TABLE 12-continued

Compounds with similar structures and/or bioactivities with celastrol and gambogic acid found using PubChem open chemistry database.

| Celastrol (CID 122724) | PubChem CID | Gambogic Acid (CID 16072310) | PubChem CID |
|---|---|---|---|
| QGWDYPREORDRIT-XYMLVX-MESA-N | 60103590 | PYCHDQHGAJKLEB-ALPBHPBSSA-N | 71718272 |
| XLZGVFDYBDKLSJ-HKUCNJHLSA-N | 59492093 | XTQBIQOZQZIJJW-HQCJEUBQSA-N | 71718866 |
| INHUILMVLIXIOP-LLYX-LEJJSA-N | 59428287 | CTSIBWDVPNXDDY-WSOPLZEESA-N | 71718874 |
| OZKBTRIBGQYSPM-VRAWMDIMSA-N | 59350382 | GSULQLPVUMJWJN-YWJDODGHSA-N | 71718876 |
| PNZQDIUZNCHSAL-ZRCCSVPJSA-N | 58338790 | OSDWBDHHKBVHAI-CNADFBRCSA-N | 71717053 |
| ILAWPUDRPIJSHC-CDKFMWKUSA-N | 58338787 | BZRJTOIKOJHZGQ-ALPBHPBSSA-N | 71716428 |
| QGWDYPREORDRIT-OUMY-WODESA-N | 57321836 | QSJAAIXXDPZJDI-QVZJNGHZSA-N | 71717051 |
| FGUPEMLTKNSPDS-WYUYVVTISA-N | 56847557 | KLEWBUIXEFWIOX-QBEIJZEMSA-N | 71717031 |
| TZYINTOVRMOTDT-WXPPGMDDSA-N | 56847496 | NPPZUPSAZVYWJX-RGAUDQMMSA-N | 71716434 |
| JKZDPNSGTLVKFS-JSJVQHDDSA-N | 25197171 | CRZXNKVWVIOGLG-KCJGJVMNSA-N | 71717027 |
| PPBNDNNFAYLUKF-SUNMMQ-DUSA-N | 25197168 | MGBNLVNNMKFWHO-MNDRQJQGSA-N | 71717026 |
| XAWKZQBUEYUMJQ-WXPPGMDDSA-N | 118404337 | PJRSCTLUXRMVLG-LPIQBNQASA-N | 71717025 |
| LMRBFTMNXRSIDU-AN-CVDJAISA-N | 56846808 | YR.DRRMNQYXEQF-TYTBCFIUSA-N | 71716450 |
| GKBQZTNFLYSBDI-HKUCNJHLSA-N | 90922624 | LKTCFJPAKUCNIB-QBEIJZEMSA-N | 71716443 |
| KTHCLZLOFJSMHN-NGXGXHCGSA-N | 68029427 | YKSIZBBLYFQODP-YWJDODGHSA-N | 71716435 |
| XFFJOOGKLFMNFN-NOZRFFRFSA-N | 68029424 | FJYQZSOKEMDMHD-RGAUDQMMSA-N | 71720740 |
| MEVHISVZZRNRNQ-HJJL-TIBASA-N | 67406451 | VOYHKSWHADONRT-UHFFFAOYSA-N | 117591472 |
| QGWDYPREORDRIT-GWEJSANNSA-N | 60103581 | VJXSSTZKBZWPPU-UHFFFAOYSA-N | 117591470 |
| CWNGKYCBOAGDTO-MIZ-XVQKXSA-N | 59546528 | FWOBTOPXTHIFAR-UHFFFAOYSA-N | 117591530 |
| HMWZFAJRZJAGAL-CDKFMWKUSA-N | 58338783 | PEVFZCIVSYJXJJ-UHFFFAOYSA-N | 117591589 |
| RZBXUSAFLXVWGM-AN-CVDJAISA-N | 56847608 | YPFPFCJFKUOQMA-UHFFFAOYSA-N | 117592388 |
| WDJQPABVFANMAQ-XIR-GYHLMSA-N | 118408890 | DQPKYEHRFQDOLK-RWPPGCTJSA-N | 118737825 |
| QGWDYPREORDRIT-BPTQZAATSA-N | 54227450 | ZYUWYMMXGSCUQT-UHFFFAOYSA-N | 117591047 |
| YGLDJGRHKCVIQN-ZRCCSVPJSA-N | 46184627 | YANZBSJNCIQKSX-ZFHAUAHYSA-N | 118737828 |
| DHGOQCNNFIELMK-AB-JUJWBKSA-N | 42630196 | KJBDNAFUXXSLAD-UHFFFAOYSA-N | 117590910 |
| HKRKUMPPXYIXCF-JSJVQHDDSA-N | 25197278 | AICGDFMIRHRSPB-MMEAOPOPSA-N | 118737829 |

TABLE 12-continued

Compounds with similar structures and/or bioactivities with celastrol and gambogic acid found using PubChem open chemistry database.

| Celastrol (CID 122724) | PubChem CID | Gambogic Acid (CID 16072310) | PubChem CID |
|---|---|---|---|
| ZEXSHDSVCZQLCO-WFVGHVPHSA-N | 25197169 | CXFIQFGADOTDPF-CMLKYFHXSA-N | 76311369 |
| QGWDYPREORDRIT-ZUZO-HOKMSA-N | 21118757 | XUYFKRZDNDQABJ-XDSJHDTISA-N | 71718887 |
| 11-Oxooleanonic acid | 11576389 | BAHZVPGPIWTLLZ-RGAUDQMMSA-N | 71720723 |
| KQJSQWZMSAGSHN-AHWKKI-ARSA-N | 58636951 | UEMVXKVCUBRCBG-KCJGJVMNSA-N | 71720719 |
| KQJSQWZMSAGSHN-WDVYO-DBHSA-N | 118655639 | XAUUFNQHVHEWRB-RGAUDQMMSA-N | 71720718 |
| YDUSFXWVWNIQDZ-IGTS-BUIGSA-N | 118404346 | YGVBIDJABJLVOL-DGTITLQCSA-N | 71720708 |
| HCAYAMHXSDCPTR-MRZDQBBQSA-N | 118404343 | COEJNDYMOAUIJK-JCJNIYCKSA-N | 71720089 |
| KQJSQWZMSAGSHN-MRHUJCAJSA-N | 90233238 | JESNVXLQVMHXLZ-JSJFTWSHSA-N | 71720088 |
| FESQODXDXOHLEO-JNEFGXKCSA-N | 71249962 | XTBWCIYKONYIDG-AQOIPSNVSA-N | 71720068 |
| SMYCYEXFRJMQLW-ANQVMFJUSA-N | 71167315 | WSCCRZWUYZCJAZ-KAJKVYITSA-N | 71719495 |
| FMTPULGTIHBJRT-LGVWSN-LESA-N | 69574940 | LWIGRTRTVVPXOZ-XDSJHDTISA-N | 71719493 |
| UAJBCGCAPNHLHM-QUYLDEAFSA-N | 68028959 | ZMMPPBWNSJCZGR-QVZJNGHZSA-N | 71719492 |
| LLKPYONQSFCTMG-IGTS-BUIGSA-N | 123598084 | XCRBRZWMQVMPIY-KENSWSBLSA-N | 23629033 |
| UQSBWMQFUNJXTI-AZUGTCGHSA-N | 58338788 | BIMUUWRNJBALEP-AWNOVZCOSA-N | 45268895 |
| REKHQMDGAPXWJP-AN-CVDJAISA-N | 56847556 | DBWZFQAUMYEWML-WWZJDETNSA-N | 45267910 |
| GBQYERWLNHTHAH-ZRCCSVPJSA-N | 56847495 | 34-Hydroxy-gambogic acid | 45267909 |
| VMVBZDHQRFGSLA-FAWNWTIBSA-N | 56846810 | DXSGQRROBDYCSJ-YVMJPLCQSA-N | 45267154 |
| AQKDBFWJOPNOKZ-MTWWMYJUSA-N | 53656716 | XRBAWHATHDIBFU-XOSCNRPVSA-N | 45266948 |
| MXMNIRXPSWDEED-GTKR-WHGSSA-N | 25197170 | XCRBRZWMQVMPIY-OQOGLVOPSA-N | 44583737 |
| RPGDRWMPFKEMPI-JSJVQHDDSA-N | 25177624 | JBRMVLBIZUTECR-FXRUCJBFSA-N | 44403668 |
| QGWDYPREORDRIT-OHHDNCQJSA-N | 16401165 | VZQQLPACAVHZQT-OLZUXEKSSA-N | 44403667 |
| GYUVZGGERRSPQY-UHKCKZ-GUSA-N | 66583327 | Gambogenific acid | 25208911 |
| SYLIRTRYLBYOBO-JJWQIEBTSA-N | 91408393 | UQHRXFAVXKZFRU-RGAUDQMMSA-N | 71716426 |
| VDDPQVQCXWFZJM-LD-LRJHFFSA-N | 91367949 | RIFZOYVQOFHOCS-WIKVJIRTSA-N | 16758013 |
| LSSXGFNMUHCIAI-WXPPGMDDSA-N | 91190512 | REDMIYQFNIRTDF-LARDOQITSA-N | 5469880 |
| SYLIRTRYLBYOBO-AHWKKI-ARSA-N | 91065125 | VLADFNOTLYCWMW-UHFFFAOYSA-N | 52916109 |

TABLE 12-continued

Compounds with similar structures and/or bioactivities with celastrol and gambogic acid found using PubChem open chemistry database.

| Celastrol (CID 122724) | PubChem CID | Gambogic Acid (CID 16072310) | PubChem CID |
|---|---|---|---|
| WNCVCMKJUFWTFA-OWDORJPTSA-N | 71249923 | XZPYBDPGHSLINX-UHFFFAOYSA-N | 52916002 |
| QGWDYPREORDRIT-AVJZJKPBSA-N | 70532695 | Tetrahydrogambogic acid | 9917275 |
| DNLGFGXSBOIDNV-ZRCCSVPJSA-N | 67421869 | Dihydrogambogic acid | 6857793 |
| URDWIVHPIKIQNK-JJWQIEBTSA-N | 66583411 | HHOLRSVIZVDOIV-OXFPAKKDSA-N | 52949100 |
| WJLHDYQXCJXZGV-WXPPGMDDSA-N | 91463431 | XUYFKRZDNDQABJ-DLPQTZSGSA-N | 57400963 |
| QGWDYPREORDRIT-WBTUSMEDSA-N | 60103570 | HHVDVNJHGHGGHI-LDNSNGAXSA-N | 57394941 |
| QGWDYPREORDRIT-VPHAENBISA-N | 57301674 | YTIQONQLSSBXHE-MOWCMFFRSA-N | 70691871 |
| QOGSXJHNNDQXSS-ZHITZLKESA-N | 57051700 | LWIGRTRTVVPXOZ-DLPQTZSGSA-N | 57393978 |
| LMHNQDYMADJAAM-CDKFMWKUSA-N | 56847555 | TZXRZTWZRWZRQS-WSOPLZEESA-N | 71716427 |
| GICPBFRHOLICHK-UHKCKZGUSA-N | 56847494 | LPYYTLGGSMEQMH-ZSJJNDTGSA-N | 45269643 |
| WWKHRRYBBUOLCO-CDKFMWKUSA-N | 25197277 | Cochinchinoxanthone | 53355017 |
| QGWDYPREORDRIT-MQLBBMOOSA-N | 18637982 | BKRLQHWNGLIVCW-NFWYAXIXSA-N | 52945436 |
| | | 33-ChlorogambogellicAcid | 52943021 |
| | | GBQLXOPZKHBGOY-SCWSFWMSSA-N | 46886397 |
| | | DRRWWKSGTSQOON-WIRZGQEJSA-N | 46886396 |
| | | QYRPARUSUFWOPG-HBWLMKOJSA-N | 45272280 |
| | | GITYGECAVAWXHS-FZGWIHBJSA-N | 45272279 |
| | | (9,10)-Dihydroxy-gambogic acid | 45270476 |
| | | 7-Methoxyisomorellinol | 45269745 |
| | | ONKMNKXXFSJVSP-UHFFFAOYSA-N | 117591965 |
| | | PLPLFPMHLSHHDS-UHFFFAOYSA-N | 117593100 |
| | | MUQLGQHFYINEFE-UHFFFAOYSA-N | 117592428 |
| | | YHHMSCSXVOQXAF-UHFFFAOYSA-N | 117592536 |
| | | IVZPDDZYGYQLHF-UHFFFAOYSA-N | 117592735 |
| | | RZRZWSHHUHKZRH-UHFFFAOYSA-N | 117592761 |
| | | XCNLXYWAJHGEPU-UHFFFAOYSA-N | 117592772 |
| | | HAZSRZGEUAECEB-UHFFFAOYSA-N | 117592892 |
| | | PWVDTBGVDGFEKA-UHFFFAOYSA-N | 117592295 |
| | | IIJYFDSGSZVXFL-LQEUQGNQSA-N | 118753349 |
| | | XXHKTHKJENJGLT-UHFFFAOYSA-N | 117592031 |
| | | DQLSLPKMHSAVGY-UHFFFAOYSA-N | 117592271 |
| | | HEZLRSFHGIYFNV-UHFFFAOYSA-N | 117592219 |

TABLE 12-continued

Compounds with similar structures and/or bioactivities with celastrol and gambogic acid found using PubChem open chemistry database.

| Celastrol (CID 122724) | PubChem CID | Gambogic Acid (CID 16072310) | PubChem CID |
|---|---|---|---|
| | | WVBHHKPTCIYZRW-UHFFFAOYSA-N | 117592147 |
| | | ANXHWYZDFGXCSL-UHFFFAOYSA-N | 117592105 |
| | | FEUKMNUTHOBIFJ-UHFFFAOYSA-N | 117592081 |
| | | JEHWFPNSWRPRFY-UHFFFAOYSA-N | 117593116 |
| | | NBOTXPPFMTZDJX-UHFFFAOYSA-N | 117593375 |
| | | RIZDOCXODMLFMH-UHFFFAOYSA-N | 117593544 |
| | | RJZOSQYZDIYLOD-UHFFFAOYSA-N | 117593652 |
| | | CIMLDIMAIQTAAF-UHFFFAOYSA-N | 117593685 |
| | | SLOASZPUTSRJOS-UHFFFAOYSA-N | 117594239 |
| | | KQBIZWOEXACMRJ-UHFFFAOYSA-N | 117594907 |
| | | HQPAKWNGDAIVMM-UHFFFAOYSA-N | 117594911 |
| | | XITFXYOJRIAYLM-UHFFFAOYSA-N | 117595036 |
| | | UUNPNKKRLMOBNZ-UHFFFAOYSA-N | 117595578 |
| | | XWFNYKWKDWAAMZ-QKBJRNKPSA-N | 118707564 |
| | | ZISRIFHOONSTEW-XQUYNDDWSA-N | 118753102 |
| | | MQXZYUNEWMQRJD-MIRSFJNZSA-N | 118753301 |
| | | WCBINTABDRSBOM-BXQNXPOQSA-N | 118753302 |
| | | TZPROOSLUNQHV-YBSJKGMBSA-N | 118753348 |
| | | Scortechinone A | 44559179 |
| | | 9,10-Dihydrogambogic Acid | 71459533 |
| | | GEZHEQNLKAOMCA-UOONSFDBSA-N | 58209843 |
| | | Gambogic acid amide | 16725080 |
| | | REDMIYQFNIRTDF-UCQKPKSFSA-N | 5475311 |
| | | Acetyl isoallogambogic acid | 6857765 |
| | | Gamboginic acid, methyl ester | 23806091 |
| | | REDMIYQFNIRTDF-OZWPVNNZSA-N | 44449776 |
| | | Decahydro-Ga | 44449798 |
| | | Tetrahydro-Ga | 44449824 |
| | | UYPYPAISERHQAO-PBBIOFTGSA-N | 44452392 |
| | | FNJGRUCXYDWBQQ-UHFFFAOYSA-N | 117591871 |
| | | Scortechinone B | 44559180 |
| | | Scortechinone I | 44559181 |
| | | Scortechinone-Q | 44559270 |
| | | Scortechinone R | 44559271 |
| | | Scortechinone S | 44559272 |
| | | Bractatin | 44583731 |
| | | 1-O-Methylbractatin | 44583733 |

TABLE 12-continued

Compounds with similar structures and/or bioactivities with celastrol and gambogic acid found using PubChem open chemistry database.

| Celastrol (CID 122724) | PubChem CID | Gambogic Acid (CID 16072310) | PubChem CID |
|---|---|---|---|
| | | Methyl 8, 8a-dihydromorellate | 45268013 |
| | | YTIQONQLSSBXHE-OGRXGPJBSA-N | 70687664 |
| | | OLVQCRKEVCKWSS-WNDIJKFFSA-N | 71717041 |
| | | UPJGOGQGKKPFQF-VJEMJKLZSA-N | 71720078 |
| | | WNQJCSUJMQRMEE-KWXZSCLYSA-N | 76315019 |
| | | FBNIACMJHDKGKH-UHFFFAOYSA-N | 117591045 |
| | | MRFFDQCGXSUJFO-UHFFFAOYSA-N | 117591692 |
| | | KGPHOVCVHPOWBR-UHFFFAOYSA-N | 117591869 |
| | | GEZHEQNLKAOMCA-UBYIDDGGSA-N | 91332450 |
| | | QOZHTUAZXBIGBU-WRXOINPPSA-N | 117647595 |
| | | GEZHEQNLKAOMCA-KSZVLNGESA-N | 91351716 |
| | | GEZHEQNLKAOMCA-IGPPFNQUSA-N | 91356587 |
| | | GEZHEQNLKAOMCA-WQMCTBSRSA-N | 91395869 |
| | | REDMIYQFNIRTDF-CLWCGEPSSA-N | 91421299 |
| | | DVTLNRRWCRGSEB-QLMUFRIZSA-N | 91507797 |
| | | DCUBEADPOQPJCP-WWYBWCOQSA-N | 91525565 |
| | | 30-Hydroxygambogic acid | 102004804 |
| | | CCEGWRPYDCDELZ-JDHSLWBYSA-N | 117640037 |
| | | REDMIYQFNIRTDF-UVYBHTOASA-N | 117640050 |
| | | CXFIQFGADOTDPF-VAVNHFACSA-N | 91116286 |
| | | GEZHEQNLKAOMCA-QSNZZALHSA-N | 91081424 |
| | | MNNVIONVHRRQPF-IGPPFNQUSA-N | 90998876 |
| | | CGTWSSOGZQAVNI-YUTXIDHZSA-N | 90956184 |
| | | MNNVIONVHRRQPF-QSNZZALHSA-N | 90904334 |
| | | GEZHEQNLKAOMCA-BMAVOULBSA-N | 90837811 |
| | | MFUIGIDUBRLELJ-RHDRSXQYSA-N | 90802529 |
| | | FAEQAXFMLPWRFS-UHFFFAOYSA-N | 90793624 |
| | | XAPLNRWTXVBXJO-UHFFFAOYSA-N | 89737453 |
| | | AAEQTEKIFSEBLF-JCDNVTHQSA-N | 123214118 |
| | | IQDYCICYXWCEEX-QTFYUPPWSA-N | 89593387 |
| | | PHWVEYPUZJUGEV-OAWOWVGUSA-N | 121241349 |
| | | IWZRSTDKYHZSQF-SDRUQSECSA-N | 88870689 |
| | | AORIIYVDTXBCHV-YCVDEPICSA-N | 123197254 |
| | | JTEORTUOYDVEOM-FOQNCPQJSA-N | 123187933 |
| | | GCHJONZZLLRAEM-IGQYWBJASA-N | 123186661 |
| | | LPPVILAKSVOTHC-VABJNMDGSA-N | 123168249 |
| | | DUZIVTBZXZNFKW-LGYDYSPQSA-N | 123153387 |

TABLE 12-continued

Compounds with similar structures and/or bioactivities with celastrol and gambogic acid found using PubChem open chemistry database.

| Celastrol (CID 122724) | PubChem CID | Gambogic Acid (CID 16072310) | PubChem CID |
|---|---|---|---|
| | | XDJCBNWCKIBHCH-JLZOOELISA-N | 123146135 |
| | | IWZRSTDKYHZSQF-FBFXOJLPSA-N | 123143901 |
| | | UJPXBLUJNQMYIY-VRJUNHGMSA-N | 122542892 |
| | | FHJLQIOSAMVKBE-UTKNUOMGSA-N | 121241350 |
| | | MPVLKYHKVPLUBC-WRXOINPPSA-N | 117649446 |
| | | RUOIRPONLNREJT-IXTCAIOQSA-N | 121241347 |
| | | RUOIRPONLNREJT-GAZVMYCTSA-N | 121241346 |
| | | WVBSIKJNTVCEQJ-NBQSLMHUSA-N | 121241345 |
| | | RCWNBHCZYXWDOV-WPKINVRVSA-N | 121241344 |
| | | WTHZNKDLVYBPIU-XKZIYDEJSA-N | 121241343 |
| | | VZXLWEWYBUGLJA-KCZYMQEJSA-N | 118218885 |
| | | KWSMUTWPBWYJTJ-GBFWCEHUSA-N | 118215929 |
| | | YTINOMMNLVRQDZ-ODZJVPPQSA-N | 118215928 |
| | | PNVQUHOJEOSPST-CZHHEZJISA-N | 117649448 |
| | | AORIIYVDTXBCHV-NTXDIHSUSA-N | 88870699 |
| | | TZPSXPDSLJISGI-JSTMFIRTSA-N | 88870710 |
| | | SYPMLUQDIRBAJH-DPGBVESVSA-N | 88870709 |
| | | TZPSXPDSLJISGI-SMCHVARRSA-N | 88870708 |
| | | KIIICIKEPTYGHX-HQTPSEOASA-N | 88870707 |
| | | KIIICIKEPTYGHX-WLVTUAKASA-N | 88870706 |
| | | SYPMLUQDIRBAJH-GKPRHQBLSA-N | 88870705 |
| | | MPUTYJMBORRTBJ-BJGVHYDOSA-N | 88870704 |
| | | GCHJONZZLLRAEM-ZWNPRXLMSA-N | 88870703 |
| | | AORIIYVDTXBCHV-XENTYZTMSA-N | 88870702 |
| | | LPPVILAKSVOTHC-MGXSGBCKSA-N | 88870701 |
| | | XTMOYKJZVWYKPJ-BEYSKSGQSA-N | 88870711 |
| | | XDJCBNWCKIBHCH-USNSJPIISA-N | 88870698 |
| | | PVGHFWKFADSYSJ-MUUFOGJZSA-N | 88870697 |
| | | TZPSXPDSLJISGI-FZVGPGJDSA-N | 88870696 |
| | | DUZIVTBZXZNFKW-DJXAADCISA-N | 88870695 |
| | | FMCZWXSKOSSEHP-DJXAADCISA-N | 88870694 |
| | | DUZIVTBZXZNFKW-HAAYKULCSA-N | 88870693 |
| | | KIIICIKEPTYGHX-LNYPENFMSA-N | 88870692 |
| | | KLXFRVJTZKOFKV-SXQTYUKPSA-N | 88870691 |
| | | TZPSXPDSLJISGI-OUIKJMRCSA-N | 88870690 |
| | | XIDKYIKGGBTUPH-LFVJCYFKSA-N | 126602554 |
| | | PVGHFWKFADSYSJ-VSBOKRGHSA-N | 88870721 |

TABLE 12-continued

Compounds with similar structures and/or bioactivities with celastrol and gambogic acid found using PubChem open chemistry database.

| Celastrol (CID 122724) | PubChem CID | Gambogic Acid (CID 16072310) | PubChem CID |
| --- | --- | --- | --- |
| | | AFLHWBGXZWEULQ-PKAZHMFMSA-N | 89410167 |
| | | DUEZXUMGZFEZCZ-OYKKKHCWSA-N | 89409368 |
| | | KFTSCWCFQNHXEF-OYKKKHCWSA-N | 89409366 |
| | | MPUTYJMBORRTBJ-ZRJUZVLNSA-N | 88870748 |
| | | IWZRSTDKYHZSQF-SAJNXLGZSA-N | 88870747 |
| | | AORIIYVDTXBCHV-PKRKJABKSA-N | 88870746 |
| | | KLXFRVJTZKOFKV-PQINOVKQSA-N | 88870744 |
| | | MVRLZFHWUTWTPZ-OAWOWVGUSA-N | 88870743 |
| | | IWZRSTDKYHZSQF-WASDJRSKSA-N | 88870742 |
| | | XDJCBNWCKIBHCH-FXXVQEQYSA-N | 88870740 |
| | | VJGFCQXTEBDXCL-XYGWBWBKSA-N | 89410235 |
| | | FJTHIYKOKGKDFM-YECKHLLKSA-N | 88870720 |
| | | MPUTYJMBORRTBJ-ZFGQNZLVSA-N | 88870719 |
| | | GCHJONZZLLRAEM-RHZAVJPWSA-N | 88870718 |
| | | FQCIAFWZLWMCNQ-HSULCKAZSA-N | 88870717 |
| | | XTMOYKJZVWYKPJ-REPUEAQBSA-N | 88870716 |
| | | SYPMLUQDIRBAJH-VGRXJTFRSA-N | 88870715 |
| | | NHNBZYVAEYGXJD-PYOCCJRJSA-N | 88870714 |
| | | KKKVOYLLLKLJGN-MWJHYMAZSA-N | 88870713 |
| | | FMCZWXSKOSSEHP-XENTYZTMSA-N | 88870712 |
| | | FJTHIYKOKGKDFM-WHJBVOODSA-N | 123809343 |
| | | GFZFBIVRUFOXDE-RAKWAVLCSA-N | 123867307 |
| | | JTEORTUOYDVEOM-AKJUZXHISA-N | 123858966 |
| | | KLXFRVJTZKOFKV-RWJQYVGMSA-N | 123858384 |
| | | XTMOYKJZVWYKPJ-IIIUNIONSA-N | 123851264 |
| | | COVMVPHACFXMAX-NJEUQTODSA-N | 123849167 |
| | | PVGHFWKFADSYSJ-QFSWFWNDSA-N | 123845773 |
| | | TZPSXPDSLJISGI-OWMZLRFQSA-N | 123844233 |
| | | DUZIVTBZXZNFKW-YCVDEPICSA-N | 123821973 |
| | | AORIIYVDTXBCHV-UOVBMFSZSA-N | 123819800 |
| | | IWZRSTDKYHZSQF-0WDHWTJPSA-N | 123811651 |
| | | KWSMUTWPBWYJTJ-GTUNQJGZSA-N | 123867860 |
| | | XTMOYKJZVWYKPJ-ZPHHXPIHSA-N | 123801882 |
| | | IWZRSTDKYHZSQF-STFZBRADSA-N | 123799471 |
| | | FMCZWXSKQSSEHP-LGYDYSPQSA-N | 123783895 |
| | | MPUTYJMBORRTBJ-UIVVFIOZSA-N | 123768632 |
| | | FMCZWXSKQSSEHP-NRBGCZKASA-N | 123764889 |

TABLE 12-continued

Compounds with similar structures and/or bioactivities with celastrol and gambogic acid found using PubChem open chemistry database.

| Celastrol (CID 122724) | PubChem CID | Gambogic Acid (CID 16072310) | PubChem CID |
|---|---|---|---|
| | | TZPSXPDSLJISGI-HHTAKYNCSA-N | 123747944 |
| | | FJTHIYKOKGKDFM-VABJNMDGSA-N | 123730782 |
| | | COQAPWLZSHQTKA-WQXODUOJSA-N | 123725925 |
| | | SYPMLUQDIRBAJH-QHKZOBPHSA-N | 123713443 |
| | | GCHJONZZLLRAEM-MNTUFJQYSA-N | 123689815 |
| | | GEZHEQNLKAOMCA-MAKUZWOISA-N | 123970099 |
| | | MPUTYJMBORRTBJ-GQPSOBIZSA-N | 124083343 |
| | | MVRLZFHWUTWTPZ-PLUQQRNKSA-N | 124083342 |
| | | TZNZFVPLCOBOHE-SRHIZFSVSA-N | 124083341 |
| | | KRGVLKLMSZLNJD-CZBSRGPZSA-N | 124083340 |
| | | UNPJLJMTRSOEBG-YTJXBEJASA-N | 124083339 |
| | | MPUTYJMBORRTBJ-ORYAWNIFSA-N | 124011815 |
| | | NHNBZYVAEYGXJD-WQXODUOJSA-N | 124009406 |
| | | FMCZWXSKQSSEHP-UOVBMFSZSA-N | 124004813 |
| | | XDJCBNWCKIBHCH-PCCITZADSA-N | 123995047 |
| | | IWZRSTDKYHZSQF-IVPRPUKMSA-N | 123970404 |
| | | PVGHFWKFADSYSJ-AHWIIWHVSA-N | 123672510 |
| | | REDMIYQFNIRTDF-SNSZSSRMSA-N | 123962837 |
| | | NFVXKLYWFCNBCO-BIDYHREASA-N | 123946655 |
| | | FQCIAFWZLWMCNQ-MZQQFRDZSA-N | 123931583 |
| | | FMCZWXSKQSSEHP-YCVDEPICSA-N | 123926824 |
| | | SYPMLUQDIRBAJH-JKFLJFCISA-N | 123921560 |
| | | SYPMLUQDIRBAJH-MXTXYYSDSA-N | 123903462 |
| | | KIIICIKEPTYGHX-KAXRJKLWSA-N | 123902138 |
| | | KLXFRVJTZKOFKV-XLPBWHEJSA-N | 123898922 |
| | | KKKVOYLLLKUIGN-QHQAMMJOSA-N | 123885028 |
| | | GEZHEQNLKAOMCA-RAKWAVLCSA-N | 123307604 |
| | | TZPSXPDSLJISGI-GTHFLSHASA-N | 123415116 |
| | | KIIICIKEPTYGHX-FEHYYDPSSA-N | 123392802 |
| | | KIIICIKEPTYGHX-QGNRMNGYSA-N | 123385862 |
| | | FBJVPBMWPVODRO-PCCITZADSA-N | 123363376 |
| | | GEZHEQNLKAOMCA-ADCYJAEYSA-N | 123352107 |
| | | DUZIVTBZXZNFKW-UOVBMFSZSA-N | 123351208 |
| | | SYPMLUQDIRBAJH-KUWKLSGISA-N | 123340327 |
| | | AORIIYVDTXBCHV-NRBGCZKASA-N | 123338137 |
| | | TZPSXPDSLJISGI-OYYJVTFHSA-N | 123324331 |
| | | COVMVPHACFXMAX-WJQTUEGHSA-N | 123322435 |

TABLE 12-continued

Compounds with similar structures and/or bioactivities with celastrol and gambogic acid found using PubChem open chemistry database.

| Celastrol (CID 122724) | PubChem CID | Gambogic Acid (CID 16072310) | PubChem CID |
|---|---|---|---|
| | | AORIIYVDTXBCHV-NWODWGALSA-N | 123437820 |
| | | NHNBZYVAEYGXJD-RNLYVTMESA-N | 123307294 |
| | | XDJCBNWCKIBHCH-MEXQKCLWSA-N | 123306297 |
| | | QOZHTUAZXBIGBU-UHFFFAOYSA-N | 123299953 |
| | | SYPMLUQDIRBAJH-CFCCRWGCSA-N | 123290623 |
| | | UWZMGTSPGQXAAP-WQXODUOJSA-N | 123272237 |
| | | NFVXKLYWFCNBCO-VDMQVCGESA-N | 123263934 |
| | | BYSLEZZCJZXNQG-RWJQYVGMSA-N | 123248797 |
| | | DUEZXUMGZFEZCZ-UHFFFAOYSA-N | 123248044 |
| | | HWTUJOKAWVHJCJ-OPUOJSSUSA-N | 123242824 |
| | | RCWNBHCZYXWDOV-KBGSTRFQSA-N | 123550305 |
| | | XDJCBNWCKIBHCH-RAKWAVLCSA-N | 123661979 |
| | | SYPMLUQDIRBAJH-XZGVVOIPSA-N | 123658150 |
| | | UWZMGTSPGQXAAP-RNLYVTMESA-N | 123650727 |
| | | KFTSCWCFQNHXEF-UHFFFAOYSA-N | 123649704 |
| | | KIIICIKEPTYGHX-ILHXXLRDSA-N | 123628892 |
| | | GEZHEQNLKAOMCA-VRYKAPMJSA-N | 123626409 |
| | | AORIIYVDTXBCHV-LGYDYSPQSA-N | 123615972 |
| | | DUZIVTBZXZNFKW-NRBGCZKASA-N | 123581184 |
| | | GEZHEQNLKAOMCA-CCZYIYSKSA-N | 123570917 |
| | | XTMOYKJZVWYKPJ-NVDLISELSA-N | 123554777 |
| | | BYSLEZZCJZXNQG-TYTNRNEYSA-N | 123234071 |
| | | PVGHFWKFADSYSJ-KFMJCXDSSA-N | 123549300 |
| | | PVGHFWKFADSYSJ-JTFGTGAKSA-N | 123542499 |
| | | AAEQTEKIFSEBLF-DZGHJPMGSA-N | 123522015 |
| | | FQCIAFWZLWMCNQ-MLFAQUDHSA-N | 123514172 |
| | | XTMOYKJZVWYKPJ-GMLGDLCKSA-N | 123504656 |
| | | MPUTYJMBORRTBJ-WHGJWNQISA-N | 123494893 |
| | | RCWNBHCZYXWDOV-NWPLKAIBSA-N | 123475850 |
| | | YTINOMMNLVRQDZ-MCGXLDAJSA-N | 123469661 |
| | | GEZHEQNLKAOMCA-BIDYHREASA-N | 123464815 |
| | | IWZRSTDKYHZSQF-GATNSQFVSA-N | 58545200 |
| | | RCWNBHCZYXWDOV-YZYLOZNXSA-N | 58545211 |
| | | SYPMLUQDIRBAJH-HYTANOMUSA-N | 58545210 |
| | | XTMOYKJZVWYKPJ-ZOLZCLEESA-N | 58545209 |
| | | GEZHEQNLKAOMCA-BSGXHHMHSA-N | 58545208 |
| | | AORIIYVDTXBCHV-NTJOPWEGSA-N | 58545207 |

TABLE 12-continued

Compounds with similar structures and/or bioactivities with celastrol and gambogic acid found using PubChem open chemistry database.

| Celastrol (CID 122724) | PubChem CID | Gambogic Acid (CID 16072310) | PubChem CID |
|---|---|---|---|
| | | UWZMGTSPGQXAAP-CAQBGEGQSA-N | 58545206 |
| | | VZQQLPACAVHZQT-IYYXIFPBSA-N | 58545204 |
| | | DMEVOSRJMNDQOB-XKZIYDEJSA-N | 58545203 |
| | | DUZIVTBZXZNFKW-SMSNCEFTSA-N | 58545202 |
| | | COVMVPHACFXMAX-PWZQPALBSA-N | 58545201 |
| | | KLXFRVJTZKOFKV-XFTJLXKISA-N | 58545213 |
| | | AAEQTEKIFSEBLF-CEGNIYDJSA-N | 58545199 |
| | | KIIICIKEPTYGHX-FBQUOBMKSA-N | 58545198 |
| | | IWZRSTDKYHZSQF-HJBKNYNFSA-N | 58545197 |
| | | FJTHIYKOKGKDFM-IDACPZNESA-N | 58545196 |
| | | PVGHFWKFADSYSJ-SZYQWLCWSA-N | 58545195 |
| | | KIIICIKEPTYGHX-ASZVOQTMSA-N | 58545193 |
| | | AORIIYVDTXBCHV-SMSNCEFTSA-N | 58545192 |
| | | SYPMLUQDIRBAJH-WVJIZLELSA-N | 58545190 |
| | | GEZHEQNLKAOMCA-ITMOWBSKSA-N | 58545188 |
| | | TZPSXPDSLJISGI-IOHWOTBESA-N | 58545187 |
| | | LPPVILAKSVOTHC-IDACPZNESA-N | 58545228 |
| | | CXFIQFGADOTDPF-DLLRBFTDSA-N | 59248849 |
| | | RAWMYNQUVMHIBX-IADYIPOJSA-N | 59060966 |
| | | MFUIGIDUBRLELJ-SJZKZEADSA-N | 58802103 |
| | | MKRYDGCYDKJGSE-OMRLFUBUSA-N | 58802102 |
| | | MVRLZFHWUTWTPZ-UZAZBKDBSA-N | 58554586 |
| | | KIIICIKEPTYGHX-MGTQMBPOSA-N | 58554585 |
| | | MPUTYJMBORRTBJ-QMNYGIFOSA-N | 58554584 |
| | | KKKVOYLLLKLJGN-JTZZIZQTSA-N | 58545231 |
| | | PHWVEYPUZJUGEV-UZAZBKDBSA-N | 58545230 |
| | | SYPMLUQDIRBAJH-GUGAKOSKSA-N | 58545229 |
| | | FQCIAFWZLWMCNQ-PJEVLYNISA-N | 58545186 |
| | | HWTUJOKAWVHJCJ-OFNKHKRGSA-N | 58545227 |
| | | MPUTYJMBORRTBJ-UCUGODPPSA-N | 58545224 |
| | | NHNBZYVAEYGXJD-SORCPTHGSA-N | 58545221 |
| | | XTMOYKJZVWYKPJ-JBZGCEAXSA-N | 58545220 |
| | | BYSLEZZCJZXNQG-PSRDIXOWSA-N | 58545219 |
| | | XDJCBNWCKIBHCH-ASCSEZEHSA-N | 58545218 |
| | | TZPSXPDSLJISGI-HEERNYNQSA-N | 58545217 |
| | | COQAPWLZSHQTKA-CAQBGEGQSA-N | 58545215 |
| | | DUZIVTBZXZNFKW-NTJOPWEGSA-N | 58545214 |

TABLE 12-continued

Compounds with similar structures and/or bioactivities with celastrol and gambogic acid found using PubChem open chemistry database.

| Celastrol (CID 122724) | PubChem CID | Gambogic Acid (CID 16072310) | PubChem CID |
|---|---|---|---|
| | | VDSCKSOYNLTQSY-KKQCBWBVSA-N | 6710618 |
| | | MNNVIONVHRRQPF-HMMDVQROSA-N | 16750435 |
| | | MNNVIONVHRRQPF-JDFKUOOISA-N | 16750413 |
| | | GEZHEQNLKAOMCA-ZEYIWNDBSA-N | 11556381 |
| | | KCALBYYRHOKKBO-QDTIIGTASA-N | 11468283 |
| | | DWYQBZCXZCGVHI-YSMPRRRNSA-N | 11422617 |
| | | KVXKEBWQNIIKMB-MTJSOVHGSA-N | 11308419 |
| | | AANGJSKPBIKCLU-ITYLOYPMSA-N | 9896558 |
| | | MFUIGIDUBRLELJ-UCQKPKSFSA-N | 9895689 |
| | | KYPSMUUXSFJTAR-HEEAUFFFSA-N | 9851944 |
| | | LFSCNWNADRUBLS-UHFFFAOYSA-N | 6710687 |
| | | GEZHEQNLKAOMCA-DTWORVFFSA-N | 16750462 |
| | | COQAPWLZSHQTKA-FRMWRBSQSA-N | 6419330 |
| | | VDSCKSOYNLTQSY-KKQCBWBVSA-N | 6710618 |
| | | Isomorellic acid | 6419329 |
| | | VZQQLPACAVHZQT-RNLYVTMESA-N | 6325059 |
| | | CXFIQFGADOTDPF-LPYMAVHISA-N | 6284659 |
| | | VZXLWEWYBUGLJA-UHFFFAOYSA-N | 5205218 |
| | | CXFIQFGADOTDPF-UHFFFAOYSA-N | 5149277 |
| | | COVMVPHACFXMAX-UHFFFAOYSA-N | 550587 |
| | | COQAPWLZSHQTKA-RNLYVTMESA-N | 442607 |
| | | GEZHEQNLKAOMCA-PCCITZADSA-N | 442595 |
| | | REDMIYQFNIRTDF-UHFFFAOYSA-N | 421874 |
| | | PZOHDYPLDDMKLL-BRXPKNJNSA-N | 56595878 |
| | | FMCZWXSKQSSEHP-NTJOPWEGSA-N | 58545185 |
| | | FMCZWXSKQSSEHP-SMSNCEFTSA-N | 58545184 |
| | | GCHJONZZLLRAEM-VSNLTSTASA-N | 58545183 |
| | | XDJCBNWCKIBHCH-KKCBTXSASA-N | 58545182 |
| | | PVGHFWKFADSYSJ-QEDXCBQSSA-N | 58545181 |
| | | NFVXKLYWFCNBCO-UOONSFDBSA-N | 58209844 |
| | | CGTWSSOGZQAVNI-NXHYFTOVSA-N | 57941599 |
| | | GEZHEQNLKAOMCA-AOJNUVNQSA-N | 57845639 |
| | | REDMIYQFNIRTDF-YOXDLCKMSA-N | 57586028 |
| | | QHQBTUGYLFRMGB-UHFFFAOYSA-N | 57332076 |
| | | GEZHEQNLKAOMCA-WOMUXGJCSA-N | 59248851 |
| | | AAEQTEKIFSEBLF-CPNRCEQSSA-N | 56595835 |
| | | DRCNCMDYOLGEQM-BRXPKNJNSA-N | 54764387 |

TABLE 12-continued

Compounds with similar structures and/or bioactivities with celastrol and gambogic acid found using PubChem open chemistry database.

| Celastrol (CID 122724) | PubChem CID | Gambogic Acid (CID 16072310) | PubChem CID |
|---|---|---|---|
| | | PVRRTDHRPRHFPD-BRXPKNJNSA-N | 54764299 |
| | | JTEORTUOYDVEOM-LMZOBULNSA-N | 25134602 |
| | | UYPYPAISERHQAO-XKZIYDEJSA-N | 23391922 |
| | | YXDVFXVYFZUHNH-OYKKKHCWSA-N | 23391915 |
| | | WCBINTABDRSBOM-BKUYFWCQSA-N | 23391867 |
| | | CAZOJRLTSYFYHR-HMAPJEAMSA-N | 23391861 |
| | | IQYGGNGWJAGSBX-QTSGYQIKSA-N | 21603452 |
| | | BZFVSJCAEZAUPC-UHFFFAOYSA-N | 76658597 |
| | | GAIPRNHDISFSOS-UHFFFAOYSA-N | 78056261 |
| | | JMMQRHVWNJXTCK-UHFFFAOYSA-N | 78056259 |
| | | ZOKLYUGLUJUVLW-UHFFFAOYSA-N | 78056187 |
| | | SUOOENMABGOQCH-UHFFFAOYSA-N | 78056180 |
| | | KCYKVBCVFBSOKZ-UHFFFAOYSA-N | 77153183 |
| | | JAWDBXPEURIBJV-UHFFFAOYSA-N | 77152099 |
| | | GUASLOULTWPTKR-UHFFFAOYSA-N | 76658664 |
| | | SUFYIURUDYGNLI-UHFFFAOYSA-N | 76658661 |
| | | WCVGFLPSZFYRCL-UHFFFAOYSA-N | 76658621 |
| | | KRUKCSSBDGDWBK-UHFFFAOYSA-N | 76658617 |
| | | FSSXEBRQIMPUGN-UHFFFAOYSA-N | 78056262 |
| | | YHKGUOGCUACMHC-UHFFFAOYSA-N | 76658582 |
| | | BVWTXTULIJKQBW-UHFFFAOYSA-N | 76658577 |
| | | UYPYPAISERHQAO-UHFFFAOYSA-N | 74047027 |
| | | YXDVFXVYFZUHNH-UHFFFAOYSA-N | 74047023 |
| | | WCBINTABDRSBOM-UHFFFAOYSA-N | 74046984 |
| | | CAZOJRLTSYFYHR-UHFFFAOYSA-N | 74046983 |
| | | RCWNBHCZYXWDOV-UHFFFAOYSA-N | 73008268 |
| | | KCALBYYRHOKKBO-UHFFFAOYSA-N | 72973410 |
| | | DWYQBZCXZCGVHI-UHFFFAOYSA-N | 72955606 |
| | | KVXKEBWQNIIKMB-UHFFFAOYSA-N | 72795177 |
| | | AORIIYVDTXBCHV-HAAYKULCSA-N | 88870677 |
| | | IWZRSTDKYHZSQF-SEXUYDOESA-N | 88870687 |
| | | NHNBZYVAEYGXJD-BUZUJXMISA-N | 88870686 |
| | | KIIICIKEPTYGHX-GWVHQLHWSA-N | 88870685 |
| | | SYPMLUQDIRBAJH-VWXYWCCPSA-N | 88870684 |
| | | XTMOYKJZVWYKPJ-XPIJMDORSA-N | 88870683 |
| | | SYPMLUQDIRBAJH-QNAMZJFPSA-N | 88870682 |
| | | XTMOYKJZVWYKPJ-KZHARUQXSA-N | 88870681 |

TABLE 12-continued

Compounds with similar structures and/or bioactivities with celastrol and gambogic acid found using PubChem open chemistry database.

| Celastrol (CID 122724) | PubChem CID | Gambogic Acid (CID 16072310) | PubChem CID |
|---|---|---|---|
| | | HWTUJOKAWVHJCJ-KJLFQBLLSA-N | 88870680 |
| | | PHWVEYPUZJUGEV-PLUQQRNKSA-N | 88870679 |
| | | AORIIYVDTXBCHV-DJXAADCISA-N | 88870678 |
| | | RAWMYNQUVMHIBX-UHFFFAOYSA-N | 72503918 |
| | | XDJCBNWCKIBHCH-NDZGPYJESA-N | 88870676 |
| | | PVGHFWKFADSYSJ-SQHFVPGGSA-N | 88870675 |
| | | PVGHFWKFADSYSJ-CZBSRGPZSA-N | 88870674 |
| | | DUZIVTBZXZNFKW-XENTYZTMSA-N | 88870673 |
| | | FMCZWXSKQSSEHP-NTXDIHSUSA-N | 88870672 |
| | | FMCZWXSKQSSEHP-HAAYKULCSA-N | 88870671 |
| | | DUZIVTBZXZNFKW-NTXDIHSUSA-N | 88870670 |
| | | FJTHIYKOKGKDFM-MGXSGBCKSA-N | 88870669 |
| | | AANGJSKPBIKCLU-UHFFFAOYSA-N | 85062448 |
| | | GEZHEQNLKAOMCA-FSLBZXJLSA-N | 66603456 |
| | | GEZHEQNLKAOMCA-DDBFOHIYSA-N | 70639874 |
| | | Deoxymorellin | 70639873 |
| | | BYSLEZZCJZXNQG-FEOFYTQISA-N | 70639871 |
| | | GEZHEQNLKAOMCA-ZESOCHHDSA-N | 70639869 |
| | | Isomorellinol | 70639868 |
| | | AAEQTEKIFSEBLF-HABQCUFLSA-N | 70639867 |
| | | CXFIQFGADOTDPF-DXJQLTJMSA-N | 70235747 |
| | | GEZHEQNLKAOMCA-WFPDQCIUSA-N | 70235746 |
| | | KCYKVBCVFBSOKZ-KPKJPENVSA-N | 66612138 |
| | | JAWDBXPEURIBJV-WUXMJOGZSA-N | 66603468 |
| | | UWZMGTSPGQXAAP-XVQCHYCYSA-N | 70639876 |
| | | LWIGRTRTVVPXOZ-FNUJIKEJSA-N | 66561235 |
| | | GEZHEQNLKAOMCA-UTDYKPHNSA-N | 66509103 |
| | | COQAPWLZSHQTKA-XVQCHYCYSA-N | 59895966 |
| | | LWIGRTRTVVPXOZ-BVLCDUKVSA-N | 59895965 |
| | | QDXKAHJQAXFABR-JQJLJWNFSA-N | 59895964 |
| | | GEZHEQNLKAOMCA-HWOJJXKDSA-N | 59895963 |
| | | DCUBEADPOQPJCP-YGJDYZIVSA-N | 59607534 |
| | | HNEQMSDUEKZLSM-HGSFHZCQSA-N | 59248855 |

TABLE 12-continued

Compounds with similar structures and/or bioactivities with celastrol and gambogic acid found using PubChem open chemistry database.

| Celastrol (CID 122724) | PubChem CID | Gambogic Acid (CID 16072310) | PubChem CID |
|---|---|---|---|
| | | LJFULGOYVXFMAL-SSQGKGTLSA-N | 59248854 |
| | | QGMGFULXKBKTCL-KIXMQPMBSA-N | 70641345 |
| | | MFUIGIDUBRLELJ-UHFFFAOYSA-N | 72428343 |
| | | MKRYDGCYDKJGSE-UHFFFAOYSA-N | 72428342 |
| | | NTOPURIAGNZMKL-IMRQLAEWSA-N | 71262488 |
| | | FSSXEBRQIMPUGN-UCQKPKSFSA-N | 71261269 |
| | | GAIPRNHDISFSOS-HMAPJEAMSA-N | 71261268 |
| | | JMMQRHVWNJXTCK-UCQKPKSFSA-N | 71261266 |
| | | ZOKLYUGLLJUVLW-ITYLOYPMSA-N | 71261175 |
| | | SUOOENMABGOQCH-ITYLOYPMSA-N | 71261168 |
| | | MFUIGIDUBRLELJ-LOSVMQNTSA-N | 71215924 |
| | | WCILAHSZCPIJPY-NTDTWHTNSA-N | 70968535 |
| | | FQCIAFWZLWMCNQ-JTWMGGOBSA-N | 88870688 |
| | | BLDWFKHVHHINGR-BBHBLYOZSA-N | 70641343 |
| | | NPTGLFQRDIIEBF-IZWSUVCCSA-N | 70641230 |
| | | NPTGLFQRDIIEBF-BXIWITQHSA-N | 70641229 |
| | | JEGOOEVCLQIINX-IWBBQFJISA-N | 70641225 |
| | | IXIIUJBIELTYTO-WECGGMARSA-N | 70641219 |
| | | FGVLMIINZOOWDO-BRWUPGPDSA-N | 70641217 |
| | | AAEQTEKIFSEBLF-WXZUYDNESA-N | 70639883 |
| | | Desoxygambogenin | 70639878 |
| | | COVMVPHACFXMAX-GJFVWJTOSA-N | 70639877 |

Gambogic Acid Remedies the Levels of CTXLP-Associated Pathological Markers CaV2.2 CCAT and Nogo-A FIG. 56 highlights than not only CTXLP is reduced in the presence of gambogic acid, but that the drug treatment also restores CaV2.2 CCAT expression (known to be suppressed by CTXLP, FIG. 47). Furthermore, we demonstrate show that gambogic acid is a potent inhibitor of Nogo-A (which inhibits remyelination) expression in cancerous NCCIT cells (FIG. 56). As the decrease in Nogo-A expression directly correlates with a drop in CTXLP expression, this therapeutic strategy may also reduce pathogenic Nogo-A expression in ALS (FIG. 42). Nogo-A inhibitors have been previously identified, such as green tea polyphenols and other natural product extracts[151]. Proteolytic turnover of Nogo-A is a physiological mechanism to reduce Nogo-A levels[152]. Gambogic acid may reduce Nogo-A expression by having an effect of CTXLP-driven pathology or a more direct effect on specific protein turnover[153,154].

Development of Cell and Animal Models to Investigate CTXLP Pathogenesis

Identification of CTXLP-Encoding ERVK Loci in Primate Genomes and Their Human Homologues Our close relatives also encode ERVK, but some ERVK loci are unique to humans. Examination of the ERVK content of three non-human primate genomes, Pan troglodytes (Common chimpanzee), Gorilla gorilla gorilla (Western lowland gorilla), and Cercocebus atys (Sooty Mangabey) shows that CTXLP is not limited to humans.

The most recent genomic assembly for each primate species was searched for CTXLP in the same manner as the human genome (Table 13). panTro5 and gorGor5 were retrieved from UCSC, and Caty_1.0 was retrieved from NCBI. Chimpanzee ERVK were identified using UCSC table panTro5.nestedRepeats, but no such table exists for the Gorilla or Sooty Mangabey. Gorilla and Mangabey ERVK were identified directly from RepeatMasker output. To reduce the number of small ERV fragments to be BLASTed and to increase the accuracy of orthology predictions by including flanking genomic regions, the loci annotated in RepeatMasker were extended by 1000 bp to either side and then any less than 10 bp apart were merged.

TABLE 13

ERVK and CTXLP loci in primates.

| | Orthologous ERVK fragments identified by BLAST | | | | Number of PF08087* and PF13804* Loci by Species | | |
|---|---|---|---|---|---|---|---|
| | H. sapiens | P. troglodytes | G. gorilla | C. atys | Species | CTXLP | Env |
| H. sapiens | 7358 | 6060 | 5853 | 2585 | H. sapiens | 28 | 383 |
| P. triglodytes | 6060 | 7389 | 5812 | 2581 | P. troglodytes | 33 | 402 |
| G gorilla | 5853 | 5812 | 6504 | 2562 | G gorilla | 39 | 318 |
| C atys | 2585 | 2581 | 2565 | 7411 | C atys | 31 | 379 |

The expected relationship between the four species is displayed by the number of orthologs recognized. Humans are most closely related to Chimpanzees, then to Gorillas, and most distantly to the Sooty Mangabey. We can see in the second table that the number of CTXLP and Env positive ERVK loci varies minimally between species.

Figure 59:
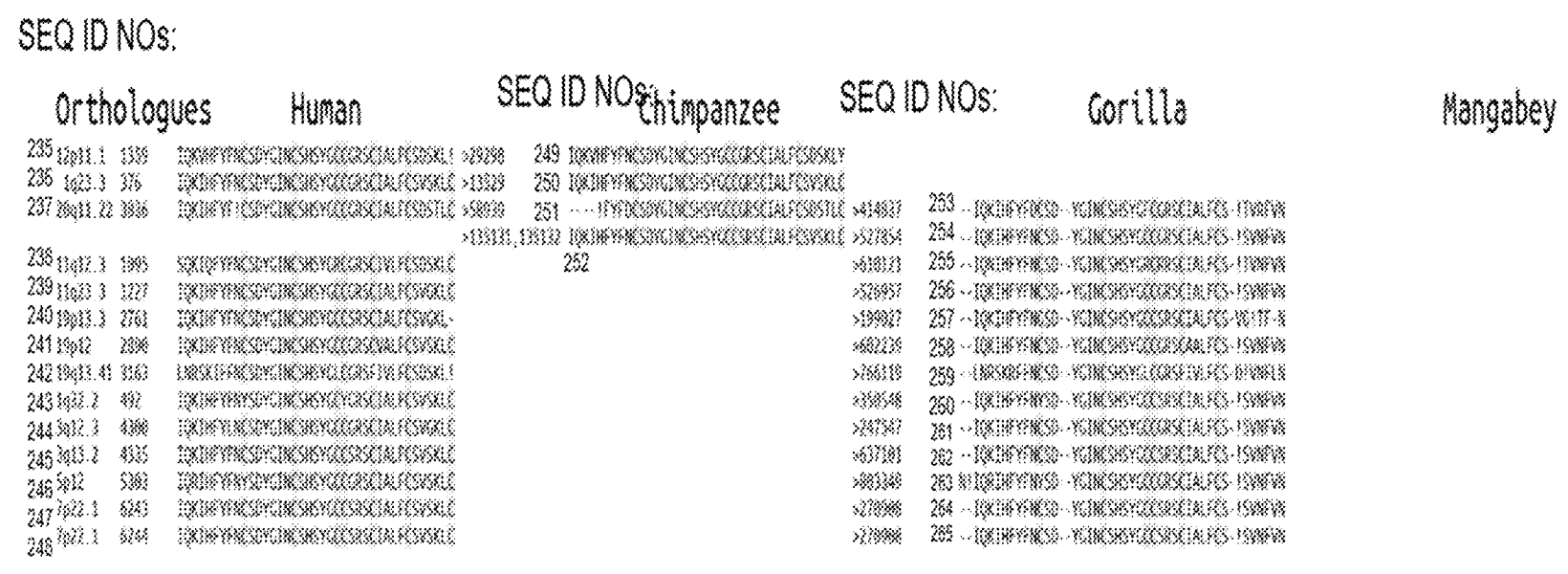
Figure 59:
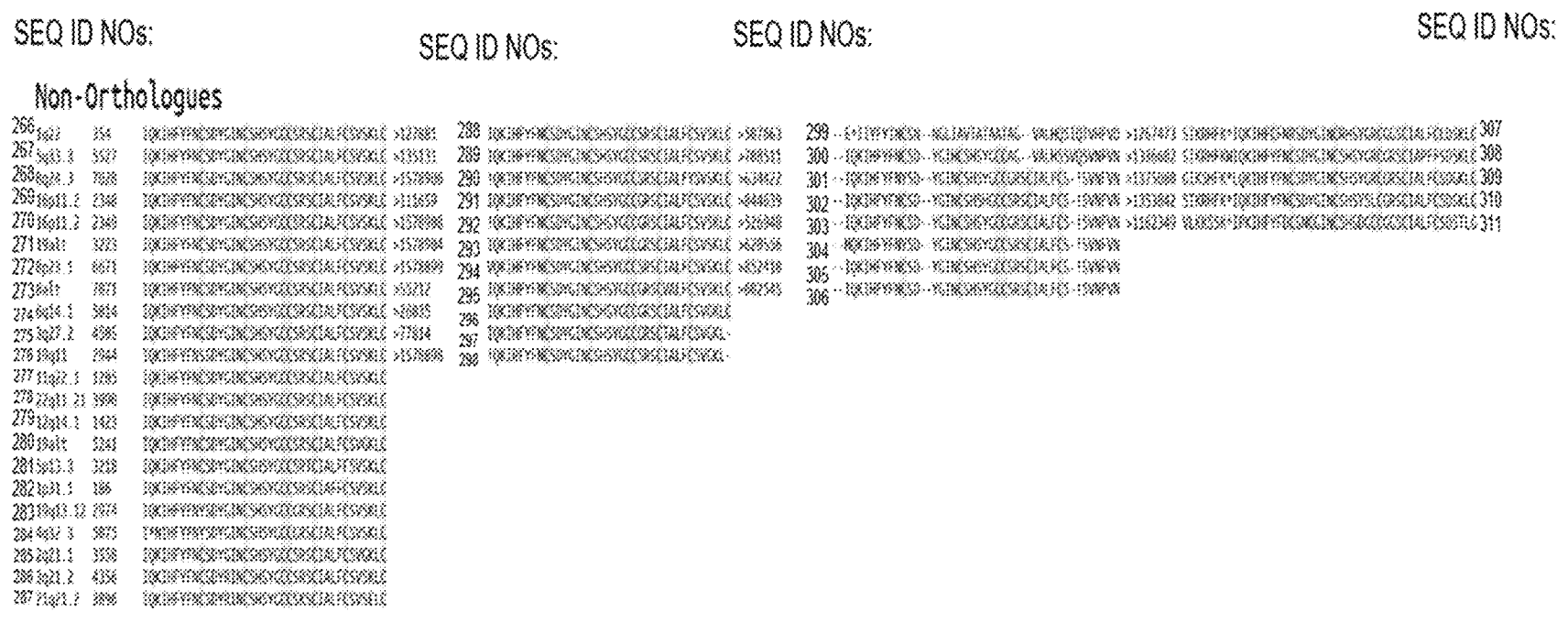

Only two human CTXLP+ loci are present in all four species. There is also 1 mangabey locus present in all four. No loci were CTXLP+ and present in all four species. FIG. 59 depicts MUSCLE alignments of tBLASTx results from loci in human, chimpanzee, gorilla, and mangabey where an orthologue in at least one species encodes a Toxin_18+ ORF. The first four alignments are split in two, where the top half contains sequences belonging to orthologous sets aligned horizontally, and the bottom half contains the remaining sequences from each species. The fifth alignment is tBLASTx results for the cd-hit cluster representative sequence of the largest cluster of Toxin_18+ ORFs from each species. Only tBLASTx results for loci which encoded a representative sequence of a cluster containing more than one member were included. This alignment was generated by MUSCLE, then curated so that the Cys residues of chimpanzee_108932 aligned better with the other sequences. FIG. 60 suggests that there is more conservation between orthologues in different species than between paralogues from the same species. This pattern is much more apparent for CTXLP than for Env reading frame, where CTXLP appear to be under diversifying selection as indicated by increased dissimilarity between the CTXLP reading frame as compared to the Env reading frame of given sequences. differences are smaller if present at all. Taken together, this suggests that non-human primates are viable models for CTXLP research.

Murine Model of ERVK CTXLP

Figure 57:
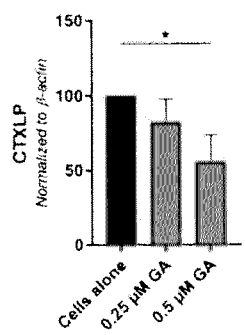
FIG. 57 depicts that endogenous levels of CTXLP in human astrocytes can be depleted in the presence of gambogic acid. Human astrocytic cell line SVGA were treated with increasing doses of gambogic acid in the low micromolar range (0.25 and 0.5 μM).
Figure 62:
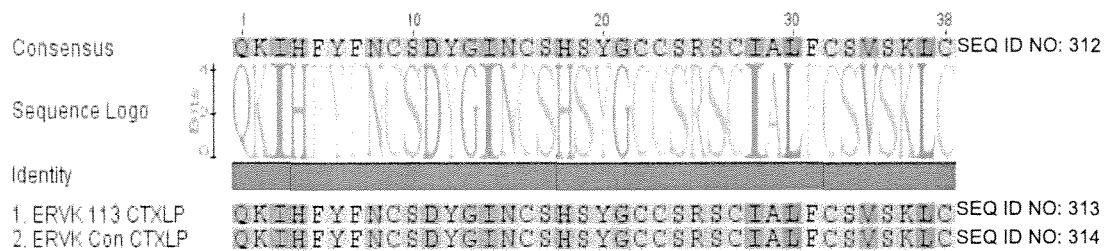
FIG. 62 depicts an alignment of ERVK113 CTXLP sequence and the ERVK Consensus sequence found in the ERVK envelope transgenic mice. Note the similarity and retention of key cysteine motif.

Avindra Nath's group has successfully developed a murine model which supports the neurotoxic potential of the ERVK envelope gene towards motor neurons[69]. ERVK env gene transgenic mice exhibit progressive motor dysfunction and hallmark pathology associated with ALS such decreased motor cortex volume and injury to pyramidal neurons and anterior horn cells in the spinal cord. This murine model is a solid platform for ERVK research, yet it remains unclear whether pathology and clinical outcomes were driven by canonical retroviral envelope proteins or CTXLP. This is because the insert used to generate the transgenic mice has the capacity to encode CTXLP (FIGS. 57 and 58). However, these mice do represent a putative model of CTXLP-driven neuropathology and neurodegeneration.

Drosophila Models of ERVK Env Gene Products, Including CTXLP

Drosophila (fruit flies) are a widely-used model organism, often used to study the cellular effects of pathogenic human viruses[155]. Moreover, TDP-43 null and TDP-43 mutant flies develop measurable motor deficits[156-158], making this model an exceptional tool to evaluate the impact of ERVK on ALS-like neuropathology and clinical outcomes. In collaboration with Dr. Alberto Civetta (University of Winnipeg), have designed an animal model system in which the ERVK proteins are transgenically expressed in Drosophila melanogaster.

ERVK Env, SU, TM and CTXLP open reading frames have been cloned (by GenScript, USA) into a pUAST vector (Drosophila Genomic Resource Center, #1000), allowing for Gal4 control of transgene expression patterns (see section above on design of custom CTXLP, SU and Env vectors). Generation of an ERVK protein transgenic flies is outsourced to BestGene Inc. (Chino Hills, CA). Flies will be crossed with neuronal (ELAV[156]), glia (repol[159]) or astrocyte (aIrm[160])-restricted Gal4 fly strains (Bloomington Drosophila Stock Center 8760, 7415 & 67032, respectively) to generate flies selectively expressing cell-type specific ERVK proteins. For each experimental group, lifespan analysis and locomotor impairment (# of walks/focal) will be monitored as previously described[156,161,162] ENREF 80. To perform pathological examinations, flies will be cold-sacrificed, heads removed, and tissue either flash frozen for western blot or fixed for immunohistochemical analyses. Biological readouts will be correlated with survival and motor-impairment metrics, as to assess how pathological events track with clinical outcomes. In a second series of experiments, fly models exhibiting clinical impairment will be used to assess the efficacy of a panel of CTXLP inhibitors, such as celastrol and gambogic acid (FIGS. 54-58). Inhibitors will be dissolved in DMSO and spiked into standard fly food just before solidification, at therapeutic concentrations of drug. Impact of drug administration on neuropathology and clinical outcomes will be evaluated.

Human Tissue Culture Models of CTXLP Expression

CTXLP was detectable in all human cell lines assayed (SVGA, ReNcell CX, NCCIT, T47D, cancer cell line panel), with varying degrees of expression. Based on the data shown above (FIGS. 54-58), ERVK CTXLP-expressing NCCIT teratocarcinoma cells are a viable model for drug screening applications. Additionally, we have developed a transient vector (pcDNA3.1, FIGS. 46 and 52) and a drug (cumate)-inducible lentiviral system (SBI SparQ QM812B-1[163]) allowing for stable overexpression of ERVK CTXLP, SU and Env. By using the feeder-independent pluripotent stem cell line WA09 (WiCell, mTeSR™ 1/Matrigel™ Platform) we can establish cerebral organoids, as previously described[164]. The above described protocols will form the foundation for generating ERVK CTXLP-expressing cerebral organoids, a human, druggable, three-dimensional brain model. Lentivirus transduction and flow cytometry selection will be used to generate WA09 stem cells containing the previously described cumate-inducible CTXLP vector. To establish a model of ERVK CTXLP-mediated pathology in intact cerebral tissue, these genetically modified WA09 cells will be grown to maximally sized cerebral organoids in the absence of cumate. Both wild-type and CTXLP-inducible cerebral organoids will be treated with varying doses of cumate, to allow for dose-response and time course experiments. Other potential human systems to study CTXLP in the future includes patient-derived human induced pluripotent stem cells systems[165-167].

In summary, Human tissue and animal models for the study of CTXLP in ALS and cancer are needed. We are actively working to further develop our human tissue culture models. In addition, together with Dr. Alberto Civetta, we are in the process of developing a model in *Drosophilia* at the University of Winnipeg. Importantly, we will continue to pursue mammalian models with our collaborators which offer an opportunity to explore multiple features of pathogenesis as we continue to elucidate the processes involved in CTXLP pathogenesis.

Discussion

Endogenous retroviruses (ERVs) are host genetic elements, representing approximately 8% of human genomic DNA. ERV activation can benefit their host, or in other contexts are proposed to be involved in pathogenesis and disease[6]. Our interest in ERVK and the CTXLP protein lies in its association to motor neuron conditions such as Amyotrophic Lateral Sclerosis (ALS), as well in cancers.

ERVK is known to be up-regulated in the neurons of many individuals with ALS[67,89,90,168]. The motor impairment in ALS is linked to calcium channel dysfunction, which is considered a viable therapeutic target. Thus, we were particularly intrigued by the CTXLP region of the ERVK genome when we discovered that it encoded a conotoxin-like peptide indicative of a pathogenic mechanism in ERVK associated disease. O-superfamily conotoxins are known to inhibit voltage gated calcium ion channels[169]. These channels are predominantly expressed at the presynaptic terminal of neural synapses[170]. When an impulse reaches this region, they allow calcium ions into the neuron, thereby increasing calcium ion concentration. This increase in concentration leads to fusion of synaptic vesicles containing neurotransmitters with the presynaptic membrane. The neurotransmitters are then released into the synaptic cleft where they bind to receptors on the postsynaptic terminal and stimulate downstream signaling. Inhibition of these channels with conotoxins can lead to tremors and an inhibition of motor function[23,24]. Our findings indicate that ERVK CTXLP may likewise be able to inhibit VGCCs and their calcium channel-associated transcriptional regulator (CCAT) and elicit similar responses resulting in impaired motor function.

It may be that ERVK CTXLP was previously implicated in ALS pathology. Notably, a 1997 study found that sera from 5 out of 6 ALS patients was able to reduce calcium ion currents when applied to mouse dorsal root ganglia[171]. The sera from a variety of disease control groups did not exhibit any effect on calcium ion currents. The authors concluded that "serum factors" from ALS patients can be passively transferred to affect calcium ion channel activity. It is possible that ERVK CTXLP may be the mediator of this effect. If this was the case, the protein would either have to be produced in non-brain cells or tissues. ERVK reverse transcriptase has been detected in the serum of many ALS patients[172,173]. If this enzyme originates from ERVK, it would demonstrate that ERVK proteins enter the serum during ALS. Thus, it would be possible that CTXLP could be present in the serum as well. In addition, a compromised blood-brain barrier observed in ALS and other neurology inflammatory events would allow CTXLP to cross into the serum[174].

Conotoxins are able to specifically inhibit ion channels of certain types of neurons[169], which may correlate with the loss of motor function and neurocognitive decline that is observed in ALS[175]. Other neurotoxin models have been proposed as etiological agents of ALS. The most prominent example is the suspected link between beta-N-methylamino-L-alanine (BMAA), a neurotoxin produced by a group of terrestrial cyanobacterial symbionts in cycad plants, and ALS (or an ALS-like syndrome)[176]. However, large scale spatial clustering of individuals with ALS has been inconsistent with the range of BMAA-producing cyanobacteria and other suspected environmental risk factors (although small, regional concordances have been identified)[176]. That is, no yet-proposed neurotoxin etiology has been able to explain the vast majority of cases of ALS. Therefore, although an environmental neurotoxin model for ALS makes sense at a physiological level, a genetic-based model (with environmental/epigenetic influence) seems more likely at an epidemiological level. A genetically-encoded neurotoxin etiology of ALS, such as ERVK CTXLP, would be consistent with both of these approaches. This model would not rely on the requirement to identify unique genes in individuals with ALS, as the different phenotypes (having ALS or not having it) could be caused by differential expression of the same genetic material. Additionally, two active ERVK loci unique to ALS patients have been identified[90]. It is possible that the CTXLP proteins of these loci are more functional than other ERVK sequences. Another alternative possibility is that insertional polymorphisms or single nucleotide polymorphisms result in differential ERVK CTXLP production or function. Thus, it is possible that sequence variation in ALS patients leads to differentially functional ERVK CTXLP proteins.

Additionally, there are several seemingly disparate features of conotoxin toxicity and ALS pathophysiology that would have to be resolved in order for such a link to be possible. For instance, calcium ion concentrations in the neurons of many ALS patients are elevated[175,177]. Since omega-conotoxins inhibit calcium influx into neurons[169], elevated calcium levels are the opposite of what would normally be expected in an ERVK CTXLP etiology of ALS[175]. However, it may be possible that these two features are not inconsistent, as many factors (aside from VGCCs) control neuronal calcium ion concentrations[170]. For instance, calcium-binding proteins such as calbindin-D28K and parvalbumin are absent in motor neurons lost early in ALS[170,177]. These proteins were present in significantly higher concentrations in healthy motor neurons, and in those affected later in the course of the disease[170]. Impaired mitochondrial calcium buffering has also been observed in ALS neurons[170,177].

Apart from pathology associated with VGCC disruption, we have also shown that CTXLP expression is correlated with elevated Nogo-A in the spinal cord of patients with ALS. Nogo-A is a key regulator of oligodendrocyte precursor cell (OPC) differentiation, ultimately negatively impacting remyelination and tissue repair. Demyelinated spinal cord lesions show an increased abundance of Nogo-A+ OPCs, yet the inability of OPCs to mature is proposed as the mechanism driving a non-permissive environment leading to remyelination failure[103-107]. Additionally, Nogo-A favours a pro-inflammatory context[123], one that would promote ERVK expression via modulation of NF-κB and pro-inflammatory cytokine secretion[67].

Nogo-A is implicated in a variety of neurological conditions, such as spinal cord injury, peripheral neuropathies, stroke, temporal lobe epilepsy, Alzheimer's disease, ALS, MS and schizophrenia[101,108-110]. Nogo-A has been identified as a prognostic marker and therapeutic target in ALS due to its substantial expression in muscle tissue from patients with motor neuron disease[111,112]. Mechanistically, Nogo-A expression destabilizes neuromuscular junctions[113-116]. Indeed, clinical trials using human anti-Nogo-A antibodies have been performed (ATI 355 from Novartis Pharma and Ozanezumab and GSK1223249 from GlaxoSmithKline)[101,117,118]. These therapies were designed to target Nogo-A expression in the periphery (intravenous infusions), but may fail to block Nogo-A expression in the CNS, thus explaining the negative results in Phase II clinical ALS trials with Ozanezumab[119,120]. Yet, anti-Nogo-A and remyelination-based therapies may be of value in the treatment of CTXLP+ disease states.

As ERVK CTXLP is present in the tissues of ALS patients, it may be used as a biomarker for the disease. This is significant given that ALS is often difficult to diagnose in its initial stages[175]. Furthermore, if it is found to be an etiological agent of disease, ERVK CTXLP levels could be useful in assessing disease progression or prognosis. Perhaps most importantly, therapeutics could be designed to target it in order to reduce motor function deficits and increase longevity. For instance, a humanized monoclonal antibody could be designed against ERVK CTXLP for intravenous immunoglobulin (IVIG) therapy. Alternatively, small molecule inhibitors, such as MAEs celastrol and gambogic acid, could be used to target ERVK CTXLP DNA binding, gene transactivation effects, enhancement of NF-κB expression and modulation of pathogenic biomarkers. If ERVK CTXLP is found to play pathological roles in other diseases, for example spinal cord injury, multiple sclerosis, schizophrenia or cancers to name a few, this avenue of research could have implications on the diagnosis and treatment of these diseases as well.

ERVK expression is up-regulated in schizophrenia and bipolar disorders[178] (unpublished data). This may be worth investigating further if ERVK CTXLP production is confirmed, given the fact that omega-conotoxins can cause emotional distress and prolonged delirium with psychotic features[24,179].

Additionally, HIV and HTLV infections are known to lead to up-regulation of ERVK expression[180,181]. Both of these infections are associated with poorly understood, reversible ALS-like syndromes in a small number of patients[182-184]. HIV-associated ALS can be treated effectively with highly active antiretroviral therapy (HAART)[182,183]. It is possible that ERVK CTXLP is a pathological contributor to exogenous retrovirus infections and these ALS-like diseases.

Many cancers are associated with ERVK expression[185]. Evidence that increased ERVK CTXLP expression occurs in cancers cells implicates this viral protein in oncogenesis and possibly metastasis. Specifically, the induction of NF-κB is likely a key feature of ERVK CTXLP activity which may facilitate cancer development and progression[186,187].

Together, the results of this analysis provide a basis for further research into the ERVK genome and the relationship between ERVK and inflammatory disease. Given the possible correlations between ERVK CTXLP and disease pathology, this line of research deserves further study.

FIGS. 63-65 summarize possible implications of our discoveries.

REFERENCES

1. Hohn, O., Hanke, K. & Bannert, N. HERV-K(HML-2), the Best Preserved Family of HERVs: Endogenization, Expression, and Implications in Health and Disease. Frontiers in oncology 3, 246 (2013).
2. Lesbats, P., Engelman, A. N. & Cherepanov, P. Retroviral DNA Integration. Chemical reviews (2016).
3. Christensen, T. HERVs in neuropathogenesis. J Neuroimmune Pharmacol 5, 326-335 (2010).
4. Weiss, R. A. The discovery of endogenous retroviruses. Retrovirology 3, 67 (2006).
5. Lokossou, A. G., Toudic, C. & Barbeau, B. Implication of human endogenous retrovirus envelope proteins in placental functions. Viruses 6, 4609-4627 (2014).
6. Manghera, M., Ferguson, J. & Douville, R. Endogenous retrovirus-K and nervous system diseases. Curr Neurol Neurosci Rep 14, 488 (2014).
7. Macfarlane, C. & Simmonds, P. Allelic variation of HERV-K(HML-2) endogenous retroviral elements in human populations. J Mol Evol 59, 642-656 (2004).
8. Shin, W., et al. Human-specific HERV-K insertion causes genomic variations in the human genome. PLoS One 8, e60605 (2013).
9. Marchi, E., Kanapin, A., Magiorkinis, G. & Belshaw, R. Unfixed endogenous retroviral insertions in the human population. J Virol 88, 9529-9537 (2014).
10. Seifarth, W., et al. Comprehensive analysis of human endogenous retrovirus transcriptional activity in human tissues with a retrovirus-specific microarray. J Virol 79, 341-352 (2005).
11. Griffiths, D. J. Endogenous retroviruses in the human genome sequence. Genome Biol 2, REVIEWS1017 (2001).
12. Buzdin, A., Kovalskaya-Alexandrova, E., Gogvadze, E. & Sverdlov, E. At least 50% of human-specific HERV-K (HML-2) long terminal repeats serve in vivo as active promoters for host nonrepetitive DNA transcription. J Virol 80, 10752-10762 (2006).
13. Ruggieri, A., et al. Human endogenous retrovirus HERV-K(HML-2) encodes a stable signal peptide with biological properties distinct from Rec. Retrovirology 6, 17 (2009).
14. Denne, M., et al. Physical and functional interactions of human endogenous retrovirus proteins Np9 and rec with the promyelocytic leukemia zinc finger protein. J Virol 81, 5607-5616 (2007).
15. Contreras-Galindo, R., et al. Characterization of human endogenous retroviral elements in the blood of HIV-1-infected individuals. J Virol 86, 262-276 (2012).
16. Dewannieux, M., Blaise, S. & Heidmann, T. Identification of a functional envelope protein from the HERV-K family of human endogenous retroviruses. J Virol 79, 15573-15577 (2005).
17. Julien, J. P., et al. Crystal structure of a soluble cleaved HIV-1 envelope trimer. Science 342, 1477-1483 (2013).
18. Daly, N. L. & Craik, D. J. Bioactive cystine knot proteins. Curr Opin Chem Biol 15, 362-368 (2011).
19. Iyer, S. & Acharya, K. R. Tying the knot: the cystine signature and molecular-recognition processes of the vascular endothelial growth factor family of angiogenic cytokines. FEBS J 278, 4304-4322 (2011).
20. McNulty, J. C., et al. Structures of the agouti signaling protein. J Mol Biol 346, 1059-1070 (2005).
21. Zhu, S., Darbon, H., Dyason, K., Verdonck, F. & Tytgat, J. Evolutionary origin of inhibitor cystine knot peptides. FASEB J 17, 1765-1767 (2003).
22. Becker, S. & Terlau, H. Toxins from cone snails: properties, applications and biotechnological production. Appl Microbiol Biotechnol 79, 1-9 (2008).
23. Anderson, P. D. Bioterrorism: toxins as weapons. Journal of pharmacy practice 25, 121-129 (2012).

24. Obafemi, A. & Roth, B. Prolonged delirium with psychotic features from omega conotoxin toxicity. Pain Med 14, 447-448 (2013).

25. Norton, R. S. & Olivera, B. M. Conotoxins down under. Toxicon 48, 780-798 (2006).

26. Su, S. C., et al. Regulation of N-type voltage-gated calcium channels and presynaptic function by cyclin-dependent kinase 5. Neuron 75, 675-687 (2012).

27. Adams, D. J. & Berecki, G. Mechanisms of conotoxin inhibition of N-type (Ca(v)2.2) calcium channels. Biochim Biophys Acta 1828, 1619-1628 (2013).

28. Eldridge, R., Li, Y. & Miller, L. K. Characterization of a baculovirus gene encoding a small conotoxinlike polypeptide. J Virol 66, 6563-6571 (1992).

29. Gracy, J., et al. KNOTTIN: the knottin or inhibitor cystine knot scaffold in 2007. Nucleic Acids Res 36, D314-319 (2008).

30. Kearse, M., et al. Geneious Basic: an integrated and extendable desktop software platform for the organization and analysis of sequence data. Bioinformatics 28, 1647-1649 (2012).

31. Pettersen, E. F., et al. UCSF Chimera—a visualization system for exploratory research and analysis. Journal of computational chemistry 25, 1605-1612 (2004).

32. Daly, N. L., Rosengren, K. J., Henriques, S. T. & Craik, D. J. NMR and protein structure in drug design: application to cyclotides and conotoxins. Eur Biophys J 40, 359-370 (2011).

33. Jiang, L., et al. 111In-labeled cystine-knot peptides based on the Agouti-related protein for targeting tumor angiogenesis. J Biomed Biotechnol 2012, 368075 (2012).

34. Li, D., et al. Function and solution structure of hainantoxin-I, a novel insect sodium channel inhibitor from the Chinese bird spider Selenocosmia hainana. FEBS Lett 555, 616-622 (2003).

35. Sato, K., et al. Binding of Ala-scanning analogs of omega-conotoxin MVIIC to N- and P/Q-type calcium channels. FEBS Lett 469, 147-150 (2000).

36. Jackson, P. J., et al. Structural and molecular evolutionary analysis of Agouti and Agouti-related proteins. Chem Biol 13, 1297-1305 (2006).

37. Bagashev, A. & Sawaya, B. E. Roles and functions of HIV-1 Tat protein in the CNS: an overview. Virol J 10, 358 (2013).

38. Kruman, II, Nath, A. & Mattson, M. P. HIV-1 protein Tat induces apoptosis of hippocampal neurons by a mechanism involving caspase activation, calcium overload, and oxidative stress. Exp Neurol 154, 276-288 (1998).

39. Popper, S. J., et al. Lower human immunodeficiency virus (HIV) type 2 viral load reflects the difference in pathogenicity of HIV-1 and HIV-2. J Infect Dis 180, 1116-1121 (1999).

40. Dhamija, N., Choudhary, D., Ladha, J. S., Pillai, B. & Mitra, D. Tat predominantly associates with host promoter elements in HIV-1-infected T-cells—regulatory basis of transcriptional repression of c-Rel. FEBS J 282, 595-610 (2015).

41. Kim, J., Yoon, J. H. & Kim, Y. S. HIV-1 Tat interacts with and regulates the localization and processing of amyloid precursor protein. PLoS One 8, e77972 (2013).

42. Gonzalez-Hernandez, M. J., et al. Regulation of the human endogenous retrovirus K (HML-2) transcriptome by the HIV-1 Tat protein. J Virol 88, 8924-8935 (2014).

43. Subramanian, R. P., Wildschutte, J. H., Russo, C. & Coffin, J. M. Identification, characterization, and comparative genomic distribution of the HERV-K (HML-2) group of human endogenous retroviruses. Retrovirology 8, 90 (2011).

44. Gifford, R. & Tristem, M. The evolution, distribution and diversity of endogenous retroviruses. Virus Genes 26, 291-315 (2003).

45. Barbulescu, M., et al. Many human endogenous retrovirus K (HERV-K) proviruses are unique to humans. Curr Biol 9, 861-868 (1999).

46. Schmitt, K., Reichrath, J., Roesch, A., Meese, E. & Mayer, J. Transcriptional profiling of human endogenous retrovirus group HERV-K(HML-2) loci in melanoma. Genome biology and evolution 5, 307-328 (2013).

47. Dinkel, H., et al. ELM 2016—data update and new functionality of the eukaryotic linear motif resource. Nucleic Acids Res 44, D294-300 (2016).

48. Vagner, S., et al. Alternative translation initiation of the Moloney murine leukemia virus mRNA controlled by internal ribosome entry involving the p57/PTB splicing factor. J Biol Chem 270, 20376-20383 (1995).

49. Buck, C. B., et al. The human immunodeficiency virus type 1 gag gene encodes an internal ribosome entry site. J Virol 75, 181-191 (2001).

50. Lopez-Lastra, M., Rivas, A. & Barria, M. I. Protein synthesis in eukaryotes: the growing biological relevance of cap-independent translation initiation. Biol Res 38, 121-146 (2005).

51. Boulikas, T. Putative nuclear localization signals (NLS) in protein transcription factors. J Cell Biochem 55, 32-58 (1994).

52. Chang, K. C. Revealing −1 programmed ribosomal frameshifting mechanisms by single-molecule techniques and computational methods. Comput Math Methods Med 2012, 569870 (2012).

53. Touriol, C., et al. Generation of protein isoform diversity by alternative initiation of translation at non-AUG codons. Biol Cell 95, 169-178 (2003).

54. Buee, L., Bussiere, T., Buee-Scherrer, V., Delacourte, A. & Hof, P. R. Tau protein isoforms, phosphorylation and role in neurodegenerative disorders. Brain Res Brain Res Rev 33, 95-130 (2000).

55. Ueki, N., Someya, K., Matsuo, Y., Wakamatsu, K. & Mukai, H. Cryptides: functional cryptic peptides hidden in protein structures. Biopolymers 88, 190-198 (2007).

56. Ho, O. & Green, W. R. Cytolytic CD8+ T cells directed against a cryptic epitope derived from a retroviral alternative reading frame confer disease protection. J Immunol 176, 2470-2475 (2006).

57. Garrison, K. E., et al. Transcriptional errors in human immunodeficiency virus type 1 generate targets for T-cell responses. Clin Vaccine Immunol 16, 1369-1371 (2009).

58. Brinzevich, D., et al. HIV-1 interacts with human endogenous retrovirus K (HML-2) envelopes derived from human primary lymphocytes. J Virol 88, 6213-6223 (2014).

59. Terry, S. N., et al. Expression of HERV-K108 envelope interferes with HIV-1 production. Virology 509, 52-59 (2017).

60. Hanke, K., et al. Reconstitution of the ancestral glycoprotein of human endogenous retrovirus k and modulation of its functional activity by truncation of the cytoplasmic domain. J Virol 83, 12790-12800 (2009).

61. Lemaitre, C., Harper, F., Pierron, G., Heidmann, T. & Dewannieux, M. The HERV-K human endogenous retrovirus envelope protein antagonizes Tetherin antiviral activity. J Virol 88, 13626-13637 (2014).

62. Kesidou, E., Lagoudaki, R., Touloumi, O., Poulatsidou, K. N. & Simeonidou, C. Autophagy and neurodegenerative disorders. Neural Regen Res 8, 2275-2283 (2013).

63. Jang, G. Y., et al. Transglutaminase 2 suppresses apoptosis by modulating caspase 3 and NF-kappaB activity in hypoxic tumor cells. Oncogene 29, 356-367 (2010).

64. Manghera, M. & Douville, R. N. Endogenous retrovirus-K promoter: a landing strip for inflammatory transcription factors? Retrovirology 10, 16 (2013).

65. Manghera, M., Ferguson, J. & Douville, R. ERVK polyprotein processing and reverse transcriptase expression in human cell line models of neurological disease. Viruses 7, 320-332 (2015).

66. Manghera, M., Ferguson-Parry, J. & Douville, R. N. TDP-43 regulates endogenous retrovirus-K viral protein accumulation. Neurobiol Dis 94, 226-236 (2016).

67. Manghera, M., Ferguson-Parry, J., Lin, R. & Douville, R. N. NF-kappaB and IRF1 Induce Endogenous Retrovirus K Expression via Interferon-Stimulated Response Elements in Its 5' Long Terminal Repeat. J Virol 90, 9338-9349 (2016).

68. Bhat, R. K., et al. Human Endogenous Retrovirus-K (II) Envelope Induction Protects Neurons during HIV/AIDS. PLoS One 9, e97984 (2014).

69. Li, W., et al. Human endogenous retrovirus-K contributes to motor neuron disease. Science translational medicine 7, 307ra153 (2015).

70. Zhou, J., Callapina, M., Goodall, G. J. & Brune, B. Functional integrity of nuclear factor kappaB, phosphatidylinositol 3'-kinase, and mitogen-activated protein kinase signaling allows tumor necrosis factor alpha-evoked Bcl-2 expression to provoke internal ribosome entry site-dependent translation of hypoxia-inducible factor 1alpha. Cancer Res 64, 9041-9048 (2004).

71. Szilagyi, A. & Skolnick, J. Efficient prediction of nucleic acid binding function from low-resolution protein structures. J Mol Biol 358, 922-933 (2006).

72. Marsili, G., et al. On the role of interferon regulatory factors in HIV-1 replication. Ann N Y Acad Sci 1010, 29-42 (2003).

73. Williams, B. R. Transcriptional regulation of interferon-stimulated genes. Eur J Biochem 200, 1-11 (1991).

74. Garcia, J. A., Harrich, D., Pearson, L., Mitsuyasu, R. & Gaynor, R. B. Functional domains required for tat-induced transcriptional activation of the HIV-1 long terminal repeat. EMBO J 7, 3143-3147 (1988).

75. Keller, G., Gross, C., Kelleher, M. & Winge, D. R. Functional independence of the two cysteine-rich activation domains in the yeast Mac1 transcription factor. J Biol Chem 275, 29193-29199 (2000).

76. Vocero-Akbani, A., Lissy, N. A. & Dowdy, S. F. Transduction of full-length Tat fusion proteins directly into mammalian cells: analysis of T cell receptor activation-induced cell death. Methods Enzymol 322, 508-521 (2000).

77. Sheehy, N., et al. Functional analysis of human T lymphotropic virus type 2 Tax proteins. Retrovirology 3, 20 (2006).

78. Hardiman, O., et al. Amyotrophic lateral sclerosis. Nat Rev Dis Primers 3, 17071 (2017).

79. Eisen, A., et al. Cortical influences drive amyotrophic lateral sclerosis. J Neurol Neurosurg Psychiatry 88, 917-924 (2017).

80. Cappello, V. & Francolini, M. Neuromuscular Junction Dismantling in Amyotrophic Lateral Sclerosis. Int J Mol Sci 18(2017).

81. Moisse, K. & Strong, M. J. Innate immunity in amyotrophic lateral sclerosis. Biochim Biophys Acta 1762, 1083-1093 (2006).

82. McCombe, P. A. & Henderson, R. D. The Role of immune and inflammatory mechanisms in ALS. Curr Mol Med 11, 246-254 (2011).

83. Scotter, E. L., Chen, H. J. & Shaw, C. E. TDP-43 Proteinopathy and ALS: Insights into Disease Mechanisms and Therapeutic Targets. Neurotherapeutics 12, 352-363 (2015).

84. Kwong, L. K., Neumann, M., Sampathu, D. M., Lee, V. M. & Trojanowski, J. Q. TDP-43 proteinopathy: the neuropathology underlying major forms of sporadic and familial frontotemporal lobar degeneration and motor neuron disease. Acta Neuropathol 114, 63-70 (2007).

85. Leal, S. S. & Gomes, C. M. Calcium dysregulation links ALS defective proteins and motor neuron selective vulnerability. Frontiers in cellular neuroscience 9, 225 (2015).

86. Zhou, T., et al. Implications of white matter damage in amyotrophic lateral sclerosis (Review). Mol Med Rep 16, 4379-4392 (2017).

87. Tognatta, R. & Miller, R. H. Contribution of the oligodendrocyte lineage to CNS repair and neurodegenerative pathologies. Neuropharmacology 110, 539-547 (2016).

88. Poniatowski, L. A., et al. Analysis of the Role of CX3CL1 (Fractalkine) and Its Receptor CX3CR1 in Traumatic Brain and Spinal Cord Injury: Insight into Recent Advances in Actions of Neurochemokine Agents. Mol Neurobiol 54, 2167-2188 (2017).

89. Manghera, M., Ferguson-Parry, J. & Douville, R. N. TDP-43 regulates endogenous retrovirus-K viral protein accumulation. Neurobiol Dis 94, 226-236 (2016).

90. Douville, R., Liu, J., Rothstein, J. & Nath, A. Identification of active loci of a human endogenous retrovirus in neurons of patients with amyotrophic lateral sclerosis. Ann Neurol 69, 141-151 (2011).

91. Hurtado, A. P., Rengifo, A. C. & Torres-Fernández, O. Immunohistochemical Overexpression of MAP-2 in the Cerebral Cortex of Rabies-Infected Mice. International Journal of Morphology 33, 465-470 (2015).

92. Monroy-Gomez, J., Santamaria, G. & Torres-Fernandez, O. Overexpression of MAP2 and NF-H Associated with Dendritic Pathology in the Spinal Cord of Mice Infected with Rabies Virus. Viruses 10(2018).

93. Timmermann, D. B., Westenbroek, R. E., Schousboe, A. & Catterall, W. A. Distribution of high-voltage-activated calcium channels in cultured gamma-aminobutyric acidergic neurons from mouse cerebral cortex. J Neurosci Res 67, 48-61 (2002).

94. McTigue, D. M. & Tripathi, R. B. The life, death, and replacement of oligodendrocytes in the adult CNS. J Neurochem 107, 1-19 (2008).

95. Othman, A., et al. Olig1 is expressed in human oligodendrocytes during maturation and regeneration. Glia 59, 914-926 (2011).

96. Chong, S. Y. & Chan, J. R. Tapping into the glial reservoir: cells committed to remaining uncommitted. J Cell Biol 188, 305-312 (2010).

97. Watkins, T. A., Emery, B., Mulinyawe, S. & Barres, B. A. Distinct stages of myelination regulated by gamma-secretase and astrocytes in a rapidly myelinating CNS coculture system. Neuron 60, 555-569 (2008).

98. de Faria, O., Jr., Gonsalvez, D., Nicholson, M. & Xiao, J. Activity-dependent central nervous system myelination throughout life. J Neurochem (2018).

99. Fancy, S. P., et al. Dysregulation of the Wnt pathway inhibits timely myelination and remyelination in the mammalian CNS. Genes Dev 23, 1571-1585 (2009).

100. Arnett, H. A., et al. bHLH transcription factor Olig1 is required to repair demyelinated lesions in the CNS. Science 306, 2111-2115 (2004).

101. Schmandke, A., Schmandke, A. & Schwab, M. E. Nogo-A: Multiple Roles in CNS Development, Maintenance, and Disease. Neuroscientist 20, 372-386 (2014).

102. Pernet, V., Joly, S., Christ, F., Dimou, L. & Schwab, M. E. Nogo-A and myelin-associated glycoprotein differently regulate oligodendrocyte maturation and myelin formation. J Neurosci 28, 7435-7444 (2008).

103. Miron, V. E., Kuhlmann, T. & Antel, J. P. Cells of the oligodendroglial lineage, myelination, and remyelination. Biochim Biophys Acta 1812, 184-193 (2011).

104. Talbott, J. F., et al. Endogenous Nkx2.2+/Olig2+ oligodendrocyte precursor cells fail to remyelinate the demyelinated adult rat spinal cord in the absence of astrocytes. Exp Neurol 192, 11-24 (2005).

105. Cafferty, W. B. & Strittmatter, S. M. The Nogo-Nogo receptor pathway limits a spectrum of adult CNS axonal growth. J Neurosci 26, 12242-12250 (2006).

106. Kuhlmann, T., et al. Differentiation block of oligodendroglial progenitor cells as a cause for remyelination failure in chronic multiple sclerosis. Brain 131, 1749-1758 (2008).

107. Theotokis, P., et al. Time course and spatial profile of Nogo-A expression in experimental autoimmune encephalomyelitis in C57BL/6 mice. J Neuropathol Exp Neurol 71, 907-920 (2012).

108. Wojcik, S., Engel, W. K. & Askanas, V. Increased expression of Noga-A in ALS muscle biopsies is not unique for this disease. Acta myologica: myopathies and cardiomyopathies: official journal of the Mediterranean Society of Myology/edited by the Gaetano Conte Academy for the study of striated muscle diseases 25, 116-118 (2006).

109. Teng, F. Y. & Tang, B. L. Nogo signaling and non-physical injury-induced nervous system pathology. J Neurosci Res 79, 273-278 (2005).

110. McDonald, C. L., Bandtlow, C. & Reindl, M. Targeting the Nogo receptor complex in diseases of the central nervous system. Curr Med Chem 18, 234-244 (2011).

111. Dupuis, L., et al. Nogo provides a molecular marker for diagnosis of amyotrophic lateral sclerosis. Neurobiol Dis 10, 358-365 (2002).

112. Pradat, P. F., et al. Muscle Nogo-A expression is a prognostic marker in lower motor neuron syndromes. Ann Neurol 62, 15-20 (2007).

113. Sui, Y. P., Zhang, X. X., Lu, J. L. & Sui, F. New Insights into the Roles of Nogo-A in CNS Biology and Diseases. Neurochem Res 40, 1767-1785 (2015).

114. Bruneteau, G., et al. Endplate denervation correlates with Nogo-A muscle expression in amyotrophic lateral sclerosis patients. Annals of clinical and translational neurology 2, 362-372 (2015).

115. Bros-Facer, V., et al. Treatment with an antibody directed against Nogo-A delays disease progression in the SOD1G93A mouse model of Amyotrophic lateral sclerosis. Hum Mol Genet 23, 4187-4200 (2014).

116. Jokic, N., et al. The neurite outgrowth inhibitor Nogo-A promotes denervation in an amyotrophic lateral sclerosis model. EMBO Rep 7, 1162-1167 (2006).

117. Ineichen, B. V., et al. Nogo-A Antibodies for Progressive Multiple Sclerosis. CNS Drugs 31, 187-198 (2017).

118. Meininger, V., et al. Safety, pharmacokinetic, and functional effects of the nogo-a monoclonal antibody in amyotrophic lateral sclerosis: a randomized, first-in-human clinical trial. PLoS One 9, e97803 (2014).

119. Meininger, V., et al. Safety and efficacy of ozanezumab in patients with amyotrophic lateral sclerosis: a randomised, double-blind, placebo-controlled, phase 2 trial. Lancet Neurol 16, 208-216 (2017).

120. Wills, A. M. Blockade of the neurite outgrowth inhibitor Nogo-A in amyotrophic lateral sclerosis. Lancet Neurol 16, 175-176 (2017).

121. Amy, M., et al. A common functional allele of the Nogo receptor gene, reticulon 4 receptor (RTN4R), is associated with sporadic amyotrophic lateral sclerosis in a French population. Amyotrophic lateral sclerosis & frontotemporal degeneration 16, 490-496 (2015).

122. Buss, A., et al. Sequential loss of myelin proteins during Wallerian degeneration in the human spinal cord. Brain 128, 356-364 (2005).

123. Fang, Y., et al. The Nogo/Nogo Receptor (NgR) Signal Is Involved in Neuroinflammation through the Regulation of Microglial Inflammatory Activation. J Biol Chem 290, 28901-28914 (2015).

124. Ghosh, S. & Dass, J. F. Study of pathway cross-talk interactions with NF-kappaB leading to its activation via ubiquitination or phosphorylation: A brief review. Gene 584, 97-109 (2016).

125. Yang, X. D. & Sun, S. C. Targeting signaling factors for degradation, an emerging mechanism for TRAF functions. Immunol Rev 266, 56-71 (2015).

126. Gomez-Ospina, N., Tsuruta, F., Barreto-Chang, O., Hu, L. & Dolmetsch, R. The C terminus of the L-type voltage-gated calcium channel Ca(V)1.2 encodes a transcription factor. Cell 127, 591-606 (2006).

127. Gomez-Ospina, N., et al. A promoter in the coding region of the calcium channel gene CACNA1C generates the transcription factor CCAT. PLoS One 8, e60526 (2013).

128. Nielsen, K. J., Schroeder, T. & Lewis, R. Structure-activity relationships of omega-conotoxins at N-type voltage-sensitive calcium channels. J Mol Recognit 13, 55-70 (2000).

129. Takata, T., et al. Clinical significance of caspase-3 expression in pathologic-stage I, nonsmall-cell lung cancer. Int J Cancer 96 Suppl, 54-60 (2001).

130. Pu, X., et al. Caspase-3 and caspase-8 expression in breast cancer: caspase-3 is associated with survival. Apoptosis 22, 357-368 (2017).

131. Chen, H., et al. Prognostic value of Caspase-3 expression in cancers of digestive tract: a meta-analysis and systematic review. Int J Clin Exp Med 8, 10225-10234 (2015).

132. Wurzer, W. J., et al. Caspase 3 activation is essential for efficient influenza virus propagation. EMBO J 22, 2717-2728 (2003).

133. Do, T., et al. Three-dimensional imaging of HIV-1 virological synapses reveals membrane architectures involved in virus transmission. J Virol 88, 10327-10339 (2014).

134. Narayan, V., et al. Celastrol inhibits Tat-mediated human immunodeficiency virus (HIV) transcription and replication. J Mol Biol 410, 972-983 (2011).

135. Kalantari, P., Narayan, V., Henderson, A. J. & Prabhu, K. S. 15-Deoxy-Delta12,14-prostaglandin J2 inhibits HIV-1 transactivating protein, Tat, through covalent modification. FASEB J 23, 2366-2373 (2009).

136. Cascao, R., Fonseca, J. E. & Moita, L. F. Celastrol: A Spectrum of Treatment Opportunities in Chronic Diseases. Front Med (Lausanne) 4, 69 (2017).

137. Salminen, A., Lehtonen, M., Paimela, T. & Kaarniranta, K. Celastrol: Molecular targets of Thunder God Vine. Biochem Biophys Res Commun 394, 439-442 (2010).

138. Tao, X., Sun, Y. & Zhong, N. [Treatment of rheumatoid arthritis with low doses of multi-glycosides of Tripterygium wilfordii]. Zhong Xi Yi Jie He Za Zhi 10, 289-291, 261-282 (1990).

139. Venkatesha, S. H., Astry, B., Nanjundaiah, S. M., Yu, H. & Moudgil, K. D. Suppression of autoimmune arthritis by Celastrus-derived Celastrol through modulation of pro-inflammatory chemokines. Bioorg Med Chem 20, 5229-5234 (2012).

140. Fang, Z., et al. High-Throughput Study of the Effects of Celastrol on Activated Fibroblast-Like Synoviocytes from Patients with Rheumatoid Arthritis. Genes 8(2017).

141. Paris, D., et al. Reduction of beta-amyloid pathology by celastrol in a transgenic mouse model of Alzheimer's disease. J Neuroinflammation 7, 17 (2010).

142. Kashyap, D., et al. Molecular targets of celastrol in cancer: Recent trends and advancements. Critical reviews in oncology/hematology 128, 70-81 (2018).

143. Reutrakul, V., et al. Cytotoxic and anti-HIV-1 caged xanthones from the resin and fruits of Garcinia hanburyi. Planta Med 73, 33-40 (2007).

144. Banik, K., et al. Therapeutic potential of gambogic acid, a caged xanthone, to target cancer. Cancer Lett 416, 75-86 (2018).

145. Kashyap, D., Mondal, R., Tuli, H. S., Kumar, G. & Sharma, A. K. Molecular targets of gambogic acid in cancer: recent trends and advancements. Tumour biology: the journal of the International Society for Oncodevelopmental Biology and Medicine 37, 12915-12925 (2016).

146. Jang, S. W., et al. Gambogic amide, a selective agonist for TrkA receptor that possesses robust neurotrophic activity, prevents neuronal cell death. Proc Natl Acad Sci USA 104, 16329-16334 (2007).

147. Fu, Q., Li, C. & Yu, L. Gambogic acid inhibits spinal cord injury and inflammation through suppressing the p38 and Akt signaling pathways. Mol Med Rep 17, 2026-2032 (2018).

148. Wang, J., Gines, S., MacDonald, M. E. & Gusella, J. F. Reversal of a full-length mutant huntingtin neuronal cell phenotype by chemical inhibitors of polyglutamine-mediated aggregation. BMC Neurosci 6, 1 (2005).

149. Chen, S. R., et al. A Mechanistic Overview of Triptolide and Celastrol, Natural Products from Tripterygium wilfordii Hook F. Frontiers in pharmacology 9, 104 (2018).

150. Saini, P., Ganugula, R., Arora, M. & Kumar, M. N. The Next Generation Non-competitive Active Polyester Nanosystems for Transferrin Receptor-mediated Peroral Transport Utilizing Gambogic Acid as a Ligand. Scientific reports 6, 29501 (2016).

151. Fan, T. K., Gundimeda, U., Mack, W. J. & Gopalakrishna, R. Counteraction of Nogo-A and axonal growth inhibitors by green tea polyphenols and other natural products. Neural Regen Res 11, 545-546 (2016).

152. Sepe, M., et al. Proteolytic control of neurite outgrowth inhibitor NOGO-A by the cAMP/PKA pathway. Proc Natl Acad Sci USA 111, 15729-15734 (2014).

153. Yu, X. J., Zhao, Q., Wang, X. B., Zhang, J. X. & Wang, X. B. Gambogenic acid induces proteasomal degradation of CIP2A and sensitizes hepatocellular carcinoma to anticancer agents. Oncol Rep 36, 3611-3618 (2016).

154. Wang, J., et al. Gambogic acid-induced degradation of mutant p53 is mediated by proteasome and related to CHIP. J Cell Biochem 112, 509-519 (2011).

155. Hughes, T. T., et al. *Drosophila* as a genetic model for studying pathogenic human viruses. Virology 423, 1-5 (2012).

156. Krug, L., et al. Retrotransposon activation contributes to neurodegeneration in a *Drosophila* TDP-43 model of ALS. PLoS Genet 13, e1006635 (2017).

157. Chang, J. C., Hazelett, D. J., Stewart, J. A. & Morton, D. B. Motor neuron expression of the voltage-gated calcium channel cacophony restores locomotion defects in a *Drosophila*, TDP-43 loss of function model of ALS. Brain Res 1584, 39-51 (2014).

158. Estes, P. S., et al. Motor neurons and glia exhibit specific individualized responses to TDP-43 expression in a *Drosophila* model of amyotrophic lateral sclerosis. Dis Model Mech 6, 721-733 (2013).

159. Ghosh, A., et al. Targeted ablation of oligodendrocytes triggers axonal damage. PLoS One 6, e22735 (2011).

160. Huang, Y., Ng, F. S. & Jackson, F. R. Comparison of larval and adult *Drosophila* astrocytes reveals stage-specific gene expression profiles. G3 (Bethesda) 5, 551-558 (2015).

161. Civetta, A. & Clark, A. G. Correlated effects of sperm competition and postmating female mortality. Proc Natl Acad Sci USA 97, 13162-13165 (2000).

162. Civetta, A., Montooth, K. L. & Mendelson, M. Quantitative trait loci and interaction effects responsible for variation in female postmating mortality in *Drosophila* simulans and D. sechellia introgression lines. Heredity (Edinb) 94, 94-100 (2005).

163. Mullick, A., et al. The cumate gene-switch: a system for regulated expression in mammalian cells. BMC biotechnology 6, 43 (2006).

164. Lancaster, M. A., et al. Cerebral organoids model human brain development and microcephaly. Nature 501, 373-379 (2013).

165. Rosati, J., et al. Establishment of stable iPS-derived human neural stem cell lines suitable for cell therapies. Cell death & disease 9, 937 (2018).

166. Dimos, J. T., et al. Induced pluripotent stem cells generated from patients with ALS can be differentiated into motor neurons. Science 321, 1218-1221 (2008).

167. Egawa, N., et al. Drug screening for ALS using patient-specific induced pluripotent stem cells. Science translational medicine 4, 145ra104 (2012).

168. Douville, R. N. & Nath, A. Human Endogenous Retrovirus-K and TDP-43 Expression Bridges ALS and HIV Neuropathology. Frontiers in microbiology 8, 1986 (2017).

169. Olivera, B. M. & Teichert, R. W. Diversity of the neurotoxic Conus peptides: a model for concerted pharmacological discovery. Mol Intery 7, 251-260 (2007).

170. Marambaud, P., Dreses-Werringloer, U. & Vingt-deux, V. Calcium signaling in neurodegeneration. Molecular neurodegeneration 4, 20 (2009).

171. Yan, H. D., Lim, W., Lee, K. W. & Kim, J. Sera from amyotrophic lateral sclerosis patients reduce high-voltage activated Ca2+ currents in mice dorsal root ganglion neurons. Neurosci Lett 235, 69-72 (1997).

172. MacGowan, D. J., Scelsa, S. N. & Waldron, M. An ALS-like syndrome with new HIV infection and complete response to antiretroviral therapy. Neurology 57, 1094-1097 (2001).

173. McCormick, A. L., Brown, R. H., Jr., Cudkowicz, M. E., Al-Chalabi, A. & Garson, J. A. Quantification of reverse transcriptase in ALS and elimination of a novel retroviral candidate. Neurology 70, 278-283 (2008).

174. Garbuzova-Davis, S. & Sanberg, P. R. Blood-CNS Barrier Impairment in ALS patients versus an animal model. Frontiers in cellular neuroscience 8, 21 (2014).

175. Mitchell, J. D. & Borasio, G. D. Amyotrophic lateral sclerosis. Lancet 369, 2031-2041 (2007).

176. Caller, T. A., et al. Spatial clustering of amyotrophic lateral sclerosis and the potential role of BMAA. Amyotroph Lateral Scler 13, 25-32 (2012).

177. Appel, S. H., Beers, D., Siklos, L., Engelhardt, J. I. & Mosier, D. R. Calcium: the Darth Vader of ALS. Amyotroph Lateral Scler Other Motor Neuron Disord 2 Suppl 1, S47-54 (2001).

178. Frank, O., et al. Human endogenous retrovirus expression profiles in samples from brains of patients with schizophrenia and bipolar disorders. J Virol 79, 10890-10901 (2005).

179. Thompson, J. C., Dunbar, E. & Laye, R. R. Treatment challenges and complications with ziconotide monotherapy in established pump patients. Pain physician 9, 147-152 (2006).

180. Toufaily, C., Landry, S., Leib-Mosch, C., Rassart, E. & Barbeau, B. Activation of LTRs from different human endogenous retrovirus (HERV) families by the HTLV-1 tax protein and T-cell activators. Viruses 3, 2146-2159 (2011).

181. Vincendeau, M., et al. Modulation of human endogenous retrovirus (HERV) transcription during persistent and de novo HIV-1 infection. Retrovirology 12, 27 (2015).

182. Verma, A. & Berger, J. R. ALS syndrome in patients with HIV-1 infection. J Neurol Sci 240, 59-64 (2006).

183. Alfahad, T. & Nath, A. Retroviruses and amyotrophic lateral sclerosis. Antiviral Res 99, 180-187 (2013).

184. Matsuzaki, T., et al. HTLV-I-associated myelopathy (HAM)/tropical spastic paraparesis (TSP) with amyotrophic lateral sclerosis-like manifestations. J Neurovirol 6, 544-548 (2000).

185. Anwar, S. L., Wulaningsih, W. & Lehmann, U. Transposable Elements in Human Cancer: Causes and Consequences of Deregulation. Int J Mol Sci 18(2017).

186. Vlahopoulos, S. A., et al. Dynamic aberrant NF-kappaB spurs tumorigenesis: a new model encompassing the microenvironment. Cytokine Growth Factor Rev 26, 389-403 (2015).

187. Bradford, J. W. & Baldwin, A. S. IKK/nuclear factor-kappaB and oncogenesis: roles in tumor-initiating cells and in the tumor microenvironment. Adv Cancer Res 121, 125-145 (2014).

REFERENCES

1. Eldridge, R., Li, Y. & Miller, L. K. Characterization of a baculovirus gene encoding a small conotoxinlike polypeptide. J Virol 66, 6563-6571 (1992).

2. Gracy, J., et al. KNOTTIN: the knottin or inhibitor cystine knot scaffold in 2007. Nucleic Acids Res 36, D314-319 (2008).

3. Kearse, M., et al. Geneious Basic: an integrated and extendable desktop software platform for the organization and analysis of sequence data. Bioinformatics 28, 1647-1649 (2012).

4. Pettersen, E. F., et al. UCSF Chimera—a visualization system for exploratory research and analysis. Journal of computational chemistry 25, 1605-1612 (2004).

5. Dinkel, H., et al. ELM 2016—data update and new functionality of the eukaryotic linear motif resource. Nucleic Acids Res 44, D294-300 (2016).

6. Brohawn, D. G., O'Brien, L. C. & Bennett, J. P., Jr. RNAseq Analyses Identify Tumor Necrosis Factor-Mediated Inflammation as a Major Abnormality in ALS Spinal Cord. PLoS One 11, e0160520 (2016).

7. Nielsen, K. J., Schroeder, T. & Lewis, R. Structure-activity relationships of omega-conotoxins at N-type voltage-sensitive calcium channels. J Mol Recognit 13, 55-70 (2000).

8. Li, W., et al. Human endogenous retrovirus-K contributes to motor neuron disease. Science translational medicine 7, 307ra153 (2015).

The embodiments described herein are intended to be examples only. Alterations, modifications and variations can be effected to the particular embodiments by those of skill in the art. The scope of the claims should not be limited by the particular embodiments set forth herein, but should be construed in a manner consistent with the specification as a whole.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A method for treating or preventing a condition or disorder associated with ω-conotoxin-like protein(CTXLP) in a subject, comprising administering to a subject in need thereof a therapeutically effective amount of active agent optionally in a physiological carrier, or a pharmaceutically acceptable salt thereof, wherein the active agent blocks or inhibits CTXLP activity and/or CTXLP associated pathology, wherein said condition or disorder is an infectious disease or cancer,
   wherein said active agent comprises a Michael acceptor electrophile (MAE), gambogic acid, celastrol, a small molecule inhibitor of HIV Tat, curcumin, rosmarinic acid, 15-deoxy-Δ(12,14)-prostaglandin J(2) (15d-PGJ (2), a cyclopentenone prostaglandin (CyPG), N-acetyl-cysteine amide (NACA), or D-penicillamine; a sulfhydryl compound with chelating properties, N-(2-Mercapto-propionyl)-glycin (MPG), 2,3-Dimercapto-propanol (DMP), 2,3-Dimercapto-propane-sulfonic acid (DMPS), Nitric oxide (NO), or a sulphated polysaccharide; or a Thioredoxin reductase 1 (TRR1) inhibitor, B5 (curcumin analog), a small molecule or antibody reversing CTXLP blockade on oligodendrocyte precursor cell maturation and oligodendrocyte myelination, clemastine fumarate, a small molecule enhancer of expression or activity of CaV2.2 or its calcium channel associated transcription regulator (CaV2.2 CCAT) of expression or activity, EGTA, or glutamate.

2. The method of claim 1, wherein said infectious disease is herpes simplex virus (HSV) infection, human immunodeficiency virus (HIV) infection, Epstein-Barr virus (EBV) infection, human T-lymphotropic virus (HTLV) infection, *Toxoplasma Gondii* infection, or prion disease.

3. The method of claim 1, wherein said cancer is breast cancer, chronic myelogenous leukemia, colon cancer, gastric cancer, a germ cell tumor, a germinogenic tongue tumor, a gonadoblastoma, hepatocellular carcinoma, adenocarcinoma, epithloid carcinoma, Acute T-cell leukemia, leukemia, lymphoma, T-cell lymphoma, Burkitt's lymphoma, neuroepithelioma, melanoma, myelodysplastic syndrome, nasopharyngeal carcinoma, ovarian cancer, pancreatic cancer, prostate cancer, testicular cancer, lung cancer, stomach cancer, skin cancer, a trophoblastic tumor, tumorigenesis, thyroid adenoma, or ERVK in a cancerous tissue.

4. The method of claim 1, further comprising administering a human anti-Nogo-A antibody.

5. A method for treating or preventing a condition or disorder associated with endogenous retrovirus-K (ERVK) in a subject, comprising measuring an amount of CTXLP polypeptide, CTXLP activity, or CTXLP mRNA; and administering to a subject in need thereof a therapeutically effective amount of an active agent optionally in a physiological carrier or a pharmaceutically acceptable salt thereof when the amount of CTXLP polypeptide, or CTXLP activity, or CTXLP mRNA is high, optionally compared to a control, wherein the active agent blocks or inhibits the CTXLP activity and/or CTXLP associated pathology, wherein said condition or disorder is an infection disease or a cancer,
   wherein said active agent comprises a Michael acceptor electrophile (MAE), gambogic acid, celastrol, a small molecule inhibitor of HIV Tat, curcumin, rosmarinic acid, 15-deoxy-Δ(12,14)-prostaglandin J(2) (15d-PGJ (2), a cyclopentenone prostaglandin (CyPG), N-acetyl-cysteine amide (NACA), or D-penicillamine; a sulfhydryl compound with chelating properties, N-(2-Mercapto-propionyl)-glycin (MPG), 2,3-Dimercapto-propanol (DMP), 2,3-Dimercapto-propane-sulfonic acid (DMPS), Nitric oxide (NO), or a sulphated polysaccharide; or a Thioredoxin reductase 1 (TRR1) inhibitor, B5 (curcumin analog), a small molecule or antibody reversing CTXLP blockade on oligodendrocyte precursor cell maturation and oligodendrocyte myelination, clemastine fumarate, a small molecule enhancer of expression or activity of CaV2.2 or its calcium channel associated transcription regulator (CaV2.2 CCAT) of expression or activity, EGTA, or glutamate.

6. A method for treating or preventing a condition or disorder associated with ERVK comprising administering to a subject in need thereof a therapeutically effective amount of an active agent optionally in a physiological carrier, or a pharmaceutically acceptable salt thereof, wherein the active agent blocks or inhibits CTXLP activity and/or CTXLP associated pathology, wherein said condition or disorder is an infectious disease or cancer, wherein said active agent comprises a Michael acceptor electrophile (MAE), gambogic acid, celastrol, a small molecule inhibitor of HIV Tat, curcumin, rosmarinic acid, 15-deoxy-Δ(12,14)-prostaglandin J(2) (15d-PGJ (2), a cyclopentenone prostaglandin (CyPG), N-acetyl-cysteine amide (NACA), or D-penicillamine; a sulfhydryl compound with chelating properties, N-(2-Mercapto-propionyl)-glycin (MPG), 2,3-Dimercapto-propanol (DMP), 2,3-Dimercapto-propane-sulfonic acid (DMPS), Nitric oxide (NO), or a sulphated polysaccharide; or a Thioredoxin reductase 1 (TRR1) inhibitor, B5 (curcumin analog), a small molecule or antibody reversing CTXLP blockade on oligodendrocyte precursor cell maturation and oligodendrocyte myelination, clemastine fumarate, a small molecule enhancer of expression or activity of CaV2.2 or its calcium channel associated transcription regulator (CaV2.2 COAT) of expression or activity, EGTA, or glutamate.

7. The method of claim 6, wherein said infection disease is HSV infection, HIV infection, EBV infection, HTLV infection, *Toxoplasma Gondii* infection, or prion disease.

8. The method of claim 6, wherein said cancer is breast cancer, chronic myelogenous leukemia, colon cancer, gastric cancer, a germ cell tumor, a germinogenic tongue tumor, a gonadoblastoma, hepatocellular carcinoma, adenocarcinoma, epithloid carcinoma, Acute T-cell leukemia, leukemia, lymphoma, T-cell lymphoma, Burkitt's lymphoma, neuroepithelioma, melanoma, myelodysplastic syndrome, nasopharyngeal carcinoma, ovarian cancer, pancreatic cancer, prostate cancer, testicular cancer, lung cancer, stomach cancer, skin cancer, a trophoblastic tumor, tumorigenesis, thyroid adenoma, or ERVK in a cancerous tissue.

9. The method of claim 6, further comprising administering a human anti-Nogo-A antibody.

* * * * *

SEQUENCE LISTING

```
<160> NUMBER OF SEQ ID NOS: 318

<210> SEQ ID NO 1
<211> LENGTH: 30
<212> TYPE: PRT
<213> ORGANISM: Endogenous retrovirus K (from homo sapiens)

<400> SEQUENCE: 1

Cys Ser Asp Tyr Gly Ile Asn Cys Ser His Ser Tyr Gly Cys Cys Ser
1               5                   10                  15

Arg Ser Cys Ile Ala Leu Phe Cys Ser Val Ser Lys Leu Cys
            20                  25                  30

<210> SEQ ID NO 2
<211> LENGTH: 503
<212> TYPE: PRT
<213> ORGANISM: Endogenous retrovirus K (from homo sapiens)
```

-continued

<400> SEQUENCE: 2

```
Met Asn Pro Ser Glu Met Gln Arg Lys Ala Pro Pro Arg Arg Arg
1               5                   10                  15

His Arg Asn Arg Ala Pro Leu Thr His Lys Met Asn Lys Met Val Thr
                20                  25                  30

Ser Glu Glu Gln Met Lys Leu Pro Ser Thr Lys Lys Ala Glu Pro Pro
            35                  40                  45

Thr Trp Ala Gln Leu Lys Lys Leu Thr Gln Leu Ala Thr Lys Tyr Leu
50                  55                  60

Glu Asn Thr Lys Val Thr Gln Thr Pro Glu Ser Met Leu Leu Ala Ala
65                  70                  75                  80

Leu Met Ile Val Ser Met Val Val Ser Leu Pro Met Pro Ala Gly Ala
                85                  90                  95

Ala Ala Ala Asn Tyr Thr Tyr Trp Ala Tyr Val Pro Phe Pro Pro Leu
                100                 105                 110

Ile Arg Ala Val Thr Trp Met Asp Asn Pro Ile Glu Ile Tyr Val Asn
                115                 120                 125

Asp Ser Val Trp Val Pro Gly Pro Thr Asp Asp Cys Cys Pro Ala Lys
            130                 135                 140

Pro Glu Glu Glu Gly Met Met Ile Asn Ile Ser Ile Gly Tyr Arg Tyr
145                 150                 155                 160

Pro Pro Ile Cys Leu Gly Arg Ala Pro Gly Cys Leu Met Pro Ala Val
                165                 170                 175

Gln Asn Trp Leu Val Glu Val Pro Thr Val Ser Pro Ile Ser Arg Phe
                180                 185                 190

Thr Tyr His Met Val Ser Gly Met Ser Leu Arg Pro Arg Val Asn Tyr
            195                 200                 205

Leu Gln Asp Phe Ser Tyr Gln Arg Ser Leu Lys Phe Arg Pro Lys Gly
            210                 215                 220

Lys Pro Cys Pro Lys Glu Ile Pro Lys Glu Ser Lys Asn Thr Glu Val
225                 230                 235                 240

Leu Val Trp Glu Glu Cys Val Ala Asn Ser Ala Val Ile Leu Gln Asn
                245                 250                 255

Asn Glu Phe Gly Thr Leu Ile Asp Trp Ala Pro Arg Gly Gln Phe Tyr
            260                 265                 270

His Asn Cys Ser Gly Gln Thr Gln Ser Cys Pro Ser Ala Gln Val Ser
            275                 280                 285

Pro Ala Val Asp Ser Asp Leu Thr Glu Ser Leu Asp Lys His Lys His
            290                 295                 300

Lys Lys Leu Gln Ser Phe Tyr Pro Trp Glu Trp Gly Glu Lys Gly Ile
305                 310                 315                 320

Ser Thr Ala Arg Pro Lys Ile Ile Ser Pro Val Ser Gly Pro Glu His
                325                 330                 335

Pro Glu Leu Trp Arg Leu Thr Val Ala Ser His His Ile Arg Ile Trp
            340                 345                 350

Ser Gly Asn Gln Thr Leu Glu Thr Arg Asp Arg Lys Pro Phe Tyr Thr
            355                 360                 365

Ile Asp Leu Asn Ser Ser Leu Thr Val Pro Leu Gln Ser Cys Val Lys
            370                 375                 380

Pro Pro Tyr Met Leu Val Val Gly Asn Ile Val Ile Lys Pro Asp Ser
385                 390                 395                 400

Gln Thr Ile Thr Cys Glu Asn Cys Arg Leu Leu Thr Cys Ile Asp Ser
```

-continued

```
                405                 410                 415
Thr Phe Asn Trp Gln His Arg Ile Leu Leu Val Arg Ala Arg Glu Gly
            420                 425                 430

Val Trp Ile Pro Val Ser Met Asp Arg Pro Trp Glu Ala Ser Pro Ser
            435                 440                 445

Val His Ile Leu Thr Glu Val Leu Lys Gly Val Leu Asn Arg Ser Lys
            450                 455                 460

Arg Gln Lys Ile His Phe Tyr Phe Asn Cys Ser Asp Tyr Gly Ile Asn
465                 470                 475                 480

Cys Ser His Ser Tyr Gly Cys Cys Ser Arg Ser Cys Ile Ala Leu Phe
                485                 490                 495

Cys Ser Val Ser Lys Leu Cys
                500

<210> SEQ ID NO 3
<211> LENGTH: 465
<212> TYPE: PRT
<213> ORGANISM: Endogenous retrovirus K (from homo sapiens)

<400> SEQUENCE: 3

Met Asn Pro Ser Glu Met Gln Arg Lys Ala Pro Pro Arg Arg Arg Arg
1               5                   10                  15

His Arg Asn Arg Ala Pro Leu Thr His Lys Met Asn Lys Met Val Thr
            20                  25                  30

Ser Glu Glu Gln Met Lys Leu Pro Ser Thr Lys Lys Ala Glu Pro Pro
        35                  40                  45

Thr Trp Ala Gln Leu Lys Lys Leu Thr Gln Leu Ala Thr Lys Tyr Leu
    50                  55                  60

Glu Asn Thr Lys Val Thr Gln Thr Pro Glu Ser Met Leu Leu Ala Ala
65                  70                  75                  80

Leu Met Ile Val Ser Met Val Val Ser Leu Pro Met Pro Ala Gly Ala
                85                  90                  95

Ala Ala Ala Asn Tyr Thr Tyr Trp Ala Tyr Val Pro Phe Pro Pro Leu
            100                 105                 110

Ile Arg Ala Val Thr Trp Met Asp Asn Pro Ile Glu Ile Tyr Val Asn
        115                 120                 125

Asp Ser Val Trp Val Pro Gly Pro Thr Asp Asp Cys Cys Pro Ala Lys
    130                 135                 140

Pro Glu Glu Glu Gly Met Met Ile Asn Ile Ser Ile Gly Tyr Arg Tyr
145                 150                 155                 160

Pro Pro Ile Cys Leu Gly Arg Ala Pro Gly Cys Leu Met Pro Ala Val
                165                 170                 175

Gln Asn Trp Leu Val Glu Val Pro Thr Val Ser Pro Ile Ser Arg Phe
            180                 185                 190

Thr Tyr His Met Val Ser Gly Met Ser Leu Arg Pro Arg Val Asn Tyr
        195                 200                 205

Leu Gln Asp Phe Ser Tyr Gln Arg Ser Leu Lys Phe Arg Pro Lys Gly
    210                 215                 220

Lys Pro Cys Pro Lys Glu Ile Pro Lys Glu Ser Lys Asn Thr Glu Val
225                 230                 235                 240

Leu Val Trp Glu Glu Cys Val Ala Asn Ser Ala Val Ile Leu Gln Asn
                245                 250                 255

Asn Glu Phe Gly Thr Leu Ile Asp Trp Ala Pro Arg Gly Gln Phe Tyr
            260                 265                 270
```

```
His Asn Cys Ser Gly Gln Thr Gln Ser Cys Pro Ser Ala Gln Val Ser
            275                 280                 285

Pro Ala Val Asp Ser Asp Leu Thr Glu Ser Leu Asp Lys His Lys His
290                 295                 300

Lys Lys Leu Gln Ser Phe Tyr Pro Trp Glu Trp Gly Lys Gly Ile
305                 310                 315                 320

Ser Thr Ala Arg Pro Lys Ile Ile Ser Pro Val Ser Gly Pro Glu His
                325                 330                 335

Pro Glu Leu Trp Arg Leu Thr Val Ala Ser His His Ile Arg Ile Trp
            340                 345                 350

Ser Gly Asn Gln Thr Leu Glu Thr Arg Asp Arg Lys Pro Phe Tyr Thr
            355                 360                 365

Ile Asp Leu Asn Ser Ser Leu Thr Val Pro Leu Gln Ser Cys Val Lys
370                 375                 380

Pro Pro Tyr Met Leu Val Val Gly Asn Ile Val Ile Lys Pro Asp Ser
385                 390                 395                 400

Gln Thr Ile Thr Cys Glu Asn Cys Arg Leu Leu Thr Cys Ile Asp Ser
                405                 410                 415

Thr Phe Asn Trp Gln His Arg Ile Leu Leu Val Arg Ala Arg Glu Gly
            420                 425                 430

Val Trp Ile Pro Val Ser Met Asp Arg Pro Trp Glu Ala Ser Pro Ser
            435                 440                 445

Val His Ile Leu Thr Glu Val Leu Lys Gly Val Leu Asn Arg Ser Lys
            450                 455                 460
Arg
465

<210> SEQ ID NO 4
<211> LENGTH: 26
<212> TYPE: PRT
<213> ORGANISM: Conus geographus

<400> SEQUENCE: 4

Cys Lys Ser Pro Gly Ser Ser Cys Ser Pro Thr Ser Tyr Asn Cys Cys
1               5                   10                  15

Arg Ser Cys Asn Pro Tyr Thr Lys Arg Cys
            20                  25

<210> SEQ ID NO 5
<211> LENGTH: 26
<212> TYPE: PRT
<213> ORGANISM: Conus geographus

<400> SEQUENCE: 5

Cys Lys Ser Pro Gly Ser Ser Cys Ser Pro Thr Ser Tyr Asn Cys Cys
1               5                   10                  15

Arg Ser Cys Asn Pro Tyr Thr Lys Arg Cys
            20                  25

<210> SEQ ID NO 6
<211> LENGTH: 26
<212> TYPE: PRT
<213> ORGANISM: Conus geographus

<400> SEQUENCE: 6

Cys Lys Ser Pro Gly Ser Ser Cys Ser Pro Thr Ser Tyr Asn Cys Cys
1               5                   10                  15

Arg Ser Cys Asn Pro Tyr Thr Lys Arg Cys
```

```
                     20                  25

<210> SEQ ID NO 7
<211> LENGTH: 26
<212> TYPE: PRT
<213> ORGANISM: Conus geographus

<400> SEQUENCE: 7

Cys Lys Ser Pro Gly Thr Pro Cys Ser Arg Gly Met Arg Asp Cys Cys
1               5                   10                  15

Thr Ser Cys Leu Leu Tyr Ser Asn Lys Cys
            20                  25

<210> SEQ ID NO 8
<211> LENGTH: 25
<212> TYPE: PRT
<213> ORGANISM: Conus magus

<400> SEQUENCE: 8

Cys Lys Gly Lys Gly Ala Lys Cys Ser Arg Leu Met Tyr Asp Cys Cys
1               5                   10                  15

Thr Gly Ser Cys Arg Ser Gly Lys Cys
            20                  25

<210> SEQ ID NO 9
<211> LENGTH: 25
<212> TYPE: PRT
<213> ORGANISM: Conus magus

<400> SEQUENCE: 9

Cys Lys Gly Lys Gly Ala Ser Cys His Arg Thr Ser Tyr Asp Cys Cys
1               5                   10                  15

Thr Gly Ser Cys Asn Arg Gly Lys Cys
            20                  25

<210> SEQ ID NO 10
<211> LENGTH: 25
<212> TYPE: PRT
<213> ORGANISM: Conus textile

<400> SEQUENCE: 10

Cys Lys Gln Ser Gly Glu Met Cys Asn Leu Leu Asp Gln Asn Cys Cys
1               5                   10                  15

Asp Gly Tyr Cys Ile Val Leu Val Cys
            20                  25

<210> SEQ ID NO 11
<211> LENGTH: 25
<212> TYPE: PRT
<213> ORGANISM: Autographa californica nucleopolyhedrovirus

<400> SEQUENCE: 11

Cys Ala Glu Thr Gly Ala Val Cys His Asn Asp Glu Cys Cys Ser Gly
1               5                   10                  15

Ala Cys Ser Pro Ile Phe Asn Tyr Cys
            20                  25

<210> SEQ ID NO 12
<211> LENGTH: 24
<212> TYPE: PRT
<213> ORGANISM: Endogenous retrovirus K (from homo sapiens)

<400> SEQUENCE: 12
```

Cys Ser Asp Tyr Gly Ile Asn Cys Ser His Ser Tyr Gly Cys Cys Ser
1               5                   10                  15

Arg Ser Cys Ile Ala Leu Phe Cys
            20

<210> SEQ ID NO 13
<211> LENGTH: 24
<212> TYPE: PRT
<213> ORGANISM: Endogenous retrovirus K (from homo sapiens)

<400> SEQUENCE: 13

Cys Ser Asp Tyr Gly Ile Asn Cys Ser His Ser Tyr Gly Cys Cys Ser
1               5                   10                  15

Arg Ser Cys Ile Ala Leu Phe Cys
            20

<210> SEQ ID NO 14
<211> LENGTH: 24
<212> TYPE: PRT
<213> ORGANISM: Antheraea pernyi nuclear polyhedrosis virus

<400> SEQUENCE: 14

Cys Thr Glu Asp Gly Arg Asn Cys Gln Tyr Ser Tyr Glu Cys Cys Ser
1               5                   10                  15

Gly Ala Cys Ser Ala Leu Phe Cys
            20

<210> SEQ ID NO 15
<211> LENGTH: 24
<212> TYPE: PRT
<213> ORGANISM: Ectropis obliqua nucleopolyhedrovirus

<400> SEQUENCE: 15

Cys Thr Glu Thr Gly Arg Asn Cys Lys Tyr Ser Tyr Glu Cys Cys Ser
1               5                   10                  15

Asn Ala Cys Ser Ala Ala Phe Cys
            20

<210> SEQ ID NO 16
<211> LENGTH: 24
<212> TYPE: PRT
<213> ORGANISM: Helicoverpa armigera granulovirus

<400> SEQUENCE: 16

Cys Thr Glu Thr Gly Arg Asn Cys Gln Tyr Ser Tyr Glu Cys Cys Ser
1               5                   10                  15

Gly Ala Cys Ser Ala Val Phe Cys
            20

<210> SEQ ID NO 17
<211> LENGTH: 24
<212> TYPE: PRT
<213> ORGANISM: Orgyia pseudotsugata multicapsid polyhedrosis virus

<400> SEQUENCE: 17

Cys Thr Glu Thr Gly Arg Asn Cys Gln Tyr Ser Tyr Glu Cys Cys Ser
1               5                   10                  15

Gly Ala Cys Ser Ala Ala Phe Cys
            20

<210> SEQ ID NO 18

```
<211> LENGTH: 24
<212> TYPE: PRT
<213> ORGANISM: Samia cynthia nucleopolyhedrovirus

<400> SEQUENCE: 18

Cys Thr Glu Asp Gly Arg Asn Cys Gln Tyr Asn Tyr Glu Cys Cys Ser
1               5                   10                  15

Gly Ala Cys Ser Ala Leu Phe Cys
            20

<210> SEQ ID NO 19
<211> LENGTH: 24
<212> TYPE: PRT
<213> ORGANISM: Apocheima cinerarium nucleopolyhedrovirus

<400> SEQUENCE: 19

Cys Thr Glu Thr Gly Arg Asn Cys Lys Tyr Ser Tyr Glu Cys Cys Ser
1               5                   10                  15

Gly Ala Cys Ser Ala Ala Phe Cys
            20

<210> SEQ ID NO 20
<211> LENGTH: 24
<212> TYPE: PRT
<213> ORGANISM: Hyphantria cunea nuclear polyhedrosis virus

<400> SEQUENCE: 20

Cys Thr Glu Thr Gly Lys Asn Cys Lys Tyr Ser Tyr Glu Cys Cys Ser
1               5                   10                  15

Gly Ala Cys Ser Ala Ala Phe Cys
            20

<210> SEQ ID NO 21
<211> LENGTH: 24
<212> TYPE: PRT
<213> ORGANISM: Anticarsia gemmatalis multiple nucleopolyhedrovirus

<400> SEQUENCE: 21

Cys Thr Glu Thr Gly Arg Asn Cys Lys Tyr Ser Tyr Glu Cys Cys Ser
1               5                   10                  15

Gly Ala Cys Ser Ala Val Phe Cys
            20

<210> SEQ ID NO 22
<211> LENGTH: 24
<212> TYPE: PRT
<213> ORGANISM: Mamestra configurata nucleopolyhedrovirus A

<400> SEQUENCE: 22

Cys Thr Asp Thr Gly Arg Asn Cys Lys Tyr Ser Tyr Glu Cys Cys Ser
1               5                   10                  15

Gly Ala Cys Ser Ala Ala Phe Cys
            20

<210> SEQ ID NO 23
<211> LENGTH: 24
<212> TYPE: PRT
<213> ORGANISM: Xestia c-nigrum granulosis virus

<400> SEQUENCE: 23

Cys Thr Glu Thr Gly Arg Asn Cys Gln Tyr Ser Tyr Glu Cys Cys Ser
1               5                   10                  15
```

```
Gly Ala Cys Ser Ala Ala Phe Cys
            20
```

<210> SEQ ID NO 24
<211> LENGTH: 30
<212> TYPE: PRT
<213> ORGANISM: Endogenous retrovirus K (from homo sapiens)

<400> SEQUENCE: 24

```
Cys Ser Asp Tyr Gly Ile Asn Cys Ser His Ser Tyr Gly Cys Cys Ser
1               5                   10                  15

Arg Ser Cys Ile Ala Leu Phe Cys Ser Val Ser Lys Leu Cys
            20                  25                  30
```

<210> SEQ ID NO 25
<211> LENGTH: 84
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid

<400> SEQUENCE: 25

```
Met Lys Ala Ser Met Phe Leu Ala Leu Ala Gly Leu Val Leu Leu Phe
1               5                   10                  15

Val Val Cys Tyr Ala Ser Glu Ser Glu Glu Lys Glu Phe Pro Arg Glu
            20                  25                  30

Leu Leu Ser Lys Ile Phe Ala Val Asp Asp Phe Lys Gly Glu Glu Arg
        35                  40                  45

Glu Cys Arg Gly Phe Gly Gly Cys Pro Gly Thr Xaa Asp Cys Cys
    50                  55                  60

Lys Xaa Leu Xaa Cys Lys Xaa Lys Xaa Lys Xaa Cys Lys Trp Asp Gly
65                  70                  75                  80

Thr Phe Ser Lys
```

<210> SEQ ID NO 26
<211> LENGTH: 30
<212> TYPE: PRT
<213> ORGANISM: Endogenous retrovirus K (from homo sapiens)

<400> SEQUENCE: 26

```
Cys Ser Asp Tyr Gly Ile Asn Cys Ser His Ser Tyr Gly Cys Cys Ser
1               5                   10                  15
```

```
Arg Ser Cys Ile Ala Leu Phe Cys Ser Val Ser Lys Leu Cys
            20                  25                  30

<210> SEQ ID NO 27
<211> LENGTH: 83
<212> TYPE: PRT
<213> ORGANISM: Selenocosmia hainana

<400> SEQUENCE: 27

Met Lys Ala Ser Met Phe Leu Ala Leu Ala Gly Leu Val Leu Leu Phe
1               5                   10                  15

Val Val Cys Tyr Ala Ser Glu Ser Glu Glu Lys Glu Phe Pro Arg Glu
            20                  25                  30

Leu Ile Ser Lys Ile Phe Ala Val Asp Asp Phe Lys Gly Glu Glu Arg
        35                  40                  45

Glu Cys Lys Gly Phe Gly Lys Ser Cys Val Pro Gly Lys Asn Glu Cys
    50                  55                  60

Cys Ser Gly Tyr Ala Cys Asn Ser Arg Asp Lys Trp Cys Lys Val Leu
65                  70                  75                  80

Leu Gly Lys

<210> SEQ ID NO 28
<211> LENGTH: 83
<212> TYPE: PRT
<213> ORGANISM: Selenocosmia hainana

<400> SEQUENCE: 28

Met Lys Ala Ser Met Phe Leu Ala Leu Ala Gly Leu Val Leu Leu Phe
1               5                   10                  15

Val Val Gly Tyr Ala Ser Glu Ser Glu Glu Lys Glu Phe Pro Arg Glu
            20                  25                  30

Leu Leu Ser Lys Ile Phe Ala Val Asp Asp Phe Lys Gly Glu Glu Arg
        35                  40                  45

Gly Cys Lys Gly Phe Gly Asp Ser Cys Thr Pro Gly Lys Asn Glu Cys
    50                  55                  60

Cys Pro Asn Tyr Ala Cys Ser Ser Lys His Lys Trp Cys Lys Val Tyr
65                  70                  75                  80

Leu Gly Lys

<210> SEQ ID NO 29
<211> LENGTH: 36
<212> TYPE: PRT
<213> ORGANISM: Selenocosmia hainana
<220> FEATURE:
<221> NAME/KEY: misc_feature
<222> LOCATION: (36)..(36)
<223> OTHER INFORMATION: Xaa can be any naturally occurring amino acid

<400> SEQUENCE: 29

Glu Cys Leu Gly Phe Gly Lys Gly Cys Asn Pro Ser Asn Asp Gln Cys
1               5                   10                  15

Cys Lys Ser Ser Asn Leu Val Cys Ser Arg Lys His Arg Trp Cys Lys
            20                  25                  30

Tyr Glu Ile Xaa
        35

<210> SEQ ID NO 30
<211> LENGTH: 68
<212> TYPE: PRT
<213> ORGANISM: Selenocosmia hainana
```

```
<400> SEQUENCE: 30

Met Asn Met Lys Ile Leu Val Leu Val Ala Val Leu Cys Leu Val Val
1               5                  10                 15

Ser Thr His Ala Glu Arg His Ser Lys Thr Asp Met Glu Asp Met Glu
            20                  25                  30

Asp Ser Pro Met Ile Gln Glu Arg Lys Cys Leu Pro Pro Gly Lys Pro
            35                  40                  45

Cys Tyr Gly Ala Thr Gln Lys Ile Pro Cys Cys Gly Val Cys Ser His
50                  55                  60

Asn Lys Cys Thr
65

<210> SEQ ID NO 31
<211> LENGTH: 35
<212> TYPE: PRT
<213> ORGANISM: Selenocosmia hainana

<400> SEQUENCE: 31

Glu Cys Leu Gly Phe Gly Lys Gly Cys Asn Pro Ser Asn Asp Gln Cys
1               5                  10                 15

Cys Lys Ser Ala Asn Leu Val Cys Ser Arg Lys His Arg Trp Cys Lys
            20                  25                  30

Tyr Glu Ile
        35

<210> SEQ ID NO 32
<211> LENGTH: 33
<212> TYPE: PRT
<213> ORGANISM: Plesiophrictus guangxiensis

<400> SEQUENCE: 32

Glu Cys Arg Lys Met Phe Gly Gly Cys Ser Val Asp Ser Asp Cys Cys
1               5                  10                 15

Ala His Leu Gly Cys Lys Pro Thr Leu Lys Tyr Cys Ala Trp Asp Gly
            20                  25                  30

Thr

<210> SEQ ID NO 33
<211> LENGTH: 36
<212> TYPE: PRT
<213> ORGANISM: Plesiophrictus guangxiensis

<400> SEQUENCE: 33

Asp Gly Glu Cys Gly Gly Phe Trp Trp Lys Cys Gly Ser Gly Lys Pro
1               5                  10                 15

Ala Cys Cys Pro Lys Tyr Val Cys Ser Pro Lys Trp Gly Leu Cys Asn
            20                  25                  30

Phe Pro Met Pro
        35

<210> SEQ ID NO 34
<211> LENGTH: 35
<212> TYPE: PRT
<213> ORGANISM: Grammostola rosea

<400> SEQUENCE: 34

Glu Cys Arg Tyr Leu Phe Gly Gly Cys Lys Thr Thr Ser Asp Cys Cys
1               5                  10                 15
```

```
Lys His Leu Gly Cys Lys Phe Arg Asp Lys Tyr Cys Ala Trp Asp Phe
            20                  25                  30

Thr Phe Ser
        35

<210> SEQ ID NO 35
<211> LENGTH: 35
<212> TYPE: PRT
<213> ORGANISM: Grammostola rosea

<400> SEQUENCE: 35

Glu Cys Arg Tyr Leu Phe Gly Gly Cys Lys Thr Thr Ala Asp Cys Cys
1               5                   10                  15

Lys His Leu Gly Cys Lys Phe Arg Asp Lys Tyr Cys Ala Trp Asp Phe
            20                  25                  30

Thr Phe Ser
        35

<210> SEQ ID NO 36
<211> LENGTH: 34
<212> TYPE: PRT
<213> ORGANISM: Scodra griseipes

<400> SEQUENCE: 36

Thr Cys Arg Tyr Leu Phe Gly Gly Cys Lys Thr Thr Ala Asp Cys Cys
1               5                   10                  15

Lys His Leu Ala Cys Arg Ser Asp Gly Lys Tyr Cys Ala Trp Asp Gly
            20                  25                  30

Thr Phe

<210> SEQ ID NO 37
<211> LENGTH: 87
<212> TYPE: PRT
<213> ORGANISM: Grammostola spatulata

<400> SEQUENCE: 37

Met Lys Ala Gln Ile Phe Val Val Leu Gly Leu Ala Ala Leu Ser
1               5                   10                  15

Val Leu Cys Tyr Gly Ser Glu Ala Asp Glu Ser Ala Leu His Glu Glu
            20                  25                  30

Ile Phe Gln Leu Leu Ala Ala Ser Asp Glu Val Pro Lys Pro Gln Glu
            35                  40                  45

Arg Asp Cys Val Arg Phe Trp Gly Lys Cys Ser Gln Thr Ser Asp Cys
        50                  55                  60

Cys Pro His Leu Ala Cys Lys Ser Lys Trp Pro Arg Asn Ile Cys Val
65                  70                  75                  80

Trp Asp Gly Ser Val Gly Lys
                85

<210> SEQ ID NO 38
<211> LENGTH: 81
<212> TYPE: PRT
<213> ORGANISM: Selenocosmia huwena

<400> SEQUENCE: 38

Met Arg Ala Ser Met Phe Leu Ala Leu Ala Gly Leu Val Leu Leu Phe
1               5                   10                  15

Val Val Cys Tyr Ala Ser Glu Ser Glu Glu Lys Glu Phe Pro Arg Glu
            20                  25                  30
```

```
Leu Leu Phe Lys Phe Phe Ala Val Asp Asp Phe Lys Gly Glu Glu Arg
            35                  40                  45

Ala Cys Lys Gly Val Phe Asp Ala Cys Thr Pro Gly Lys Asn Glu Cys
 50                  55                  60

Cys Pro Asn Arg Val Cys Ser Asp Lys His Lys Trp Cys Lys Trp Lys
 65                  70                  75                  80

Leu

<210> SEQ ID NO 39
<211> LENGTH: 69
<212> TYPE: PRT
<213> ORGANISM: Artificial Sequence
<220> FEATURE:
<223> OTHER INFORMATION: Synthetic Construct

<400> SEQUENCE: 39

Met Leu Thr Ala Ala Val Leu Ser Cys Ala Leu Leu Leu Ala Leu Pro
 1               5                  10                  15

Ala Thr Arg Gly Ala Gln Met Gly Leu Ala Pro Met Glu Gly Ile Arg
            20                  25                  30

Arg Pro Asp Gln Ala Leu Leu Pro Glu Leu Pro Gly Leu Gly Leu Arg
            35                  40                  45

Ala Pro Leu Lys Lys Thr Thr Ala Glu Gln Ala Glu Glu Asp Leu Leu
 50                  55                  60

Gln Glu Ala Gln Ala
 65

<210> SEQ ID NO 40
<211> LENGTH: 69
<212> TYPE: PRT
<213> ORGANISM: Homo sapiens

<400> SEQUENCE: 40

Met Leu Thr Ala Ala Val Leu Ser Cys Ala Leu Leu Leu Ala Leu Pro
 1               5                  10                  15

Ala Thr Arg Gly Ala Gln Met Gly Leu Ala Pro Met Glu Gly Ile Arg
            20                  25                  30

Arg Pro Asp Gln Ala Leu Leu Pro Glu Leu Pro Gly Leu Gly Leu Arg
            35                  40                  45

Ala Pro Leu Lys Lys Thr Thr Ala Glu Gln Ala Glu Glu Asp Leu Leu
 50                  55                  60

Gln Glu Ala Gln Ala
 65

<210> SEQ ID NO 41
<211> LENGTH: 63
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(14)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (20)..(23)
<223> OTHER INFORMATION: Xaa can be any naturally occurring amino acid
<220> FEATURE:
```

```
<221> NAME/KEY: misc_feature
<222> LOCATION: (26)..(31)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (45)..(47)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (54)..(57)
<223> OTHER INFORMATION: Xaa can be any naturally occurring amino acid

<400> SEQUENCE: 41

Leu Ala Glu Val Xaa Xaa Xaa Xaa Xaa Xaa Xaa Xaa Xaa Ser Xaa
1               5                   10                  15

Xaa Cys Val Xaa Xaa Xaa Xaa Ser Cys Xaa Xaa Xaa Xaa Xaa Cys
            20                  25                  30

Cys Asp Pro Cys Ala Xaa Cys Tyr Cys Arg Phe Phe Xaa Xaa Xaa Cys
            35                  40                  45

Tyr Cys Arg Xaa Leu Xaa Xaa Xaa Xaa Asn Pro Cys Ser Arg Thr
    50                  55                  60

<210> SEQ ID NO 42
<211> LENGTH: 63
<212> TYPE: PRT
<213> ORGANISM: Homo sapiens

<400> SEQUENCE: 42

Leu Ala Glu Val Leu Asp Leu Gln Asp Arg Glu Pro Arg Ser Ser Arg
1               5                   10                  15

Arg Cys Val Arg Leu His Glu Ser Cys Leu Gly Gln Gln Val Pro Cys
            20                  25                  30

Cys Asp Pro Cys Ala Thr Cys Tyr Cys Arg Phe Phe Asn Ala Phe Cys
            35                  40                  45

Tyr Cys Arg Lys Leu Gly Thr Ala Met Asn Pro Cys Ser Arg Thr
    50                  55                  60

<210> SEQ ID NO 43
<211> LENGTH: 53
<212> TYPE: PRT
<213> ORGANISM: Homo sapiens

<400> SEQUENCE: 43

Lys Lys Val Val Arg Pro Arg Thr Pro Leu Ser Ala Pro Cys Val Ala
1               5                   10                  15

Thr Arg Asn Ser Cys Lys Pro Pro Ala Pro Ala Cys Cys Asp Pro Cys
            20                  25                  30

Ala Ser Cys Tyr Cys Arg Phe Phe Arg Ser Ala Cys Tyr Cys Arg Val
            35                  40                  45

Leu Ser Leu Asn Cys
    50

<210> SEQ ID NO 44
<211> LENGTH: 30
<212> TYPE: PRT
<213> ORGANISM: Artificial Sequence
```

```
<220> FEATURE:
<223> OTHER INFORMATION: Synthetic Construct

<400> SEQUENCE: 44

Cys Ser Asp Tyr Gly Ile Asn Cys Ser His Ser Tyr Gly Cys Cys Ser
1               5                   10                  15

Arg Ser Cys Ile Ala Leu Phe Cys Ser Val Ser Lys Leu Cys
            20                  25                  30

<210> SEQ ID NO 45
<211> LENGTH: 74
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (73)..(74)
<223> OTHER INFORMATION: Xaa can be any naturally occurring amino acid

<400> SEQUENCE: 45

Phe Ala Ala Gly Gly Tyr Asn Xaa Glu Xaa Leu Val Val Ile Xaa Glu
1               5                   10                  15

Glu Val Trp Gln Arg Ser Xaa Cys Gln Pro Arg Glu Thr Leu Val Xaa
            20                  25                  30

Val Xaa Xaa Glu Tyr Pro Asp Glu Thr Xaa Thr Xaa Phe Lys Pro Ser
        35                  40                  45

Cys Val Xaa Val Xaa Arg Cys Gly Gly Cys Cys Asn Asp Glu Xaa Leu
```

```
                      50                  55                  60

Glu Cys Val Pro Thr Glu Thr Ser Xaa Xaa
65                  70

<210> SEQ ID NO 46
<211> LENGTH: 24
<212> TYPE: PRT
<213> ORGANISM: Endogenous retrovirus K (from homo sapiens)

<400> SEQUENCE: 46

Cys Ser Asp Tyr Gly Ile Asn Cys Ser His Ser Tyr Gly Cys Cys Ser
1               5                   10                  15

Arg Ser Cys Ile Ala Leu Phe Cys
            20

<210> SEQ ID NO 47
<211> LENGTH: 74
<212> TYPE: PRT
<213> ORGANISM: Homo sapiens

<400> SEQUENCE: 47

Met Ala Glu Gly Gly Gly Gln Asn His His Glu Val Val Lys Phe Met
1               5                   10                  15

Asp Val Tyr Gln Arg Ser Tyr Cys His Pro Ile Glu Thr Leu Val Asp
            20                  25                  30

Ile Phe Gln Glu Tyr Pro Asp Glu Ile Glu Tyr Ile Phe Lys Pro Ser
        35                  40                  45

Cys Val Pro Leu Met Arg Cys Gly Gly Cys Asn Asp Glu Gly Leu
    50                  55                  60

Glu Cys Val Pro Thr Glu Glu Ser Asn Ile
65                  70

<210> SEQ ID NO 48
<211> LENGTH: 71
<212> TYPE: PRT
<213> ORGANISM: Homo sapiens

<400> SEQUENCE: 48

Asp Ala Pro Gly His Gln Arg Lys Val Val Ser Trp Ile Asp Val Tyr
1               5                   10                  15

Thr Arg Ala Thr Cys Gln Pro Arg Glu Val Val Val Pro Leu Thr Val
            20                  25                  30

Glu Leu Met Gly Thr Val Ala Lys Gln Leu Val Pro Ser Cys Val Thr
        35                  40                  45

Val Gln Arg Cys Gly Gly Cys Cys Pro Asp Asp Gly Leu Glu Cys Val
    50                  55                  60

Pro Thr Gly Gln His Gln Val
65                  70

<210> SEQ ID NO 49
<211> LENGTH: 73
<212> TYPE: PRT
<213> ORGANISM: Homo sapiens

<400> SEQUENCE: 49

Phe Ala Ala Ala His Tyr Asn Thr Glu Ile Leu Lys Ser Ile Asp Asn
1               5                   10                  15

Glu Trp Arg Lys Thr Gln Cys Met Pro Arg Glu Val Cys Ile Asp Val
            20                  25                  30
```

```
Gly Lys Glu Phe Gly Val Ala Thr Asn Thr Phe Phe Lys Pro Pro Cys
        35                  40                  45

Val Ser Val Tyr Arg Cys Gly Gly Cys Cys Asn Ser Glu Gly Leu Gln
    50                  55                  60

Cys Met Asn Thr Ser Thr Ser Tyr Leu
65                  70

<210> SEQ ID NO 50
<211> LENGTH: 73
<212> TYPE: PRT
<213> ORGANISM: Homo sapiens

<400> SEQUENCE: 50

Phe Ala Ala Thr Phe Tyr Asp Ile Glu Thr Leu Lys Val Ile Asp Glu
1               5                   10                  15

Glu Trp Gln Arg Thr Gln Cys Ser Pro Arg Glu Thr Cys Val Glu Val
            20                  25                  30

Ala Ser Glu Leu Gly Lys Ser Thr Asn Thr Phe Phe Lys Pro Pro Cys
        35                  40                  45

Val Asn Val Phe Arg Cys Gly Gly Cys Cys Asn Glu Glu Ser Leu Ile
    50                  55                  60

Cys Met Asn Thr Ser Thr Ser Tyr Ile
65                  70

<210> SEQ ID NO 51
<211> LENGTH: 73
<212> TYPE: PRT
<213> ORGANISM: Homo sapiens

<400> SEQUENCE: 51

Leu His Gln Tyr Leu Leu Asn Ala Asp Ser Asn Thr Lys Gly Trp Ser
1               5                   10                  15

Glu Val Leu Lys Gly Ser Glu Cys Lys Pro Arg Pro Ile Val Val Pro
            20                  25                  30

Val Ser Glu Thr His Pro Glu Leu Thr Ser Gln Arg Phe Asn Pro Pro
        35                  40                  45

Cys Val Thr Leu Met Arg Cys Gly Gly Cys Cys Asn Asp Glu Ser Leu
    50                  55                  60

Glu Cys Val Pro Thr Glu Glu Val Asn
65                  70

<210> SEQ ID NO 52
<211> LENGTH: 63
<212> TYPE: PRT
<213> ORGANISM: Vipera ammodytes
<220> FEATURE:
<221> NAME/KEY: misc_feature
<222> LOCATION: (1)..(1)
<223> OTHER INFORMATION: Xaa can be any naturally occurring amino acid

<400> SEQUENCE: 52

Xaa Val Arg Pro Phe Leu Glu Val His Glu Arg Ser Ala Cys Gln Ala
1               5                   10                  15

Arg Glu Thr Leu Val Pro Ile Leu Gln Glu Tyr Pro Asp Glu Ile Ser
            20                  25                  30

Asp Ile Phe Arg Pro Ser Cys Val Ala Val Leu Arg Cys Ser Gly Cys
        35                  40                  45

Cys Thr Asp Glu Ser Leu Lys Cys Thr Pro Val Gly Lys His Thr
    50                  55                  60
```

-continued

<210> SEQ ID NO 53
<211> LENGTH: 73
<212> TYPE: PRT
<213> ORGANISM: Homo sapiens

<400> SEQUENCE: 53

Ser Ala Gly Asn Gly Ser Ser Glu Val Glu Val Val Pro Phe Gln Glu
1               5                   10                  15

Val Trp Gly Arg Ser Tyr Cys Arg Ala Leu Glu Arg Leu Val Asp Val
            20                  25                  30

Val Ser Glu Tyr Pro Ser Glu Val Glu His Met Phe Ser Pro Ser Cys
        35                  40                  45

Val Ser Leu Leu Arg Cys Thr Gly Cys Cys Gly Asp Glu Asn Leu His
    50                  55                  60

Cys Val Pro Val Glu Thr Ala Asn Val
65                  70

<210> SEQ ID NO 54
<211> LENGTH: 96
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(36)
<223> OTHER INFORMATION: Xaa can be any naturally occurring amino acid
<220> FEATURE:
<221> NAME/KEY: misc_feature
<222> LOCATION: (38)..(45)
<223> OTHER INFORMATION: Xaa can be any naturally occurring amino acid
<220> FEATURE:
<221> NAME/KEY: misc_feature
<222> LOCATION: (47)..(49)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (68)..(69)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:

```
<221> NAME/KEY: misc_feature
<222> LOCATION: (79)..(80)
<223> OTHER INFORMATION: Xaa can be any naturally occurring amino acid
<220> FEATURE:
<221> NAME/KEY: misc_feature
<222> LOCATION: (82)..(83)
<223> OTHER INFORMATION: Xaa can be any naturally occurring amino acid
<220> FEATURE:
<221> NAME/KEY: misc_feature
<222> LOCATION: (85)..(87)
<223> OTHER INFORMATION: Xaa can be any naturally occurring amino acid
<220> FEATURE:
<221> NAME/KEY: misc_feature
<222> LOCATION: (89)..(92)
<223> OTHER INFORMATION: Xaa can be any naturally occurring amino acid
<220> FEATURE:
<221> NAME/KEY: misc_feature
<222> LOCATION: (95)..(96)
<223> OTHER INFORMATION: Xaa can be any naturally occurring amino acid

<400> SEQUENCE: 54

Met Glu Thr Pro Leu Lys Glu Pro Glu Ser Ser Leu Glu Ser Tyr Asn
1               5                   10                  15

Glu Pro Ser Ser Cys Thr Ser Glu Arg Asp Val Thr Xaa Glx Xaa Xaa
            20                  25                  30

Xaa Xaa Xaa Xaa Glu Xaa Xaa Xaa Xaa Xaa Xaa Xaa Pro Xaa Xaa
        35                  40                  45

Xaa Cys Xaa Asn Xaa Cys Tyr Cys Lys Xaa Cys Cys Xaa His Cys Gln
    50                  55                  60

Xaa Cys Phe Xaa Xaa Lys Gly Leu Gly Ile Xaa Tyr Xaa Arg Xaa Xaa
65                  70                  75                  80

Arg Xaa Xaa Arg Xaa Xaa Xaa Pro Xaa Xaa Xaa Xaa Thr His Xaa Xaa
                85                  90                  95

<210> SEQ ID NO 55
<211> LENGTH: 30
<212> TYPE: PRT
<213> ORGANISM: Endogenous retrovirus K (from homo sapiens)

<400> SEQUENCE: 55

Cys Ser Asp Tyr Gly Ile Asn Cys Ser His Ser Tyr Gly Cys Cys Ser
1               5                   10                  15

Arg Ser Cys Ile Ala Leu Phe Cys Ser Val Ser Lys Leu Cys
            20                  25                  30

<210> SEQ ID NO 56
<211> LENGTH: 67
<212> TYPE: PRT
<213> ORGANISM: Human immunodeficiency virus type 1

<400> SEQUENCE: 56

Met Glu Pro Val Asn Pro Arg Leu Glu Pro Trp Lys His Pro Gly Ser
1               5                   10                  15

Gln Pro Arg Thr Pro Cys Asn Thr Cys Tyr Cys Lys Lys Cys Cys Phe
            20                  25                  30

His Cys Gln Tyr Cys Phe Thr Thr Lys Gly Leu Gly Ile Ser Tyr Gly
        35                  40                  45

Arg Lys Lys Arg Lys Gln Arg Gln Lys Ala Pro Gln Gly Ser Gln Thr
    50                  55                  60

His Gln Ala
65

<210> SEQ ID NO 57
```

```
<211> LENGTH: 94
<212> TYPE: PRT
<213> ORGANISM: Human immunodeficiency virus type 2

<400> SEQUENCE: 57

Met Glu Thr Pro Leu Lys Glu Pro Glu Ser Ser Leu Glu Ser Tyr Asn
1               5                   10                  15

Glu Pro Ser Ser Cys Thr Ser Glu Arg Asp Val Thr Ala Gln Glu Arg
            20                  25                  30

Ala Lys Gln Gly Glu Leu Leu Ala Gln Leu His Arg Pro Leu Glu
        35                  40                  45

Ala Cys Thr Asn Ser Cys Tyr Cys Lys Gln Cys Ser Tyr His Cys Gln
    50                  55                  60

Leu Cys Phe Leu Lys Lys Gly Leu Gly Ile Trp Tyr Ala Arg Gln Gly
65                  70                  75                  80

Arg Arg Arg Arg Thr Pro Arg Lys Thr Lys Thr His Pro Pro
                85                  90

<210> SEQ ID NO 58
<211> LENGTH: 36
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 58

Xaa Xaa Ser Xaa Lys Ser Ile Ser Thr Arg Thr Gly Asp Ser Gln Pro
1               5                   10                  15

Thr Lys Lys Gln Lys Lys Thr Pro Glu Thr Thr Val Val Ser Ala Cys
            20                  25                  30

Gly Leu Gly His
        35

<210> SEQ ID NO 59
<211> LENGTH: 4
<212> TYPE: PRT
<213> ORGANISM: Human immunodeficiency virus type 1

<400> SEQUENCE: 59

Ser Leu Ser Lys
1

<210> SEQ ID NO 60
<211> LENGTH: 36
<212> TYPE: PRT
<213> ORGANISM: Human immunodeficiency virus type 2

<400> SEQUENCE: 60

Pro Ala Ser Asp Lys Ser Ile Ser Thr Arg Thr Gly Asp Ser Gln Pro
1               5                   10                  15

Thr Lys Lys Gln Lys Lys Thr Pro Glu Thr Thr Val Val Ser Ala Cys
            20                  25                  30

Gly Leu Gly His
        35
```

<210> SEQ ID NO 61
<211> LENGTH: 30
<212> TYPE: PRT
<213> ORGANISM: Artificial Sequence
<220> FEATURE:
<223> OTHER INFORMATION: Synthetic Construct

<400> SEQUENCE: 61

Cys Ser Asp Tyr Gly Ile Asn Cys Ser His Ser Tyr Gly Cys Cys Ser
1               5                   10                  15

Arg Ser Cys Ile Ala Leu Phe Cys Ser Val Ser Lys Leu Cys
            20                  25                  30

<210> SEQ ID NO 62
<211> LENGTH: 30
<212> TYPE: PRT
<213> ORGANISM: Endogenous retrovirus K (from homo sapiens)

<400> SEQUENCE: 62

Cys Ser Asp Tyr Gly Ile Asn Cys Ser His Ser Tyr Gly Cys Cys Ser
1               5                   10                  15

Arg Ser Cys Ile Ala Leu Phe Cys Ser Val Ser Lys Leu Cys
            20                  25                  30

<210> SEQ ID NO 63
<211> LENGTH: 30
<212> TYPE: PRT
<213> ORGANISM: Endogenous retrovirus K (from homo sapiens)

<400> SEQUENCE: 63

Cys Ser Asp Tyr Gly Ile Asn Cys Ser His Ser Tyr Gly Cys Cys Ser
1               5                   10                  15

Arg Ser Cys Ile Ala Leu Phe Cys Ser Val Ser Lys Leu Cys
            20                  25                  30

<210> SEQ ID NO 64
<211> LENGTH: 30
<212> TYPE: PRT
<213> ORGANISM: Endogenous retrovirus K (from homo sapiens)

<400> SEQUENCE: 64

Cys Ser Asp Tyr Gly Ile Asn Cys Ser His Ser Tyr Gly Cys Cys Ser
1               5                   10                  15

Arg Ser Cys Ile Ala Leu Phe Cys Ser Val Ser Lys Leu Cys
            20                  25                  30

<210> SEQ ID NO 65
<211> LENGTH: 30
<212> TYPE: PRT
<213> ORGANISM: Endogenous retrovirus K (from homo sapiens)

<400> SEQUENCE: 65

Cys Ser Asp Tyr Gly Ile Asn Cys Ser His Ser Tyr Gly Cys Cys Ser
1               5                   10                  15

Arg Ser Cys Ile Ala Leu Phe Cys Ser Val Ser Lys Leu Cys
            20                  25                  30

<210> SEQ ID NO 66
<211> LENGTH: 30
<212> TYPE: PRT
<213> ORGANISM: Endogenous retrovirus K (from homo sapiens)

<400> SEQUENCE: 66

-continued

Cys Ser Asp Tyr Gly Ile Asn Cys Ser His Ser Tyr Gly Cys Cys Ser
1               5                   10                  15

Arg Ser Cys Ile Ala Leu Phe Cys Ser Val Ser Lys Leu Cys
            20                  25                  30

<210> SEQ ID NO 67
<211> LENGTH: 30
<212> TYPE: PRT
<213> ORGANISM: Endogenous retrovirus K (from homo sapiens)

<400> SEQUENCE: 67

Cys Ser Asp Tyr Gly Ile Asn Cys Ser His Ser Tyr Gly Cys Cys Ser
1               5                   10                  15

Arg Ser Cys Ile Ala Leu Phe Cys Ser Val Ser Lys Leu Cys
            20                  25                  30

<210> SEQ ID NO 68
<211> LENGTH: 30
<212> TYPE: PRT
<213> ORGANISM: Endogenous retrovirus K (from homo sapiens)

<400> SEQUENCE: 68

Cys Ser Asp Tyr Gly Ile Asn Cys Ser His Ser Tyr Gly Cys Cys Ser
1               5                   10                  15

Arg Ser Cys Ile Ala Leu Phe Cys Ser Val Ser Lys Leu Cys
            20                  25                  30

<210> SEQ ID NO 69
<211> LENGTH: 30
<212> TYPE: PRT
<213> ORGANISM: Endogenous retrovirus K (from homo sapiens)

<400> SEQUENCE: 69

Cys Ser Asp Tyr Gly Ile Asn Cys Ser His Ser Tyr Gly Cys Cys Ser
1               5                   10                  15

Arg Ser Cys Ile Ala Leu Phe Cys Ser Val Ser Lys Leu Cys
            20                  25                  30

<210> SEQ ID NO 70
<211> LENGTH: 30
<212> TYPE: PRT
<213> ORGANISM: Endogenous retrovirus K (from homo sapiens)

<400> SEQUENCE: 70

Cys Ser Asp Tyr Gly Ile Asn Cys Ser His Ser Tyr Gly Cys Cys Ser
1               5                   10                  15

Arg Ser Cys Ile Ala Leu Phe Cys Ser Val Ser Lys Leu Cys
            20                  25                  30

<210> SEQ ID NO 71
<211> LENGTH: 30
<212> TYPE: PRT
<213> ORGANISM: Endogenous retrovirus K (from homo sapiens)

<400> SEQUENCE: 71

Cys Ser Asp Tyr Gly Ile Asn Cys Ser His Ser Tyr Gly Cys Cys Ser
1               5                   10                  15

Arg Ser Cys Ile Ala Leu Phe Cys Ser Val Ser Lys Leu Cys
            20                  25                  30

<210> SEQ ID NO 72

<211> LENGTH: 30
<212> TYPE: PRT
<213> ORGANISM: Endogenous retrovirus K (from homo sapiens)

<400> SEQUENCE: 72

Cys Ser Asp Tyr Gly Ile Asn Cys Ser His Ser Tyr Gly Cys Cys Ser
1               5                   10                  15

Arg Ser Cys Ile Ala Leu Phe Cys Ser Val Ser Lys Leu Cys
            20                  25                  30

<210> SEQ ID NO 73
<211> LENGTH: 30
<212> TYPE: PRT
<213> ORGANISM: Endogenous retrovirus K (from homo sapiens)

<400> SEQUENCE: 73

Cys Ser Asp Tyr Gly Ile Asn Cys Ser His Ser Tyr Gly Cys Cys Ser
1               5                   10                  15

Arg Ser Cys Ile Ala Leu Phe Cys Ser Val Ser Lys Leu Cys
            20                  25                  30

<210> SEQ ID NO 74
<211> LENGTH: 30
<212> TYPE: PRT
<213> ORGANISM: Endogenous retrovirus K (from homo sapiens)

<400> SEQUENCE: 74

Cys Ser Asp Tyr Gly Ile Asn Cys Ser His Ser Tyr Gly Cys Cys Ser
1               5                   10                  15

Arg Ser Cys Ile Ala Leu Phe Cys Ser Val Ser Lys Leu Cys
            20                  25                  30

<210> SEQ ID NO 75
<211> LENGTH: 30
<212> TYPE: PRT
<213> ORGANISM: Endogenous retrovirus K (from homo sapiens)

<400> SEQUENCE: 75

Cys Ser Asp Tyr Gly Ile Asn Cys Ser His Ser Tyr Gly Cys Cys Ser
1               5                   10                  15

Arg Ser Cys Ile Ala Leu Phe Cys Ser Val Ser Lys Leu Cys
            20                  25                  30

<210> SEQ ID NO 76
<211> LENGTH: 30
<212> TYPE: PRT
<213> ORGANISM: Endogenous retrovirus K (from homo sapiens)

<400> SEQUENCE: 76

Cys Ser Asp Tyr Gly Ile Asn Cys Ser His Ser Tyr Gly Cys Cys Gly
1               5                   10                  15

Arg Ser Cys Ile Ala Leu Phe Cys Ser Val Gly Lys Leu Cys
            20                  25                  30

<210> SEQ ID NO 77
<211> LENGTH: 30
<212> TYPE: PRT
<213> ORGANISM: Endogenous retrovirus K (from homo sapiens)

<400> SEQUENCE: 77

Cys Ser Asp Tyr Gly Ile Asn Cys Ser His Ser Tyr Gly Cys Cys Gly
1               5                   10                  15

-continued

Arg Ser Cys Ile Ala Leu Phe Cys Ser Val Gly Lys Leu Cys
            20                  25                  30

<210> SEQ ID NO 78
<211> LENGTH: 30
<212> TYPE: PRT
<213> ORGANISM: Endogenous retrovirus K (from homo sapiens)

<400> SEQUENCE: 78

Cys Ser Asp Tyr Gly Ile Asn Cys Ser His Ser Tyr Gly Cys Cys Ser
1               5                   10                  15

Arg Ser Cys Ile Ala Leu Phe Cys Ser Val Gly Lys Leu Cys
            20                  25                  30

<210> SEQ ID NO 79
<211> LENGTH: 30
<212> TYPE: PRT
<213> ORGANISM: Endogenous retrovirus K (from homo sapiens)

<400> SEQUENCE: 79

Cys Ser Asp Tyr Gly Ile Asn Cys Ser His Ser Tyr Gly Cys Cys Ser
1               5                   10                  15

Arg Ser Cys Ile Ala Leu Phe Cys Ser Val Gly Lys Leu Cys
            20                  25                  30

<210> SEQ ID NO 80
<211> LENGTH: 30
<212> TYPE: PRT
<213> ORGANISM: Endogenous retrovirus K (from homo sapiens)

<400> SEQUENCE: 80

Cys Ser Asp Tyr Gly Ile Asn Cys Ser His Ser Tyr Gly Cys Cys Gly
1               5                   10                  15

Arg Ser Cys Ile Ala Leu Phe Cys Ser Val Ser Lys Leu Cys
            20                  25                  30

<210> SEQ ID NO 81
<211> LENGTH: 30
<212> TYPE: PRT
<213> ORGANISM: Endogenous retrovirus K (from homo sapiens)

<400> SEQUENCE: 81

Cys Ser Asp Tyr Gly Ile Asn Cys Ser His Ser Tyr Gly Cys Cys Ser
1               5                   10                  15

Arg Ser Cys Ile Ala Phe Phe Cys Ser Val Ser Lys Leu Cys
            20                  25                  30

<210> SEQ ID NO 82
<211> LENGTH: 30
<212> TYPE: PRT
<213> ORGANISM: Endogenous retrovirus K (from homo sapiens)

<400> SEQUENCE: 82

Cys Ser Asp Tyr Arg Ile Asn Cys Ser His Ser Tyr Gly Cys Cys Ser
1               5                   10                  15

Arg Ser Cys Ile Ala Leu Phe Cys Ser Val Ser Lys Leu Cys
            20                  25                  30

<210> SEQ ID NO 83
<211> LENGTH: 30
<212> TYPE: PRT
<213> ORGANISM: Endogenous retrovirus K (from homo sapiens)

```
<400> SEQUENCE: 83

Cys Ser Asp Tyr Gly Ile Asn Cys Ser His Ser Tyr Gly Cys Cys Gly
1               5                   10                  15

Arg Ser Cys Val Ala Leu Phe Cys Ser Val Ser Lys Leu Cys
            20                  25                  30

<210> SEQ ID NO 84
<211> LENGTH: 30
<212> TYPE: PRT
<213> ORGANISM: Endogenous retrovirus K (from homo sapiens)

<400> SEQUENCE: 84

Cys Ser Asp Tyr Gly Ile Asn Cys Ser His Ser Tyr Gly Cys Cys Gly
1               5                   10                  15

Arg Ser Cys Ile Ala Leu Phe Cys Ser Asp Ser Thr Leu Cys
            20                  25                  30

<210> SEQ ID NO 85
<211> LENGTH: 30
<212> TYPE: PRT
<213> ORGANISM: Endogenous retrovirus K (from homo sapiens)

<400> SEQUENCE: 85

Cys Ser Asp Tyr Gly Ile Asn Cys Ser His Ser Tyr Gly Cys Cys Asn
1               5                   10                  15

Arg Ser Cys Ile Ala Leu Phe Cys Ser Val Ser Lys Leu Cys
            20                  25                  30

<210> SEQ ID NO 86
<211> LENGTH: 30
<212> TYPE: PRT
<213> ORGANISM: Endogenous retrovirus K (from homo sapiens)

<400> SEQUENCE: 86

Cys Ser Asp Tyr Arg Ile Asn Cys Ser His Ser Tyr Gly Cys Cys Ser
1               5                   10                  15

Lys Ser Cys Ile Ala Leu Phe Cys Ser Val Ser Glu Leu Cys
            20                  25                  30

<210> SEQ ID NO 87
<211> LENGTH: 86
<212> TYPE: PRT
<213> ORGANISM: Endogenous retrovirus K (from homo sapiens)

<400> SEQUENCE: 87

Met Val Thr Pro Val Thr Trp Met Asp Asn Pro Ile Glu Tyr Tyr Val
1               5                   10                  15

Asn Asp Ser Val Trp Val Pro Gly Pro Thr Asp Asp Arg Cys Pro Ala
            20                  25                  30

Lys Pro Glu Glu Glu Gly Met Met Ile Asn Ile Ser Ile Gly Tyr His
        35                  40                  45

Tyr Pro Pro Ile Cys Leu Gly Arg Ala Pro Gly Cys Leu Met Pro Ala
    50                  55                  60

Val Gln Asn Trp Leu Val Glu Val Pro Thr Val Ser Pro Asn Ser Arg
65                  70                  75                  80

Phe Thr Tyr His Met Val
                85

<210> SEQ ID NO 88
<211> LENGTH: 86
```

<212> TYPE: PRT
<213> ORGANISM: Endogenous retrovirus K (from homo sapiens)

<400> SEQUENCE: 88

Ser Gly Met Ser Leu Arg Pro Arg Val Asn Cys Leu Gln Asp Phe Ser
1               5                   10                  15

Tyr Gln Arg Ser Leu Lys Phe Arg Pro Lys Gly Lys Thr Cys Pro Lys
                20                  25                  30

Glu Ile Pro Lys Gly Ser Lys Asn Thr Glu Val Leu Val Trp Glu Glu
            35                  40                  45

Cys Val Ala Asn Ser Val Val Ile Leu Gln Asn Asn Glu Phe Gly Thr
50                  55                  60

Ile Ile Asp Trp Ala Pro Arg Gly Gln Phe Tyr His Asn Cys Ser Cys
65                  70                  75                  80

Gln Thr Gln Ser Cys Pro
                85

<210> SEQ ID NO 89
<211> LENGTH: 86
<212> TYPE: PRT
<213> ORGANISM: Endogenous retrovirus K (from homo sapiens)

<400> SEQUENCE: 89

Ser Ala Gln Val Ser Pro Ala Val Asp Ser Asp Leu Thr Glu Ser Leu
1               5                   10                  15

Asp Lys His Lys His Lys Lys Leu Gln Ser Phe Tyr Leu Trp Glu Trp
                20                  25                  30

Glu Glu Lys Gly Ile Ser Thr Pro Arg Pro Lys Ile Ile Ser Pro Val
            35                  40                  45

Ser Gly Pro Glu His Pro Glu Leu Trp Arg Leu Thr Val Ala Ser His
50                  55                  60

His Ile Arg Ile Trp Ser Gly Asn Gln Thr Leu Glu Thr Arg Tyr Arg
65                  70                  75                  80

Lys Pro Phe Tyr Thr Ile
                85

<210> SEQ ID NO 90
<211> LENGTH: 86
<212> TYPE: PRT
<213> ORGANISM: Endogenous retrovirus K (from homo sapiens)

<400> SEQUENCE: 90

Asp Leu Asn Ser Ile Leu Thr Val Pro Leu Gln Ser Cys Tyr Lys Pro
1               5                   10                  15

Pro Tyr Met Leu Val Val Gly Asn Ile Val Ile Lys Pro Ala Ser Gln
                20                  25                  30

Thr Ile Thr Cys Glu Asn Gly Arg Leu Phe Thr Cys Ile Asp Ser Thr
            35                  40                  45

Phe Asn Trp Gln His Arg Ile Leu Leu Val Arg Ala Arg Glu Gly Met
50                  55                  60

Trp Ile Pro Val Ser Thr Asp Arg Pro Trp Glu Ala Ser Pro Ser Ile
65                  70                  75                  80

His Ile Leu Thr Glu Ile
                85

<210> SEQ ID NO 91
<211> LENGTH: 86
<212> TYPE: PRT

<213> ORGANISM: Endogenous retrovirus K (from homo sapiens)

<400> SEQUENCE: 91

```
Leu Lys Gly Val Leu Asn Arg Ser Lys Arg Phe Ile Phe Thr Leu Ile
1               5                   10                  15
Ala Val Ile Met Gly Leu Ile Ala Val Thr Ala Thr Ala Ala Val Ala
            20                  25                  30
Gly Val Ala Leu His Ser Ser Val Gln Ser Val Asn Phe Val Asn Tyr
        35                  40                  45
Trp Gln Lys Asn Ser Thr Arg Leu Trp Asn Ser Gln Ser Ser Ile Asp
50                  55                  60
Gln Lys Leu Ala Ser Gln Ile Asn Asp Leu Arg Gln Thr Val Ile Trp
65                  70                  75                  80
Met Gly Asp Arg Leu Met
                85
```

<210> SEQ ID NO 92
<211> LENGTH: 39
<212> TYPE: PRT
<213> ORGANISM: Endogenous retrovirus K (from homo sapiens)

<400> SEQUENCE: 92

```
Ile Gln Lys Ile His Phe Tyr Phe Asn Cys Ser Asp Tyr Gly Ile Asn
1               5                   10                  15
Cys Ser His Ser Tyr Gly Cys Cys Gly Arg Ser Cys Ile Ala Leu Phe
            20                  25                  30
Cys Ser Val Ser Lys Leu Cys
        35
```

<210> SEQ ID NO 93
<211> LENGTH: 86
<212> TYPE: PRT
<213> ORGANISM: Endogenous retrovirus K (from homo sapiens)

<400> SEQUENCE: 93

```
Thr Leu Glu His His Phe Gln Leu Gln Cys Asp Trp Asn Thr Ser Asp
1               5                   10                  15
Phe Cys Ile Thr Pro Gln Ile Tyr Asn Glu Ser Glu His His Trp Asp
            20                  25                  30
Met Val Arg Arg His Leu Gln Gly Arg Glu Asp Asn Leu Thr Leu Asp
        35                  40                  45
Ile Ser Lys Leu Lys Glu Gln Ile Phe Glu Ala Ser Lys Ala His Leu
50                  55                  60
Asn Leu Val Pro Gly Thr Glu Ala Ile Ala Gly Val Ala Asp Gly Leu
65                  70                  75                  80
Ala Asn Leu Asn Pro Val
                85
```

<210> SEQ ID NO 94
<211> LENGTH: 44
<212> TYPE: PRT
<213> ORGANISM: Endogenous retrovirus K (from homo sapiens)

<400> SEQUENCE: 94

```
Thr Trp Ile Lys Thr Ile Arg Ser Thr Met Ile Ile Asn Leu Ile Leu
1               5                   10                  15
Ile Val Val Cys Leu Phe Cys Leu Leu Val Cys Arg Cys Thr Gln
            20                  25                  30
```

-continued

```
Gln Leu Arg Arg Asp Ser Asp Ile Glu Asn Gly Pro
        35                  40

<210> SEQ ID NO 95
<211> LENGTH: 39
<212> TYPE: PRT
<213> ORGANISM: Endogenous retrovirus K (from homo sapiens)

<400> SEQUENCE: 95

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
        35

<210> SEQ ID NO 96
<211> LENGTH: 6
<212> TYPE: PRT
<213> ORGANISM: Endogenous retrovirus K (from homo sapiens)

<400> SEQUENCE: 96

Lys Ile His Phe Tyr Phe
1               5

<210> SEQ ID NO 97
<211> LENGTH: 6
<212> TYPE: PRT
<213> ORGANISM: Endogenous retrovirus K (from homo sapiens)

<400> SEQUENCE: 97

His Phe Tyr Phe Asn Cys
1               5

<210> SEQ ID NO 98
<211> LENGTH: 6
<212> TYPE: PRT
<213> ORGANISM: Endogenous retrovirus K (from homo sapiens)

<400> SEQUENCE: 98

Cys Ser Asp Tyr Gly Ile
1               5

<210> SEQ ID NO 99
<211> LENGTH: 6
<212> TYPE: PRT
<213> ORGANISM: Endogenous retrovirus K (from homo sapiens)

<400> SEQUENCE: 99

Ser Asp Tyr Gly Ile Asn
1               5

<210> SEQ ID NO 100
<211> LENGTH: 7
<212> TYPE: PRT
<213> ORGANISM: Endogenous retrovirus K (from homo sapiens)

<400> SEQUENCE: 100

Ser Asp Tyr Gly Ile Asn Cys
1               5

<210> SEQ ID NO 101
<211> LENGTH: 6
<212> TYPE: PRT
```

<213> ORGANISM: Endogenous retrovirus K (from homo sapiens)

<400> SEQUENCE: 101

Asp Tyr Gly Ile Asn Cys
1               5

<210> SEQ ID NO 102
<211> LENGTH: 6
<212> TYPE: PRT
<213> ORGANISM: Endogenous retrovirus K (from homo sapiens)

<400> SEQUENCE: 102

Ser His Ser Tyr Gly Cys
1               5

<210> SEQ ID NO 103
<211> LENGTH: 7
<212> TYPE: PRT
<213> ORGANISM: Endogenous retrovirus K (from homo sapiens)

<400> SEQUENCE: 103

Ser His Ser Tyr Gly Cys Cys
1               5

<210> SEQ ID NO 104
<211> LENGTH: 8
<212> TYPE: PRT
<213> ORGANISM: Endogenous retrovirus K (from homo sapiens)

<400> SEQUENCE: 104

Ser His Ser Tyr Gly Cys Cys Ser
1               5

<210> SEQ ID NO 105
<211> LENGTH: 6
<212> TYPE: PRT
<213> ORGANISM: Endogenous retrovirus K (from homo sapiens)

<400> SEQUENCE: 105

His Ser Tyr Gly Cys Cys
1               5

<210> SEQ ID NO 106
<211> LENGTH: 7
<212> TYPE: PRT
<213> ORGANISM: Endogenous retrovirus K (from homo sapiens)

<400> SEQUENCE: 106

His Ser Tyr Gly Cys Cys Ser
1               5

<210> SEQ ID NO 107
<211> LENGTH: 6
<212> TYPE: PRT
<213> ORGANISM: Endogenous retrovirus K (from homo sapiens)

<400> SEQUENCE: 107

Ser Tyr Gly Cys Cys Ser
1               5

<210> SEQ ID NO 108
<211> LENGTH: 6
<212> TYPE: PRT
<213> ORGANISM: Endogenous retrovirus K (from homo sapiens)

```
<400> SEQUENCE: 108

Gly Cys Cys Ser Arg Ser
1               5

<210> SEQ ID NO 109
<211> LENGTH: 6
<212> TYPE: PRT
<213> ORGANISM: Endogenous retrovirus K (from homo sapiens)

<400> SEQUENCE: 109

Ser Arg Ser Cys Ile Ala
1               5

<210> SEQ ID NO 110
<211> LENGTH: 6
<212> TYPE: PRT
<213> ORGANISM: Endogenous retrovirus K (from homo sapiens)

<400> SEQUENCE: 110

Arg Ser Cys Ile Ala Leu
1               5

<210> SEQ ID NO 111
<211> LENGTH: 6
<212> TYPE: PRT
<213> ORGANISM: Endogenous retrovirus K (from homo sapiens)

<400> SEQUENCE: 111

Ser Cys Ile Ala Leu Phe
1               5

<210> SEQ ID NO 112
<211> LENGTH: 6
<212> TYPE: PRT
<213> ORGANISM: Endogenous retrovirus K (from homo sapiens)

<400> SEQUENCE: 112

Leu Phe Cys Ser Val Ser
1               5

<210> SEQ ID NO 113
<211> LENGTH: 9
<212> TYPE: PRT
<213> ORGANISM: Endogenous retrovirus K (from homo sapiens)

<400> SEQUENCE: 113

Leu Phe Cys Ser Val Ser Lys Leu Cys
1               5

<210> SEQ ID NO 114
<211> LENGTH: 6
<212> TYPE: PRT
<213> ORGANISM: Endogenous retrovirus K (from homo sapiens)

<400> SEQUENCE: 114

Ser Val Ser Lys Leu Cys
1               5

<210> SEQ ID NO 115
<211> LENGTH: 24
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 115

Cys Thr Xaa Tyr Gly Xaa Asn Cys Xaa Xaa Ser Tyr Glu Cys Cys Ser
1               5                   10                  15

Xaa Xaa Cys Ser Xaa Gly Phe Cys
            20

<210> SEQ ID NO 116
<211> LENGTH: 24
<212> TYPE: PRT
<213> ORGANISM: Endogenous retrovirus K (from homo sapiens)

<400> SEQUENCE: 116

Cys Ser Asp Tyr Gly Ile Asn Cys Ser His Ser Tyr Gly Cys Cys Ser
1               5                   10                  15

Arg Ser Cys Ile Ala Leu Phe Cys
            20

<210> SEQ ID NO 117
<211> LENGTH: 26
<212> TYPE: PRT
<213> ORGANISM: Perigonia lusca single nucleopolyhedrovirus

<400> SEQUENCE: 117

Cys Thr Glu Asn Gly Arg Asn Cys Lys Tyr Ser Tyr Glu Cys Cys Ser
1               5                   10                  15

Gln Ala Cys Ser Ala Val Phe Gly Phe Cys
            20                  25

<210> SEQ ID NO 118
<211> LENGTH: 26
<212> TYPE: PRT
<213> ORGANISM: Hemileuca sp. Nucleopolyhedrovirus

<400> SEQUENCE: 118

Cys Thr Glu Thr Gly Arg Asn Cys Lys Tyr Ser Asp Glu Cys Cys Ser
1               5                   10                  15

Gly Ala Cys Ser Ala Ala Phe Gly Phe Cys
            20                  25

<210> SEQ ID NO 119
<211> LENGTH: 24
<212> TYPE: PRT
<213> ORGANISM: Conus textile

<400> SEQUENCE: 119

Cys Pro Asp Tyr Thr Glu Pro Cys Ser His Ala His Glu Cys Cys Ser
```

```
1               5                  10                  15
Trp Asn Cys Tyr Asn Gly His Cys
            20

<210> SEQ ID NO 120
<211> LENGTH: 24
<212> TYPE: PRT
<213> ORGANISM: Conus ventricosus

<400> SEQUENCE: 120

Cys Leu Ala Ser Gly Glu Thr Cys Trp Arg Asp Thr Ser Cys Cys Ser
1               5                   10                  15

Phe Ser Cys Thr Asn Asn Val Cys
            20

<210> SEQ ID NO 121
<211> LENGTH: 39
<212> TYPE: PRT
<213> ORGANISM: Endogenous retrovirus K (from homo sapiens)

<400> SEQUENCE: 121

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
            35

<210> SEQ ID NO 122
<211> LENGTH: 39
<212> TYPE: PRT
<213> ORGANISM: Endogenous retrovirus K (from homo sapiens)

<400> SEQUENCE: 122

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Gly Lys Leu Cys
            35

<210> SEQ ID NO 123
<211> LENGTH: 39
<212> TYPE: PRT
<213> ORGANISM: Endogenous retrovirus K (from homo sapiens)

<400> SEQUENCE: 123

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Phe Phe
            20                  25                  30

Cys Ser Val Ser Lys Leu Cys
            35

<210> SEQ ID NO 124
<211> LENGTH: 39
<212> TYPE: PRT
<213> ORGANISM: Endogenous retrovirus K (from homo sapiens)

<400> SEQUENCE: 124

Ile Gln Lys Ile His Phe Tyr Phe Asn Cys Ser Asp Tyr Arg Ile Asn
```

-continued

```
                1               5                  10                  15
Cys Ser His Ser Tyr Gly Cys Cys Ser Arg Ser Cys Ile Ala Leu Phe
                20                  25                  30
Cys Ser Val Ser Lys Leu Cys
            35

<210> SEQ ID NO 125
<211> LENGTH: 39
<212> TYPE: PRT
<213> ORGANISM: Endogenous retrovirus K (from homo sapiens)

<400> SEQUENCE: 125

Ile Gln Lys Ile His Phe Tyr Phe Asn Cys Ser Asp Tyr Gly Ile Asn
1               5                  10                  15
Cys Ser His Ser Tyr Gly Cys Cys Ser Arg Thr Cys Ile Ala Leu Phe
                20                  25                  30
Phe Ser Val Ser Lys Leu Cys
            35

<210> SEQ ID NO 126
<211> LENGTH: 39
<212> TYPE: PRT
<213> ORGANISM: Endogenous retrovirus K (from homo sapiens)

<400> SEQUENCE: 126

Ile Gln Lys Ile His Phe Tyr Phe Asn Ser Ser Asp Tyr Gly Ile Asn
1               5                  10                  15
Cys Ser His Ser Tyr Gly Cys Cys Ser Arg Ser Cys Ile Ala Leu Phe
                20                  25                  30
Cys Ser Val Ser Lys Leu Cys
            35

<210> SEQ ID NO 127
<211> LENGTH: 39
<212> TYPE: PRT
<213> ORGANISM: Endogenous retrovirus K (from homo sapiens)

<400> SEQUENCE: 127

Ile Gln Lys Ile His Phe Tyr Phe Asn Cys Ser Asp Tyr Arg Ile Asn
1               5                  10                  15
Cys Ser His Ser Tyr Gly Cys Cys Ser Lys Ser Cys Ile Ala Leu Phe
                20                  25                  30
Cys Ser Val Ser Glu Leu Cys
            35

<210> SEQ ID NO 128
<211> LENGTH: 39
<212> TYPE: PRT
<213> ORGANISM: Endogenous retrovirus K (from homo sapiens)

<400> SEQUENCE: 128

Ile Gln Lys Ile His Phe Tyr Leu Asn Cys Ser Asp Tyr Gly Ile Asn
1               5                  10                  15
Cys Ser His Ser Tyr Gly Cys Cys Gly Arg Ser Cys Ile Ala Leu Phe
                20                  25                  30
Cys Ser Val Gly Lys Leu Cys
            35

<210> SEQ ID NO 129
<211> LENGTH: 39
```

-continued

```
<212> TYPE: PRT
<213> ORGANISM: Endogenous retrovirus K (from homo sapiens)

<400> SEQUENCE: 129

Ile Gln Lys Ile His Phe Tyr Phe Asn Cys Ser Asp Tyr Gly Ile Asn
1               5                   10                  15

Cys Ser His Ser Tyr Gly Cys Cys Gly Arg Ser Cys Ile Ala Leu Phe
            20                  25                  30

Cys Ser Val Ser Lys Leu Cys
        35

<210> SEQ ID NO 130
<211> LENGTH: 39
<212> TYPE: PRT
<213> ORGANISM: Endogenous retrovirus K (from homo sapiens)

<400> SEQUENCE: 130

Ile Gln Lys Ile His Phe Tyr Phe Asn Cys Ser Asp Tyr Gly Ile Asn
1               5                   10                  15

Cys Ser His Ser Tyr Gly Cys Cys Gly Arg Ser Cys Ile Ala Leu Phe
            20                  25                  30

Cys Ser Val Gly Lys Leu Cys
        35

<210> SEQ ID NO 131
<211> LENGTH: 39
<212> TYPE: PRT
<213> ORGANISM: Endogenous retrovirus K (from homo sapiens)

<400> SEQUENCE: 131

Ile Gln Lys Ile His Phe Tyr Phe Asn Cys Ser Asp Tyr Gly Ile Asn
1               5                   10                  15

Cys Ser His Ser Tyr Gly Cys Cys Gly Arg Ser Cys Val Ala Leu Phe
            20                  25                  30

Cys Ser Val Ser Lys Leu Cys
        35

<210> SEQ ID NO 132
<211> LENGTH: 39
<212> TYPE: PRT
<213> ORGANISM: Endogenous retrovirus K (from homo sapiens)

<400> SEQUENCE: 132

Ile Gln Lys Val His Phe Tyr Phe Asn Cys Ser Asp Tyr Gly Ile Asn
1               5                   10                  15

Cys Ser His Ser Tyr Gly Cys Cys Gly Arg Ser Cys Ile Ala Leu Phe
            20                  25                  30

Cys Ser Asp Ser Lys Leu Tyr
        35

<210> SEQ ID NO 133
<211> LENGTH: 63
<212> TYPE: PRT
<213> ORGANISM: Endogenous retrovirus K (from homo sapiens)

<400> SEQUENCE: 133

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30
```

```
Cys Ser Val Gly Lys Leu Leu Met Ile Gly Lys Lys Ile Leu Gln Asp
         35                  40                  45

Tyr Gly Ile His Asn Leu Val Leu Ile Lys Asn Trp Gln Ile Lys
 50                  55                  60
```

<210> SEQ ID NO 134
<211> LENGTH: 30
<212> TYPE: PRT
<213> ORGANISM: Endogenous retrovirus K (from homo sapiens)

<400> SEQUENCE: 134

```
Met Ser Asp Tyr Gly Ile Asn Cys Ser His Ser Tyr Gly Cys Cys Gly
 1               5                  10                  15

Arg Ser Cys Ile Ala Leu Phe Cys Ser Asp Ser Thr Leu Cys
             20                  25                  30
```

<210> SEQ ID NO 135
<211> LENGTH: 39
<212> TYPE: PRT
<213> ORGANISM: Endogenous retrovirus K (from homo sapiens)

<400> SEQUENCE: 135

```
Ile Gln Lys Ile Gln Phe Tyr Phe Asn Cys Ser Asp Tyr Gly Ile Asn
 1               5                  10                  15

Cys Ser His Ser Tyr Gly Arg Cys Gly Arg Ser Cys Ile Val Leu Phe
             20                  25                  30

Cys Ser Asp Ser Lys Leu Cys
         35
```

<210> SEQ ID NO 136
<211> LENGTH: 153
<212> TYPE: DNA
<213> ORGANISM: Endogenous retrovirus K (from homo sapiens)

<400> SEQUENCE: 136

```
gtattaaaag gtgttttaaa tagatccaaa agattcattt ttactttaat tgcagtgatt      60
atgggattaa ttgcagtcac agctacggct gctgtagcag gagttgcatt gcactcttct     120
gttcagtcag taaactttgt taatgattgg caa                                  153
```

<210> SEQ ID NO 137
<211> LENGTH: 51
<212> TYPE: PRT
<213> ORGANISM: Endogenous retrovirus K (from homo sapiens)

<400> SEQUENCE: 137

```
Val Leu Lys Gly Val Leu Asn Arg Ser Lys Arg Phe Ile Phe Thr Leu
 1               5                  10                  15

Ile Ala Val Ile Met Gly Leu Ile Ala Val Thr Ala Thr Ala Ala Val
             20                  25                  30

Ala Gly Val Ala Leu His Ser Ser Val Gln Ser Val Asn Phe Val Asn
         35                  40                  45

Asp Trp Gln
 50
```

<210> SEQ ID NO 138
<211> LENGTH: 47
<212> TYPE: PRT
<213> ORGANISM: Endogenous retrovirus K (from homo sapiens)

<400> SEQUENCE: 138

```
Ile Lys Arg Cys Phe Lys Ile Gln Lys Ile His Phe Tyr Phe Asn Cys
1               5                   10                  15

Ser Asp Tyr Gly Ile Asn Cys Ser His Ser Tyr Gly Cys Ser Arg
            20                  25                  30

Ser Cys Ile Ala Leu Phe Cys Ser Val Ser Lys Leu Cys Leu Ala
        35                  40                  45
```

<210> SEQ ID NO 139
<211> LENGTH: 8
<212> TYPE: PRT
<213> ORGANISM: Endogenous retrovirus K (from homo sapiens)

<400> SEQUENCE: 139

```
Thr Glu Val Leu Trp Glu Glu Cys
1               5
```

<210> SEQ ID NO 140
<211> LENGTH: 8
<212> TYPE: PRT
<213> ORGANISM: Endogenous retrovirus K (from homo sapiens)

<400> SEQUENCE: 140

```
Lys Gly Val Leu Ile Gln Lys Ile
1               5
```

<210> SEQ ID NO 141
<211> LENGTH: 8
<212> TYPE: PRT
<213> ORGANISM: Endogenous retrovirus K (from homo sapiens)

<400> SEQUENCE: 141

```
Pro Tyr Met Leu Val Val Gly Asn
1               5
```

<210> SEQ ID NO 142
<211> LENGTH: 8
<212> TYPE: PRT
<213> ORGANISM: Endogenous retrovirus K (from homo sapiens)

<400> SEQUENCE: 142

```
Trp Leu Val Glu Val Pro Thr Val
1               5
```

<210> SEQ ID NO 143
<211> LENGTH: 8
<212> TYPE: PRT
<213> ORGANISM: Endogenous retrovirus K (from homo sapiens)

<400> SEQUENCE: 143

```
Val Pro Leu Gln Ser Cys Val Lys
1               5
```

<210> SEQ ID NO 144
<211> LENGTH: 8
<212> TYPE: PRT
<213> ORGANISM: Endogenous retrovirus K (from homo sapiens)

<400> SEQUENCE: 144

```
Phe Tyr Leu Trp Glu Trp Glu Glu
1               5
```

<210> SEQ ID NO 145
<211> LENGTH: 8
<212> TYPE: PRT

<213> ORGANISM: Endogenous retrovirus K (from homo sapiens)

<400> SEQUENCE: 145

His Asn Cys Ser Gly Gln Thr Gln
1               5

<210> SEQ ID NO 146
<211> LENGTH: 8
<212> TYPE: PRT
<213> ORGANISM: Endogenous retrovirus K (from homo sapiens)

<400> SEQUENCE: 146

Lys Lys Leu Gln Ser Phe Tyr Leu
1               5

<210> SEQ ID NO 147
<211> LENGTH: 8
<212> TYPE: PRT
<213> ORGANISM: Endogenous retrovirus K (from homo sapiens)

<400> SEQUENCE: 147

Val Ile Leu Gln Asn Asn Glu Phe
1               5

<210> SEQ ID NO 148
<211> LENGTH: 8
<212> TYPE: PRT
<213> ORGANISM: Endogenous retrovirus K (from homo sapiens)

<400> SEQUENCE: 148

Val Ser Pro Asn Ser Arg Phe Thr
1               5

<210> SEQ ID NO 149
<211> LENGTH: 8
<212> TYPE: PRT
<213> ORGANISM: Endogenous retrovirus K (from homo sapiens)

<400> SEQUENCE: 149

His Ile Leu Thr Glu Ile Leu Lys
1               5

<210> SEQ ID NO 150
<211> LENGTH: 8
<212> TYPE: PRT
<213> ORGANISM: Endogenous retrovirus K (from homo sapiens)

<400> SEQUENCE: 150

Gln Thr Leu Glu Thr Arg Tyr Arg
1               5

<210> SEQ ID NO 151
<211> LENGTH: 8
<212> TYPE: PRT
<213> ORGANISM: Endogenous retrovirus K (from homo sapiens)

<400> SEQUENCE: 151

Gln Ser Phe Tyr Leu Trp Glu Trp
1               5

<210> SEQ ID NO 152
<211> LENGTH: 8
<212> TYPE: PRT
<213> ORGANISM: Endogenous retrovirus K (from homo sapiens)

```
<400> SEQUENCE: 152

His His Ile Arg Ile Trp Ser Gly
1               5

<210> SEQ ID NO 153
<211> LENGTH: 8
<212> TYPE: PRT
<213> ORGANISM: Endogenous retrovirus K (from homo sapiens)

<400> SEQUENCE: 153

Val Trp Val Pro Gly Pro Thr Asp
1               5

<210> SEQ ID NO 154
<211> LENGTH: 8
<212> TYPE: PRT
<213> ORGANISM: Endogenous retrovirus K (from homo sapiens)

<400> SEQUENCE: 154

Ser Gly Pro Glu His Pro Glu Leu
1               5

<210> SEQ ID NO 155
<211> LENGTH: 8
<212> TYPE: PRT
<213> ORGANISM: Endogenous retrovirus K (from homo sapiens)

<400> SEQUENCE: 155

Lys Gly Ile Ser Thr Pro Arg Pro
1               5

<210> SEQ ID NO 156
<211> LENGTH: 8
<212> TYPE: PRT
<213> ORGANISM: Endogenous retrovirus K (from homo sapiens)

<400> SEQUENCE: 156

Met Val Ser Gly Met Ser Leu Arg
1               5

<210> SEQ ID NO 157
<211> LENGTH: 8
<212> TYPE: PRT
<213> ORGANISM: Endogenous retrovirus K (from homo sapiens)

<400> SEQUENCE: 157

Phe Thr Tyr His Met Val Ser Gly
1               5

<210> SEQ ID NO 158
<211> LENGTH: 8
<212> TYPE: PRT
<213> ORGANISM: Endogenous retrovirus K (from homo sapiens)

<400> SEQUENCE: 158

Asn Pro Ile Glu Val Tyr Val Asn
1               5

<210> SEQ ID NO 159
<211> LENGTH: 8
<212> TYPE: PRT
<213> ORGANISM: Endogenous retrovirus K (from homo sapiens)

<400> SEQUENCE: 159
```

-continued

```
Pro Pro Tyr Met Leu Val Val Gly
1               5

<210> SEQ ID NO 160
<211> LENGTH: 8
<212> TYPE: PRT
<213> ORGANISM: Endogenous retrovirus K (from homo sapiens)

<400> SEQUENCE: 160

Met Pro Ala Val Gln Asn Trp Leu
1               5

<210> SEQ ID NO 161
<211> LENGTH: 8
<212> TYPE: PRT
<213> ORGANISM: Endogenous retrovirus K (from homo sapiens)

<400> SEQUENCE: 161

Arg Pro Lys Gly Lys Thr Cys Pro
1               5

<210> SEQ ID NO 162
<211> LENGTH: 8
<212> TYPE: PRT
<213> ORGANISM: Endogenous retrovirus K (from homo sapiens)

<400> SEQUENCE: 162

Cys Pro Ser Ala Gln Val Ser Pro
1               5

<210> SEQ ID NO 163
<211> LENGTH: 8
<212> TYPE: PRT
<213> ORGANISM: Endogenous retrovirus K (from homo sapiens)

<400> SEQUENCE: 163

Asn Thr Glu Val Leu Trp Glu Glu
1               5

<210> SEQ ID NO 164
<211> LENGTH: 8
<212> TYPE: PRT
<213> ORGANISM: Endogenous retrovirus K (from homo sapiens)

<400> SEQUENCE: 164

Thr Pro Arg Pro Lys Ile Ile Ser
1               5

<210> SEQ ID NO 165
<211> LENGTH: 8
<212> TYPE: PRT
<213> ORGANISM: Endogenous retrovirus K (from homo sapiens)

<400> SEQUENCE: 165

Met Val Ser Gly Met Ser Leu Arg
1               5

<210> SEQ ID NO 166
<211> LENGTH: 8
<212> TYPE: PRT
<213> ORGANISM: Endogenous retrovirus K (from homo sapiens)

<400> SEQUENCE: 166

Ala Pro Arg Gly Gln Phe Tyr His
1               5
```

```
<210> SEQ ID NO 167
<211> LENGTH: 8
<212> TYPE: PRT
<213> ORGANISM: Endogenous retrovirus K (from homo sapiens)

<400> SEQUENCE: 167

Thr Pro Val Thr Trp Met Asp Asn
1               5

<210> SEQ ID NO 168
<211> LENGTH: 8
<212> TYPE: PRT
<213> ORGANISM: Endogenous retrovirus K (from homo sapiens)

<400> SEQUENCE: 168

Ser Gly Met Ser Leu Arg Pro Arg
1               5

<210> SEQ ID NO 169
<211> LENGTH: 8
<212> TYPE: PRT
<213> ORGANISM: Endogenous retrovirus K (from homo sapiens)

<400> SEQUENCE: 169

Val Ala Asn Ser Val Val Ile Leu
1               5

<210> SEQ ID NO 170
<211> LENGTH: 8
<212> TYPE: PRT
<213> ORGANISM: Endogenous retrovirus K (from homo sapiens)

<400> SEQUENCE: 170

Lys Pro Pro Tyr Met Leu Val Val
1               5

<210> SEQ ID NO 171
<211> LENGTH: 8
<212> TYPE: PRT
<213> ORGANISM: Endogenous retrovirus K (from homo sapiens)

<400> SEQUENCE: 171

Val Asp Ser Asp Leu Thr Glu Ser
1               5

<210> SEQ ID NO 172
<211> LENGTH: 8
<212> TYPE: PRT
<213> ORGANISM: Endogenous retrovirus K (from homo sapiens)

<400> SEQUENCE: 172

Glu Glu Glu Gly Met Met Ile Asn
1               5

<210> SEQ ID NO 173
<211> LENGTH: 8
<212> TYPE: PRT
<213> ORGANISM: Endogenous retrovirus K (from homo sapiens)

<400> SEQUENCE: 173

Ser Ile His Ile Leu Thr Glu Ile
1               5
```

```
<210> SEQ ID NO 174
<211> LENGTH: 8
<212> TYPE: PRT
<213> ORGANISM: Endogenous retrovirus K (from homo sapiens)

<400> SEQUENCE: 174

Met Val Thr Pro Val Thr Trp Met
1               5

<210> SEQ ID NO 175
<211> LENGTH: 8
<212> TYPE: PRT
<213> ORGANISM: Endogenous retrovirus K (from homo sapiens)

<400> SEQUENCE: 175

Val Lys Pro Pro Tyr Met Leu Val
1               5

<210> SEQ ID NO 176
<211> LENGTH: 8
<212> TYPE: PRT
<213> ORGANISM: Endogenous retrovirus K (from homo sapiens)

<400> SEQUENCE: 176

Ser Asp Tyr Gly Ile Asn Cys Ser
1               5

<210> SEQ ID NO 177
<211> LENGTH: 8
<212> TYPE: PRT
<213> ORGANISM: Endogenous retrovirus K (from homo sapiens)

<400> SEQUENCE: 177

Val Val Gly Asn Ile Val Ile Lys
1               5

<210> SEQ ID NO 178
<211> LENGTH: 8
<212> TYPE: PRT
<213> ORGANISM: Endogenous retrovirus K (from homo sapiens)

<400> SEQUENCE: 178

Leu Ile Gln Lys Ile His Phe Tyr
1               5

<210> SEQ ID NO 179
<211> LENGTH: 8
<212> TYPE: PRT
<213> ORGANISM: Endogenous retrovirus K (from homo sapiens)

<400> SEQUENCE: 179

Leu Thr Val Pro Leu Gln Ser Cys
1               5

<210> SEQ ID NO 180
<211> LENGTH: 8
<212> TYPE: PRT
<213> ORGANISM: Endogenous retrovirus K (from homo sapiens)

<400> SEQUENCE: 180

His Arg Ile Leu Leu Val Arg Ala
1               5

<210> SEQ ID NO 181
<211> LENGTH: 8
```

```
<212> TYPE: PRT
<213> ORGANISM: Endogenous retrovirus K (from homo sapiens)

<400> SEQUENCE: 181

Leu Lys Gly Val Leu Ile Gln Lys
1               5

<210> SEQ ID NO 182
<211> LENGTH: 8
<212> TYPE: PRT
<213> ORGANISM: Endogenous retrovirus K (from homo sapiens)

<400> SEQUENCE: 182

Glu Glu Gly Met Met Ile Asn Ile
1               5

<210> SEQ ID NO 183
<211> LENGTH: 6
<212> TYPE: PRT
<213> ORGANISM: Endogenous retrovirus K (from homo sapiens)

<400> SEQUENCE: 183

Ser Val Ser Lys Leu Cys
1               5

<210> SEQ ID NO 184
<211> LENGTH: 8
<212> TYPE: PRT
<213> ORGANISM: Endogenous retrovirus K (from homo sapiens)

<400> SEQUENCE: 184

Cys Pro Ser Ala Gln Val Ser Pro
1               5

<210> SEQ ID NO 185
<211> LENGTH: 8
<212> TYPE: PRT
<213> ORGANISM: Endogenous retrovirus K (from homo sapiens)

<400> SEQUENCE: 185

Cys Val Ala Asn Ser Val Val Ile
1               5

<210> SEQ ID NO 186
<211> LENGTH: 8
<212> TYPE: PRT
<213> ORGANISM: Endogenous retrovirus K (from homo sapiens)

<400> SEQUENCE: 186

Lys Pro Ala Ser Gln Thr Ile Thr
1               5

<210> SEQ ID NO 187
<211> LENGTH: 8
<212> TYPE: PRT
<213> ORGANISM: Endogenous retrovirus K (from homo sapiens)

<400> SEQUENCE: 187

Pro Pro Tyr Met Leu Val Val Gly
1               5

<210> SEQ ID NO 188
<211> LENGTH: 8
<212> TYPE: PRT
<213> ORGANISM: Endogenous retrovirus K (from homo sapiens)
```

```
<400> SEQUENCE: 188

Val Val Ile Leu Gln Asn Asn Glu
1               5

<210> SEQ ID NO 189
<211> LENGTH: 8
<212> TYPE: PRT
<213> ORGANISM: Endogenous retrovirus K (from homo sapiens)

<400> SEQUENCE: 189

Arg Phe Thr Tyr His Met Val Ser
1               5

<210> SEQ ID NO 190
<211> LENGTH: 8
<212> TYPE: PRT
<213> ORGANISM: Endogenous retrovirus K (from homo sapiens)

<400> SEQUENCE: 190

Pro Glu Leu Trp Arg Leu Thr Val
1               5

<210> SEQ ID NO 191
<211> LENGTH: 8
<212> TYPE: PRT
<213> ORGANISM: Endogenous retrovirus K (from homo sapiens)

<400> SEQUENCE: 191

Ile Ser Pro Val Ser Gly Pro Glu
1               5

<210> SEQ ID NO 192
<211> LENGTH: 8
<212> TYPE: PRT
<213> ORGANISM: Endogenous retrovirus K (from homo sapiens)

<400> SEQUENCE: 192

Ile Gln Lys Ile His Phe Tyr Phe
1               5

<210> SEQ ID NO 193
<211> LENGTH: 8
<212> TYPE: PRT
<213> ORGANISM: Endogenous retrovirus K (from homo sapiens)

<400> SEQUENCE: 193

Asn Ser Val Val Ile Leu Gln Asn
1               5

<210> SEQ ID NO 194
<211> LENGTH: 8
<212> TYPE: PRT
<213> ORGANISM: Endogenous retrovirus K (from homo sapiens)

<400> SEQUENCE: 194

Arg Ser Cys Ile Ala Leu Phe Cys
1               5

<210> SEQ ID NO 195
<211> LENGTH: 8
<212> TYPE: PRT
<213> ORGANISM: Endogenous retrovirus K (from homo sapiens)

<400> SEQUENCE: 195
```

Tyr Pro Pro Ile Cys Leu Gly Arg
1               5

<210> SEQ ID NO 196
<211> LENGTH: 8
<212> TYPE: PRT
<213> ORGANISM: Endogenous retrovirus K (from homo sapiens)

<400> SEQUENCE: 196

Asn Asp Ser Val Trp Val Pro Gly
1               5

<210> SEQ ID NO 197
<211> LENGTH: 8
<212> TYPE: PRT
<213> ORGANISM: Endogenous retrovirus K (from homo sapiens)

<400> SEQUENCE: 197

Ile Leu Leu Val Arg Ala Arg Glu
1               5

<210> SEQ ID NO 198
<211> LENGTH: 8
<212> TYPE: PRT
<213> ORGANISM: Endogenous retrovirus K (from homo sapiens)

<400> SEQUENCE: 198

Met Ile Asn Ile Ser Ile Gly Tyr
1               5

<210> SEQ ID NO 199
<211> LENGTH: 8
<212> TYPE: PRT
<213> ORGANISM: Endogenous retrovirus K (from homo sapiens)

<400> SEQUENCE: 199

Tyr Met Leu Val Val Gly Asn Ile
1               5

<210> SEQ ID NO 200
<211> LENGTH: 8
<212> TYPE: PRT
<213> ORGANISM: Endogenous retrovirus K (from homo sapiens)

<400> SEQUENCE: 200

Tyr His Met Val Ser Gly Met Ser
1               5

<210> SEQ ID NO 201
<211> LENGTH: 8
<212> TYPE: PRT
<213> ORGANISM: Endogenous retrovirus K (from homo sapiens)

<400> SEQUENCE: 201

Ser His His Ile Arg Ile Trp Ser
1               5

<210> SEQ ID NO 202
<211> LENGTH: 8
<212> TYPE: PRT
<213> ORGANISM: Endogenous retrovirus K (from homo sapiens)

<400> SEQUENCE: 202

Gly Val Leu Ile Gln Lys Ile His 1               5

<210> SEQ ID NO 203
<211> LENGTH: 8
<212> TYPE: PRT
<213> ORGANISM: Endogenous retrovirus K (from homo sapiens)

<400> SEQUENCE: 203

Met Pro Ala Val Gln Asn Trp Leu
1               5

<210> SEQ ID NO 204
<211> LENGTH: 8
<212> TYPE: PRT
<213> ORGANISM: Endogenous retrovirus K (from homo sapiens)

<400> SEQUENCE: 204

Gly Met Met Ile Asn Ile Ser Ile
1               5

<210> SEQ ID NO 205
<211> LENGTH: 8
<212> TYPE: PRT
<213> ORGANISM: Endogenous retrovirus K (from homo sapiens)

<400> SEQUENCE: 205

Val Thr Pro Val Thr Trp Met Asp
1               5

<210> SEQ ID NO 206
<211> LENGTH: 8
<212> TYPE: PRT
<213> ORGANISM: Endogenous retrovirus K (from homo sapiens)

<400> SEQUENCE: 206

Leu Thr Val Ala Ser His His Ile
1               5

<210> SEQ ID NO 207
<211> LENGTH: 8
<212> TYPE: PRT
<213> ORGANISM: Endogenous retrovirus K (from homo sapiens)

<400> SEQUENCE: 207

Gly Thr Ile Ile Asp Trp Ala Pro
1               5

<210> SEQ ID NO 208
<211> LENGTH: 8
<212> TYPE: PRT
<213> ORGANISM: Endogenous retrovirus K (from homo sapiens)

<400> SEQUENCE: 208

Asn Ile Ser Ile Gly Tyr His Tyr
1               5

<210> SEQ ID NO 209
<211> LENGTH: 8
<212> TYPE: PRT
<213> ORGANISM: Endogenous retrovirus K (from homo sapiens)

<400> SEQUENCE: 209

Asn Thr Glu Val Leu Trp Glu Glu
1               5

<210> SEQ ID NO 210
<211> LENGTH: 8
<212> TYPE: PRT
<213> ORGANISM: Endogenous retrovirus K (from homo sapiens)

<400> SEQUENCE: 210

Trp Ile Pro Val Ser Thr Asp Arg
1               5

<210> SEQ ID NO 211
<211> LENGTH: 8
<212> TYPE: PRT
<213> ORGANISM: Endogenous retrovirus K (from homo sapiens)

<400> SEQUENCE: 211

Pro Arg Pro Lys Ile Ile Ser Pro
1               5

<210> SEQ ID NO 212
<211> LENGTH: 8
<212> TYPE: PRT
<213> ORGANISM: Endogenous retrovirus K (from homo sapiens)

<400> SEQUENCE: 212

Gly Gln Phe Tyr His Asn Cys Ser
1               5

<210> SEQ ID NO 213
<211> LENGTH: 8
<212> TYPE: PRT
<213> ORGANISM: Endogenous retrovirus K (from homo sapiens)

<400> SEQUENCE: 213

Glu Gly Met Met Ile Asn Ile Ser
1               5

<210> SEQ ID NO 214
<211> LENGTH: 8
<212> TYPE: PRT
<213> ORGANISM: Endogenous retrovirus K (from homo sapiens)

<400> SEQUENCE: 214

Pro Tyr Met Leu Val Val Gly Asn
1               5

<210> SEQ ID NO 215
<211> LENGTH: 8
<212> TYPE: PRT
<213> ORGANISM: Endogenous retrovirus K (from homo sapiens)

<400> SEQUENCE: 215

Ile Asp Leu Asn Ser Ile Leu Thr
1               5

<210> SEQ ID NO 216
<211> LENGTH: 8
<212> TYPE: PRT
<213> ORGANISM: Endogenous retrovirus K (from homo sapiens)

<400> SEQUENCE: 216

Ile Glu Val Tyr Val Asn Asp Ser
1               5

<210> SEQ ID NO 217

-continued

```
<211> LENGTH: 8
<212> TYPE: PRT
<213> ORGANISM: Endogenous retrovirus K (from homo sapiens)

<400> SEQUENCE: 217

Ile Arg Ile Trp Ser Gly Asn Gln
1               5

<210> SEQ ID NO 218
<211> LENGTH: 8
<212> TYPE: PRT
<213> ORGANISM: Endogenous retrovirus K (from homo sapiens)

<400> SEQUENCE: 218

Val Thr Trp Met Asp Asn Pro Ile
1               5

<210> SEQ ID NO 219
<211> LENGTH: 8
<212> TYPE: PRT
<213> ORGANISM: Endogenous retrovirus K (from homo sapiens)

<400> SEQUENCE: 219

Arg Phe Thr Tyr His Met Val Ser
1               5

<210> SEQ ID NO 220
<211> LENGTH: 8
<212> TYPE: PRT
<213> ORGANISM: Endogenous retrovirus K (from homo sapiens)

<400> SEQUENCE: 220

Ser Ile Gly Tyr His Tyr Pro Pro
1               5

<210> SEQ ID NO 221
<211> LENGTH: 8
<212> TYPE: PRT
<213> ORGANISM: Endogenous retrovirus K (from homo sapiens)

<400> SEQUENCE: 221

His Arg Ile Leu Leu Val Arg Ala
1               5

<210> SEQ ID NO 222
<211> LENGTH: 8
<212> TYPE: PRT
<213> ORGANISM: Endogenous retrovirus K (from homo sapiens)

<400> SEQUENCE: 222

Pro Pro Tyr Met Leu Val Val Gly
1               5

<210> SEQ ID NO 223
<211> LENGTH: 8
<212> TYPE: PRT
<213> ORGANISM: Endogenous retrovirus K (from homo sapiens)

<400> SEQUENCE: 223

Gln Ser Phe Tyr Leu Trp Glu Trp
1               5

<210> SEQ ID NO 224
<211> LENGTH: 8
<212> TYPE: PRT
```

-continued

<213> ORGANISM: Endogenous retrovirus K (from homo sapiens)

<400> SEQUENCE: 224

Arg Glu Gly Met Trp Ile Pro Val
1               5

<210> SEQ ID NO 225
<211> LENGTH: 8
<212> TYPE: PRT
<213> ORGANISM: Endogenous retrovirus K (from homo sapiens)

<400> SEQUENCE: 225

Glu Glu Gly Met Met Ile Asn Ile
1               5

<210> SEQ ID NO 226
<211> LENGTH: 8
<212> TYPE: PRT
<213> ORGANISM: Endogenous retrovirus K (from homo sapiens)

<400> SEQUENCE: 226

Cys Ser Asp Tyr Gly Ile Asn Cys
1               5

<210> SEQ ID NO 227
<211> LENGTH: 8
<212> TYPE: PRT
<213> ORGANISM: Endogenous retrovirus K (from homo sapiens)

<400> SEQUENCE: 227

Pro Val Thr Trp Met Asp Asn Pro
1               5

<210> SEQ ID NO 228
<211> LENGTH: 8
<212> TYPE: PRT
<213> ORGANISM: Endogenous retrovirus K (from homo sapiens)

<400> SEQUENCE: 228

Val Ser Gly Met Ser Leu Arg Pro
1               5

<210> SEQ ID NO 229
<211> LENGTH: 8
<212> TYPE: PRT
<213> ORGANISM: Endogenous retrovirus K (from homo sapiens)

<400> SEQUENCE: 229

Pro Arg Pro Lys Ile Ile Ser Pro
1               5

<210> SEQ ID NO 230
<211> LENGTH: 8
<212> TYPE: PRT
<213> ORGANISM: Endogenous retrovirus K (from homo sapiens)

<400> SEQUENCE: 230

Arg Ala Arg Glu Gly Met Trp Ile
1               5

<210> SEQ ID NO 231
<211> LENGTH: 8
<212> TYPE: PRT
<213> ORGANISM: Endogenous retrovirus K (from homo sapiens)

```
<400> SEQUENCE: 231

Asp Leu Thr Glu Ser Leu Asp Lys
1               5

<210> SEQ ID NO 232
<211> LENGTH: 8
<212> TYPE: PRT
<213> ORGANISM: Endogenous retrovirus K (from homo sapiens)

<400> SEQUENCE: 232

Gln Asp Phe Ser Tyr Gln Arg Ser
1               5

<210> SEQ ID NO 233
<211> LENGTH: 8
<212> TYPE: PRT
<213> ORGANISM: Endogenous retrovirus K (from homo sapiens)

<400> SEQUENCE: 233

Leu Val Arg Ala Arg Glu Gly Met
1               5

<210> SEQ ID NO 234
<211> LENGTH: 699
<212> TYPE: PRT
<213> ORGANISM: Endogenous retrovirus K (from homo sapiens)

<400> SEQUENCE: 234

Met Asn Pro Ser Glu Met Gln Arg Lys Ala Pro Pro Arg Arg Arg
1               5                   10                  15

His Arg Asn Arg Ala Pro Leu Thr His Lys Met Asn Lys Met Val Thr
                20                  25                  30

Ser Glu Glu Gln Met Lys Leu Pro Ser Thr Lys Lys Ala Glu Pro Pro
            35                  40                  45

Thr Trp Ala Gln Leu Lys Lys Leu Thr Gln Leu Ala Thr Lys Tyr Leu
    50                  55                  60

Glu Asn Thr Lys Val Thr Gln Thr Pro Glu Ser Met Leu Leu Ala Ala
65                  70                  75                  80

Leu Met Ile Val Ser Met Val Val Ser Leu Pro Met Pro Ala Gly Ala
                85                  90                  95

Ala Ala Ala Asn Tyr Thr Tyr Trp Ala Tyr Val Pro Phe Pro Pro Leu
                100                 105                 110

Ile Arg Ala Val Thr Trp Met Asp Asn Pro Ile Glu Ile Tyr Val Asn
                115                 120                 125

Asp Ser Val Trp Val Pro Gly Pro Thr Asp Asp Cys Cys Pro Ala Lys
            130                 135                 140

Pro Glu Glu Glu Gly Met Met Ile Asn Ile Ser Ile Gly Tyr Arg Tyr
145                 150                 155                 160

Pro Pro Ile Cys Leu Gly Arg Ala Pro Gly Cys Leu Met Pro Ala Val
                165                 170                 175

Gln Asn Trp Leu Val Glu Val Pro Thr Val Ser Pro Ile Ser Arg Phe
                180                 185                 190

Thr Tyr His Met Val Ser Gly Met Ser Leu Arg Pro Arg Val Asn Tyr
                195                 200                 205

Leu Gln Asp Phe Ser Tyr Gln Arg Ser Leu Lys Phe Arg Pro Lys Gly
            210                 215                 220

Lys Pro Cys Pro Lys Glu Ile Pro Lys Glu Ser Lys Asn Thr Glu Val
225                 230                 235                 240
```

```
Leu Val Trp Glu Glu Cys Val Ala Asn Ser Ala Val Ile Leu Gln Asn
                245                 250                 255

Asn Glu Phe Gly Thr Leu Ile Asp Trp Ala Pro Arg Gly Gln Phe Tyr
            260                 265                 270

His Asn Cys Ser Gly Gln Thr Gln Ser Cys Pro Ser Ala Gln Val Ser
        275                 280                 285

Pro Ala Val Asp Ser Asp Leu Thr Glu Ser Leu Asp Lys His Lys His
    290                 295                 300

Lys Lys Leu Gln Ser Phe Tyr Pro Trp Glu Trp Gly Glu Lys Gly Ile
305                 310                 315                 320

Ser Thr Ala Arg Pro Lys Ile Ile Ser Pro Val Ser Gly Pro Glu His
                325                 330                 335

Pro Glu Leu Trp Arg Leu Thr Val Ala Ser His His Ile Arg Ile Trp
            340                 345                 350

Ser Gly Asn Gln Thr Leu Glu Thr Arg Asp Arg Lys Pro Phe Tyr Thr
        355                 360                 365

Ile Asp Leu Asn Ser Ser Leu Thr Val Pro Leu Gln Ser Cys Val Lys
    370                 375                 380

Pro Pro Tyr Met Leu Val Val Gly Asn Ile Val Ile Lys Pro Asp Ser
385                 390                 395                 400

Gln Thr Ile Thr Cys Glu Asn Cys Arg Leu Leu Thr Cys Ile Asp Ser
                405                 410                 415

Thr Phe Asn Trp Gln His Arg Ile Leu Leu Val Arg Ala Arg Glu Gly
            420                 425                 430

Val Trp Ile Pro Val Ser Met Asp Arg Pro Trp Glu Ala Ser Pro Ser
        435                 440                 445

Val His Ile Leu Thr Glu Val Leu Lys Gly Val Leu Asn Arg Ser Lys
    450                 455                 460

Arg Phe Ile Phe Thr Leu Ile Ala Val Ile Met Gly Leu Ile Ala Val
465                 470                 475                 480

Thr Ala Thr Ala Ala Val Ala Gly Val Ala Leu His Ser Ser Val Gln
                485                 490                 495

Ser Val Asn Phe Val Asn Asp Trp Gln Asn Asn Ser Thr Arg Leu Trp
            500                 505                 510

Asn Ser Gln Ser Ser Ile Asp Gln Lys Leu Ala Asn Gln Ile Asn Asp
        515                 520                 525

Leu Arg Gln Thr Val Ile Trp Met Gly Asp Arg Leu Met Ser Leu Glu
    530                 535                 540

His Arg Phe Gln Leu Gln Cys Asp Trp Asn Thr Ser Asp Phe Cys Ile
545                 550                 555                 560

Thr Pro Gln Ile Tyr Asn Glu Ser Glu His His Trp Asp Met Val Arg
                565                 570                 575

Cys His Leu Gln Gly Arg Glu Asp Asn Leu Thr Leu Asp Ile Ser Lys
            580                 585                 590

Leu Lys Glu Gln Ile Phe Glu Ala Ser Lys Ala His Leu Asn Leu Val
        595                 600                 605

Pro Gly Thr Glu Ala Ile Ala Gly Val Ala Asp Gly Leu Ala Asn Leu
    610                 615                 620

Asn Thr Val Thr Trp Val Lys Thr Ile Gly Ser Thr Thr Ile Ile Asn
625                 630                 635                 640

Leu Ile Leu Ile Leu Val Cys Leu Phe Cys Leu Leu Leu Val Tyr Arg
                645                 650                 655
```

-continued

```
Cys Thr Gln Gln Leu Arg Arg Asp Ser Asp His Arg Glu Arg Ala Met
                660                 665                 670
Met Thr Met Val Val Leu Ser Lys Arg Lys Gly Gly Asn Val Gly Lys
            675                 680                 685
Ser Lys Arg Asp Gln Ile Val Thr Val Ser Val
        690                 695

<210> SEQ ID NO 235
<211> LENGTH: 38
<212> TYPE: PRT
<213> ORGANISM: Endogenous Retrovirus-K (from Homo sapiens)

<400> SEQUENCE: 235

Ile Gln Lys Val His Phe Val Phe Asn Cys Ser Asp Tyr Gly Ile Asn
1               5                   10                  15
Cys Ser His Ser Tyr Gly Cys Cys Gly Arg Ser Cys Ile Ala Leu Phe
            20                  25                  30
Cys Ser Asp Ser Lys Leu
        35

<210> SEQ ID NO 236
<211> LENGTH: 39
<212> TYPE: PRT
<213> ORGANISM: Endogenous Retrovirus-K (from Homo sapiens)

<400> SEQUENCE: 236

Ile Gln Lys Ile His Phe Tyr Phe Asn Cys Ser Asp Tyr Gly Ile Asn
1               5                   10                  15
Cys Ser His Ser Tyr Gly Cys Cys Gly Arg Ser Cys Ile Ala Leu Phe
            20                  25                  30
Cys Ser Val Ser Lys Leu Cys
        35

<210> SEQ ID NO 237
<211> LENGTH: 38
<212> TYPE: PRT
<213> ORGANISM: Endogenous Retrovirus-K (from Homo sapiens)

<400> SEQUENCE: 237

Ile Gln Lys Ile His Phe Tyr Phe Cys Ser Asp Tyr Gly Ile Asn Cys
1               5                   10                  15
Ser His Ser Tyr Gly Cys Cys Gly Arg Ser Cys Ile Ala Leu Phe Cys
            20                  25                  30
Ser Asp Ser Thr Leu Cys
        35

<210> SEQ ID NO 238
<211> LENGTH: 39
<212> TYPE: PRT
<213> ORGANISM: Endogenous Retrovirus-K (from Homo sapiens)

<400> SEQUENCE: 238

Ser Gln Lys Ile Gln Phe Tyr Phe Asn Cys Ser Asp Tyr Gly Ile Asn
1               5                   10                  15
Cys Ser His Ser Tyr Gly Arg Cys Gly Arg Ser Cys Ile Val Leu Phe
            20                  25                  30
Cys Ser Asp Ser Lys Leu Cys
        35

<210> SEQ ID NO 239
```

```
<211> LENGTH: 39
<212> TYPE: PRT
<213> ORGANISM: Endogenous Retrovirus-K (from Homo sapiens)

<400> SEQUENCE: 239

Ile Gln Lys Ile His Phe Tyr Phe Asn Cys Ser Asp Tyr Gly Ile Asn
1               5                   10                  15

Cys Ser His Ser Tyr Gly Cys Cys Gly Arg Ser Cys Ile Ala Leu Phe
            20                  25                  30

Cys Ser Val Gly Lys Leu Cys
        35

<210> SEQ ID NO 240
<211> LENGTH: 38
<212> TYPE: PRT
<213> ORGANISM: Endogenous Retrovirus-K (from Homo sapiens)

<400> SEQUENCE: 240

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Gly Lys Leu
        35

<210> SEQ ID NO 241
<211> LENGTH: 39
<212> TYPE: PRT
<213> ORGANISM: Endogenous Retrovirus-K (from Homo sapiens)

<400> SEQUENCE: 241

Ile Gln Lys Ile His Phe Tyr Phe Asn Cys Ser Asp Tyr Gly Ile Asn
1               5                   10                  15

Cys Ser His Ser Tyr Gly Cys Cys Gly Arg Ser Cys Val Ala Leu Phe
            20                  25                  30

Cys Ser Val Ser Lys Leu Cys
        35

<210> SEQ ID NO 242
<211> LENGTH: 38
<212> TYPE: PRT
<213> ORGANISM: Endogenous Retrovirus-K (from Homo sapiens)

<400> SEQUENCE: 242

Leu Asn Arg Ser Lys Ile Phe Phe Asn Cys Ser Asp Tyr Gly Thr Asn
1               5                   10                  15

Cys Ser His Ser Tyr Gly Leu Cys Gly Arg Ser Phe Ile Val Leu Phe
            20                  25                  30

Cys Ser Asp Ser Lys Leu
        35

<210> SEQ ID NO 243
<211> LENGTH: 39
<212> TYPE: PRT
<213> ORGANISM: Endogenous Retrovirus-K (from Homo sapiens)

<400> SEQUENCE: 243

Ile Gln Lys Ile His Phe Tyr Phe Asn Tyr Ser Asp Tyr Gly Ile Asn
1               5                   10                  15

Cys Ser His Ser Tyr Gly Cys Tyr Gly Arg Ser Cys Ile Ala Leu Phe
            20                  25                  30
```

-continued

Cys Ser Val Ser Lys Leu Cys
        35

<210> SEQ ID NO 244
<211> LENGTH: 39
<212> TYPE: PRT
<213> ORGANISM: Endogenous Retrovirus-K (from Homo sapiens)

<400> SEQUENCE: 244

Ile Gln Lys Ile His Phe Tyr Leu Asn Cys Ser Asp Tyr Gly Ile Asn
1               5                   10                  15

Cys Ser His Ser Tyr Gly Cys Cys Gly Arg Ser Cys Ile Ala Leu Phe
            20                  25                  30

Cys Ser Val Gly Lys Leu Cys
        35

<210> SEQ ID NO 245
<211> LENGTH: 39
<212> TYPE: PRT
<213> ORGANISM: Endogenous Retrovirus-K (from Homo sapiens)

<400> SEQUENCE: 245

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
        35

<210> SEQ ID NO 246
<211> LENGTH: 39
<212> TYPE: PRT
<213> ORGANISM: Endogenous Retrovirus-K (from Homo sapiens)

<400> SEQUENCE: 246

Ile Gln Arg Ile His Phe Tyr Phe Asn Tyr Ser Asp Tyr Gly Ile Asn
1               5                   10                  15

Cys Ser His Ser Tyr Gly Cys Cys Gly Arg Ser Cys Ile Ala Leu Phe
            20                  25                  30

Cys Ser Val Ser Lys Leu Cys
        35

<210> SEQ ID NO 247
<211> LENGTH: 39
<212> TYPE: PRT
<213> ORGANISM: Endogenous Retrovirus-K (from Homo sapiens)

<400> SEQUENCE: 247

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
        35

<210> SEQ ID NO 248
<211> LENGTH: 39
<212> TYPE: PRT
<213> ORGANISM: Endogenous Retrovirus-K (from Homo sapiens)

<400> SEQUENCE: 248

-continued

```
Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
            35

<210> SEQ ID NO 249
<211> LENGTH: 39
<212> TYPE: PRT
<213> ORGANISM: Endogenous Retrovirus-K (from Pan troglodytes)

<400> SEQUENCE: 249

Ile Gln Lys Val His Phe Tyr Phe Asn Cys Ser Asp Tyr Gly Ile Asn
1               5                   10                  15

Cys Ser His Ser Tyr Gly Cys Cys Gly Arg Ser Cys Ile Ala Leu Phe
            20                  25                  30

Cys Ser Asp Ser Lys Leu Tyr
            35

<210> SEQ ID NO 250
<211> LENGTH: 39
<212> TYPE: PRT
<213> ORGANISM: Endogenous Retrovirus-K (from Pan troglodytes)

<400> SEQUENCE: 250

Ile Gln Lys Ile His Phe Tyr Phe Asn Cys Ser Asp Tyr Gly Ile Asn
1               5                   10                  15

Cys Ser His Ser Tyr Gly Cys Cys Gly Arg Ser Cys Ile Ala Leu Phe
            20                  25                  30

Cys Ser Val Ser Lys Leu Cys
            35

<210> SEQ ID NO 251
<211> LENGTH: 34
<212> TYPE: PRT
<213> ORGANISM: Endogenous Retrovirus-K (from Pan troglodytes)

<400> SEQUENCE: 251

Phe Tyr Phe Asp Cys Ser Asp Tyr Gly Ile Asn Cys Ser His Ser Tyr
1               5                   10                  15

Gly Cys Cys Gly Arg Ser Cys Ile Ala Leu Phe Cys Ser Asp Ser Thr
            20                  25                  30

Leu Cys

<210> SEQ ID NO 252
<211> LENGTH: 39
<212> TYPE: PRT
<213> ORGANISM: Endogenous Retrovirus-K (from Pan troglodytes)

<400> SEQUENCE: 252

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
            35

<210> SEQ ID NO 253
```

```
<211> LENGTH: 40
<212> TYPE: PRT
<213> ORGANISM: Endogenous Retrovirus-K (from Gorilla gorilla gorilla)

<400> SEQUENCE: 253

Ile Gln Lys Ile His Phe Tyr Phe Asp Cys Ser Asp Tyr Gly Ile Asn
1               5                   10                  15

Cys Ser His Ser Tyr Gly Phe Cys Gly Arg Ser Cys Ile Ala Leu Phe
            20                  25                  30

Cys Ser Thr Val Arg Phe Val Asn
        35                  40

<210> SEQ ID NO 254
<211> LENGTH: 40
<212> TYPE: PRT
<213> ORGANISM: Endogenous Retrovirus-K (from Gorilla gorilla gorilla)

<400> SEQUENCE: 254

Ile Gln Lys Ile His Phe Tyr Phe Asn Cys Ser Asp Tyr Gly Ile Asn
1               5                   10                  15

Cys Ser His Ser Tyr Gly Cys Cys Gly Arg Ser Cys Ile Ala Leu Phe
            20                  25                  30

Cys Ser Ser Val Asn Phe Val Asn
        35                  40

<210> SEQ ID NO 255
<211> LENGTH: 40
<212> TYPE: PRT
<213> ORGANISM: Endogenous Retrovirus-K (from Gorilla gorilla gorilla)

<400> SEQUENCE: 255

Ile Gln Asn Ile His Phe Tyr Phe Asn Cys Ser Asp Tyr Gly Ile Asn
1               5                   10                  15

Cys Ser His Ser Tyr Gly Arg Cys Arg Arg Ser Cys Ile Ala Leu Phe
            20                  25                  30

Cys Ser Thr Val Asn Phe Val Asn
        35                  40

<210> SEQ ID NO 256
<211> LENGTH: 40
<212> TYPE: PRT
<213> ORGANISM: Endogenous Retrovirus-K (from Gorilla gorilla gorilla)

<400> SEQUENCE: 256

Ile Gln Lys Ile His Phe Tyr Phe Asn Cys Ser Asp Tyr Gly Ile Asn
1               5                   10                  15

Cys Ser His Ser Tyr Gly Cys Cys Gly Arg Ser Cys Ile Ala Leu Phe
            20                  25                  30

Cys Ser Ser Val Asn Phe Val Asn
        35                  40

<210> SEQ ID NO 257
<211> LENGTH: 39
<212> TYPE: PRT
<213> ORGANISM: Endogenous Retrovirus-K (from Gorilla gorilla gorilla)

<400> SEQUENCE: 257

Ile Gln Lys Ile His Phe Tyr Phe Asn Gly Ser Asp Tyr Gly Ile Asn
1               5                   10                  15

Cys Ser His Ser Tyr Gly Cys Cys Ser Arg Ser Cys Ile Ala Leu Phe
            20                  25                  30
```

Cys Ser Val Gly Thr Phe Asn
        35

<210> SEQ ID NO 258
<211> LENGTH: 40
<212> TYPE: PRT
<213> ORGANISM: Endogenous Retrovirus-K (from Gorilla gorilla gorilla)

<400> SEQUENCE: 258

Ile Gln Lys Ile His Phe Tyr Phe Asn Cys Ser Asp Tyr Gly Ile Asn
1               5                   10                  15

Cys Ser His Ser Tyr Gly Cys Cys Gly Arg Ser Cys Ala Ala Leu Phe
            20                  25                  30

Cys Ser Ser Val Asn Phe Val Asn
        35                  40

<210> SEQ ID NO 259
<211> LENGTH: 40
<212> TYPE: PRT
<213> ORGANISM: Endogenous Retrovirus-K (from Gorilla gorilla gorilla)

<400> SEQUENCE: 259

Leu Asn Arg Ser Lys Arg Phe Phe Asn Cys Ser Asp Tyr Gly Thr Asn
1               5                   10                  15

Cys Ser His Ser Tyr Gly Leu Cys Gly Arg Ser Phe Ile Val Leu Phe
            20                  25                  30

Cys Ser Asp Val Asn Phe Leu Asn
        35                  40

<210> SEQ ID NO 260
<211> LENGTH: 40
<212> TYPE: PRT
<213> ORGANISM: Endogenous Retrovirus-K (from Gorilla gorilla gorilla)

<400> SEQUENCE: 260

Ile Gln Lys Ile His Phe Tyr Phe Asn Tyr Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Ser Val Asn Phe Val Asn
        35                  40

<210> SEQ ID NO 261
<211> LENGTH: 40
<212> TYPE: PRT
<213> ORGANISM: Endogenous Retrovirus-K (from Gorilla gorilla gorilla)

<400> SEQUENCE: 261

Ile Gln Lys Ile His Phe Tyr Phe Asn Cys Ser Asp Tyr Gly Ile Asn
1               5                   10                  15

Cys Ser His Ser Tyr Gly Cys Cys Gly Arg Ser Cys Ile Ala Leu Phe
            20                  25                  30

Cys Ser Ser Val Asn Phe Val Asn
        35                  40

<210> SEQ ID NO 262
<211> LENGTH: 40
<212> TYPE: PRT
<213> ORGANISM: Endogenous Retrovirus-K (from Gorilla gorilla gorilla)

<400> SEQUENCE: 262

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Ser Val Asn Phe Val Asn
        35                  40

<210> SEQ ID NO 263
<211> LENGTH: 41
<212> TYPE: PRT
<213> ORGANISM: Endogenous Retrovirus-K (from Gorilla gorilla gorilla)

<400> SEQUENCE: 263

Asn Ile Gln Arg Ile His Phe Tyr Phe Asn Tyr Ser Asp Tyr Gly Ile
1               5                   10                  15

Asn Cys Ser His Ser Tyr Gly Cys Cys Gly Arg Ser Cys Ile Ala Leu
            20                  25                  30

Phe Cys Ser Ser Val Asn Phe Val Asn
        35                  40

<210> SEQ ID NO 264
<211> LENGTH: 40
<212> TYPE: PRT
<213> ORGANISM: Endogenous Retrovirus-K (from Gorilla gorilla gorilla)

<400> SEQUENCE: 264

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Asn Phe Val Asn
        35                  40

<210> SEQ ID NO 265
<211> LENGTH: 40
<212> TYPE: PRT
<213> ORGANISM: Endogenous Retrovirus-K (from Gorilla gorilla gorilla)

<400> SEQUENCE: 265

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Ser Val Asn Phe Val Asn
        35                  40

<210> SEQ ID NO 266
<211> LENGTH: 39
<212> TYPE: PRT
<213> ORGANISM: Endogenous Retrovirus-K (from Homo sapiens)

<400> SEQUENCE: 266

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
        35

```
<210> SEQ ID NO 267
<211> LENGTH: 39
<212> TYPE: PRT
<213> ORGANISM: Endogenous Retrovirus-K (from Homo sapiens)

<400> SEQUENCE: 267

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
        35

<210> SEQ ID NO 268
<211> LENGTH: 39
<212> TYPE: PRT
<213> ORGANISM: Endogenous Retrovirus-K (from Homo sapiens)

<400> SEQUENCE: 268

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
        35

<210> SEQ ID NO 269
<211> LENGTH: 39
<212> TYPE: PRT
<213> ORGANISM: Endogenous Retrovirus-K (from Homo sapiens)

<400> SEQUENCE: 269

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
        35

<210> SEQ ID NO 270
<211> LENGTH: 39
<212> TYPE: PRT
<213> ORGANISM: Endogenous Retrovirus-K (from Homo sapiens)

<400> SEQUENCE: 270

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
        35

<210> SEQ ID NO 271
<211> LENGTH: 39
<212> TYPE: PRT
<213> ORGANISM: Endogenous Retrovirus-K (from Homo sapiens)

<400> SEQUENCE: 271

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
```

```
                20                  25                  30

Cys Ser Val Ser Lys Leu Cys
        35

<210> SEQ ID NO 272
<211> LENGTH: 39
<212> TYPE: PRT
<213> ORGANISM: Endogenous Retrovirus-K (from Homo sapiens)

<400> SEQUENCE: 272

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
        35

<210> SEQ ID NO 273
<211> LENGTH: 39
<212> TYPE: PRT
<213> ORGANISM: Endogenous Retrovirus-K (from Homo sapiens)

<400> SEQUENCE: 273

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
        35

<210> SEQ ID NO 274
<211> LENGTH: 39
<212> TYPE: PRT
<213> ORGANISM: Endogenous Retrovirus-K (from Homo sapiens)

<400> SEQUENCE: 274

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
        35

<210> SEQ ID NO 275
<211> LENGTH: 39
<212> TYPE: PRT
<213> ORGANISM: Endogenous Retrovirus-K (from Homo sapiens)

<400> SEQUENCE: 275

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
        35

<210> SEQ ID NO 276
<211> LENGTH: 39
<212> TYPE: PRT
<213> ORGANISM: Endogenous Retrovirus-K (from Homo sapiens)
```

<400> SEQUENCE: 276

Ile Gln Lys Ile His Phe Tyr Phe Asn Ser Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
        35

<210> SEQ ID NO 277
<211> LENGTH: 39
<212> TYPE: PRT
<213> ORGANISM: Endogenous Retrovirus-K (from Homo sapiens)

<400> SEQUENCE: 277

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
        35

<210> SEQ ID NO 278
<211> LENGTH: 39
<212> TYPE: PRT
<213> ORGANISM: Endogenous Retrovirus-K (from Homo sapiens)

<400> SEQUENCE: 278

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
        35

<210> SEQ ID NO 279
<211> LENGTH: 39
<212> TYPE: PRT
<213> ORGANISM: Endogenous Retrovirus-K (from Homo sapiens)

<400> SEQUENCE: 279

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
        35

<210> SEQ ID NO 280
<211> LENGTH: 39
<212> TYPE: PRT
<213> ORGANISM: Endogenous Retrovirus-K (from Homo sapiens)

<400> SEQUENCE: 280

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Gly Lys Leu Cys
        35

<210> SEQ ID NO 281
<211> LENGTH: 39
<212> TYPE: PRT
<213> ORGANISM: Endogenous Retrovirus-K (from Homo sapiens)

<400> SEQUENCE: 281

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Thr Cys Ile Ala Leu Phe
                20                  25                  30

Phe Ser Val Ser Lys Leu Cys
            35

<210> SEQ ID NO 282
<211> LENGTH: 39
<212> TYPE: PRT
<213> ORGANISM: Endogenous Retrovirus-K (from Homo sapiens)

<400> SEQUENCE: 282

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Phe Phe
                20                  25                  30

Cys Ser Val Ser Lys Leu Cys
            35

<210> SEQ ID NO 283
<211> LENGTH: 39
<212> TYPE: PRT
<213> ORGANISM: Endogenous Retrovirus-K (from Homo sapiens)

<400> SEQUENCE: 283

Ile Gln Lys Ile His Phe Tyr Phe Asn Tyr Ser Asp Tyr Gly Ile Asn
1               5                   10                  15

Cys Ser His Ser Tyr Gly Cys Cys Gly Arg Ser Cys Ile Ala Leu Phe
                20                  25                  30

Cys Ser Val Ser Lys Leu Cys
            35

<210> SEQ ID NO 284
<211> LENGTH: 38
<212> TYPE: PRT
<213> ORGANISM: Endogenous Retrovirus-K (from Homo sapiens)

<400> SEQUENCE: 284

Ile Asn Ile His Phe Tyr Phe Asn Tyr Ser Asp Tyr Gly Ile Asn Cys
1               5                   10                  15

Ser His Ser Tyr Gly Cys Cys Gly Arg Ser Cys Ile Ala Leu Phe Cys
                20                  25                  30

Ser Val Ser Lys Leu Cys
            35

<210> SEQ ID NO 285
<211> LENGTH: 39
<212> TYPE: PRT
<213> ORGANISM: Endogenous Retrovirus-K (from Homo sapiens)

<400> SEQUENCE: 285

Ile Gln Lys Ile His Phe Tyr Phe Asn Cys Ser Asp Tyr Gly Ile Asn
1               5                   10                  15

```
Cys Ser His Ser Tyr Gly Cys Cys Ser Arg Ser Cys Ile Ala Leu Phe
            20                  25                  30

Cys Ser Val Gly Lys Leu Cys
        35

<210> SEQ ID NO 286
<211> LENGTH: 39
<212> TYPE: PRT
<213> ORGANISM: Endogenous Retrovirus-K (from Homo sapiens)

<400> SEQUENCE: 286

Ile Gln Lys Ile His Phe Tyr Phe Asn Cys Ser Asp Tyr Arg Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
        35

<210> SEQ ID NO 287
<211> LENGTH: 39
<212> TYPE: PRT
<213> ORGANISM: Endogenous Retrovirus-K (from Homo sapiens)

<400> SEQUENCE: 287

Ile Gln Lys Ile His Phe Tyr Phe Asn Cys Ser Asp Tyr Arg Ile Asn
1               5                   10                  15

Cys Ser His Ser Tyr Gly Cys Cys Ser Lys Ser Cys Ile Ala Leu Phe
            20                  25                  30

Cys Ser Val Ser Glu Leu Cys
        35

<210> SEQ ID NO 288
<211> LENGTH: 39
<212> TYPE: PRT
<213> ORGANISM: Endogenous Retrovirus-K (from Pan troglodytes)

<400> SEQUENCE: 288

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
        35

<210> SEQ ID NO 289
<211> LENGTH: 39
<212> TYPE: PRT
<213> ORGANISM: Endogenous Retrovirus-K (from Pan troglodytes)

<400> SEQUENCE: 289

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
        35

<210> SEQ ID NO 290
<211> LENGTH: 38
<212> TYPE: PRT
<213> ORGANISM: Endogenous Retrovirus-K (from Pan troglodytes)
```

<400> SEQUENCE: 290

Gln Lys Ile His Phe Tyr Phe Asn Cys Ser Asp Tyr Gly Ile Asn Cys
1               5                   10                  15

Ser His Ser Tyr Gly Cys Cys Ser Arg Ser Cys Ile Ala Leu Phe Tyr
            20                  25                  30

Ser Val Ser Lys Leu Cys
        35

<210> SEQ ID NO 291
<211> LENGTH: 39
<212> TYPE: PRT
<213> ORGANISM: Endogenous Retrovirus-K (from Pan troglodytes)

<400> SEQUENCE: 291

Ile Gln Lys Ile His Phe Tyr Phe Asn Cys Ser Asp Tyr Gly Ile Asn
1               5                   10                  15

Cys Ser His Ser Tyr Gly Cys Cys Gly Arg Ser Cys Ile Ala Leu Phe
            20                  25                  30

Cys Ser Val Ser Lys Leu Cys
        35

<210> SEQ ID NO 292
<211> LENGTH: 38
<212> TYPE: PRT
<213> ORGANISM: Endogenous Retrovirus-K (from Pan troglodytes)

<400> SEQUENCE: 292

Gln Lys Ile His Phe Tyr Phe Asn Cys Ser Asp Tyr Gly Ile Asn Cys
1               5                   10                  15

Ser His Ser Tyr Gly Cys Cys Gly Arg Ser Cys Ile Ala Leu Phe Cys
            20                  25                  30

Ser Val Ser Lys Leu Cys
        35

<210> SEQ ID NO 293
<211> LENGTH: 39
<212> TYPE: PRT
<213> ORGANISM: Endogenous Retrovirus-K (from Pan troglodytes)

<400> SEQUENCE: 293

Ile Gln Lys Ile His Phe Tyr Phe Asn Cys Ser Asp Tyr Gly Ile Asn
1               5                   10                  15

Cys Ser His Ser Tyr Gly Cys Cys Gly Arg Ser Cys Ile Ala Leu Phe
            20                  25                  30

Cys Ser Val Ser Lys Leu Cys
        35

<210> SEQ ID NO 294
<211> LENGTH: 39
<212> TYPE: PRT
<213> ORGANISM: Endogenous Retrovirus-K (from Pan troglodytes)

<400> SEQUENCE: 294

Val Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Ser Lys Leu Cys
        35

<210> SEQ ID NO 295
<211> LENGTH: 39
<212> TYPE: PRT
<213> ORGANISM: Endogenous Retrovirus-K (from Pan troglodytes)

<400> SEQUENCE: 295

Ile Gln Lys Ile His Phe Tyr Phe Asn Cys Ser Asp Tyr Gly Ile Asn
1               5                   10                  15

Cys Ser His Ser Tyr Gly Cys Cys Gly Arg Ser Cys Val Ala Leu Phe
            20                  25                  30

Cys Ser Val Ser Lys Leu Cys
        35

<210> SEQ ID NO 296
<211> LENGTH: 39
<212> TYPE: PRT
<213> ORGANISM: Endogenous Retrovirus-K (from Pan troglodytes)

<400> SEQUENCE: 296

Ile Gln Lys Ile His Phe Tyr Phe Asn Cys Ser Asp Tyr Gly Ile Asn
1               5                   10                  15

Cys Ser His Ser Tyr Gly Cys Cys Gly Arg Ser Cys Ile Ala Leu Phe
            20                  25                  30

Cys Ser Val Gly Lys Leu Cys
        35

<210> SEQ ID NO 297
<211> LENGTH: 38
<212> TYPE: PRT
<213> ORGANISM: Endogenous Retrovirus-K (from Pan troglodytes)

<400> SEQUENCE: 297

Ile Gln Lys Ile His Phe Tyr Phe Asn Cys Ser Asp Tyr Gly Ile Asn
1               5                   10                  15

Cys Ser His Ser Tyr Gly Cys Cys Gly Arg Ser Cys Thr Ala Leu Phe
            20                  25                  30

Cys Ser Val Gly Lys Leu
        35

<210> SEQ ID NO 298
<211> LENGTH: 37
<212> TYPE: PRT
<213> ORGANISM: Endogenous Retrovirus-K (from Pan troglodytes)

<400> SEQUENCE: 298

Gln Lys Ile Arg Phe Tyr Phe Asn Cys Ser Asp Tyr Gly Ile Asn Cys
1               5                   10                  15

Ser His Ser Tyr Gly Cys Cys Ser Arg Ser Cys Ile Ala Leu Phe Cys
            20                  25                  30

Ser Val Gly Lys Leu
        35

<210> SEQ ID NO 299
<211> LENGTH: 39
<212> TYPE: PRT
<213> ORGANISM: Endogenous Retrovirus-K (from Gorilla gorilla gorilla)

<400> SEQUENCE: 299

Glu Ile Ile Tyr Phe Tyr Ile Asn Cys Ser Asn Asn Gly Leu Ile Ala
1               5                   10                  15

Val Thr Ala Thr Ala Ala Thr Ala Gly Val Ala Leu His Gln Ser Ile
            20                  25                  30

Gln Thr Val His Phe Val Asp
            35

<210> SEQ ID NO 300
<211> LENGTH: 40
<212> TYPE: PRT
<213> ORGANISM: Endogenous Retrovirus-K (from Gorilla gorilla gorilla)

<400> SEQUENCE: 300

Ile Gln Lys Ile His Phe Tyr Phe Asn Cys Ser Asp Tyr Gly Ile His
1               5                   10                  15

Cys Ser His Ser Tyr Gly Cys Cys Ala Gly Val Ala Leu His Ser Ser
            20                  25                  30

Val Gln Ser Val Asn Phe Val Asn
            35                  40

<210> SEQ ID NO 301
<211> LENGTH: 40
<212> TYPE: PRT
<213> ORGANISM: Endogenous Retrovirus-K (from Gorilla gorilla gorilla)

<400> SEQUENCE: 301

Ile Gln Lys Ile His Phe Tyr Phe Asn Tyr Ser Asp Tyr Gly Ile Asn
1               5                   10                  15

Cys Ser His Ser Tyr Gly Cys Cys Gly Arg Ser Cys Ile Ala Leu Phe
            20                  25                  30

Cys Ser Ser Val Asn Phe Val Asn
            35                  40

<210> SEQ ID NO 302
<211> LENGTH: 40
<212> TYPE: PRT
<213> ORGANISM: Endogenous Retrovirus-K (from Gorilla gorilla gorilla)

<400> SEQUENCE: 302

Ile Gln Lys Ile His Phe Tyr Phe Asn Cys Ser Asp Tyr Gly Ile Asn
1               5                   10                  15

Cys Ser His Ser His Gly Cys Cys Ser Arg Ser Cys Ile Ala Leu Phe
            20                  25                  30

Cys Ser Ser Val Asn Phe Val Asn
            35                  40

<210> SEQ ID NO 303
<211> LENGTH: 40
<212> TYPE: PRT
<213> ORGANISM: Endogenous Retrovirus-K (from Gorilla gorilla gorilla)

<400> SEQUENCE: 303

Ile Gln Lys Ile His Phe Tyr Phe Asn Cys Ser Asp Tyr Gly Ile Asn
1               5                   10                  15

Cys Ser His Ser Tyr Gly Cys Cys Gly Arg Ser Cys Ile Ala Leu Phe
            20                  25                  30

Cys Ser Ser Val Asn Phe Val Asn
            35                  40

<210> SEQ ID NO 304
<211> LENGTH: 40
<212> TYPE: PRT

<213> ORGANISM: Endogenous Retrovirus-K (from Gorilla gorilla gorilla)

<400> SEQUENCE: 304

Met Gln Lys Ile His Phe Tyr Phe Asn Tyr Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Ser Val Asn Phe Val Asn
        35                  40

<210> SEQ ID NO 305
<211> LENGTH: 40
<212> TYPE: PRT
<213> ORGANISM: Endogenous Retrovirus-K (from Gorilla gorilla gorilla)

<400> SEQUENCE: 305

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Ser Val Asn Phe Val Asn
        35                  40

<210> SEQ ID NO 306
<211> LENGTH: 40
<212> TYPE: PRT
<213> ORGANISM: Endogenous Retrovirus-K (from Gorilla gorilla gorilla)

<400> SEQUENCE: 306

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Ser Val Asn Phe Val Asn
        35                  40

<210> SEQ ID NO 307
<211> LENGTH: 46
<212> TYPE: PRT
<213> ORGANISM: Endogenous Retrovirus-K (from Cercocebus atys)

<400> SEQUENCE: 307

Ser Ile Lys Arg His Phe Lys Ile Gln Lys Ile His Phe Cys Phe Asn
1               5                   10                  15

Arg Ser Asp Tyr Gly Ile Asn Cys Arg His Ser Tyr Gly Arg Cys Gly
            20                  25                  30

Gly Ser Cys Ile Ala Leu Phe Cys Leu Asp Ser Lys Leu Cys
        35                  40                  45

<210> SEQ ID NO 308
<211> LENGTH: 47
<212> TYPE: PRT
<213> ORGANISM: Endogenous Retrovirus-K (from Cercocebus atys)

<400> SEQUENCE: 308

Ser Ile Lys Arg His Phe Lys Trp Ile Gln Lys Ile His Phe Tyr Phe
1               5                   10                  15

Asn Cys Ser Asp Tyr Gly Ile Asn Cys Ser His Ser Tyr Gly Arg Cys
            20                  25                  30

Gly Arg Ser Cys Ile Ala Pro Phe Phe Ser Asp Ser Lys Leu Cys

-continued

```
                 35                  40                  45

<210> SEQ ID NO 309
<211> LENGTH: 46
<212> TYPE: PRT
<213> ORGANISM: Endogenous Retrovirus-K (from Cercocebus atys)

<400> SEQUENCE: 309

Gly Ile Lys Ser His Phe Lys Leu Gln Lys Ile His Phe Tyr Phe Asn
1               5                   10                  15

Cys Ser Asp Tyr Gly Ile Asn Cys Ser His Ser Tyr Gly Arg Cys Gly
            20                  25                  30

Arg Ser Cys Ile Ala Leu Phe Cys Ser Asp Gly Lys Leu Cys
        35                  40                  45

<210> SEQ ID NO 310
<211> LENGTH: 46
<212> TYPE: PRT
<213> ORGANISM: Endogenous Retrovirus-K (from Cercocebus atys)

<400> SEQUENCE: 310

Ser Ile Lys Arg His Phe Lys Ile Gln Lys Ile His Phe Tyr Phe Asn
1               5                   10                  15

Cys Ser Asp Tyr Gly Ile Asn Cys Ser His Ser Tyr Ser Leu Cys Gly
            20                  25                  30

Arg Ser Cys Ile Ala Leu Phe Cys Ser Asp Ser Lys Leu Cys
        35                  40                  45

<210> SEQ ID NO 311
<211> LENGTH: 46
<212> TYPE: PRT
<213> ORGANISM: Endogenous Retrovirus-K (from Cercocebus atys)

<400> SEQUENCE: 311

Val Leu Lys Lys Ser Ser Lys Ile Pro Lys Ile His Phe Tyr Phe Asp
1               5                   10                  15

Cys Ser Asn Cys Gly Ile Asn Cys Ser His Ser Asp Gly Cys Cys Gly
            20                  25                  30

Gly Ser Cys Ile Ala Leu Phe Cys Ser Asp Ser Thr Leu Gly
        35                  40                  45

<210> SEQ ID NO 312
<211> LENGTH: 38
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (34)..(34)
<223> OTHER INFORMATION: Xaa can be any naturally occurring amino acid

<400> SEQUENCE: 312

Gln Lys Ile His Phe Tyr Phe Asn Cys Ser Asp Tyr Gly Ile Asn Cys
1               5                   10                  15

Ser His Ser Tyr Gly Cys Cys Ser Arg Ser Cys Ile Ala Leu Phe Cys
            20                  25                  30

Ser Xaa Ser Lys Leu Cys
        35

<210> SEQ ID NO 313
<211> LENGTH: 38
```

<212> TYPE: PRT
<213> ORGANISM: Endogenous Retrovirus-K (from Homo sapiens)

<400> SEQUENCE: 313

Gln Lys Ile His Phe Tyr Phe Asn Cys Ser Asp Tyr Gly Ile Asn Cys
1               5                   10                  15

Ser His Ser Tyr Gly Cys Cys Ser Arg Ser Cys Ile Ala Leu Phe Cys
            20                  25                  30

Ser Val Ser Lys Leu Cys
        35

<210> SEQ ID NO 314
<211> LENGTH: 38
<212> TYPE: PRT
<213> ORGANISM: Artificial Sequence
<220> FEATURE:
<223> OTHER INFORMATION: Synthetic Construct

<400> SEQUENCE: 314

Gln Lys Ile His Phe Tyr Phe Asn Cys Ser Asp Tyr Gly Ile Asn Cys
1               5                   10                  15

Ser His Ser Tyr Gly Cys Cys Ser Arg Ser Cys Ile Ala Leu Phe Cys
            20                  25                  30

Ser Val Ser Lys Leu Cys
        35

<210> SEQ ID NO 315
<211> LENGTH: 39
<212> TYPE: PRT
<213> ORGANISM: Artificial Sequence
<220> FEATURE:
<223> OTHER INFORMATION: Synthetic Construct

<400> SEQUENCE: 315

Ile Gln Lys Ile His Phe Tyr Phe Asn Cys Ser Asp Tyr Gly Ile Asn
1               5                   10                  15

Cys Ser His Ser Tyr Gly Cys Cys Gly Arg Ser Cys Ile Ala Leu Phe
            20                  25                  30

Cys Ser Val Gly Lys Leu Cys
        35

<210> SEQ ID NO 316
<211> LENGTH: 39
<212> TYPE: PRT
<213> ORGANISM: Artificial Sequence
<220> FEATURE:
<223> OTHER INFORMATION: Synthetic Construct

<400> SEQUENCE: 316

Ile Gln Lys Ile His Phe Tyr Phe Asn Cys Ser Asp Tyr Gly Ile Asn
1               5                   10                  15

Cys Ser His Ser Tyr Ser Leu Cys Gly Arg Ser Cys Ile Ala Leu Phe
            20                  25                  30

Cys Ser Asp Ser Lys Leu Cys
        35

<210> SEQ ID NO 317
<211> LENGTH: 39
<212> TYPE: PRT
<213> ORGANISM: Artificial Sequence
<220> FEATURE:
<223> OTHER INFORMATION: Synthetic Construct -continued

```
<400> SEQUENCE: 317

Ile Gln Lys Ile His Phe Tyr Phe Asn Cys Ser Asp Tyr Gly Ile Asn
1               5                   10                  15

Cys Ser His Ser Tyr Gly Cys Cys Gly Arg Ser Cys Ile Ala Leu Phe
            20                  25                  30

Cys Ser Val Ser Lys Leu Cys
        35

<210> SEQ ID NO 318
<211> LENGTH: 39
<212> TYPE: PRT
<213> ORGANISM: Artificial Sequence
<220> FEATURE:
<223> OTHER INFORMATION: Synthetic Construct

<400> SEQUENCE: 318

Ile Gln Lys Ile His Phe Tyr Phe Asn Cys Ser Asp Tyr Gly Ile Asn
1               5                   10                  15

Cys Ser His Ser Tyr Gly Cys Cys Ser Arg Ser Cys Ile Ala Leu Phe
            20                  25                  30

Cys Ser Val Gly Lys Leu Cys
        35
```

UNITED STATES PATENT AND TRADEMARK OFFICE
CERTIFICATE OF CORRECTION

PATENT NO. : 12,064,407 B2
APPLICATION NO. : 16/756947
DATED : August 20, 2024
INVENTOR(S) : Renée Douville et al.

It is certified that error appears in the above-identified patent and that said Letters Patent is hereby corrected as shown below:

In the Claims

Column 248, Line 43, Claim 5 replace "or CTXLP" with --CTXLP--.

Column 250, Line 4, Claim 6 replace "CaV2.2 COAT" with --CaV2.2 CCAT--.

Signed and Sealed this
Nineteenth Day of November, 2024

Katherine Kelly Vidal
*Director of the United States Patent and Trademark Office*